United States Patent
Eckhardt et al.

(10) Patent No.: US 9,120,769 B2
(45) Date of Patent: *Sep. 1, 2015

(54) ARYL- AND HETEROARYLCARBONYL DERIVATIVES OF HEXAHYDROINDENOPYRIDINE AND OCTAHYDROBENZOQUINOLINE

(71) Applicant: Boehringer Ingelheim International GmbH, Ingelheim am Rhein (DE)

(72) Inventors: Matthias Eckhardt, Biberach an der Riss (DE); Hans-Juergen Martin, Biberach an der Riss (DE); Martin Schuehle, Biberach an der Riss (DE); Sandra Sick, Biberach an der Riss (DE); Bing Shiou Yang, Southbury, CT (US)

(73) Assignee: Boehringer-Ingelheim International GmbH (DE)

(*) Notice: Subject to any disclaimer, the term of this patent is extended or adjusted under 35 U.S.C. 154(b) by 0 days.

This patent is subject to a terminal disclaimer.

(21) Appl. No.: 14/190,899

(22) Filed: Feb. 26, 2014

(65) Prior Publication Data

US 2014/0249174 A1 Sep. 4, 2014

Related U.S. Application Data

(63) Continuation of application No. 13/289,418, filed on Nov. 4, 2011, now Pat. No. 8,686,149.

(60) Provisional application No. 61/484,995, filed on May 11, 2011.

(30) Foreign Application Priority Data

Nov. 5, 2010 (WO) ................ PCT/US2010/055586

(51) Int. Cl.
A61K 31/44 (2006.01)
C07D 401/06 (2006.01)

(52) U.S. Cl.
CPC .................... C07D 401/06 (2013.01)

(58) Field of Classification Search
USPC ........................................................ 514/290
See application file for complete search history.

(56) References Cited

U.S. PATENT DOCUMENTS

| | | |
|---|---|---|
| 3,341,538 A | 9/1967 | Block et al. |
| 3,657,257 A | 4/1972 | Helsley et al. |
| 3,681,349 A | 8/1972 | Schwan et al. |
| 3,703,529 A | 11/1972 | Cavalla et al. |
| 3,708,497 A | 1/1973 | Kamiya et al. |
| 3,919,047 A | 11/1975 | Vidic et al. |
| 3,931,194 A | 1/1976 | Merz et al. |
| 3,981,874 A | 9/1976 | Merz et al. |
| 3,982,005 A | 9/1976 | Merz et al. |
| 4,009,171 A | 2/1977 | Albertson |
| 4,087,532 A | 5/1978 | Merz et al. |
| 4,108,857 A | 8/1978 | Albertson |
| 4,293,556 A | 10/1981 | Merz et al. |
| 6,368,816 B2 | 4/2002 | Walker et al. |
| 6,838,253 B2 | 1/2005 | Walker et al. |
| 6,946,487 B2 | 9/2005 | Walker et al. |
| 7,087,400 B2 | 8/2006 | Walker et al. |
| 7,122,531 B2 | 10/2006 | Walker et al. |
| 7,122,532 B2 | 10/2006 | Walker et al. |
| 7,129,231 B2 | 10/2006 | Walker et al. |
| 7,276,520 B2 | 10/2007 | Nargund et al. |
| 7,799,782 B2 | 9/2010 | Munson et al. |
| 7,897,773 B2 | 3/2011 | Aletru et al. |
| 8,048,825 B2 | 11/2011 | Hino et al. |
| 8,497,281 B2* | 7/2013 | Eckhardt et al. ............. 514/290 |
| 2006/0089349 A1 | 4/2006 | Gundertofte et al. |
| 2007/0197530 A1 | 8/2007 | Li et al. |

(Continued)

FOREIGN PATENT DOCUMENTS

| | | |
|---|---|---|
| DE | 2105743 A1 | 8/1972 |
| DE | 2108954 A1 | 9/1972 |

(Continued)

OTHER PUBLICATIONS

Brittain's publication, pp. 348-361, 1999.*
Acta Polonaie Pharmaceutica 1987, 39, p. 411-414.
Acta Poloniae Pharmaceutica 1982, 39, p. 61-64.
Acta Poloniae Pharmaceutica 1986, 43, p. 403-405.
Anantanarayan, Ashok, et al., Chemical Abstract Document No. 133:4656 (2000), 4pp.
Chem. Ber. 1976, 109, p. 2657-2669.
Database File Registry (online), Chemical Abstracts Service, Columbus, Ohio 2007, Database accession No. 958599-31-0 abstract (ISA).

(Continued)

*Primary Examiner* — Rei-Tsang Shiao
(74) *Attorney, Agent, or Firm* — McCarter & English LLP; Steven G. Davis; Michael J. DeGrazia

(57) ABSTRACT

The present invention relates to compounds defined by formula I

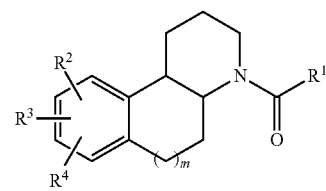

wherein the variables $R^1$, $R^2$, $R^3$, $R^4$, and m are defined as in claim 1, possessing valuable pharmacological activity. Particularly, the compounds are inhibitors of 11β-hydroxysteroid dehydrogenase (HSD) 1 and thus are suitable for treatment and prevention of diseases which can be influenced by inhibition of this enzyme, such as metabolic diseases, in particular diabetes type 2, obesity, and dyslipidemia.

6 Claims, 8 Drawing Sheets

(56) References Cited

U.S. PATENT DOCUMENTS

| | | |
|---|---|---|
| 2011/0105504 A1 | 5/2011 | Claremon et al. |
| 2011/0136800 A1 | 6/2011 | Eckhardt et al. |
| 2011/0263583 A1 | 10/2011 | Claremon et al. |
| 2012/0108579 A1 | 5/2012 | Renz et al. |
| 2012/0157488 A1 | 6/2012 | Eckhardt et al. |

FOREIGN PATENT DOCUMENTS

| | | |
|---|---|---|
| DE | 2229695 A1 | 1/1974 |
| DE | 2338369 A1 | 2/1975 |
| DE | 2354002 A1 | 5/1975 |
| DE | 2411382 A1 | 9/1975 |
| DE | 2437610 A1 | 2/1976 |
| DE | 2828039 A1 | 1/1980 |
| DE | 10034623 A1 | 1/2002 |
| EP | 0847275 A1 | 6/1998 |
| EP | 0928789 A1 | 7/1999 |
| EP | 1864971 A1 | 12/2007 |
| EP | 1935420 A1 | 6/2008 |
| GB | 1077711 A | 8/1967 |
| JP | 2007140188 A | 6/2007 |
| WO | 96/37494 A1 | 11/1996 |
| WO | 97/07789 A1 | 3/1997 |
| WO | 98/22462 A1 | 5/1998 |
| WO | 0031063 A1 | 6/2000 |
| WO | 01/55063 A1 | 8/2001 |
| WO | 03/097608 A2 | 11/2003 |
| WO | 2004/089896 A1 | 10/2004 |
| WO | 2005/108361 A1 | 11/2005 |
| WO | 2006/024628 A1 | 3/2006 |
| WO | 2006/040329 A1 | 4/2006 |
| WO | 2006/044174 A1 | 4/2006 |
| WO | 2007/051810 A2 | 5/2007 |
| WO | 2007051811 A2 | 5/2007 |
| WO | 2007/076055 A2 | 7/2007 |
| WO | 2007/081570 A2 | 7/2007 |
| WO | 2007/124337 A1 | 11/2007 |
| WO | 2007/127693 A1 | 11/2007 |
| WO | 2007/127763 A2 | 11/2007 |
| WO | 2008/000951 A2 | 1/2008 |
| WO | 2008/046758 A2 | 4/2008 |
| WO | 2008/106128 A2 | 9/2008 |
| WO | 2008110196 A1 | 9/2008 |
| WO | 2009/017664 A1 | 2/2009 |
| WO | 2009/017671 A1 | 2/2009 |
| WO | 2009/061498 A1 | 5/2009 |
| WO | 2009/063061 A2 | 5/2009 |
| WO | 2009/100872 A1 | 8/2009 |
| WO | 2009/102428 A2 | 8/2009 |
| WO | 2009/102460 A2 | 8/2009 |
| WO | 2009/117109 A1 | 9/2009 |
| WO | 2009/134400 A1 | 11/2009 |
| WO | 2010/010157 A2 | 1/2010 |
| WO | 2010/011314 A1 | 1/2010 |

OTHER PUBLICATIONS

Database File Registry (online), Chemical Abstracts Service, Columbus, Ohio 2007, Database accession No. 958625-83-7 abstract (ISA).
Database File Registry (online), Chemical Abstracts Service, Columbus, Ohio 2007, Database accession No. 958629-14-6 abstract (ISA).
Database File Registry (online), Chemical Abstracts Service, Columbus, Ohio 2007, Database accession No. 958629-22-6 abstract (ISA).
Database File Registry (online), Chemical Abstracts Service, Columbus, Ohio 2007, Database accession No. 958629-39-5 abstract (ISA).
Database File Registry (online), Chemical Abstracts Service, Columbus, Ohio 2007, Database accession No. 958696-32-7 abstract (ISA).
Database File Registry (online), Chemical Abstracts Service, Columbus, Ohio 2007, Database accession No. 958696-39-4 abstract (ISA).
Database File Registry (online), Chemical Abstracts Service, Columbus, Ohio 2007, Database accession No. 958700-63-5 abstract (ISA).
Demarinis R.M. et.al., Journal of Medicinal Chemistry 1981, vol. 24, No. 12, pp. 1432-1437.
Harno et.al., Trends in Endocrinology and Metabolism, Elsevier Science Publishing, New York 2010, vol. 21, No. 10, pp. 619-627 (ISA).
Helsley, Grover C., Chemical Abstract Document No. 77:5360 (1972), 2 pp.
Hembrough, Todd A., Chemical Abstract Document No. 147:134403 (2007), 1 page.
Heterocycles 1980, 14, p. 1983-1988.
Hughes, Katherine A., 11-Beta-Hydroxysteroid Dehydrogenase Type 1 (11Beta-HSD1) Inhibitors in Type 2 Diabetes Mellitus and Obesity, Expert Opin. Investig. Drugs, 17(4):481-496, (2008).
International Preliminary Report on Patentability for PCT/US2009/002653, issued Nov. 2, 2010.
International Search Report and Written Opinion for PCT/US2009/002653, completed Jun. 23, 2009.
J. Med. Chem. 1979, 22, p. 537-553.
Rosenstock et.al. Diabetes Care Jul. 2010 LNKD-PUBMED:20413513, vol.33, No. 7, pp. 1516-1522 (ISA P01-2676).
Synthesis 2007, p. 161-163.
Taddayon et.al., Expert opinion on Investigational Drugs Ashley Publication Ltd. 2003, vol. 12, No. 3, pp. 307-324 (ISA).
Tetrahedron 2007, 63, p. 7523-7531.
Britain, 1999, pp. 348-361.

\* cited by examiner

ARYL- AND HETEROARYLCARBONYL DERIVATIVES OF HEXAHYDROINDENOPYRIDINE AND OCTAHYDROBENZOQUINOLINE

RELATED APPLICATIONS

This application is a divisional of U.S. patent application Ser. No. 13/289,418, filed Nov. 4, 2011, now U.S. Pat. No. 8,686,149, which claims the benefit of U.S. Provisional Application Ser. No. 61/484,995, filed May 11, 2011. U.S. patent application Ser. No. 13/289,418 also claims priority to International Application Serial No. PCT/US2010/055586, filed Nov. 5, 2010. The entire teachings of each of these applications are incorporated herein by reference.

FIELD OF THE INVENTION

The present invention relates to hexahydroindenopyridines and octahydrobenzoquinolines and their use as inhibitors of 11β-hydroxysteroid dehydrogenase 1 (HSD 1), to pharmaceutical compositions containing said compounds as well as their use for the treatment of metabolic disorders like metabolic syndrome, diabetes, obesity, and dyslipidemia. In addition, the invention relates to processes for preparing a pharmaceutical composition as well as a compound according to the invention.

BACKGROUND OF THE INVENTION

In the literature, compounds which have an inhibitory effect on the enzyme 11β-hydroxysteroid dehydrogenase (HSD) 1 are proposed for the treatment of the metabolic syndrome, in particular diabetes type 2, obesity, and dyslipidemia.

In *Bulletin of the Chemical Society of Japan* 1959, 32, p. 1005-7 and *Journal of Organic Chemistry* 1964, 29, p. 1419-24, the compounds of the following structures have been disclosed:

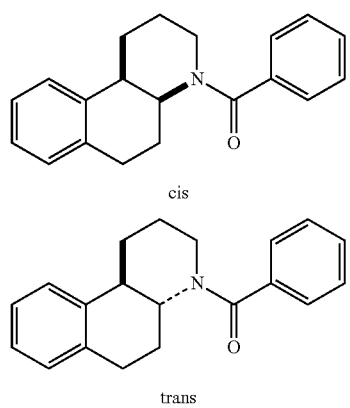

In *Journal of Organic Chemistry* 1984, 49, p. 2504-6 a chromatographic method to separate enantiomers of heterocyclic amines, inter alia the enantiomers of the following racemic compound are disclosed:

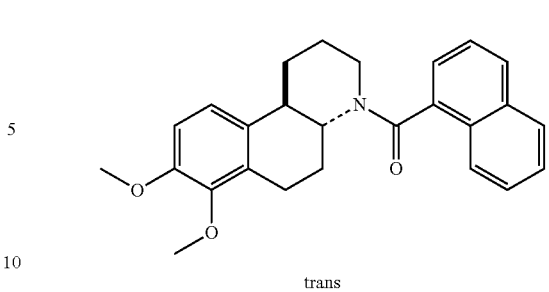

In *Journal of Medicinal Chemistry* 1981, 24, p. 1432-7 the following compound is described as an intermediate in order to separate cis- and trans-isomer:

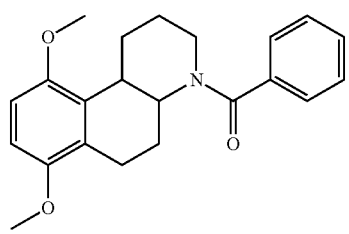 [SMILES: COc1ccc(OC)c2c1CCC1C2CCCN1C(=O)c1ccccc1]

AIM OF THE INVENTION

It has been surprisingly found that compounds of the present invention have not only an inhibitory effect on HSD 1 in vitro and/or in vivo but also possess significant metabolic stability which makes them suitable to be used as medicaments. Accordingly, aim of the present invention is to discover hexahydroindenopyridines and octahydrobenzoquinolines having an inhibitory effect on HSD 1 in vitro and/or in vivo and possessing suitable pharmacological and pharmacokinetic properties to use them as medicaments.

A further aspect of the present invention is to provide new pharmaceutical compositions which are suitable for the prevention and/or treatment of metabolic disorders.

A further aspect of the invention relates to the physiologically acceptable salts of the compounds of general formula I according to this invention with inorganic or organic acids or bases.

In a further aspect this invention relates to pharmaceutical compositions, containing at least one compound of general formula I or a physiologically acceptable salt according to the invention, optionally together with one or more inert carriers and/or diluents.

In a further aspect this invention relates to the compounds according to general formula I or the physiologically acceptable salts thereof for treatment or prevention of diseases or conditions which can be influenced by inhibiting the enzyme 11β-hydroxysteroid dehydrogenase (HSD) 1, such as metabolic disorders.

In a further aspect this invention relates to the use of at least one compound according to general formula I or a physiologically acceptable salt thereof for preparing a pharmaceutical composition which is suitable for the treatment or prevention of diseases or conditions which can be influenced by inhibiting the enzyme 11β-hydroxysteroid dehydrogenase (HSD) 1, such as metabolic disorders.

Other aims of the present invention will become apparent to the skilled man directly from the foregoing and following remarks.

DETAILED DESCRIPTION

Figure 1:
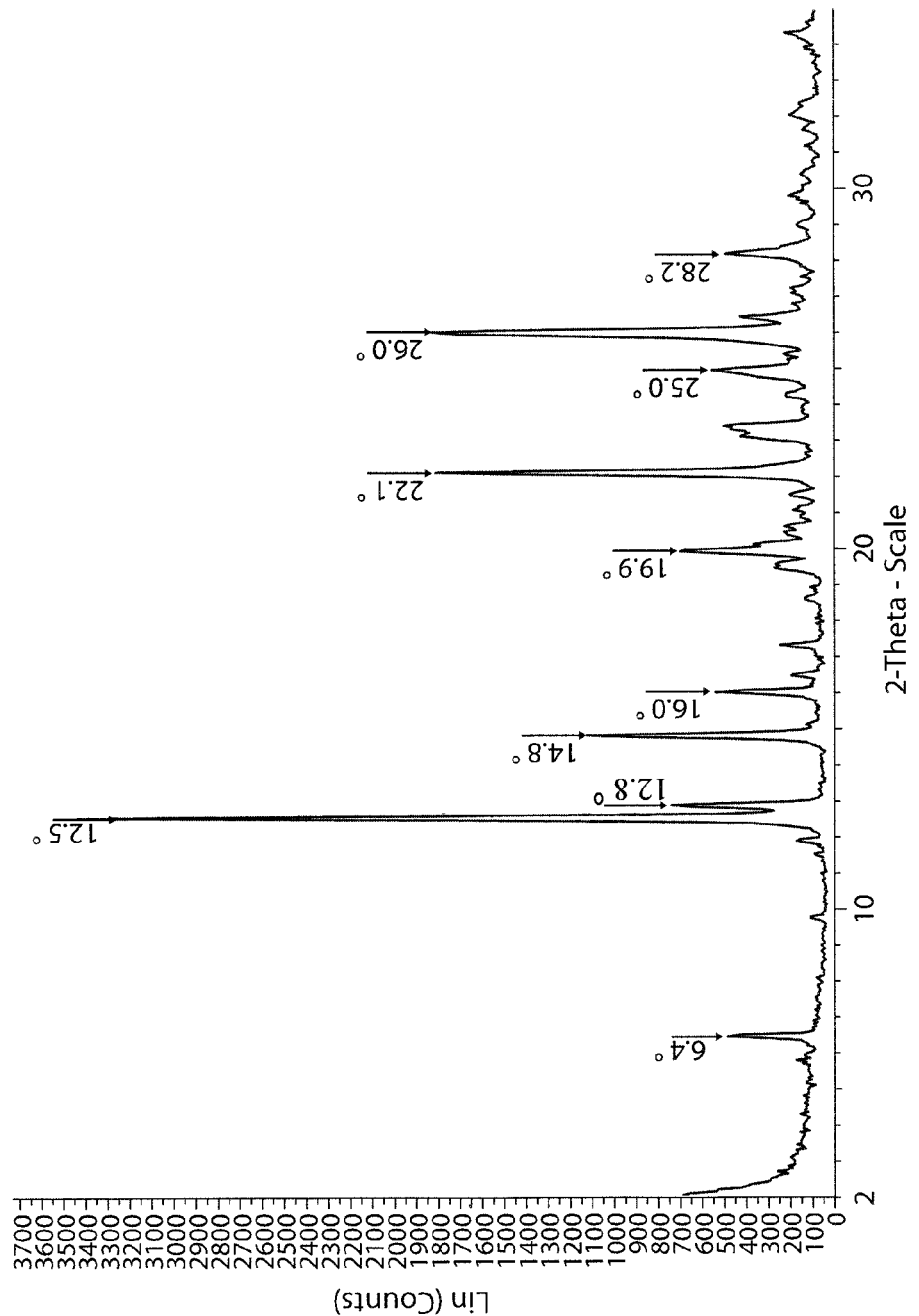
FIG. 1 is an XRPD pattern obtained from a sample of Form I of the compound of formula (II).

In a first aspect the present invention relates to compounds of general formula I

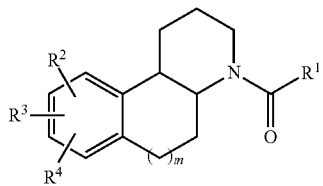

wherein $R^1$ is selected from the group $R^{1a}$ consisting of
phenyl, naphthyl, pyrrolyl, furanyl, thienyl, pyridyl, indolyl, benzofuranyl, benzothiophenyl, quinolinyl, isoquinolinyl,
wherein in the pyrrolyl, furanyl, thienyl, and pyridyl group optionally 1 or 2 CH groups may be replaced by N, and wherein in the indolyl, benzofuranyl, benzothiophenyl, quinolinyl, and isoquinolinyl group 1 to 3 CH groups may optionally be replaced by N,
2-oxo-1,2-dihydro-pyridinyl, 4-oxo-1,4-dihydro-pyridinyl, 3-oxo-2,3-dihydro-pyridazinyl, 3,6-dioxo-1,2,3,6-tetrahydro-pyridazinyl, 2-oxo-1,2-dihydro-pyrimidinyl, 4-oxo-3,4-dihydro-pyrimidinyl, 1,2,3,4-tetrahydro-2,4-dioxo-pyrimidinyl, 2-oxo-1,2-dihydro-pyrazinyl, 2,3-dioxo-1,2,3,4-tetrahydro-pyrazinyl, indanyl, 1-oxo-indanyl, 2,3-dihydro-indolyl, 2,3-dihydro-isoindolyl, 2-oxo-2,3-dihydro-indolyl, 1-oxo-2,3-di-hydro-isoindolyl, 2,3-dihydrobenzofuranyl, 2-oxo-2,3-dihydrobenzimidazolyl, 2-oxo-2,3-dihydro-benzoxazolyl, benzo[1,3]dioxolyl, 2-oxo-benzo[1,3]dioxolyl, 1,2,3,4-tetrahydro-naphthyl, 1,2,3,4-tetrahydro-quinolinyl, 2-oxo-1,2,3,4-tetrahydro-quinolinyl, 2-oxo-1,2-dihydro-quinolinyl, 4-oxo-1,4-dihydro-quinolinyl, 1,2,3,4-tetrahydro-isoquinolinyl, 1-oxo-1,2,3,4-tetrahydro-isoquinolinyl, 1-oxo-1,2-dihydro-isoquinolinyl, 4-oxo-1,4-dihydro-cinnolinyl, 2-oxo-1,2-dihydro-quinazolinyl, 4-oxo-1,4-dihydro-quinazolinyl, 2,4-dioxo-1,2,3,4-tetrahydro-quinazolinyl, 2-oxo-1,2-dihydro-quinoxalinyl, 3-oxo-1,2,3,4-tetrahydro-quinoxalinyl, 2,3-dioxo-1,2,3,4-tetrahydro-quinoxalinyl, 1-oxo-1,2-dihydro-phthalazinyl, 1,4-dioxo-1,2,3,4-tetrahydro-phthalazinyl, chromanyl, coumarinyl, 2,3-dihydro-benzo[1,4]dioxinyl, 3-oxo-3,4-dihydro-benzo[1,4]oxazinyl, tetrazolyl, 2-oxo-2,3-dihydro-benzothiazolyl, and imidazo[1,2-a]pyridinyl,
wherein the members of the group $R^{1a}$ are attached to the carbonyl group in formula I via an aromatic carbon atom and
wherein the members of the group $R^{1a}$ may optionally be substituted with one $R^5$, one to three identical and/or different $R^6$, and/or one $R^7$, provided that in case $R^1$ is a phenyl group, the substituents $R^5$, $R^6$, and/or $R^7$ are not attached to the carbon atoms next to the carbon atom which is attached to the carbonyl group in formula I;

$R^2$ is selected from the group $R^{2a}$ consisting of
hydrogen, halogen, (het)aryl, cyano, nitro, amino, hydroxy, $C_{1-6}$-alkyl, $C_{3-6}$-cycloalkyl, $C_{2-6}$-alkenyl, and $C_{2-6}$-alkynyl,
wherein in each $C_{1-6}$-alkyl-, $C_{3-6}$-cycloalkyl-, $C_{2-6}$-alkenyl- or $C_{2-6}$-alkynyl-group one $CH_2$ group may optionally be replaced by CO or $SO_2$, one $CH_2$ group optionally by O or $NR^N$ and one CH group optionally by N, and wherein each of those groups may optionally be mono- or polyfluorinated and optionally mono- or independently of each other disubstituted with
chlorine, $C_{1-3}$-alkyl, cyano, (het)aryl, amino, $C_{1-3}$-alkylamino, di-($C_{1-3}$-alkyl)-amino, hydroxy, $C_{1-3}$-alkyloxy, (het)aryloxy, $C_{1-3}$-alkylsulfanyl, $C_{1-3}$-alkylsulfinyl, or $C_{3-6}$-cycloalkyl, wherein one or two $CH_2$ groups of the $C_{3-6}$-cycloalkyl group may optionally be replaced independently of each other by carbonyl, O or $NR^N$ and one CH group optionally by N, and which may optionally be mono- or independently disubstituted with fluorine or $C_{1-3}$-alkyl;

$R^3$, $R^4$ are selected independently of each other from the group $R^{3/4a}$ consisting of hydrogen, halogen, $C_{1-3}$-alkyl, trifluoromethyl, hydroxy, $C_{1-3}$-alkyloxy, and cyano, or
$R^{3/4a}$ denotes $R^3$ and $R^4$ that are bound to adjacent carbon atoms and joined to form a methylenedioxy, ethylenedioxy, or $C_{3-5}$-alkylene group, each of which may optionally be substituted with one or two groups independently selected from fluorine and methyl, or, together with the carbon atoms they are attached, form a benzo, pyrido, pyrimido, pyrazino, pyridazino, pyrazolo, imidazo, triazolo, oxazolo, thiazolo, isoxazolo, or isothiazolo ring, each of which may optionally be substituted with one or two substituents selected independently from halogen, $C_{1-3}$-alkyl, trifluoromethyl, amino, $C_{1-3}$-alkylamino, di-($C_{1-3}$-alkyl)amino, hydroxy, and $C_{1-3}$-alkyloxy;

$R^5$ is selected from the group $R^{5a}$ consisting of
halogen, (het)aryl, cyano, nitro, amino, hydroxy, $C_{1-6}$-alkyl, $C_{3-6}$-cycloalkyl, $C_{2-6}$-alkenyl, and $C_{2-6}$-alkynyl, wherein in each group one $CH_2$ group may optionally be replaced by CO or $SO_2$, one $CH_2$ group optionally by O or $NR^N$, and one CH group optionally by N, and wherein each group may optionally be mono- or polyfluorinated and optionally mono- or independently of each other disubstituted with
chlorine, $C_{1-3}$-alkyl, cyano, (het)aryl, amino, $C_{1-3}$-alkylamino, di-($C_{1-3}$-alkyl)-amino, hydroxy, $C_{1-3}$-alkyloxy, (het)aryloxy, $C_{1-3}$-alkylsulfanyl, $C_{1-3}$-alkylsulfinyl, or $C_{3-6}$-cycloalkyl, wherein one or two $CH_2$ groups of the $C_{3-6}$-cycloalkyl group may optionally be replaced independently of each other by carbonyl, O or $NR^N$ and one CH group optionally by N, and which may optionally be mono- or independently disubstituted with fluorine or $C_{1-3}$-alkyl;

$R^6$, $R^7$ are selected independently of each other from the group $R^{6/7a}$ consisting of halogen, $C_{1-3}$-alkyl, $C_{2-3}$-alkynyl, trifluoromethyl, hydroxy, $C_{1-3}$-alkyloxy, and cyano, and/or $R^{6/7a}$ denotes one $R^6$ combined with $R^7$, which are bound to adjacent carbon atoms, that form a methylenedioxy, difluoromethylenedioxy, ethylenedioxy, $C_{3-5}$-alkylene group, or form, together with the carbon atoms they are attached, a pyrazolo, imidazo, oxazolo, isoxazolo, thiazolo, or isothiazolo ring, each of which may optionally be mono- or disubstituted independently of each other with $C_{1-3}$-alkyl, trifluoromethyl, amino, $C_{1-3}$-alkylamino, di-($C_{1-3}$-alkyl)amino, hydroxy, $C_{1-3}$-alkyloxy;

$R^N$ is selected independently of each other from the group $R^{Na}$ consisting of hydrogen, $C_{1-6}$-alkyl, $C_{3-6}$-cycloalkyl, $C_{3-6}$-alkenyl, $C_{3-6}$-alkynyl, (het)aryl, $C_{1-4}$-alkylcarbonyl, (het)arylcarbonyl, $C_{1-4}$-alkylaminocarbonyl, di-($C_{1-3}$-alkyl)-aminocarbonyl, (het)arylaminocarbonyl, $C_{1-4}$-alkyloxycarbonyl, $C_{1-4}$-alkylsulfonyl and (het) arylsulfonyl, wherein each alkyl, alkenyl and alkynyl group may optionally be mono- or polysubstituted with fluorine and optionally monosubstituted with (het)aryl, cyano, aminocarbonyl, $C_{1-3}$-alkylaminocarbonyl, di-($C_{1-3}$-alkyl)aminocarbonyl, carboxy, $C_{1-4}$-alkyloxycarbonyl, amino, $C_{1-4}$-alkylamino, di-($C_{1-3}$-alkyl)amino, $C_{1-4}$-alkylcarbonylamino, hydroxy, $C_{1-4}$-alkyloxy, $C_{1-4}$-alkylsulfanyl, $C_{1-4}$-alkylsulfinyl, or $C_{1-4}$-alkylsulfonyl;

(het)aryl is selected independently of each other from the group $HA^a$ consisting of phenyl, naphthyl, pyrrolyl, furanyl, thienyl, pyridyl, indolyl, benzofuranyl, benzothio-phenyl, quinolinyl, isoquinolinyl, wherein in the pyrrolyl, furanyl, thienyl, and pyridyl group optionally 1 or 2 CH groups may be replaced by N, and wherein in the indolyl, benzofuranyl, benzothiophenyl, quinolinyl, and isoquinolinyl group 1 to 3 CH groups optionally may be replaced by N, 2-oxo-1,2-dihydro-pyridinyl, 4-oxo-1,4-dihydro-pyridinyl, 3-oxo-2,3-dihydro-pyridazinyl, 3,6-dioxo-1,2,3,6-tetrahydro-pyridazinyl, 2-oxo-1,2-dihydro-pyrimidinyl, 4-oxo-3,4-dihydro-pyrimidinyl, 2,4-dioxo-1,2,3,4-tetrahydro-pyrimidinyl, 2-oxo-1,2-dihydro-pyrazinyl, 2,3-dioxo-1,2,3,4-tetrahydro-pyrazinyl, 2-oxo-2,3-dihydro-indolyl, 2,3-dihydrobenzo-furanyl, 2-oxo-2,3-dihydro-benzimidazolyl, 2-oxo-2,3-dihydro-benzoxazolyl, 2-oxo-1,2-dihydro-quinolinyl, 4-oxo-1,4-dihydro-quinolinyl, 1-oxo-1,2-dihydro-isoquinolinyl, 4-oxo-1,4-dihydro-cinnolinyl, 2-oxo-1,2-dihydro-quinazolinyl, 4-oxo-1,4-dihydro-quinazolinyl, 2,4-dioxo-1,2,3,4-tetrahydro-quinazolinyl, 2-oxo-1,2-dihydro-quinoxalinyl, 3-oxo-1,2,3,4-tetrahydro-quinoxalinyl, 2,3-dioxo-1,2,3,4-tetrahydro-quinoxalinyl, 1-oxo-1,2-dihydro-phthalazinyl, 1,4-dioxo-1,2,3,4-tetrahydro-phthalazinyl, chromanyl, coumarinyl, 2,3-dihydro-benzo[1,4]dioxinyl, 3-oxo-3,4-dihydro-benzo[1,4]oxazinyl, and tetrazolyl, and wherein the above-mentioned (het)aryl groups may optionally be substituted with one to three $R^{10}$ which may be identical or different;

$R^{10}$ is selected independently of each other from the group $R^{10a}$ consisting of halogen, $C_{1-3}$-alkyl, difluoromethyl, trifluoromethyl, cyano, aminocarbonyl, $C_{1-3}$-alkylaminocarbonyl, di-($C_{1-3}$-alkyl)-aminocarbonyl, carboxy, $C_{1-4}$-alkyloxycarbonyl, nitro, amino, $C_{1-3}$-alkylamino, di-($C_{1-3}$-alkyl) amino, acetylamine, methylsulfonylamino, hydroxy, $C_{1-3}$-alkyloxy, difluoromethoxy, trifluoromethoxy, methylsulfanyl, methylsulfinyl, methylsulfonyl, aminosulfonyl and phenyl, wherein the phenyl-group may optionally be substituted with 1 or 2 substituents independently of each other selected from fluorine, methyl, methoxy, cyano, and hydroxy;

m denotes 0 or 1;

and wherein the aliphatic part of the tricyclic core structure of general formula I is substituted with one or two different or identical groups $R^8$ selected independently of each other from the group $R^{8a}$ consisting of hydrogen, methyl, and ethyl;

the tautomers thereof, the stereoisomers thereof, the mixtures thereof, and the salts thereof, while the following compounds are excluded:

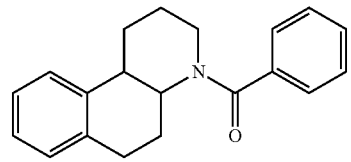

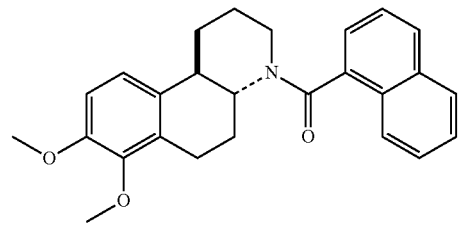

trans

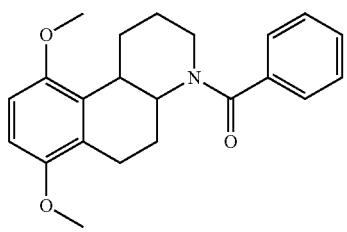

In a further aspect the present invention relates to a process for preparing the compounds of general formula I, characterized in that
a compound of general formula II

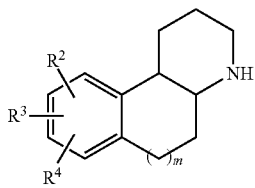

II wherein the variables $R^2$, $R^3$, $R^4$, and m are defined as hereinbefore and hereinafter,
is reacted with a compound of general formula $R^1$—CO—Y, optionally prepared in situ from the corresponding carboxylic acid (Y=OH), wherein $R^1$ is defined as hereinbefore and hereinafter and
Y is a leaving group and in particular denotes
fluorine, chlorine, bromine, cyano, $C_{1-4}$-alkoxy, $C_{2-4}$-alkenyloxy, $C_{2-4}$-alkynyloxy, $C_{1-4}$-alkylsulfanyl, arylotriazoloxy, heteroarylotriazoloxy, heteroar-N-yl, succinyl-N-oxy, $C_{1-4}$-alkylcarbonyloxy, di-($C_{1-4}$-alkyl)-aminocarbonyloxy, pyrrolylcarbonyloxy, piperidinylcarbonyloxy, morpholinylcarbonyloxy, [tri-($C_{1-4}$-alkyl)-carbamimidoyl]oxy, [di-($C_{1-4}$-alkyl)-amino][di-($C_{1-4}$-alkyl)-iminiumyl]methoxy {=[($C_{1-4}$-alkyl)$_2$N]$_2$C$^+$—O—}, (N,N'-dicyclohexyl-carbamidoyl)oxy, di-($C_{1-4}$-alkyloxy)-phosphoryloxy, bis[di-($C_{1-4}$-alkyl)-amino]-phosphoryloxy, [bis(pyrrolidin-1-yl)-phosphoryl]oxy, aryloxy, arylsulfanyl, heterosulfanyl, or heteroaryloxy,
while the alkyl, alkenyl, and alkynyl groups mentioned in the definition of the above leaving groups optionally may be mono- or polysubstituted with fluorine, chlorine, $C_{1-3}$-alkyl, or $C_{1-3}$-alkoxy,
while the aryl groups mentioned in the definition of the above leaving groups, either alone or as part of another group, denote phenyl or naphthyl and the heteroaryl groups mentioned in the definition of the above groups, either alone or as part of another group, denote pyridinyl, pyrimidinyl, triazinyl, imidazolyl, pyrazolyl, triazolyl, or tetrazolyl, whilst both, the aryl and heteroaryl groups, may optionally be mono- or polysubstituted independently of each other with fluorine, chlorine, bromine, $C_{1-3}$-alkyl, $C_{1-3}$-alkyloxy, nitro, cyano, and/or di-($C_{1-3}$-alkyl)amino,
optionally in the presence of a base such as a tertiary or an aromatic amine, e.g. ethyl-diisopropyl-amine, triethylamine, imidazole, or pyridine, or an inorganic salt, e.g. potassium carbonate or calcium oxide, and/or another additive such as 4-dimethylaminopyridine or 1-hydroxybenzotriazol, in solvents preferably selected from tetrahydrofuran, 1,2-dimethoxyethane, ether, 1,4-dioxane, N,N-dimethylformamide, N,N-dimethylacetamide, N-methylpyrrolidinone, acetonitrile, ethyl acetate, dichloromethane, 1,2-dichloroethane, toluene, benzene, and hexanes, also aqueous and alcoholic solutions may be usable for some of the combinations listed above, preferably at −10 to 120° C.;
and, if necessary, any protective group used in the reactions described above is cleaved concurrently or subsequently;
if desired, a compound of general formula I thus obtained is resolved into its stereoisomers;
if desired, a compound of general formula I thus obtained is converted into the salts thereof, particularly for pharmaceutical use into the physiologically acceptable salts thereof.

DETAILED DESCRIPTION OF THE INVENTION

Unless otherwise stated, the groups, residues, and substituents, particularly $R^1$, $R^2$, $R^3$, $R^4$, $R^5$, $R^6$, $R^7$, $R^8$, $R^{10}$, $R^N$, and m are defined as above and hereinafter. If residues, substituents, or groups occur several times in a compound they may have the same or different meanings. Some preferred meanings of groups and substituents of the compounds according to the invention will be given hereinafter.
Preferred embodiments of the invention are characterized by the following definitions:
In a further embodiment of the present invention
$R^1$ is selected from the group $R^{1b}$ consisting of
phenyl, naphthyl, pyrrolyl, furanyl, thienyl, pyridyl, indolyl, benzofuranyl, benzothio-phenyl, quinolinyl, isoquinolinyl,
wherein in the pyrrolyl, furanyl, thienyl, and pyridyl group optionally 1 CH group may be replaced by N, and wherein in the indolyl, benzofuranyl, benzothiophenyl, quinolinyl, and isoquinolinyl groups optionally 1 or 2 CH groups may be replaced by N,
indanyl, 2,3-dihydro-indolyl, 2-oxo-2,3-dihydro-indolyl, 2,3-dihydro-benzofuranyl, 2-oxo-2,3-dihydro-benzoimidazolyl, 2-oxo-2,3-dihydro-benzothiazolyl, benzo[1,3]dioxolyl, 1,2,3,4-tetrahydronaphthyl, 1,2,3,4-tetrahydroquinolinyl, 1,2,3,4-tetrahydroisoquinolinyl, 2-oxo-1,2-dihydro-quinoxalinyl, 3-oxo-1,2,3,4-tetrahydro-quinoxalinyl, chromanyl, and imidazo[1,2-a]pyridinyl,
wherein the members of the group $R^{1b}$ are attached to the carbonyl group in formula I via an aromatic carbon atom and
wherein the members of the group $R^{1b}$ may optionally be substituted with one $R^5$, one $R^6$, and/or one $R^7$, provided that in case $R^1$ is a phenyl group, the substituents $R^5$, $R^6$, and/or $R^7$ are not attached to the carbon atoms next to the carbon atom which is attached to the carbonyl group in formula I.
In a further embodiment of the present invention
$R^1$ is selected from the group $R^{1c}$ consisting of
phenyl, naphthyl, furanyl, thienyl, pyrazolyl, imidazolyl, oxazolyl, isoxazolyl, thiazolyl, isothiazolyl, pyridyl, indolyl, benzofuranyl, benzothiophenyl,
wherein in the indolyl, benzofuranyl, and benzothiophenyl group optionally 1 or 2 CH groups may be replaced by N,
indanyl, 2,3-dihydro-indolyl, 2-oxo-2,3-dihydro-indolyl, 2,3-dihydrobenzofuranyl, 2-oxo-2,3-dihydro-benzoimidazolyl, 2-oxo-2,3-dihydro-benzothiazolyl, benzo[1,3]dioxolyl, 1,2,3,4-tetrahydroquinolinyl, 2-oxo-1,2-dihydro-quinoxalinyl, chromanyl, and imidazo[1,2-a]pyridinyl,
wherein the members of the group $R^{1c}$ are attached to the carbonyl group in formula I via an aromatic carbon atom and
wherein the members of the group $R^{1c}$ may optionally be substituted with one $R^5$, one $R^6$, and/or one $R^7$, provided that in case $R^1$ is a phenyl group, the substituents $R^5$, $R^6$, and/or $R^7$ are not attached to the carbon atoms next to the carbon atom which is attached to the carbonyl group in formula I.

In a further embodiment of the present invention
$R^1$ is selected from the group $R^{1d}$ consisting of
phenyl, indolyl, 2-oxo-2,3-dihydro-indolyl, benzimidazolyl, indazolyl, imidazo[1,2-a]pyridinyl, 2-oxo-2,3-dihydro-benzoimidazolyl, 2-oxo-2,3-dihydro-benzothiazolyl, imidazopyridinyl, benzotriazolyl, benzothiazolyl and 2-oxo-1,2-dihydro-quinoxalinyl,
wherein the members of the group $R^{1d}$ are attached to the carbonyl group in formula I via an aromatic carbon atom and
wherein the members of the group $R^{1d}$ may optionally be substituted with one $R^5$, one $R^6$, and/or one $R^7$, provided that in case $R^1$ is a phenyl group, the substituents $R^5$, $R^6$, and/or $R^7$ are not attached to the carbon atoms next to the carbon atom which is attached to the carbonyl group in formula I.

In a further embodiment of the present invention
$R^1$ is selected from the group $R^{1d2}$ consisting of
4-hydroxy-phenyl, 4-amino-3-methoxy-phenyl, 3-fluoro-4-hydroxy-phenyl, 4-amino-3-chloro-phenyl, 3-chloro-4-hydroxy-phenyl, indol-3-yl, indol-5-yl, indol-6-yl, 1-methyl-indol-3-yl, benzimidazol-5-yl, 6-methyl-benzimidazol-5-yl, 7-methyl-benzimidazol-5-yl, indazol-5-yl and benzothiazol-6-yl.

In a further embodiment of the present invention
$R^1$ is selected from the group $R^{1e}$ consisting of
4-hydroxy-phenyl, 4-amino-3-methoxy-phenyl, 3-fluoro-4-hydroxy-phenyl, 4-amino-3-chloro-phenyl, 3-chloro-4-hydroxy-phenyl, indol-3-yl, indol-5-yl, indol-6-yl, 1-methyl-indol-3-yl, benzimidazol-5-yl, indazol-5-yl and benzothiazol-6-yl.

In a further embodiment of the present invention
$R^1$ is selected from the group $R^{1f}$ consisting of
benzimidazol-5-yl, 6-methyl-benzimidazol-5-yl and 7-methyl-benzimidazol-5-yl.

In a further embodiment of the present invention
$R^2$ is selected from the group $R^{2b}$ consisting of
hydrogen, halogen, (het)aryl, cyano, nitro, amino, hydroxy, $C_{2-6}$-alkynyl, $C_{1-6}$-alkyl and $C_{3-6}$-cycloalkyl,
wherein in the $C_{1-6}$-alkyl and $C_{3-6}$-cycloalkyl group one $CH_2$ group may optionally be replaced by CO or $SO_2$, one $CH_2$ group optionally by O or $NR^N$, and one CH group optionally by N, and wherein both of these groups may optionally be mono- or polyfluorinated and optionally mono- or independently of each other disubstituted with
chlorine, $C_{1-3}$-alkyl, cyano, (het)aryl, amino, $C_{1-3}$-alkylamino, di-($C_{1-3}$-alkyl)-amino, hydroxy, $C_{1-3}$-alkyloxy, (het)aryloxy, $C_{1-3}$-alkylsulfanyl, $C_{1-3}$-alkylsulfinyl, and/or $C_{3-6}$-cycloalkyl, wherein in the $C_{3-6}$-cycloalkyl group one or two $CH_2$ groups may optionally be replaced independently of each other by carbonyl, O or $NR^N$, and one CH group optionally by N, and which may optionally be mono- or independently disubstituted with fluorine or $C_{1-3}$-alkyl.

In a further embodiment of the present invention
$R^2$ is selected from the group $R^{2c}$ consisting of
hydrogen, fluorine, chlorine, bromine, $C_{1-3}$-alkyl, $C_{3-6}$-cycloalkylmethyl, cyclopropyl, (het)aryl-methyl, $C_{2-4}$-alkynyl, (het)aryl, cyano-$C_{1-3}$-alkyl, aminocarbonyl-$C_{1-3}$-alkyl, $C_{1-3}$-alkyl-aminocarbonyl-$C_{1-3}$-alkyl, di-($C_{1-3}$-alkyl)-aminocarbonyl-$C_{1-3}$-alkyl, pyrrolidin-1-yl-carbonyl-$C_{1-3}$-alkyl, piperidin-1-yl-carbonyl-$C_{1-3}$-alkyl, morpholin-4-yl-carbonyl-$C_{1-3}$-alkyl, carboxy-$C_{1-3}$-alkyl, $C_{1-3}$-alkyloxy-carbonyl-$C_{1-3}$-alkyl, $C_{1-3}$-alkylcarbonyl-amino-$C_{1-3}$-alkyl, N—($C_{1-3}$-alkyl)-$C_{1-3}$-alkylcarbonyl-amino-$C_{1-3}$-alkyl, 2-oxo-pyrrolidin-1-yl-$C_{1-3}$-alkyl, 2-oxo-piperidin-1-yl-$C_{1-3}$-alkyl, 3-oxo-morpholin-4-yl-$C_{1-3}$-alkyl, hydroxy-$C_{1-3}$-alkyl, $C_{1-3}$-alkyloxy-$C_{1-3}$-alkyl, trifluoromethyl, difluoromethyl, cyano, aminocarbonyl, $C_{1-3}$-alkyl-aminocarbonyl, di-($C_{1-3}$-alkyl)-aminocarbonyl, pyrrolidin-1-yl-carbonyl, piperidin-1-yl-carbonyl, morpholin-4-yl-carbonyl, carboxy, $C_{1-3}$-alkyloxy-carbonyl, amino, $C_{1-3}$-alkylamino, $C_{1-3}$-alkyl-carbonylamino, (het)aryl-carbonylamino, N—($C_{1-3}$-alkyl)-$C_{1-3}$-alkyl-carbonylamino, N—($C_{1-3}$-alkyl)-(het)aryl-carbonylamino, 2-oxo-pyrrolidin-1-yl, 2-oxo-piperidin-1-yl, morpholin-4-yl, 3-oxo-morpholin-4-yl, $C_{1-3}$-alkyl-sulfonylamino, N—($C_{1-3}$-alkyl)-$C_{1-3}$-alkyl-sulfonylamino, N—($C_{1-3}$-alkyl)-(het)aryl-sulfonylamino, hydroxy, $C_{1-4}$-alkyloxy, $C_{3-6}$-cycloalkyloxy, tetrahydrofuran-3-yloxy, tetrahydropyran-3-yloxy, tetrahydropyran-4-yloxy, difluoromethoxy, trifluoromethoxy, (het)aryloxy, cyano-$C_{1-3}$-alkyloxy, aminocarbonyl-$C_{1-3}$-alkyloxy, $C_{1-3}$-alkyl-aminocarbonyl-$C_{1-3}$-alkyloxy, di-($C_{1-3}$-alkyl)-aminocarbonyl-$C_{1-3}$-alkyloxy, pyrrolidin-1-yl-carbonyl-$C_{1-3}$-alkyloxy, piperidin-1-yl-carbonyl-$C_{1-3}$-alkyloxy, morpholin-4-yl-carbonyl-$C_{1-3}$-alkyloxy, carboxy-$C_{1-3}$-alkyloxy, $C_{1-3}$-alkyloxy-carbonyl-$C_{1-3}$-alkyloxy, hydroxy-$C_{1-3}$-alkyloxy, $C_{1-3}$-alkyloxy-$C_{1-3}$-alkyloxy, tetrahydrofuranyl-$C_{1-3}$-alkyloxy, tetrahydropyranyl-$C_{1-3}$-alkyloxy, $C_{1-4}$-alkylsulfonyl, $C_{3-6}$-cycloalkylsulfonyl, aminosulfonyl, $C_{1-3}$-alkyl-aminosulfonyl and di-($C_{1-3}$-alkyl)-aminosulfonyl,
wherein the above-mentioned term (het)aryl denotes phenyl, furanyl, thienyl, imidazolyl, pyrazolyl, oxazolyl, isoxazolyl, thiazolyl, triazolyl, oxadiazolyl, pyridinyl, pyrimidinyl, pyrazinyl, or pyridazinyl, all of which may optionally be mono- or disubstituted with $R^{10}$.

In a further embodiment of the present invention
$R^2$ is selected from the group $R^{2d}$ consisting of
hydrogen, fluorine, chlorine, bromine, methyl, ethynyl, cyclopropyl, $C_{3-6}$-cycloalkylmethyl, phenylmethyl, hydroxy-$C_{1-3}$-alkyl, phenyl, cyano, aminocarbonyl, methylaminocarbonyl, dimethylaminocarbonyl, pyrrolidin-1-ylcarbonyl, morpholin-4-ylcarbonyl, carboxy, methoxycarbonyl, amino, acetylamino, methylsulfonylamino, hydroxy, $C_{1-3}$-alkyloxy, phenyloxy, and pyridazinyloxy,
while the mentioned phenyl and pyridazinyl groups may optionally be monosubstituted with fluorine, methyl, cyano, or methoxy.

In a further embodiment of the present invention
$R^2$ is selected from the group $R^{2e}$ consisting of
hydrogen, fluorine, bromine, cyclohexylmethyl, phenylmethyl, 4-methoxy-phenylmethyl, hydroxymethyl, 2-hydroxyprop-2-yl, phenyl, cyano, aminocarbonyl, methylaminocarbonyl, dimethylaminocarbonyl, pyrrolidin-1-ylcarbonyl, morpholin-4-ylcarbonyl, carboxy, methoxycarbonyl, amino, hydroxy, methoxy, 4-methoxyphenoxy, and 6-methyl-pyridazin-3-yloxy.

In a further embodiment of the present invention
$R^2$ is selected from the group $R^{2f}$ consisting of
hydrogen and cyano.

In a further embodiment of the present invention
$R^3$, $R^4$ are selected independently of each other from the group $R^{3/4b}$ consisting of hydrogen, fluorine, chlorine, $C_{1-3}$-alkyl, trifluoromethyl, cyano, hydroxy, and $C_{1-3}$-alkyloxy, or
$R^{3/4b}$ denotes $R^3$ and $R^4$ that are attached to adjacent carbon atoms and joined to form a methylenedioxy or ethylenedioxy group, or, together with the carbon atoms they are attached, an imidazo, oxazolo, or a thiazolo ring, each of which may optionally be substituted with one or two substituents independently selected from methyl, dimethylamino, hydroxy, and methoxy.

In a further embodiment of the present invention $R^3$, $R^4$ are selected independently of each other from the group $R^{3/4c}$ consisting of hydrogen, fluorine, chlorine, methyl, trifluoromethyl, cyano, hydroxy, and methoxy.

In a further embodiment of the present invention $R^3$, $R^4$ are selected independently of each other from the group $R^{3/4c2}$ consisting of hydrogen, fluorine and methyl.

In a further embodiment of the present invention $R^3$, $R^4$ are selected independently of each other from the group $R^{3/4d}$ consisting of hydrogen and fluorine.

In a further embodiment of the present invention $R^5$ is selected from the group $R^{5b}$ consisting of fluorine, chlorine, bromine, $C_{1-4}$-alkyl, $C_{3-6}$-cycloalkyl-$C_{1-3}$-alkyl, $C_{3-6}$-cycloalkyl, (het)aryl-$C_{1-3}$-alkyl, (het)aryl, cyano-$C_{1-3}$-alkyl, aminocarbonyl-$C_{1-3}$-alkyl, $C_{1-3}$-alkyl-aminocarbonyl-$C_{1-3}$-alkyl, di-($C_{1-3}$-alkyl)-aminocarbonyl-$C_{1-3}$-alkyl, pyrrolidin-1-yl-carbonyl-$C_{1-3}$-alkyl, piperidin-1-yl-carbonyl-$C_{1-3}$-alkyl, piperazin-1-yl-carbonyl-$C_{1-3}$-alkyl, 4-($C_{1-3}$-alkyl)-piperazin-1-yl-carbonyl-$C_{1-3}$-alkyl, morpholin-4-yl-carbonyl-$C_{1-3}$-alkyl, carboxy-$C_{1-3}$-alkyl, $C_{1-3}$-alkyloxy-carbonyl-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, pyrrolidin-1-yl-$C_{1-3}$-alkyl, piperidin-1-yl-$C_{1-3}$-alkyl, piperazin-1-yl-$C_{1-3}$-alkyl, 4-($C_{1-3}$-alkyl)-piperazin-1-yl-$C_{1-3}$-alkyl, morpholin-4-yl-$C_{1-3}$-alkyl, $C_{1-3}$-alkylcarbonylamino-$C_{1-3}$-alkyl, (het)arylcarbonylamino-$C_{1-3}$-alkyl, 2-oxo-pyrrolidin-1-yl-$C_{1-3}$-alkyl, 2-oxo-piperidin-1-yl-$C_{1-3}$-alkyl, 2-oxo-piperazin-1-yl-$C_{1-3}$-alkyl, 3-oxo-piperazin-1-yl-$C_{1-3}$-alkyl, 2-oxo-4-($C_{1-3}$-alkyl)-piperazin-1-yl-$C_{1-3}$-alkyl, 3-oxo-4-($C_{1-3}$-alkyl)-piperazin-1-yl-$C_{1-3}$-alkyl, 3-oxo-morpholin-4-yl-$C_{1-3}$-alkyl, hydroxy-$C_{1-3}$-alkyl, $C_{1-3}$-alkyloxy-$C_{1-3}$-alkyl, (het)aryloxy-$C_{1-3}$-alkyl, difluoromethyl, trifluoromethyl, 2,2,2-trifluoro-1-hydroxyethyl, 2,2,2-trifluoro-1-hydroxy-1-methylethyl, 2,2,2-trifluoro-1-hydroxy-1-(trifluoromethyl)ethyl, cyano, aminocarbonyl, $C_{1-3}$-alkyl-aminocarbonyl, di-($C_{1-3}$-alkyl)-aminocarbonyl, (het)aryl-$C_{1-3}$-alkylaminocarbonyl, N—($C_{1-3}$-alkyl)-(het)aryl-$C_{1-3}$-alkylaminocarbonyl, (het)arylaminocarbonyl, N—($C_{1-3}$-alkyl)-(het)arylaminocarbonyl, pyrrolidin-1-yl-carbonyl, piperidin-1-yl-carbonyl, piperazin-1-yl-carbonyl, 4-($C_{1-3}$-alkyl)-piperazin-1-yl-carbonyl, morpholin-4-yl-carbonyl, carboxy, $C_{1-3}$-alkyloxy-carbonyl, nitro, amino, $C_{1-3}$-alkylamino, di-($C_{1-3}$-alkyl)amino, pyrrolidin-1-yl, piperidin-1-yl, piperazin-1-yl, 4-($C_{1-3}$-alkyl)-piperazin-1-yl, 4-($C_{1-3}$-alkylcarbonyl)-piperazin-1-yl, 4-($C_{1-3}$-alkyloxycarbonyl)-piperazin-1-yl, 4-($C_{1-3}$-alkylsulfonyl)-piperazin-1-yl, morpholin-4-yl, $C_{1-3}$-alkyl-carbonylamino, N—($C_{1-3}$-alkyl)-$C_{1-3}$-alkyl-carbonylamino, (het)arylcarbonylamino, N—($C_{1-3}$-alkyl)-(het)arylcarbonylamino, (het)aryl-$C_{1-3}$-alkyl-carbonylamino, N—($C_{1-3}$-alkyl)-(het)aryl-$C_{1-3}$-alkyl-carbonylamino, 2-oxo-pyrrolidin-1-yl, 2-oxo-piperidin-1-yl, 2-oxo-piperazin-1-yl, 2-oxo-4-($C_{1-3}$-alkyl)-piperazin-1-yl, 3-oxo-piperazin-1-yl, 3-oxo-4-($C_{1-3}$-alkyl)-piperazin-1-yl, 3-oxo-morpholin-4-yl, aminocarbonylamino, N-(aminocarbonyl)-$C_{1-3}$-alkylamino, $C_{1-3}$-alkyl-aminocarbonylamino, N—($C_{1-3}$-alkyl-aminocarbonyl)-$C_{1-3}$-alkylamino, N-[di-($C_{1-3}$-alkyl)aminocarbonyl]-$C_{1-3}$-alkylamino, di-($C_{1-3}$-alkyl)-aminocarbonyl-amino, pyrrolidin-1-yl-carbonylamino, piperidin-1-yl-carbonylamino, piperazin-1-yl-carbonylamino, 4-($C_{1-3}$-alkyl)-piperazin-1-yl-carbonylamino, morpholin-4-yl-carbonylamino, $C_{1-3}$-alkyloxy-carbonylamino, N—($C_{1-3}$-alkyl)-$C_{1-3}$-alkyloxy-carbonylamino, $C_{1-3}$-alkylsulfonylamino, N—($C_{1-3}$-alkyl)-$C_{1-3}$-alkylsulfonylamino, (het)arylsulfonylamino, N—($C_{1-3}$-alkyl)-(het)arylsulfonylamino, oxo-imidazolidin-1-yl, hydroxy, $C_{1-4}$-alkyloxy, $C_{3-6}$-cycloalkyl-$C_{1-3}$-alkyloxy, (het)aryl-$C_{1-3}$-alkyloxy, $C_{3-6}$-cycloalkyloxy, (het)aryloxy, cyano-$C_{1-3}$-alkyloxy, aminocarbonyl-$C_{1-3}$-alkyloxy, $C_{1-3}$-alkyl-aminocarbonyl-$C_{1-3}$-alkyloxy, di-($C_{1-3}$-alkyl)-aminocarbonyl-$C_{1-3}$-alkyloxy, pyrrolidin-1-yl-carbonyl-$C_{1-3}$-alkyloxy, piperidin-1-yl-carbonyl-$C_{1-3}$-alkyloxy, piperazin-1-yl-carbonyl-$C_{1-3}$-alkyloxy, 4-($C_{1-3}$-alkyl)-piperazin-1-yl-carbonyl-$C_{1-3}$-alkyloxy, morpholin-4-yl-carbonyl-$C_{1-3}$-alkyloxy, carboxy-$C_{1-3}$-alkyloxy, $C_{1-3}$-alkyloxy-carbonyl-$C_{1-3}$-alkyloxy, amino-$C_{1-3}$-alkyloxy, $C_{1-3}$-alkylamino-$C_{1-3}$-alkyloxy, di-($C_{1-3}$-alkyl)-amino-$C_{1-3}$-alkyloxy, pyrrolidin-1-yl-$C_{1-3}$-alkyloxy, piperidin-1-yl-$C_{1-3}$-alkyloxy, piperazin-1-yl-$C_{1-3}$-alkyloxy, 4-($C_{1-3}$-alkyl)-piperazin-1-yl-$C_{1-3}$-alkyloxy, morpholin-4-yl-$C_{1-3}$-alkyloxy, 2-oxo-pyrrolidin-1-yl-$C_{1-3}$-alkyloxy, 2-oxo-piperidin-1-yl-$C_{1-3}$-alkyloxy, 2-oxo-piperazin-1-yl-$C_{1-3}$-alkyloxy, 3-oxo-piperazin-1-yl-$C_{1-3}$-alkyloxy, 2-oxo-4-($C_{1-3}$-alkyl)-piperazin-1-yl-$C_{1-3}$-alkyloxy, 3-oxo-4-($C_{1-3}$-alkyl)-piperazin-1-yl-$C_{1-3}$-alkyloxy, 3-oxo-morpholin-4-yl-$C_{1-3}$-alkyloxy, hydroxy-$C_{1-3}$-alkyloxy, $C_{1-3}$-alkyloxy-$C_{1-3}$-alkyloxy, tetrahydrofuran-3-yl-oxy, tetrahydropyran-3-yl-oxy, tetrahydropyran-4-yl-oxy, tetrahydrofuranyl-$C_{1-3}$-alkyloxy, tetrahydropyranyl-$C_{1-3}$-alkyloxy, difluoromethoxy, trifluoromethoxy, $C_{1-3}$-alkylsulfanyl-$C_{1-3}$-alkyloxy, $C_{1-3}$-alkylsulfinyl-$C_{1-3}$-alkyloxy, $C_{1-3}$-alkylsulfonyl-$C_{1-3}$-alkyloxy, $C_{1-3}$-alkylsulfonyl, (het)arylsulfonyl, aminosulfonyl, $C_{1-3}$-alkyl-aminosulfonyl, di-($C_{1-3}$-alkyl)-aminosulfonyl, pyrrolidin-1-yl-sulfonyl, piperidin-1-yl-sulfonyl, morpholin-4-yl-sulfonyl, piperazin-1-yl-sulfonyl, and 4-($C_{1-3}$-alkyl)-piperazin-1-yl-sulfonyl, wherein the above-mentioned term (het)aryl is defined as hereinbefore or hereinafter.

In a further embodiment of the present invention $R^5$ is selected from the group $R^{5c}$ consisting of fluorine, chlorine, $C_{1-4}$-alkyl, (het)aryl-$C_{1-3}$-alkyl, (het)aryl, aminosulfonyl, amino-$C_{1-3}$-alkyl, $C_{1-3}$-alkylamino-$C_{1-3}$-alkyl, di-($C_{1-3}$-alkyl)-amino-$C_{1-3}$-alkyl, pyrrolidin-1-yl-$C_{1-3}$-alkyl, morpholin-4-yl-$C_{1-3}$-alkyl, $C_{1-3}$-alkylcarbonylamino-$C_{1-3}$-alkyl, (het)arylcarbonylamino-$C_{1-3}$-alkyl, 2-oxo-pyrrolidin-1-yl-$C_{1-3}$-alkyl, 3-oxo-morpholin-4-yl-$C_{1-3}$-alkyl, hydroxy-$C_{1-3}$-alkyl, $C_{1-3}$-alkyloxy-$C_{1-3}$-alkyl, 2,2,2-trifluoro-1-hydroxyethyl, 2,2,2-trifluoro-1-hydroxy-1-methylethyl, 2,2,2-trifluoro-1-hydroxy-1-trifluoromethyl-ethyl, trifluoromethyl, cyano, aminocarbonyl, $C_{1-3}$-alkyl-aminocarbonyl, di-($C_{1-3}$-alkyl)-aminocarbonyl, (het)arylaminocarbonyl, pyrrolidin-1-yl-carbonyl, piperidin-1-yl-carbonyl, piperazin-1-yl-carbonyl, morpholin-4-yl-carbonyl, 4-($C_{1-3}$-alkyl)-piperazin-1-yl-carbonyl, carboxy, $C_{1-3}$-alkyloxy-carbonyl, amino, $C_{1-3}$-alkylamino, di-($C_{1-3}$-alkyl)amino, pyrrolidin-1-yl, piperidin-1-yl, piperazin-1-yl, morpholin-4-yl, 2-oxo-pyrrolidin-1-yl, 2-oxo-piperidin-1-yl, 2-oxo-piperazin-1-yl, 3-oxo-piperazin-1-yl, 3-oxo-morpholin-4-yl, $C_{1-3}$-alkyl-carbonylamino, (het)arylcarbonylamino, aminocarbonylamino, $C_{1-3}$-alkyl-aminocarbonylamino, di-($C_{1-3}$-alkyl)aminocarbonylamino, pyrrolidin-1-yl-carbonylamino, piperidin-1-yl-carbonylamino, piperazin-1-yl-carbonylamino, morpholin-4-yl-carbonylamino, $C_{1-3}$-alkyloxy-carbonylamino, hydroxy, $C_{1-4}$-alkyloxy, hydroxy-$C_{1-3}$-alkyloxy, $C_{1-3}$-alkyloxy-$C_{1-3}$-alkyloxy, difluoromethoxy, trifluoromethoxy, and (het)aryloxy, wherein the above-mentioned term (het)aryl denotes phenyl, pyrrolyl, pyrazolyl, imidazolyl, furanyl, oxazolyl, isoxazolyl, thienyl, thiazolyl, triazolyl, oxadiazolyl, pyridyl, pyridazinyl, pyrimidinyl, and pyrazinyl, each of which may optionally be substituted with one or two $R^{10}$.

In a further embodiment of the present invention
$R^5$ is selected from the group $R^{5d}$ consisting of
fluorine, chlorine, $C_{1-3}$-alkyl, hydroxy-$C_{1-3}$-alkyl, aminocarbonyl, $C_{1-3}$-alkyl-aminocarbonyl, amino, $C_{1-3}$-alkylamino, $C_{1-3}$-alkyl-carbonylamino, hydroxy, $C_{1-3}$-alkyloxy, trifluoromethyl, difluoromethoxy, trifluoromethoxy, and aminosulfonyl.

In a further embodiment of the present invention
$R^5$ is selected from the group Rye consisting of
fluorine, chlorine, methyl, amino, hydroxy, and methoxy.

In a further embodiment of the present invention
$R^6$, $R^7$ are selected independently of each other from the group $R^{6/7b}$ consisting of
fluorine, chlorine, bromine, $C_{1-3}$-alkyl, $C_{2-3}$-alkynyl, trifluoromethyl, hydroxy, $C_{1-3}$-alkyloxy, and cyano, and/or $R^{6/7b}$ denotes one $R^6$ and $R^7$ that are attached to adjacent carbon atoms and joined to form a methylenedioxy, difluoromethylenedioxy, ethylenedioxy, or $C_{3-5}$-alkylene group.

In a further embodiment of the present invention
$R^6$, $R^7$ are selected independently of each other from the group $R^{6/7c}$ consisting of
fluorine, chlorine, methyl, ethyl, trifluoromethyl, hydroxy, methoxy, and ethoxy.

In a further embodiment of the present invention
$R^6$, $R^7$ are selected independently of each other from the group $R^{6/7d}$ consisting of
fluorine, chlorine, methyl, hydroxy, and methoxy.

In a further embodiment of the present invention
$R^{10}$ is selected independently of each other from the group $R^{1b}$ consisting of
fluorine, chlorine, bromine, $C_{1-3}$-alkyl, phenyl, difluoromethyl, trifluoromethyl, cyano, aminocarbonyl, $C_{1-3}$-alkylaminocarbonyl, di-($C_{1-3}$-alkyl)-aminocarbonyl, carboxy, $C_{1-4}$-alkyloxycarbonyl, nitro, amino, acetylamine, methylsulfonylamino, hydroxy, $C_{1-3}$-alkyloxy, difluoromethoxy, trifluoromethoxy, methylsulfanyl, methylsulfinyl, methylsulfonyl, and aminosulfonyl.

In a further embodiment of the present invention
$R^{10}$ is selected independently of each other from the group $R^{10c}$ consisting of
fluorine, chlorine, methyl, difluoromethyl, trifluoromethyl, cyano, hydroxy, methoxy, difluoromethoxy, and trifluoromethoxy.

In a further embodiment of the present invention
$R^{10}$ is selected independently of each other from the group $R^{10d}$ consisting of
fluorine, methyl, cyano, and methoxy.

In a further embodiment of the present invention
$R^N$ is selected independently of each other from the group $R^{Nb}$ consisting of
hydrogen, $C_{1-6}$-alkyl, $C_{3-6}$-cycloalkyl, $C_{3-6}$-alkenyl, phenyl, $C_{1-4}$-alkylcarbonyl, phenylcarbonyl, $C_{1-3}$-alkylaminocarbonyl, phenylaminocarbonyl, $C_{1-4}$-alkyloxycarbonyl, $C_{1-4}$-alkylsulfonyl, and phenylsulfonyl, wherein the $C_{1-6}$-alkyl group optionally may be mono- or polysubstituted with fluorine and optionally monosubstituted with phenyl, cyano, aminocarbonyl, $C_{1-3}$-alkylaminocarbonyl, di-($C_{1-3}$-alkyl)aminocarbonyl, carboxy, $C_{1-4}$-alkoxycarbonyl, $C_{1-4}$-alkylcarbonylamino, hydroxy, or $C_{1-4}$-alkoxy.

In a further embodiment of the present invention
$R^N$ is selected independently of each other from the group $R^{Nc}$ consisting of hydrogen, phenyl, $C_{1-4}$-alkylcarbonyl, phenylcarbonyl, $C_{1-3}$-alkylaminocarbonyl, phenylaminocarbonyl, $C_{1-4}$-alkyloxycarbonyl, $C_{1-4}$-alkylsulfonyl, phenylsulfonyl, and a $C_{1-4}$-alkyl group, which optionally may be mono- or polyfluorinated and optionally monosubstituted with hydroxy, $C_{1-4}$-alkoxy, cyano, or phenyl.

In a further embodiment of the present invention
$R^N$ is selected independently of each other from the group $R^{Nd}$ consisting of
hydrogen, methyl, benzyl, phenyl, acetyl, tert-butoxycarbonyl, and methylsulfonyl.

In a further embodiment of the present invention
$R^8$ is selected independently of each other from the group $R^{8b}$ consisting of
hydrogen and methyl.

In a further embodiment of the present invention
$R^8$ is selected independently of each other from the group $R^{8c}$ consisting of
hydrogen.

In a further embodiment of the present invention m is 0.

Each $R^{1x}$, $R^{2x}$, $R^{3/4x}$, $R^{5x}$, $R^{6/7x}$, $R^{Nx}$, $R^{8x}$, $R^{10x}$, m represents a characterized, individual embodiment for the corresponding substituent as described above. Thus given the above definitions, preferred individual embodiments of the first aspect of the invention are fully characterized by the term ($R^{1x}$, $R^{2x}$, $R^{3/4x}$, $R^{5x}$, $R^{6/7x}$, $R^{Nx}$, $R^{8x}$, $R^{10x}$, m), wherein for each index x an individual figure is given that ranges from "a" to the highest letter given above. Indices x and m vary independently from each other. All individual embodiments described by the term in parentheses with full permutation of the indices x and m, referring to the definitions above, shall be comprised by the present invention.

The following Table 1 shows, exemplarily and in the order of increasing preference from the first line to the last line, such embodiments E-1 to E-36 of the invention that are considered preferred. This means that embodiment E-36, represented by the entries in the last row of Table 1, is the most preferred embodiment.

TABLE 1

Preferred embodiments E-1 to E-36 of the invention

| | $R^1$ | $R^2$ | $R^3/R^4$ | $R^5$ | $R^6/R^7$ | $R^{10}$ | $R^8$ | $R^N$ | m |
|---|---|---|---|---|---|---|---|---|---|
| E-1 | $R^{1b}$ | $R^{2b}$ | $R^{3/4b}$ | $R^{5b}$ | $R^{6/7b}$ | $R^{10b}$ | $R^{8a}$ | $R^{Nb}$ | 0.1 |
| E-2 | $R^{1c}$ | $R^{2c}$ | $R^{3/4c}$ | $R^{5c}$ | $R^{6/7c}$ | $R^{10c}$ | $R^{8a}$ | —* | 0.1 |
| E-3 | $R^{1b}$ | $R^{2b}$ | $R^{3/4d}$ | $R^{5c}$ | $R^{6/7d}$ | $R^{10d}$ | $R^{8a}$ | $R^{Nd}$ | 0.1 |
| E-4 | $R^{1b}$ | $R^{2b}$ | $R^{3/4d}$ | $R^{5d}$ | $R^{6/7d}$ | $R^{10d}$ | $R^{8b}$ | $R^{Nd}$ | 0.1 |
| E-5 | $R^{1b}$ | $R^{2b}$ | $R^{3/4d}$ | $R^{5e}$ | $R^{6/7d}$ | $R^{10d}$ | $R^{8b}$ | $R^{Nd}$ | 0.1 |
| E-6 | $R^{1c}$ | $R^{2b}$ | $R^{3/4b}$ | $R^{5c}$ | $R^{6/7c}$ | $R^{10d}$ | $R^{8b}$ | $R^{Nd}$ | 0.1 |
| E-7 | $R^{1b}$ | $R^{2b}$ | $R^{3/4b}$ | $R^{5d}$ | $R^{6/7d}$ | $R^{10d}$ | $R^{8b}$ | $R^{Nd}$ | 0.1 |
| E-8 | $R^{1b}$ | $R^{2c}$ | $R^{3/4c}$ | $R^{5c}$ | $R^{6/7c}$ | $R^{10d}$ | $R^{8b}$ | —* | 0.1 |
| E-9 | $R^{1c}$ | $R^{2b}$ | $R^{3/4c}$ | $R^{5c}$ | $R^{6/7c}$ | $R^{10d}$ | $R^{8b}$ | $R^{Nd}$ | 0.1 |
| E-10 | $R^{1c}$ | $R^{2c}$ | $R^{3/4c}$ | $R^{5c}$ | $R^{6/7c}$ | $R^{10d}$ | $R^{8b}$ | —* | 0.1 |
| E-11 | $R^{1c}$ | $R^{2c}$ | $R^{3/4c}$ | $R^{5d}$ | $R^{6/7d}$ | $R^{10d}$ | $R^{8b}$ | —* | 0.1 |
| E-12 | $R^{1b}$ | $R^{2c}$ | $R^{3/4c2}$ | $R^{5c}$ | $R^{6/7c}$ | $R^{10d}$ | $R^{8b}$ | —* | 0.1 |
| E-13 | $R^{1c}$ | $R^{2b}$ | $R^{3/4c2}$ | $R^{5c}$ | $R^{6/7c}$ | $R^{10d}$ | $R^{8b}$ | $R^{Nd}$ | 0.1 |
| E-14 | $R^{1c}$ | $R^{2c}$ | $R^{3/4c2}$ | $R^{5c}$ | $R^{6/7c}$ | $R^{10d}$ | $R^{8b}$ | —* | 0.1 |
| E-15 | $R^{1c}$ | $R^{2c}$ | $R^{3/4c2}$ | $R^{5d}$ | $R^{6/7d}$ | $R^{10d}$ | $R^{8b}$ | —* | 0.1 |
| E-16 | $R^{1c}$ | $R^{2c}$ | $R^{3/4d}$ | $R^{5d}$ | $R^{6/7d}$ | $R^{10d}$ | $R^{8b}$ | —* | 0.1 |
| E-17 | $R^{1d}$ | $R^{2c}$ | $R^{3/4d}$ | $R^{5d}$ | $R^{6/7d}$ | $R^{10d}$ | $R^{8b}$ | —* | 0.1 |

TABLE 1-continued

Preferred embodiments E-1 to E-36 of the invention

|  | $R^1$ | $R^2$ | $R^3/R^4$ | $R^5$ | $R^6/R^7$ | $R^{10}$ | $R^8$ | $R^N$ | m |
|---|---|---|---|---|---|---|---|---|---|
| E-18 | $R^{1d}$ | $R^{2c}$ | $R^{3/4d}$ | $R^{5e}$ | $R^{6/7d}$ | $R^{10d}$ | $R^{8b}$ | —* | 0.1 |
| E-19 | $R^{1d}$ | $R^{2d}$ | $R^{3/4d}$ | $R^{5e}$ | $R^{6/7d}$ | —* | $R^{8b}$ | —* | 0.1 |
| E-20 | $R^{1d}$ | $R^{2e}$ | $R^{3/4d}$ | $R^{5e}$ | $R^{6/7d}$ | —* | $R^{8b}$ | —* | 0.1 |
| E-21 | $R^{1d2}$ | $R^{2e}$ | $R^{3/4d}$ | —* | —* | —* | $R^{8b}$ | —* | 0.1 |
| E-22 | $R^{1e}$ | $R^{2e}$ | $R^{3/4d}$ | —* | —* | —* | $R^{8b}$ | —* | 0.1 |
| E-23 | $R^{1e}$ | $R^{2e}$ | $R^{3/4d}$ | —* | —* | —* | $R^{8c}$ | —* | 0.1 |
| E-24 | $R^{1e}$ | $R^{2e}$ | $R^{3/4d}$ | —* | —* | —* | $R^{8c}$ | —* | 0 |
| E-25 | $R^{1d}$ | $R^{2f}$ | $R^{3/4d}$ | $R^{5e}$ | $R^{6/7d}$ | —* | $R^{8b}$ | —* | 0.1 |
| E-26 | $R^{1e}$ | $R^{2f}$ | $R^{3/4d}$ | —* | —* | —* | $R^{8b}$ | —* | 0.1 |
| E-27 | $R^{1e}$ | $R^{2f}$ | $R^{3/4d}$ | —* | —* | —* | $R^{8c}$ | —* | 0.1 |
| E-28 | $R^{1e}$ | $R^{2f}$ | $R^{3/4d}$ | —* | —* | —* | $R^{8c}$ | —* | 0 |
| E-29 | $R^{1d2}$ | $R^{2c}$ | $R^{3/4d}$ | —* | —* | $R^{10d}$ | $R^{8b}$ | —** | 0.1 |
| E-30 | $R^{1d2}$ | $R^{2d}$ | $R^{3/4d}$ | —* | —* | —* | $R^{8b}$ | —* | 0.1 |
| E-31 | $R^{1d2}$ | $R^{2e}$ | $R^{3/4d}$ | —* | —* | —* | $R^{8b}$ | —* | 0.1 |
| E-32 | $R^{1d2}$ | $R^{2f}$ | $R^{3/4d}$ | —* | —* | —* | $R^{8b}$ | —* | 0.1 |
| E-33 | $R^{1d2}$ | $R^{2f}$ | $R^{3/4d}$ | —* | —* | —* | $R^{8b}$ | —* | 0 |
| E-34 | $R^{1f}$ | $R^{2f}$ | $R^{3/4d}$ | —* | —* | —* | $R^{8b}$ | —* | 0.1 |
| E-35 | $R^{1f}$ | $R^{2f}$ | $R^{3/4d}$ | —* | —* | —* | $R^{8c}$ | —* | 0.1 |
| E-36 | $R^{1f}$ | $R^{2f}$ | $R^{3/4d}$ | —* | —* | —* | $R^{8c}$ | —* | 0 |

—*means that the respective variable does not exist in the corresponding embodiment the tautomers thereof, the stereoisomers thereof, the mixtures thereof, and the salts thereof,
while the following compounds are excluded:

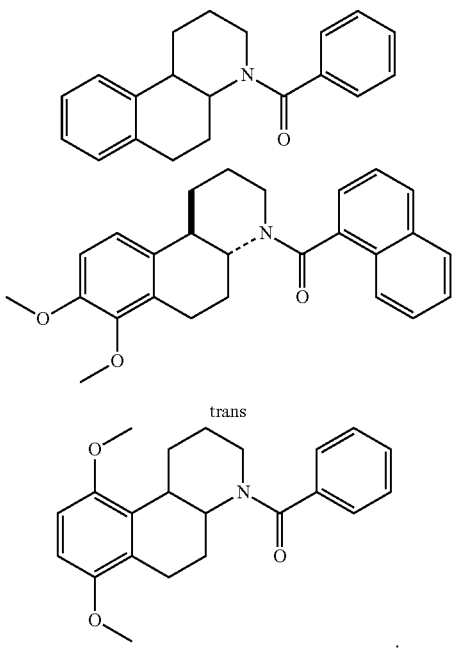

Accordingly, E-24 covers compounds of formula I, wherein
$R^1$ is selected from the group $R^{1e}$ consisting of
4-hydroxy-phenyl, 4-amino-3-methoxy-phenyl, 3-fluoro-4-hydroxy-phenyl, 4-amino-3-chloro-phenyl, 3-chloro-4-hydroxy-phenyl, indol-3-yl, indol-5-yl, indol-6-yl, 1-methyl-indol-3-yl, benzimidazol-5-yl, indazol-5-yl and benzothiazol-6-yl,
$R^2$ is selected from the group $R^{2e}$ consisting of
hydrogen, fluorine, bromine, cyclohexylmethyl, phenylmethyl, 4-methoxy-phenylmethyl, hydroxymethyl, 2-hydroxyprop-2-yl, phenyl, cyano, aminocarbonyl, methylaminocarbonyl, dimethylaminocarbonyl, pyrrolidin-1-ylcarbonyl, morpholin-4-ylcarbonyl, carboxy, methoxycarbonyl, amino, hydroxy, methoxy, 4-methoxyphenoxy, and 6-methyl-pyridazin-3-yloxy.
$R^3$, $R^4$ are selected independently of each other from the group $R^{3/4d}$ consisting of
hydrogen and fluorine,
$R^8$ is selected independently of each other from the group $R^{8c}$ consisting of
hydrogen,
and m=0,
the tautomers thereof, the stereoisomers thereof, the mixtures thereof, and the salts thereof.

Accordingly, E-28 covers compounds of formula I, wherein
$R^1$ is selected from the group $R^{1e}$ consisting of
4-hydroxy-phenyl, 4-amino-3-methoxy-phenyl, 3-fluoro-4-hydroxy-phenyl, 4-amino-3-chloro-phenyl, 3-chloro-4-hydroxy-phenyl, indol-3-yl, indol-5-yl, indol-6-yl, 1-methyl-indol-3-yl, benzimidazol-5-yl, indazol-5-yl and benzothiazol-6-yl,
$R^2$ is selected from the group $R^{2f}$ consisting of
hydrogen and cyano,
$R^3$, $R^4$ are selected independently of each other from the group $R^{3/4d}$ consisting of
hydrogen and fluorine,
$R^8$ is selected independently of each other from the group $R^{8c}$ consisting of
hydrogen,
and m=0,
the tautomers thereof, the stereoisomers thereof, the mixtures thereof, and the salts thereof.

Accordingly, E-33 covers compounds of formula I, wherein
$R^1$ is selected from the group $R^{1d2}$ consisting of
4-hydroxy-phenyl, 4-amino-3-methoxy-phenyl, 3-fluoro-4-hydroxy-phenyl, 4-amino-3-chloro-phenyl, 3-chloro-4-hydroxy-phenyl, indol-3-yl, indol-5-yl, indol-6-yl, 1-methyl-indol-3-yl, benzimidazol-5-yl, 6-methyl-benzimidazol-5-yl, 7-methyl-benzimidazol-5-yl, indazol-5-yl and benzothiazol-6-yl,
$R^2$ is selected from the group $R^{2f}$ consisting of
hydrogen and cyano,
$R^3$, $R^4$ are selected independently of each other from the group $R^{3/4d}$ consisting of
hydrogen and fluorine,
$R^8$ is selected independently of each other from the group $R^{8b}$ consisting of
hydrogen and methyl
and m=0,
the tautomers thereof, the stereoisomers thereof, the mixtures thereof, and the salts thereof.

Accordingly, E-36 covers compounds of formula I, wherein
$R^1$ is selected from the group $R^{1f}$ consisting of
benzimidazol-5-yl, 6-methyl-benzimidazol-5-yl and 7-methyl-benzimidazol-5-yl,
$R^2$ is selected from the group $R^{2f}$ consisting of
hydrogen and cyano,
$R^3$, $R^4$ are selected independently of each other from the group $R^{3/4d}$ consisting of
hydrogen and fluorine,
$R^8$ is selected independently of each other from the group $R^{8c}$ consisting of
hydrogen,
and m=0,
the tautomers thereof, the stereoisomers thereof, the mixtures thereof, and the salts thereof.

Another preferred embodiment of this invention is described by formula I.a

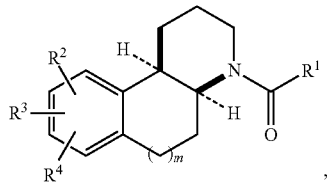

wherein the piperidine substructure and the tetraline (m=1) or indane (m=0) substructure form a cis configured tricyclic core structure, while the variables $R^1$, $R^2$, $R^3$, $R^4$, and m are defined as hereinbefore and hereinafter, their tautomers, their stereoisomers, mixtures thereof, and the salts thereof.

A further preferred embodiment of this invention is described by formula I.b

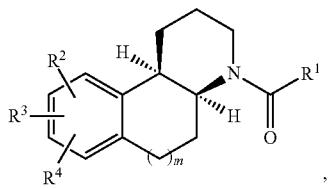

wherein the tricyclic core structure is R configured at C-10b (for m=1)/C-4a (for m=0) and S configured at C-4a (for m=1)/C-9a (for m=0), while the variables $R^1$, $R^2$, $R^3$, $R^4$, and m are defined as hereinbefore and hereinafter, their tautomers, their stereoisomers, mixtures thereof, and the salts thereof.

Accordingly, one embodiment of preferred compounds according to the invention comprises compounds of formula I.b,

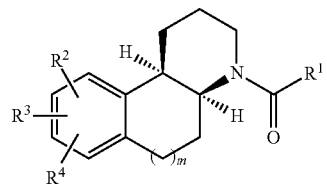

wherein
$R^1$ is selected from the group $R^{1e}$ consisting of
4-hydroxy-phenyl, 4-amino-3-methoxy-phenyl, 3-fluoro-4-hydroxy-phenyl, 4-amino-3-chloro-phenyl, 3-chloro-4-hydroxy-phenyl, indol-3-yl, indol-5-yl, indol-6-yl, 1-methyl-indol-3-yl, benzimidazol-5-yl, indazol-5-yl and benzothiazol-6-yl,
$R^2$ is selected from the group $R^{2e}$ consisting of
hydrogen, fluorine, bromine, cyclohexylmethyl, phenylmethyl, 4-methoxy-phenylmethyl, hydroxymethyl, 2-hydroxyprop-2-yl, phenyl, cyano, aminocarbonyl, methylaminocarbonyl, dimethylaminocarbonyl, pyrrolidin-1-ylcarbonyl, morpholin-4-ylcarbonyl, carboxy, methoxycarbonyl, amino, hydroxy, methoxy, 4-methoxyphenoxy, and 6-methyl-pyridazin-3-yloxy, $R^3$, $R^4$ are selected independently of each other from the group $R^{3/4d}$ consisting of
hydrogen and fluorine,
$R^8$ is selected independently of each other from the group $R^{8c}$ consisting of
hydrogen,
and m=0,
the tautomers thereof, the stereoisomers thereof, the mixtures thereof, and the salts thereof.

Another embodiment of preferred compounds according to the invention are compounds of formula I.b, wherein
$R^1$ is selected from the group $R^{1e}$ consisting of
4-hydroxy-phenyl, 4-amino-3-methoxy-phenyl, 3-fluoro-4-hydroxy-phenyl, 4-amino-3-chloro-phenyl, 3-chloro-4-hydroxy-phenyl, indol-3-yl, indol-5-yl, indol-6-yl, 1-methyl-indol-3-yl, benzimidazol-5-yl, indazol-5-yl and benzothiazol-6-yl,
$R^2$ is selected from the group $R^{2f}$ consisting of
hydrogen and cyano,
$R^3$, $R^4$ are selected independently of each other from the group $R^{3/4d}$ consisting of
hydrogen and fluorine,
$R^8$ is selected independently of each other from the group $R^{8c}$ consisting of
hydrogen,
and m=0,
the tautomers thereof, the stereoisomers thereof, the mixtures thereof, and the salts thereof.

Another embodiment of preferred compounds according to the invention are compounds of formula I.b, wherein
$R^1$ is selected from the group $R^{1f}$ consisting of
benzimidazol-5-yl, 6-methyl-benzimidazol-5-yl and 7-methyl-benzimidazol-5-yl,
$R^2$ is selected from the group $R^{2f}$ consisting of
hydrogen and cyano,
$R^3$, $R^4$ are selected independently of each other from the group $R^{3/4d}$ consisting of
hydrogen and fluorine,
$R^8$ is selected independently of each other from the group $R^{8c}$ consisting of
hydrogen,
and m=0,
the tautomers thereof, the stereoisomers thereof, the mixtures thereof, and the salts thereof.

Regarding the definitions of N-containing heteroaromatic groups, such as (het)aryl possessing one or more nitrogens within its framework, that bear a hydroxy group at the carbon atom adjacent to the nitrogen or another position of the ring which allows a mesomeric interaction with the nitrogen, these groups can form a tautomeric amide substructure which is part of the invention; the tautomeric amide obtained from combining a hydroxy group and an N-containing heteroaromatic may bear substituents other than hydrogen on the amide nitrogen. Examples of such substructures of heteroaromatic groups wherein a tautomeric amide may be formed are depicted in the following compilation:

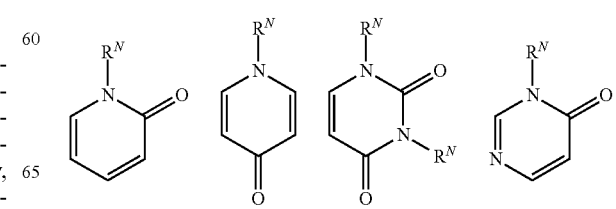

-continued

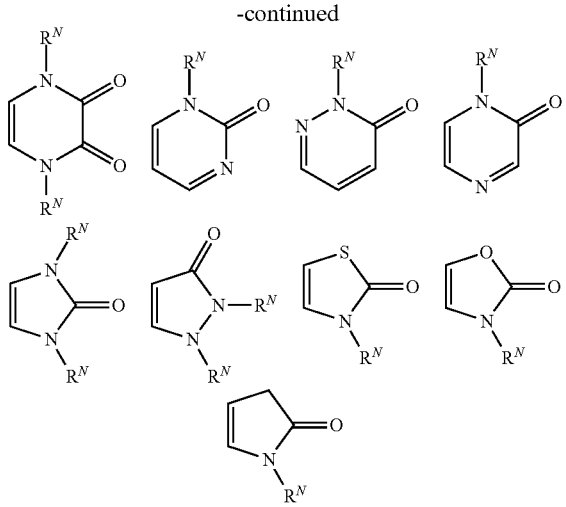

wherein $R^N$ is defined as described above. These tautomeric structures may be annelated to hereroaromatic and aromatic groups like such that are comprised by (het)aryl.

In some embodiments, the present teachings provide crystalline compounds of the following structural formula (II):

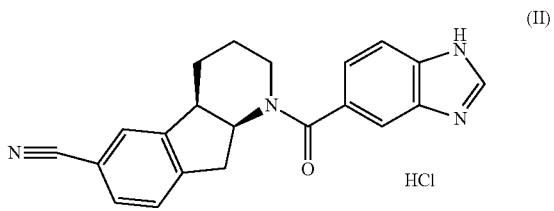

(II)

As used herein, "crystalline" refers to a solid in which molecules are arranged in an orderly repeating pattern in three dimensions. Crystalline compounds of formula (II) can be a single crystalline form or a mixture of different crystalline forms. A single crystalline form means a compound of formula (II) as a single crystal or a plurality of crystals in which each crystal has the same crystal form.

In a particular embodiment, at least a particular percentage by weight of the compound of formula (II) is a single crystalline form. Particular weight percentages include 50%, 52%, 55%, 57%, 60%, 62%, 65%, 67%, 70%, 72%, 75%, 77%, 80%, 82%, 85%, 86%, 87%, 88%, 89%, 90%, 91%, 92%, 93%, 94%, 95%, 96%, 97%, 98%, 99%, 99.5%, 99.9%, or a percentage between 50% and 100%.

When a particular percentage by weight of the compound of formula (II) is defined as a crystalline form, the-remainder of the compound of formula (II) is some combination of amorphous forms of the compound of formula (II). When a particular percentage by weight of the compound of formula (II) is defined as a single crystalline form, the-remainder of the compound of formula (II) is some combination of amorphous forms of the compound of formula (II) and/or one or more crystalline forms of the compound of formula (II) other than the single crystalline form. Examples of single crystalline forms include Forms I and II of the compound of formula (II), as well as single crystalline forms characterized by one or more properties as discussed herein.

In the following description of particular crystalline forms of the compound of formula (II), embodiments of the invention may be described with reference to a particular crystalline "Form" of the compound of formula (II). However, the particular crystalline forms may also be characterized by one or more of the characteristics of the crystalline forms as described herein, with or without regard to referencing a particular "Form".

Form I

In one embodiment, a single crystalline form of the compound of formula (II) is characterized as crystalline Form I. In another embodiment, at least a particular percentage by weight of the compound of formula (II) is crystalline Form I. Particular weight percentages include 50%, 52%, 55%, 57%, 60%, 62%, 65%, 67%, 70%, 72%, 75%, 77%, 80%, 82%, 85%, 86%, 87%, 88%, 89%, 90%, 91%, 92%, 93%, 94%, 95%, 96%, 97%, 98%, 99%, 99.5%, 99.9%, or a percentage between 50% and 100%.

In some embodiments, the crystalline form is characterized by the X-ray powder diffraction (herein referred to as "XRPD") pattern shown in FIG. 1, e.g., with values of 2Θ angles, d-spacings and relative intensities as listed in Table 1, obtained using CuKα radiation. In some embodiments, the crystalline form is characterized by one, two, three, four, five or six XRPD peaks at 2Θ angles selected from 12.5°, 12.9°, 14.8°, 20.0°, 22.2° and 26.1°. In some embodiments, the crystalline form is characterized by at least three XRPD peaks at 2Θ angles selected from 12.5°, 12.9°, 14.8°, 20.0°, 22.2° and 26.1°. In some embodiments, the crystalline form is characterized by at least four XRPD peaks at 2Θ angles selected from 12.5°, 12.9°, 14.8°, 20.0°, 22.2° and 26.1°. In some embodiments, the crystalline form is characterized by at least five XRPD peaks at 2Θ angles selected from 12.5°, 12.9°, 14.8°, 20.0°, 22.2° and 26.1°. In some embodiments, the crystalline form is characterized by XRPD peaks at 2Θ angles of 12.5°, 12.9°, 14.8°, 20.0°, 22.2° and 26.1°. In some embodiments, the crystalline form is characterized by one, two, three or four major XRPD peaks at 2Θ angles selected from 12.5°, 14.8°, 22.2° and 26.1°. In some embodiments, the crystalline form is characterized by at least three XRPD peaks at 2Θ angles selected from 12.5°, 14.8°, 22.2° and 26.1°. In some embodiments, the crystalline form is characterized by XRPD peaks at 2Θ angles of 12.5°, 14.8°, 22.2° and 26.1°. In some embodiments, the crystalline form is characterized by one, two, three or four major XRPD peaks at 2Θ angles selected from 12.5°, 14.8°, 22.2° and 26.1°. In some embodiments, the crystalline form is characterized by major XRPD peaks at 2Θ angles of 12.5°, 14.8°, 22.2° and 26.1°. It is to be understood that a specified 2Θ angle means the specified value ±0.1°.

As used herein, "major XRPD peak" refers to an XRPD peak with a relative intensity greater than 25%. Relative intensity is calculated as a ratio of the peak intensity of the peak of interest versus the peak intensity of the largest peak.

TABLE 1

XRPD Peaks from FIG. 1

| 2Θ [°] | d-value [Å] | Intensity I/I$_o$ [%] |
|---|---|---|
| 5.77 | 15.30 | 5 |
| 5.93 | 14.88 | 4 |
| 6.47 | 13.65 | 17 |
| 9.81 | 9.01 | 3 |
| 11.55 | 7.66 | 2 |
| 11.94 | 7.40 | 5 |
| 12.54 | 7.05 | 100 |
| 12.88 | 6.87 | 23 |
| 14.83 | 5.97 | 31 |

TABLE 1-continued

XRPD Peaks from FIG. 1

| 2Θ [°] | d-value [Å] | Intensity I/I$_o$ [%] |
|---|---|---|
| 16.04 | 5.52 | 12 |
| 16.54 | 5.35 | 4 |
| 17.35 | 5.11 | 5 |
| 18.67 | 4.75 | 2 |
| 19.52 | 4.54 | 5 |
| 19.59 | 4.53 | 5 |
| 19.98 | 4.44 | 21 |
| 20.20 | 4.39 | 7 |
| 20.46 | 4.34 | 5 |
| 20.66 | 4.30 | 4 |
| 20.90 | 4.25 | 3 |
| 21.14 | 4.20 | 5 |
| 21.55 | 4.12 | 4 |
| 22.18 | 4.01 | 49 |
| 23.14 | 3.84 | 8 |
| 23.26 | 3.82 | 11 |
| 23.49 | 3.78 | 10 |
| 23.99 | 3.71 | 3 |
| 24.32 | 3.66 | 4 |
| 24.91 | 3.57 | 9 |
| 25.02 | 3.56 | 14 |
| 25.39 | 3.51 | 4 |
| 26.09 | 3.41 | 60 |
| 26.52 | 3.36 | 12 |
| 26.84 | 3.32 | 2 |
| 27.10 | 3.29 | 1 |
| 27.33 | 3.26 | 2 |
| 28.30 | 3.15 | 14 |
| 29.12 | 3.06 | 3 |
| 29.91 | 2.98 | 4 |

Figure 2:
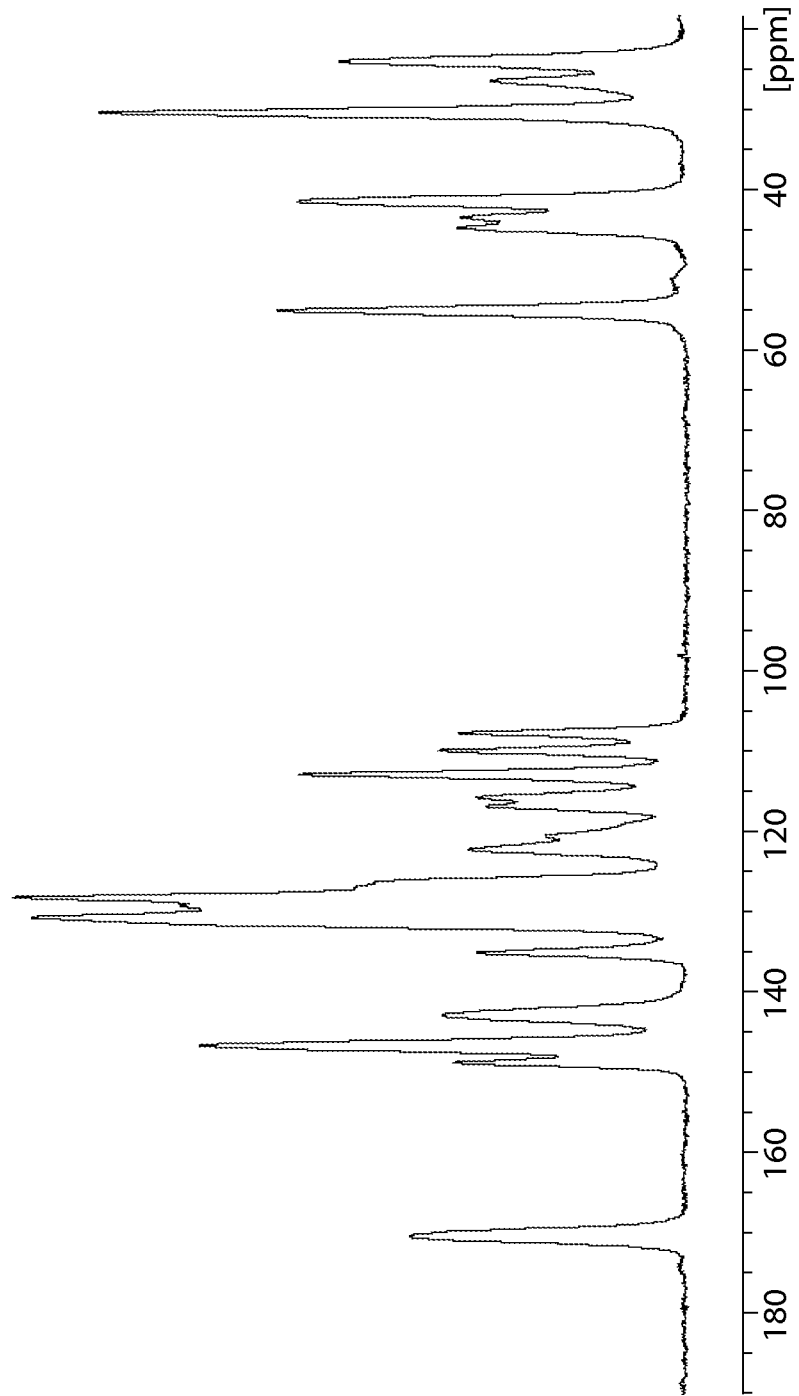
FIG. 2 is a $^{13}C$ SSNMR spectrum obtained from a sample of Form I of the compound of formula (II).

In some embodiments, the crystalline form is characterized by the $^{13}$C solid-state nuclear magnetic resonance (herein referred to as "SSNMR") pattern shown in FIG. 2, e.g., with chemical shifts as listed in Table 2, obtained using magic angle spinning. In a particular embodiment, the crystalline form is characterized by 1, 2, 3, 4, 5, 6, 7, 8, 9, 10, 11, 12, 13, 14, 15, 16, 17 or 18 $^{13}$C SSNMR peaks at chemical shifts selected from 170.3 ppm, 146.5 ppm, 142.8 ppm, 135.0 ppm, 130.6 ppm, 128.1 ppm, 122.1 ppm, 116.7 ppm, 115.6 ppm, 112.8 ppm, 109.8 ppm, 107.6 ppm, 44.6 ppm, 43.3 ppm, 41.4 ppm, 30.3 ppm, 26.3 ppm and 23.9 ppm. In one embodiment, the crystalline form is characterized by at least ten $^{13}$C SSNMR peaks at chemical shifts selected from 170.3 ppm, 146.5 ppm, 142.8 ppm, 135.0 ppm, 130.6 ppm, 128.1 ppm, 122.1 ppm, 116.7 ppm, 115.6 ppm, 112.8 ppm, 109.8 ppm, 107.6 ppm, 44.6 ppm, 43.3 ppm, 41.4 ppm, 30.3 ppm, 26.3 ppm and 23.9 ppm. In one embodiment, the crystalline form is characterized by at least fifteen $^{13}$C SSNMR peaks at chemical shifts selected from 170.3 ppm, 146.5 ppm, 142.8 ppm, 135.0 ppm, 130.6 ppm, 128.1 ppm, 122.1 ppm, 116.7 ppm, 115.6 ppm, 112.8 ppm, 109.8 ppm, 107.6 ppm, 44.6 ppm, 43.3 ppm, 41.4 ppm, 30.3 ppm, 26.3 ppm and 23.9 ppm. In one embodiment, the crystalline form is characterized by $^{13}$C SSNMR peaks at chemical shifts of 170.3 ppm, 146.5 ppm, 142.8 ppm, 135.0 ppm, 130.6 ppm, 128.1 ppm, 122.1 ppm, 116.7 ppm, 115.6 ppm, 112.8 ppm, 109.8 ppm, 107.6 ppm, 44.6 ppm, 43.3 ppm, 41.4 ppm, 30.3 ppm, 26.3 ppm and 23.9 ppm.

TABLE 2

$^{13}$C NMR Chemical Shifts from FIG 2

| Peak | Chemical Shift (ppm) |
|---|---|
| 1 | 170.3 |
| 2 | 148.7 |
| 3 | 146.5 |
| 4 | 142.8 |
| 5 | 135.0 |
| 6 | 130.6 |
| 7 | 128.1 |
| 8 | 122.1 |
| 9 | 116.7 |
| 10 | 115.6 |
| 11 | 112.8 |
| 12 | 109.8 |
| 13 | 107.6 |
| 14 | 54.9 |
| 15 | 44.6 |
| 16 | 43.3 |
| 17 | 41.4 |
| 18 | 30.3 |
| 19 | 26.3 |
| 20 | 23.9 |

Figure 3:
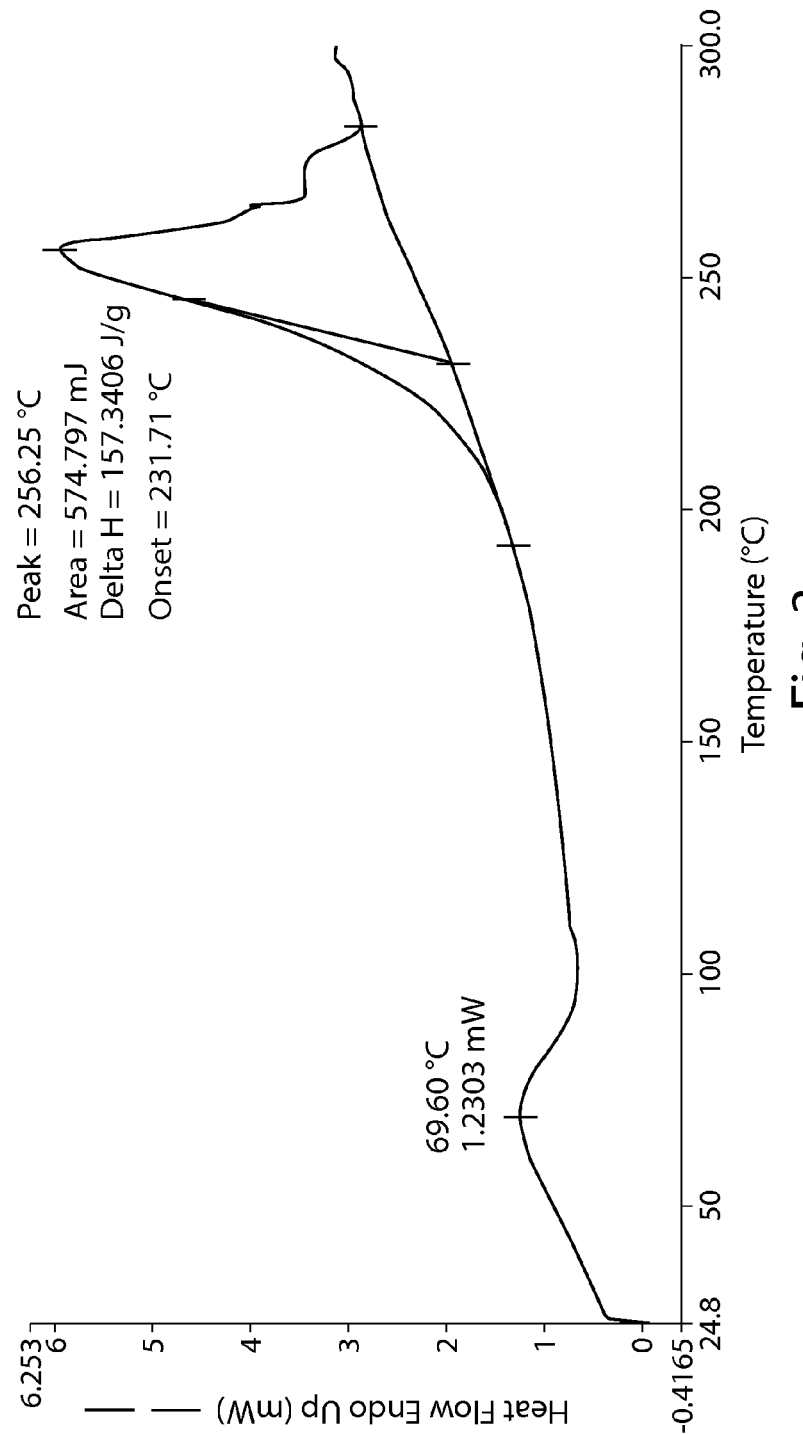
FIG. 3 is a thermal analysis profile obtained from a sample of Form I of the compound of formula (II) determined by DSC measurements.

In some embodiments, the crystalline form is characterized by an endothermic transition having an onset of about 231.7±0.5° C. in the differential scanning (herein referred to as "DSC") profile. In some embodiments, the crystalline form is characterized by a DSC profile as shown in FIG. 3. The profile plots the heat flow as a function of temperature from a sample containing Form I. The DSC is performed on the sample using a scanning rate of 10° C./minute.

Figure 4:
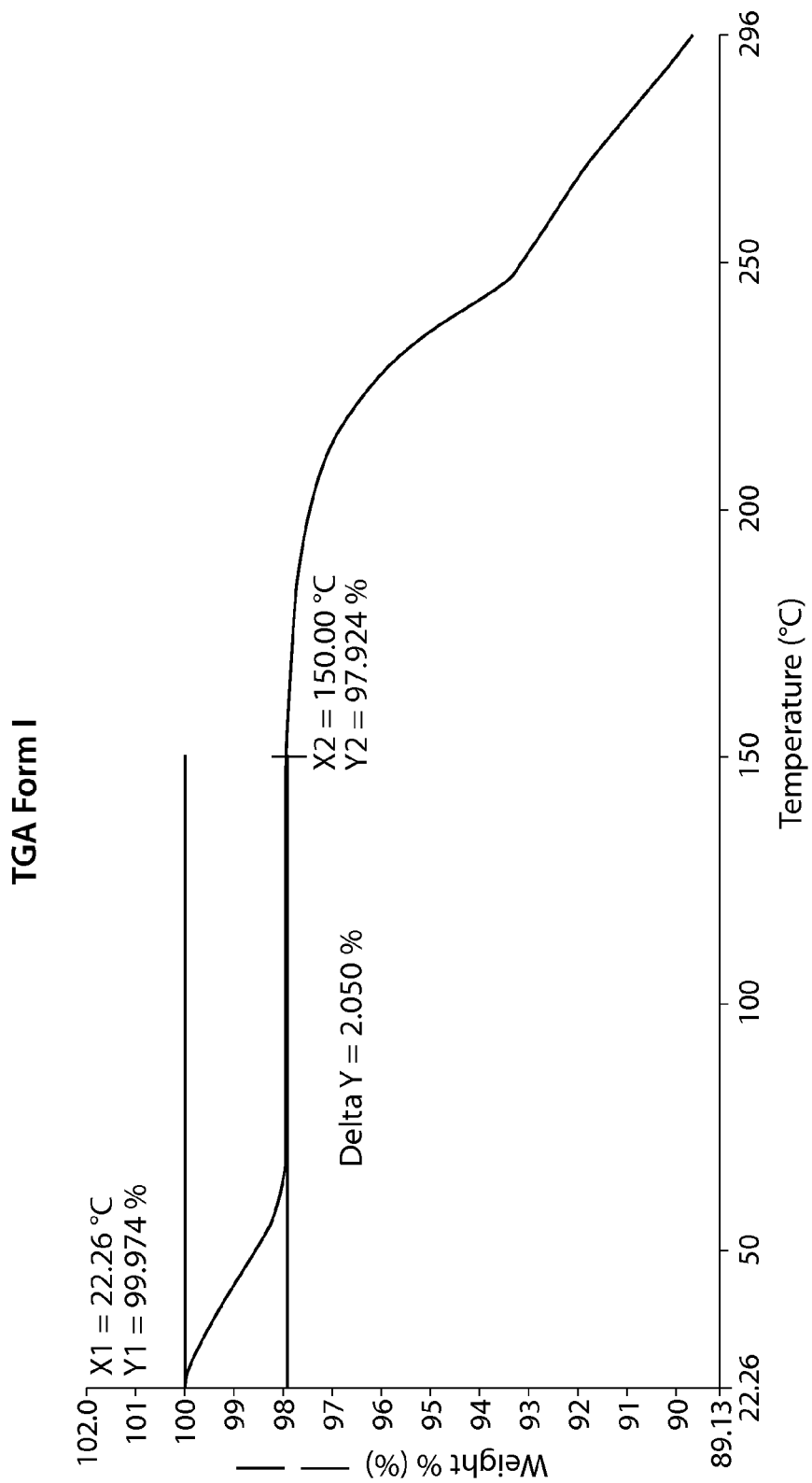
FIG. 4 is a thermal analysis profile obtained from a sample of Form I of the compound of formula (II) determined by TGA measurements.

Form I is also characterized by the thermal gravimetric analysis (herein referred to as "TGA") profile shown in FIG. 4. The profile graphs the percent loss of weight of the sample as a function of temperature with the temperature rate change being 10° C./minute. The profile shows a weight loss of approximately 2.1% as the temperature of the sample is changed from room temperature to 150° C., which indicates that Form I is anhydrous.

Form II

In one embodiment, a single crystalline form of the compound of formula (II) is characterized as crystalline Form II. In another embodiment, at least a particular percentage by weight of the compound of formula (II) is crystalline Form II. Particular weight percentages include 50%, 52%, 55%, 57%, 60%, 62%, 65%, 67%, 70%, 72%, 75%, 77%, 80%, 82%, 85%, 86%, 87%, 88%, 89%, 90%, 91%, 92%, 93%, 94%, 95%, 96%, 97%, 98%, 99%, 99.5%, 99.9%, or a percentage between 50% and 100%.

Figure 5:
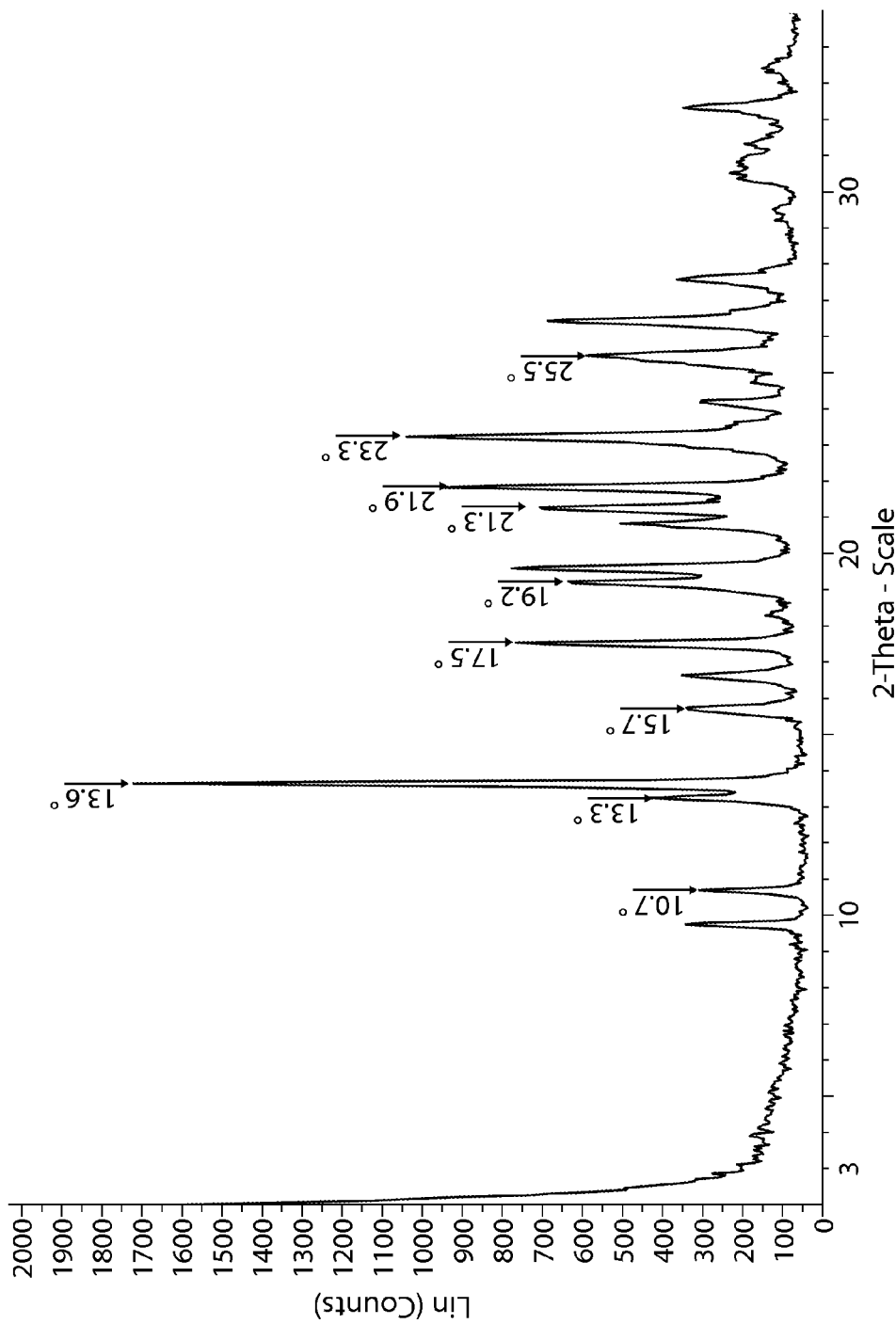
FIG. 5 is an XRPD pattern obtained from a sample of Form II of the compound of formula (II).

In some embodiments, the crystalline form is characterized by the XRPD pattern shown in FIG. 5, e.g., with values of 2Θ angles, d-spacings and relative intensities as listed in Table 3, obtained using CuKα radiation. In a particular embodiment, the crystalline form is characterized by one, two, three, four, five, six or seven, eight, nine, ten, eleven or twelve XRPD peaks at 2Θ angles selected from 13.3°, 13.7°, 15.7°, 17.6°, 19.3°, 19.7°, 20.9°, 21.3°, 21.9°, 23.3°, 25.6° and 26.5°. In a particular embodiment, the crystalline form is characterized by at least seven, eight, nine, ten or eleven XRPD peaks at 2Θ angles selected from 13.3°, 13.7°, 15.7°, 17.6°, 19.3°, 19.7°, 20.9°, 21.3°, 21.9°, 23.3°, 25.6° and 26.5°. In some embodiments, the crystalline form is characterized by XRPD peaks at 2Θ angles of 13.3°, 13.7°, 15.7°, 17.6°, 19.3°, 19.7°, 20.9°, 21.3°, 21.9°, 23.3°, 25.6° and 26.5°.

In some embodiments, the crystalline form is characterized by XRPD peaks at 2Θ angles of 13.7°, 17.6°, 21.3°, 21.9°, 23.3°, 25.6° and 26.5°. In some embodiments, the crystalline form is characterized by XRPD peaks at 2Θ angles of 13.7°, 17.6°, 19.7, 21.3°, 21.9°, 23.3°, 25.6° and 26.5°. In some embodiments, the crystalline form is characterized by XRPD peaks at 2Θ angles of 13.7°, 17.6°, 19.7, 20.9, 21.3°, 21.9°, 23.3°, 25.6° and 26.5°. In some embodiments, the crystalline form is characterized by XRPD peaks at 2Θ angles of 13.7°, 17.6°, 19.3, 19.7, 20.9, 21.3°, 21.9°, 23.3°, 25.6° and 26.5°. In some embodiments, the crystalline form is characterized by XRPD peaks at 2Θ angles of 13.3°, 13.7°, 17.6°, 19.3°, 19.7°, 20.9°, 21.3°, 21.9°, 23.3°, 25.6° and 26.5°. In some embodiments, the crystalline form is characterized by XRPD peaks at 2Θ angles of 13.3°, 13.7°, 15.7°, 17.6°, 19.3°, 19.7°, 20.9°, 21.3°, 21.9°, 23.3°, 25.6° and 26.5°. In some embodiments, the crystalline form is characterized by one, two, three, four, five, six or seven major XRPD peaks at 2Θ angles selected from 13.7°, 17.6°, 21.3°, 21.9°, 23.3°, 25.6° and 26.5°. In some embodiments, the crystalline form is characterized by major XRPD peaks at 2Θ angles of 13.7°, 17.6°, 21.3°, 21.9°, 23.3°, 25.6° and 26.5°.

TABLE 3

XRPD Peaks from FIG. 5

| 2Θ [°] | d-value [Å] | Intensity I/I$_o$ [%] |
|---|---|---|
| 9.79 | 9.03 | 19 |
| 10.73 | 8.24 | 18 |
| 12.54 | 7.05 | 3 |
| 13.31 | 6.65 | 26 |
| 13.70 | 6.46 | 100 |
| 14.83 | 5.97 | 2 |
| 15.71 | 5.63 | 20 |
| 16.68 | 5.31 | 19 |
| 17.58 | 5.04 | 40 |
| 18.41 | 4.82 | 7 |
| 19.07 | 4.65 | 10 |
| 19.27 | 4.60 | 33 |
| 19.66 | 4.51 | 39 |
| 20.88 | 4.25 | 38 |
| 21.32 | 4.16 | 48 |
| 21.56 | 4.12 | 8 |
| 21.91 | 4.05 | 50 |
| 22.99 | 3.87 | 10 |
| 23.29 | 3.82 | 56 |
| 23.61 | 3.77 | 8 |
| 24.27 | 3.66 | 19 |
| 24.89 | 3.57 | 9 |
| 25.37 | 3.51 | 15 |
| 25.55 | 3.48 | 40 |
| 26.05 | 3.42 | 5 |
| 26.50 | 3.36 | 41 |
| 26.79 | 3.32 | 10 |
| 27.68 | 3.22 | 19 |

Figure 6:
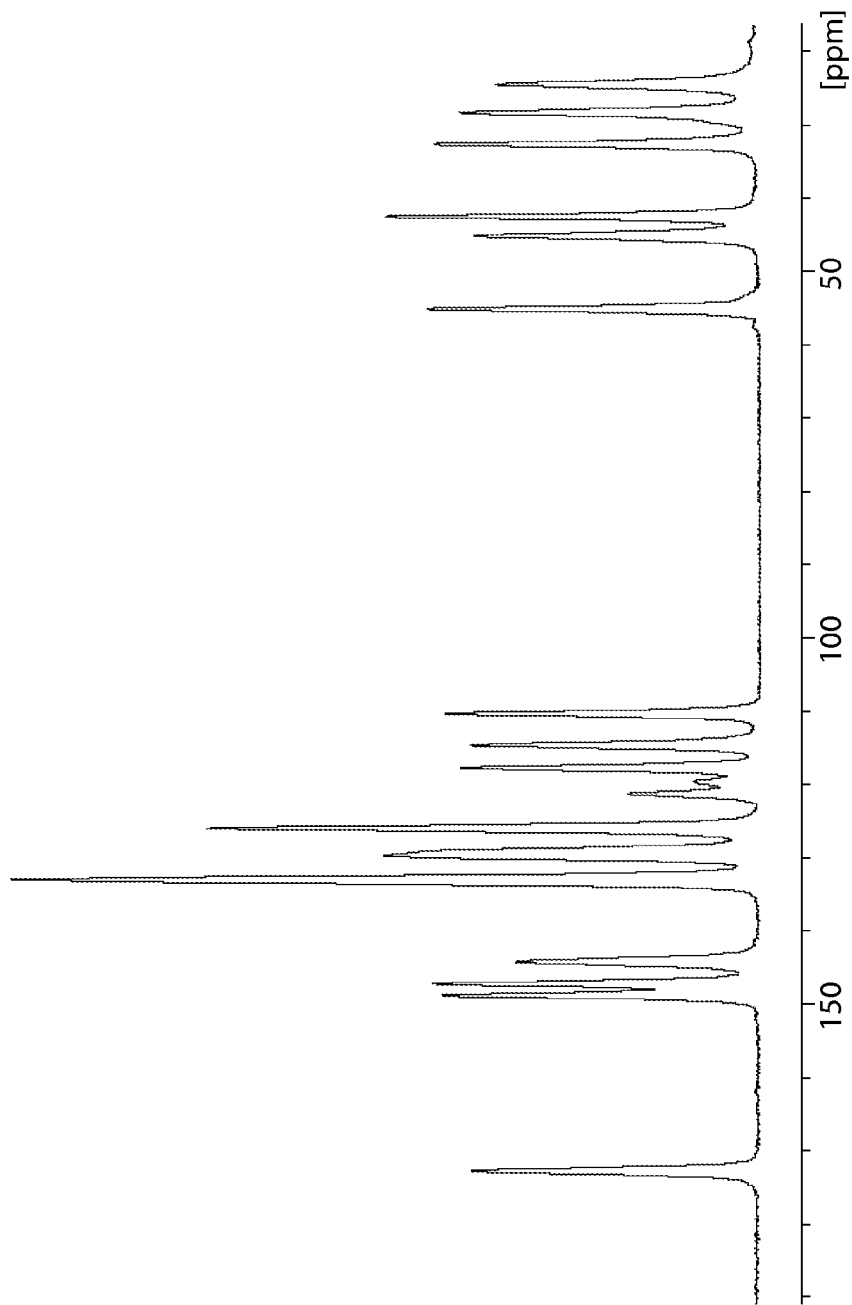
FIG. 6 is a $^{13}C$ SSNMR spectrum obtained from a sample of Form II of the compound of formula (II).

In some embodiments, the crystalline form is characterized by the $^{13}$C SSNMR pattern shown in FIG. 6, e.g., with chemical shifts as listed in Table 4, obtained using magic angle spinning. In a particular embodiment, the crystalline form is characterized by 1, 2, 3, 4, 5, 6, 7, 8, 9, 10, 11, 12, 13, 14, 15, 16, 17 or 18 $^{13}$C SSNMR peaks at chemical shifts selected from 172.6 ppm, 147.1 ppm 144.1 ppm, 132.9 ppm 129.6 ppm, 125.9 ppm 121.2 ppm, 119.5 ppm, 117.7 ppm, 114.6 ppm, 110.2 ppm, 45.1 ppm, 42.4 ppm, 32.6 ppm, 28.3 ppm and 24.4 ppm. In one embodiment, the crystalline form is characterized by at least ten $^{13}$C SSNMR peaks at chemical shifts selected from 172.6 ppm, 147.1 ppm 144.1 ppm, 132.9 ppm 129.6 ppm, 125.9 ppm 121.2 ppm, 119.5 ppm, 117.7 ppm, 114.6 ppm, 110.2 ppm, 45.1 ppm, 42.4 ppm, 32.6 ppm, 28.3 ppm and 24.4 ppm. In one embodiment, the crystalline form is characterized by at least thirteen $^{13}$C SSNMR peaks at chemical shifts selected from 172.6 ppm, 147.1 ppm 144.1 ppm, 132.9 ppm 129.6 ppm, 125.9 ppm 121.2 ppm, 119.5 ppm, 117.7 ppm, 114.6 ppm, 110.2 ppm, 45.1 ppm, 42.4 ppm, 32.6 ppm, 28.3 ppm and 24.4 ppm. In one embodiment, the crystalline form is characterized by $^{13}$C SSNMR peaks at chemical shifts of 172.6 ppm, 147.1 ppm 144.1 ppm, 132.9 ppm 129.6 ppm, 125.9 ppm 121.2 ppm, 119.5 ppm, 117.7 ppm, 114.6 ppm, 110.2 ppm, 45.1 ppm, 42.4 ppm, 32.6 ppm, 28.3 ppm and 24.4 ppm.

TABLE 4

$^{13}$C NMR Chemical Shifts from FIG. 6

| Peak | Chemical Shift (ppm) |
|---|---|
| 1 | 172.6 |
| 2 | 148.7 |
| 3 | 147.1 |
| 4 | 144.1 |
| 5 | 132.9 |
| 6 | 129.6 |
| 7 | 125.9 |
| 8 | 121.2 |
| 9 | 119.5 |
| 10 | 117.7 |
| 11 | 114.6 |
| 12 | 110.2 |
| 13 | 55.0 |
| 14 | 45.1 |
| 15 | 42.4 |
| 16 | 32.6 |
| 17 | 28.3 |
| 18 | 24.4 |

Figure 7:
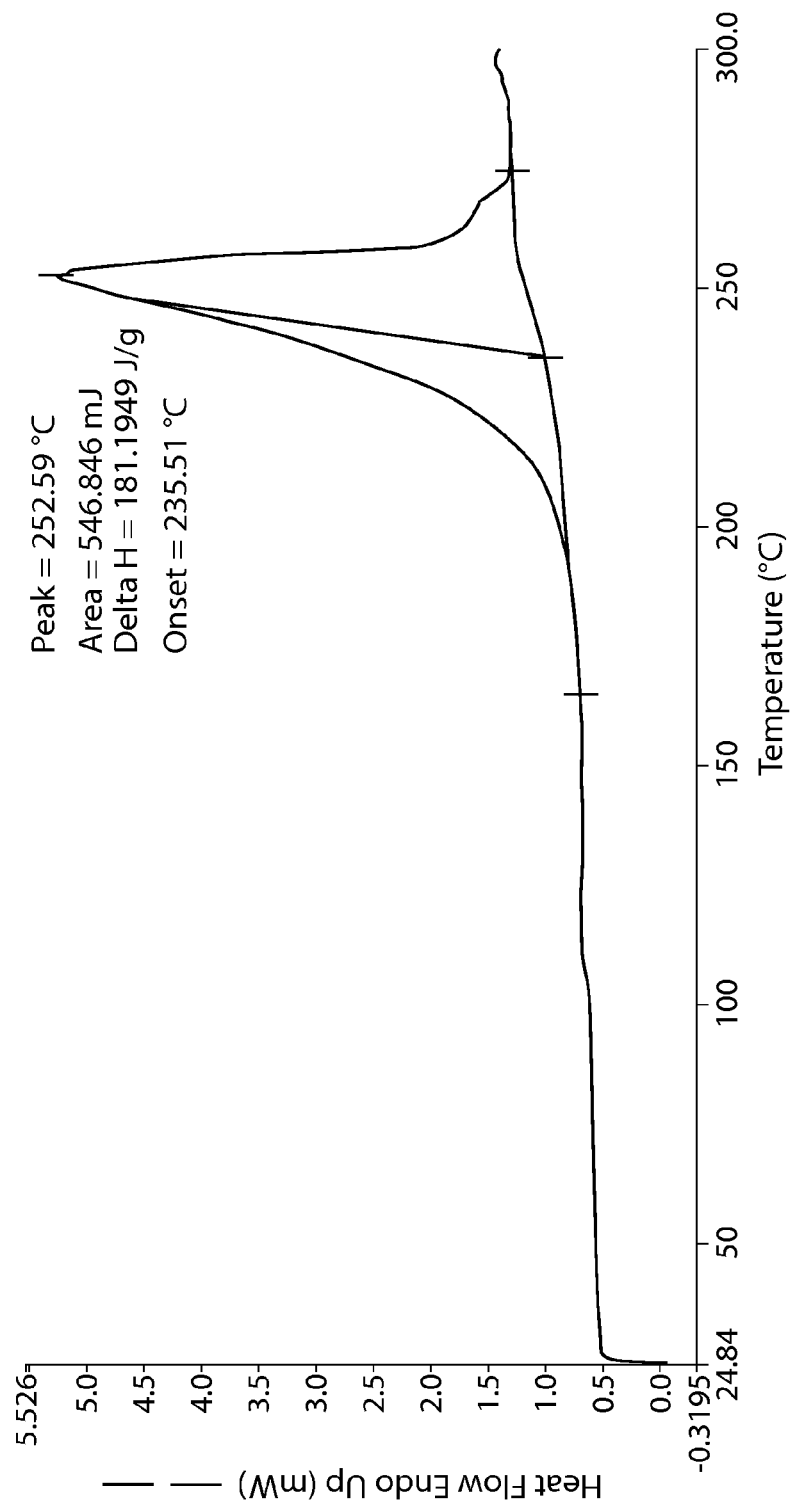
FIG. 7 is a thermal analysis profile obtained from a sample of Form II of the compound of formula (II) determined by DSC measurements.

In some embodiments, the crystalline form is characterized by an endothermic transition having an onset of about 235.5±0.5° C. in the DSC profile. In some embodiments, the crystalline form is characterized by a DSC profile as shown in FIG. 7. The profile plots the heat flow as a function of temperature from a sample containing Form II. The DSC is performed on the sample using a scanning rate of 10° C./minute.

Figure 8:
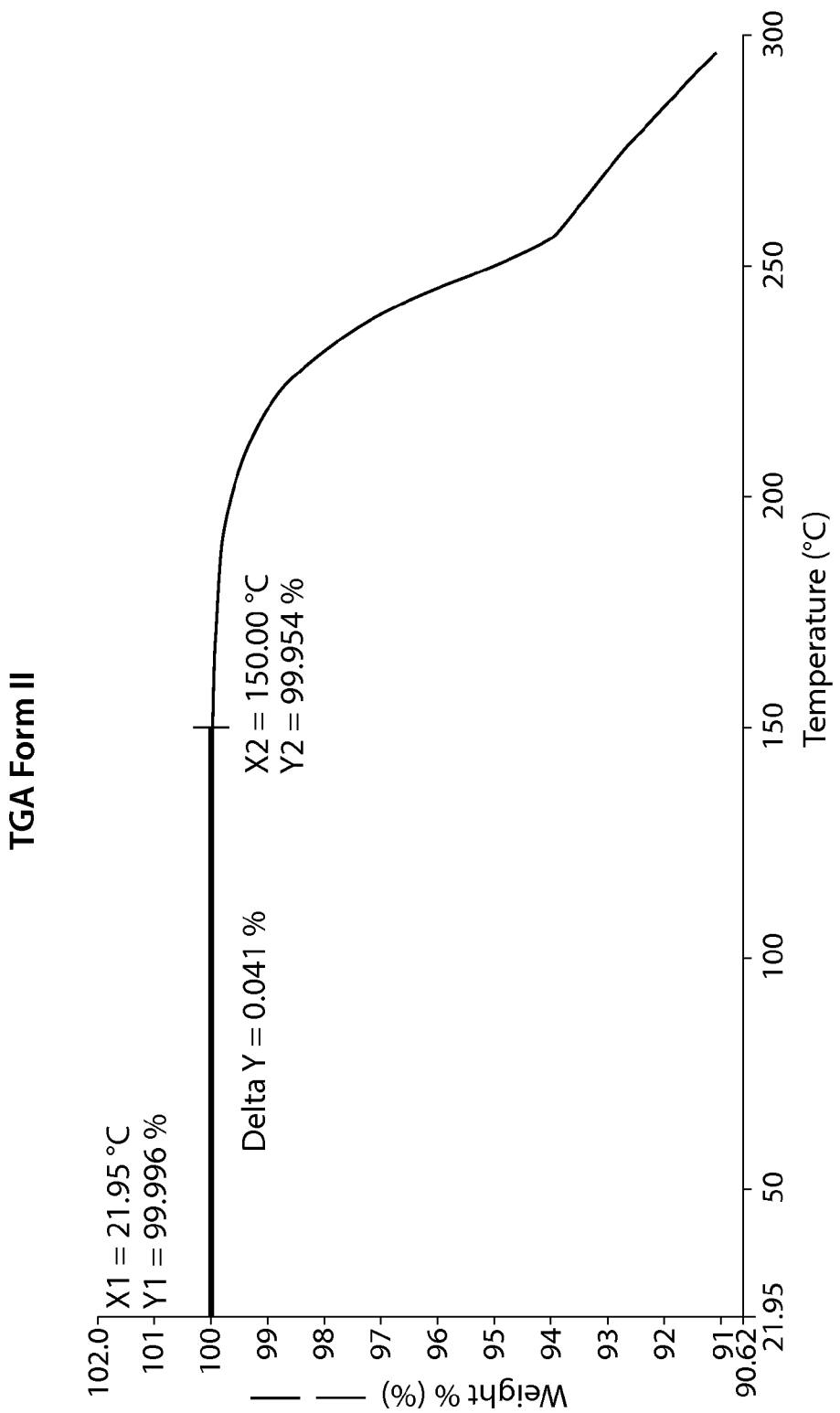
FIG. 8 is a thermal analysis profile obtained from a sample of Form II of the compound of formula (II) determined by TGA measurements.

In some embodiments, the crystalline form is characterized by the thermal gravimetric analysis (herein referred to as "TGA") profile shown in FIG. 8. The profile graphs the percent loss of weight of the sample as a function of temperature with the temperature rate change being 10° C./minute. The profile shows a weight loss of approximately 0.1% as the temperature of the sample is changed from room temperature to 150° C., which indicates that Form II is anhydrous.

Other embodiments of the invention are directed to a single crystalline form of the compound of formula (II) is characterized by a combination of the aforementioned characteristics of any of the single crystalline forms discussed herein. The characterization can be any combination of one or more of the XRPD, TGA, DSC and SSNMR described for a particular crystalline form. For example, the single crystalline form of the compound of formula (II) can be characterized by any combination of the 2Θ peaks in an XRPD scan and/or any combination of the chemical shift peaks of an SSNMR spectrum and/or any combination of information obtained from the DSC determinations and/or the weight change in a sample obtained by TGA. It is to be understood that the present teachings include any combination of analytical techniques to characterize a crystalline form.

The present teachings also include compositions which include any of the compounds described herein. In some embodiments, the present teachings provide a pharmaceutical composition including any of the compounds described herein and a pharmaceutically acceptable carrier or diluent. In some embodiments, the present teachings provide a pharmaceutical composition comprising the crystalline compound of Formula (II) and a pharmaceutically acceptable carrier or diluent.

Some terms used above and hereinafter to describe the compounds according to the invention will now be defined more closely.

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkyl-" means an aryl group which is bound to a $C_{1-3}$-alkyl group, the latter of which is bound to the core or to the group to which the substituent is attached.

In general, the attachment site of a given residue to another group shall be variable, i.e. any capable atom, bearing hydrogens to be replaced, within this residue may be the linking spot to the group being attached, unless otherwise indicated.

Unless specifically indicated, throughout the specification and the appended claims, a given chemical formula or name shall encompass all conceivable constitutional isomers and stereoisomers, including enantiomers, diastereomers, cis/trans isomers, E/Z isomers, etc., and mixtures thereof, for example, 1:1 mixtures of enantiomers (termed racemates), mixtures of different proportions of separate enantiomers, mixtures of diastereomers, or mixtures of any of the foregoing forms where such isomers exist, as well as salts, including pharmaceutically acceptable salts thereof and solvates thereof such as, for instance, hydrates, including solvates of the free compounds or solvates of a salt of the compound.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

The term "substituted" as used herein means that any one or more hydrogens on the designated atom is replaced with a selection from the indicated group, provided that the designated atom's viable valence number is not exceeded, and that the substitution results in a stable compound.

The term "partially unsaturated" as used herein means that in the designated group or moiety 1, 2, or more, preferably 1 or 2, double bonds are present. Preferably, as used herein, the term "partially unsaturated" does not cover fully unsaturated groups or moieties.

The term halogen denotes an atom selected from the group consisting of F, Cl, Br, and I.

The term $C_{1-n}$-alkyl, wherein n may have a value of 1 to 18, denotes a saturated, branched or unbranched hydrocarbon group with 1 to n C atoms. Examples of such groups include methyl, ethyl, n-propyl, iso-propyl, butyl, iso-butyl, sec-butyl, tert-butyl, n-pentyl, iso-pentyl, neo-pentyl, tert-pentyl, n-hexyl, iso-hexyl, etc.

The term "$C_{1-n}$-alkylene" wherein n is an integer of 1 to n, either alone or in combination with another radical, denotes an acyclic, straight or branched chain divalent alkyl radical containing 1 to n carbon atoms. For example, the term $C_{1-4}$-alkylene includes —(CH$_2$)—, —(CH$_2$—CH$_2$)—, —(CH(CH$_3$))—, —(CH$_2$—CH$_2$—CH$_2$)—, —(C(CH$_3$)$_2$)—, —(CH(CH$_2$CH$_3$))—, —(CH(CH$_3$)—CH$_2$)—, —(CH$_2$—CH(CH$_3$))—, —(CH$_2$—CH$_2$—CH$_2$—CH$_2$)—, —(CH$_2$—CH$_2$—CH(CH$_3$))—, —(CH(CH$_3$)—CH$_2$—CH$_2$)—, —(CH$_2$—CH(CH$_3$)—CH$_2$)—, —(CH$_2$—C(CH$_3$)$_2$)—, —(C(CH$_3$)$_2$—CH$_2$)—, —(CH(CH$_3$)—CH(CH$_3$))—, —(CH$_2$—CH(CH$_2$CH$_3$))—, —(CH(CH$_2$CH$_3$)—CH$_2$)—, —(CH(CH$_2$CH$_2$CH$_3$))—, —(CHCH(CH$_3$)$_2$)—, and —C(CH$_3$)(CH$_2$CH$_3$)—

The term $C_{2-n}$-alkenyl, wherein n has a value of 3 to 10, denotes a branched or unbranched hydrocarbon group with 2 to n C atoms and a C=C double bond. Examples of such groups include ethenyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, etc.

The term $C_{2-n}$-alkynyl, wherein n has a value of 3 to 10, denotes a branched or unbranched hydrocarbon group with 2 to n C atoms and a C≡C triple bond. Examples of such groups include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, etc. Unless otherwise stated alkynyl groups are connected to the remainder of the molecule via the C atom in position 1. Therefore terms such as 1-propynyl, 2-propynyl, 1-butynyl, etc. are equivalent to the terms 1-propyn-1-yl, 2-propyn-1-yl, 1-butyn-1-yl, etc. This also applies analogously to $C_{2-n}$-alkenyl groups.

The term $C_{1-n}$-alkoxy denotes a $C_{1-n}$-alkyl-O group, wherein $C_{1-n}$-alkyl is as hereinbefore defined. Examples of such groups include methoxy, ethoxy, n-propoxy, iso-propoxy, n-butoxy, iso-butoxy, sec-butoxy, tert-butoxy, n-pentoxy, iso-pentoxy, neo-pentoxy, tert-pentoxy, n-hexoxy, iso-hexoxy, etc.

The term $C_{1-n}$-alkylcarbonyl denotes a $C_{1-n}$-alkyl-C(=O) group, wherein $C_{1-n}$-alkyl is as hereinbefore defined. Examples of such groups include methylcarbonyl, ethylcarbonyl, n-propylcarbonyl, iso-propylcarbonyl, n-butylcarbonyl, iso-butylcarbonyl, sec-butylcarbonyl, tert-butylcarbonyl, n-pentylcarbonyl, iso-pentylcarbonyl, neo-pentylcarbonyl, tert-pentylcarbonyl, n-hexylcarbonyl, iso-hexylcarbonyl, etc.

The term $C_{3-n}$-cycloalkyl denotes a saturated mono-, bi-, tri- or spirocarbocyclic group with 3 to n C atoms. Examples of such groups include cyclopropyl, cyclobutyl, cyclopentyl, cyclohexyl, cycloheptyl, cyclooctyl, cyclononyl, cyclododecyl, bicyclo[3.2.1]octyl, spiro[4.5]decyl, norpinyl, norbonyl, norcaryl, adamantyl, etc. Preferably the term $C_{3-7}$-cycloalkyl denotes saturated monocyclic groups.

The term $C_{5-n}$-cycloalkenyl denotes a $C_{5-n}$-cycloalkyl group which is as hereinbefore defined and additionally has at least one C=C double bond.

The term $C_{3-n}$-cycloalkylcarbonyl denotes a $C_{3-n}$-cycloalkyl-C(=O) group wherein $C_{3-n}$-cycloalkyl is as hereinbefore defined.

The term $C_{3-n}$-heterocycloalkyl denotes a saturated mono-, bi-, tri- or spirocarbocyclic group, which is as hereinbefore defined, with 3-m to n-m C atoms, wherein m carbon atoms are replaced with m heteroatoms independently selected from N, NR$^N$, O, S, SO, and SO$_2$.

Examples of such groups include aziridinyl, oxiranyl, azetidinyl, oxetanyl, pyrrolidinyl, tetrahydrofuranyl, tetrahydrothiophenyl, piperidinyl, tetrahydropyranyl, tetrahydrothiopyranyl, piperazinyl, morpholinyl, 1,3-dioxanyl, 1,4-dioxanyl, thiomorpholinyl, azepanyl, oxepanyl, thiepanyl, 1-aza-bicyclo[2.2.2]octane, 1,4-diaza-bicyclo[2.2.2]octane, etc. Preferably, the term heterocycloalkyl denotes saturated monocyclic $C_{5-6}$-cycloalkyl groups wherein one or two carbon atoms are replaced with N and/or O.

The term tri-($C_{1-4}$-alkyl)silyl comprises silyl groups which have identical or two or three different alkyl groups.

The term di-($C_{1-3}$-alkyl)amino comprises amino groups which have two identical or different alkyl groups.

If groups or residues are optionally substituted, this applies to any form of the group or residue. For instance, if an alkyl group is optionally mono- or polyfluorinated this comprises also alkyl residues which are part of larger groups, e.g. alkyloxy, alkylcarbonyl, alkoxyalkyl, etc., or if a (het)aryl group is optionally mono- or polysubstituted with a certain substituent or a set of substituents this also includes (het)aryl groups which are part of larger groups, e.g. (het)aryl-$C_{1-n}$-alkyl, (het)aryloxy, (het)aryloxy-$C_{1-n}$-alkyl, (het)aryl-$C_{1-n}$-alkyloxy, etc. Accordingly, in cases where e.g. $R^2$ or $R^5$ has, for example, the meaning (het)aryloxy, while (het)aryl residues are optionally mono- or polyfluorinated and (het)aryl denotes inter alia phenyl, the meanings mono-, di-, tri-, tetra-, and pentafluorophenoxy are also comprised. The same applies to groups or residues in which a part of the group or residue is replaced by another group, e.g. a $CH_2$ group is optionally replaced by O, S, $NR^N$, CO, or $SO_2$. For instance, a residue having inter alia the meaning hydroxy-$C_{1-3}$-alkyl in which a $CH_2$ group is optionally replaced by CO (=carbonyl), this also comprises carboxy, carboxymethyl, hydroxymethylcarbonyl, 1-hydroxy-2-oxo-ethyl, carboxyethyl, 2-carboxyethyl, 1-carboxyethyl, hydroxymethylcarbonylmethyl, 1-hydroxy-2-oxo-propyl, hydroxyethylcarbonyl, (2-hydroxyethyl)carbonyl, hydroxy-3-oxo-propyl, 1-hydroxy-3-oxo-propyl, 2-hydroxy-3-oxo-propyl, (1-hydroxyethyl)-carbonyl, 2-hydroxy-1-oxo-prop-2-yl, hydroxy-2-oxo-prop-2-yl and 3-hydroxy-1-oxo-prop-2-yl. Analogously, a definition such as $C_{1-n}$-alkyl wherein one or more $CH_2$ groups are optionally replaced by, for example, carbonyl and which is optionally substituted with e.g. hydroxy or amino also comprises explicit residues having no CH and/or $CH_2$ group, e.g. carboxy and aminocarbonyl.

All atoms/elements described herein, including atoms that are part of a group, comprise all stable isotopic forms of the respective element. For instance, whenever hydrogen is mentioned, either explicitly or as part of a group such as methyl, this includes hydrogen and deuterium as stable isotopic forms of the element hydrogen.

The compounds according to the invention may be obtained using methods of synthesis known in principle. Preferably, the compounds are obtained by the following methods according to the invention which are described in more detail hereinafter.

A general route to access the core structures of the compounds of the invention is given in Scheme 1 employing a tricyclic pyridine as precursor for the tricyclic piperidine framework; $R^2$, $R^3$, $R^4$, and m have the meanings as defined hereinbefore and hereinafter. The tricyclic pyridine may be obtained from 2-indanones (m=0) or 2-tetralones (m=1) and propargylamine or a derivative thereof by combining the two starting compounds in the presence of a catalyst, such as salts or complexes of gold and copper, preferably $NaAuCl_4$ and $CuCl_2$ (see J. Org. Chem. 2003, 68, 6959-6966). The reaction is usually run in alcohols, such as ethanol, at temperatures of 20 to 120° C. through conventional heating or microwave irradiation. The pyridine structure obtained is transformed to the piperidine derivative by reduction with hydrogen in the presence of a transition metal catalyst, such as $PtO_2$, Pt/C, Pd/C, Rh/C, Raney-Ni, or mixtures thereof. Alcohols, e.g. methanol and ethanol, ethyl acetate, acetic acid, water, ether, tetrahydrofuran, 1,4-dioxane, N,N-dimethylformamide, N,N-dimethylacetamide, N-methylpyrrolidinone, hexanes, methylcyclohexane, or mixtures thereof are among the preferred solvents, optionally used in combination with additives, such as acid, e.g. trifluoroacetic acid, hydrochloric acid, and sulfuric acid, at temperatures of 10 to 150° C., preferably 20 to 80° C., and hydrogen pressures of 1 to 150 bar, preferably 1 to 20 bar. Alternatively, the reduction may be accomplished, after transforming the pyridine into a pyridinium ion by N-alkylation, N-acylation, or N-sulfonylation, by treatment with a hydride source such as $NaBH_4$ or $LiAlH_4$. The latter reagent is preferably employed in hydrocarbons, ether, tetrahydrofuran, 1,4-dioxane, benzene, or toluene, while the former is preferably used in alcohols, e.g. methanol or ethanol, and water, optionally combined with a co-solvent such as tetrahydrofuran, 1,4-dioxane, or N-methylpyrrolidinone and an additive such as acid, e.g. acetic acid, or base, e.g. sodium hydroxide.

Scheme 1. Strategy 1 to build the tricyclic skeleton

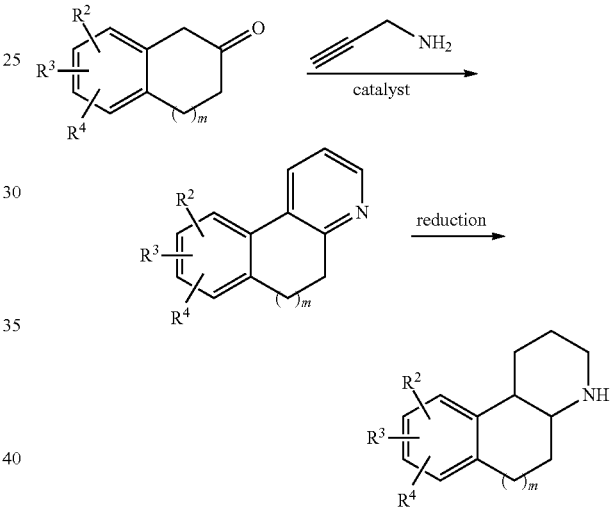

Another viable synthetic route to the tricyclic pyridine precursor described in Scheme 1 is delineated in Scheme 2; $R^2$, $R^3$, $R^4$, and m have the meanings as defined hereinbefore and hereinafter. Transition metal catalyzed coupling of a phenylmethyl (for m=0) or phenethyl (for m=1) metal derivative with a 2,3-dihalo or pseudohalo pyridine furnishes a requisite intermediate. Suited metal residues in the phenylalkyl metal derivative may be e.g. MgCl, MgBr, $B(OH)_2$, $B(OCMe_2CMe_2O)$, $BF_3K$, ZnCl, ZnBr, or ZnI, and suited halo or pseudohalo at the pyridine is preferably Cl, Br, I, $F_3CSO_3$, p-$TolSO_3$, and $MeSO_3$. Depending on the coupling partners, different catalysts may be suitable which are predominantly derived from Pd, Ni, Cu, or Fe. $Pd(PPh_3)_4$, Pd[1,1'-bis(diphenylphosphino)ferrocene]$Cl_2$, $Pd(PPh_3)_2Cl_2$, $Ni(PPh_3)_2Cl_2$, or Pd on C, nanoparticles of Pd or Fe, Pd(II), Ni(II), Fe(II), or Fe(III) salts, such as $Pd(O_2CCH_3)_2$, $PdCl_2$, $NiCl_2$, or $FeCl_3$, optionally combined with a 2-(optionally substituted phenyl)phenyl-dicyclohexyl or di-tert-butylphosphine, triphenylphosphine, tritolylphosphine, trifurylphosphine, tri-tert-butyl-phosphine, tricyclohexylphosphine, a 1,3-diaryl imidazolidinium salt, or a 1,3-diaryl dihydroimidazolidinium salt, are a few more often employed catalysts. The couplings are preferably conducted in toluene, tetrahydrofuran, 1,4-dioxane, 1,2-dimethoxyethane, N,N-dimethylformamide, N,N-dimethylacetamide, N-methylpyrrolidinone, or mixtures thereof, which, depending on the coupling partners, are optionally combined with alcohol, e.g. methanol, water, alkali metal salts, such as LiCl, NaOH, $Na_2CO_3$, $K_2CO_3$, $Cs_2CO_3$, $NaO_2CCH_3$, or $K_3PO_4$, ammonium salts, e.g. $Bu_4NCl$, or silver salts, e.g. $AgO_3SCF_3$, at temperatures of −10 to 150° C. The subsequent cyclization of the benzyl- or phenethylpyridine to the tricyclic pyridine structure may be accomplished by another transition metal catalyzed reaction, preferably Pd, e.g. derived from $Pd(O_2CC_3)_2$ or $Pd(O_2CCMe_3)_2$, and a phosphine ligand, such as e.g. di-tert-butyl-methyl-phosphine, tricyclohexylphosphine, triphenyl-phosphine, tri(4-fluorophenyl)phosphine, or 2-(2-dimethylaminophenyl)phenyl-diphenyl-phosphine. The cyclization is most preferably carried out in the presence of a potassium salt, e.g. $K_2CO_3$ or $KO_2CCH_3$, optionally combined with a silver salt, e.g. $Ag_2CO_3$ or $AgO_3SCF_3$, and/or pivalic acid in N,N-dimethylacetamide at 40 to 160° C. (see e.g. *Tetrahedron* 2008, 64, 6015-20 and references quoted therein).

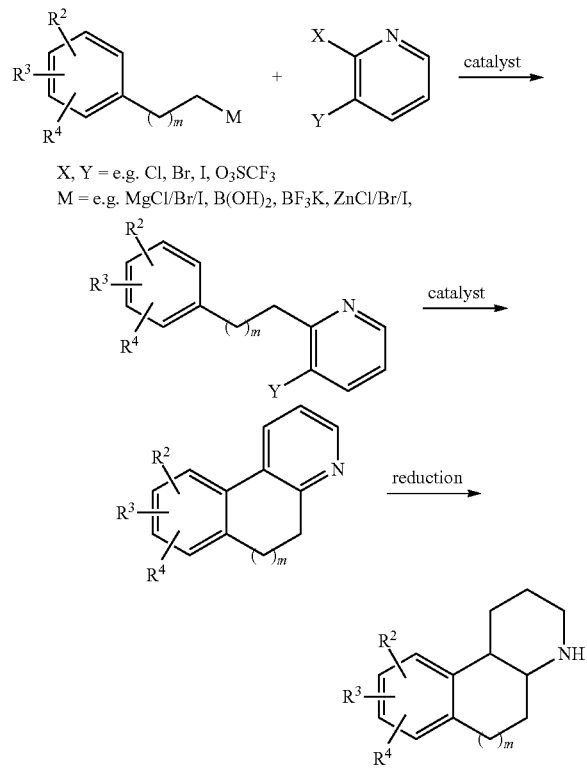

Scheme 2. Strategy 2 to build the tricyclic skeleton

An alternative strategy to access the tricyclic pyridine precursor described in Scheme 1 is described in Scheme 3; $R^2$, $R^3$, $R^4$, and m have the meanings as defined hereinbefore and hereinafter. A transition metal catalyzed coupling of a phenyl metal derivative, metal is e.g. MgCl, MgBr, $B(OH)_2$, $B(OCMe_2CMe_2O)$, $BF_3K$, ZnCl, ZnBr, or ZnI, with a pyridine-2-carboxylic acid derivative or a 3-halogen or pseudohalogen substituted pyridine-2-carboxylic acid derivative (m=0) or pyrid-2-ylacetic acid derivative (m=1), carboxylic acid derivative preferably is carboxylic acid, carboxylic ester, or carbonitrile, provides the first intermediate. Depending on the coupling partners, different catalysts may be suitable, which are preferably derived from Pd, e.g. $Pd(PPh_3)_4$, $Pd[1,1'$-bis(diphenylphosphino)ferrocene]$Cl_2$, $Pd(PPh_3)_2Cl_2$, Pd on C, nanoparticles of Pd, Pd(II) salts such as $Pd(O_2CCH_3)_2$ or $PdCl_2$, optionally combined with a 2-(optionally substituted phenyl)phenyl-dicyclohexyl or di-tert-butyl-phosphine, triphenylphosphine, tritolylphosphine, trifurylphosphine, tri-tert-butyl-phosphine, tricyclohexylphosphine, a 1,3-diaryl imidazolidinium salt, or a 1,3-diaryl dihydroimidazolidinium salt, optionally in the presence of alkali metal salts, such as LiCl, NaOH, $NaO^tBu$, $KO^tBu$, $Na_2CO_3$, $K_2CO_3$, $Cs_2CO_3$, $NaO_2CCH_3$, or $K_3PO_4$, ammonium salts, e.g. $Bu_4NCl$, and/or silver salts, e.g. $AgO_3SCF_3$, preferably employed in toluene, tetrahydrofuran, 1,4-dioxane, N,N-dimethylformamide, N,N-dimethylacetamide, N-methylpyrrolidinone, or mixtures thereof, which are optionally combined with water, at −10 to 150° C. Subsequent intramolecular Friedel-Crafts acylation establishes the tricyclic pyridine scaffold by activating the carboxy functionality, e.g. carboxylic acid, anhydride, mixed anhydride, or ester, carbonyl chloride, or nitrile, with a Lewis acid, depending on the kind of carboxy group and the electronic nature of the benzene substructure, e.g. hydrobromic acid, hydrochloric acid, sulfuric acid, phosphoric acid, trifluoroacetic acid, methanesulfonic acid, toluenesulfonic acid, trifluoromethanesulfonic acid, $SnCl_4$, $FeCl_3$, $AlBr_3$, $AlCl_3$, $SbCl_5$, $BCl_3$, $BF_3$, $ZnCl_2$, montmorillonites, $POCl_3$, and $PCl_5$, preferably in an inert solvent, e.g. acetonitrile, dichloromethane, 1,2-dichloromethane, 1,4-dioxane, 1,2-dimethoxyethane, hydrocarbons, nitrobenzene, or chlorobenzene, at 0 to 180° C. Reduction of the keto group formed thereafter is preferably conducted with hydrogen in the presence of a transition metal catalyst, e.g. Pd/C, $Pd(OH)_2$, $PtO_2$, Pt/C, or Rh/C, in alcohol, e.g. methanol, glycol, or ethanol, water, acetic acid, ethyl acetate, N-methylpyrrolidinone, tetrahydrofuran, 1,4-dioxane, ether, or mixtures thereof, optionally in the presence of acid, e.g. hydrochloric acid, at 0 to 180° C., preferably 20 to 120° C., and hydrogen pressures of 1 to 100 bar, preferably 1 to 10 bar. Alternatively, reduction of the keto group may be accomplished with a hydride, e.g. triethylsilane, borane, sodium borohydride, or lithium aluminum hydride, optionally in the presence of a Lewis acid, e.g. $BF_3$, $AlCl_3$, $InCl_3$, $SnCl_4$, $FeCl_3$, $ZnCl_2$, acetic acid, trifluoroacetic acid, hydrochloric acid, methanesulfonic acid, or trifluoromethanesulfonic acid, at 0 to 140° C.

Scheme 3. Strategy 3 to build the tricyclic skeleton

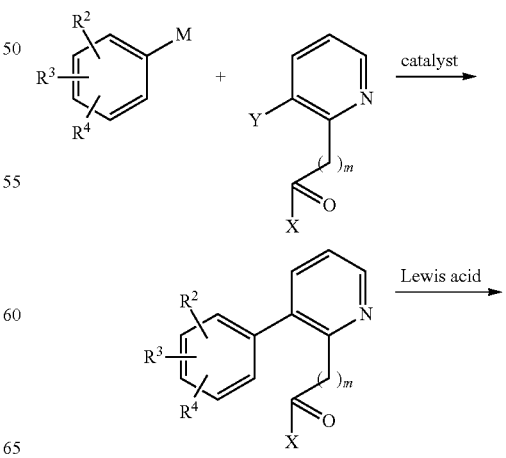

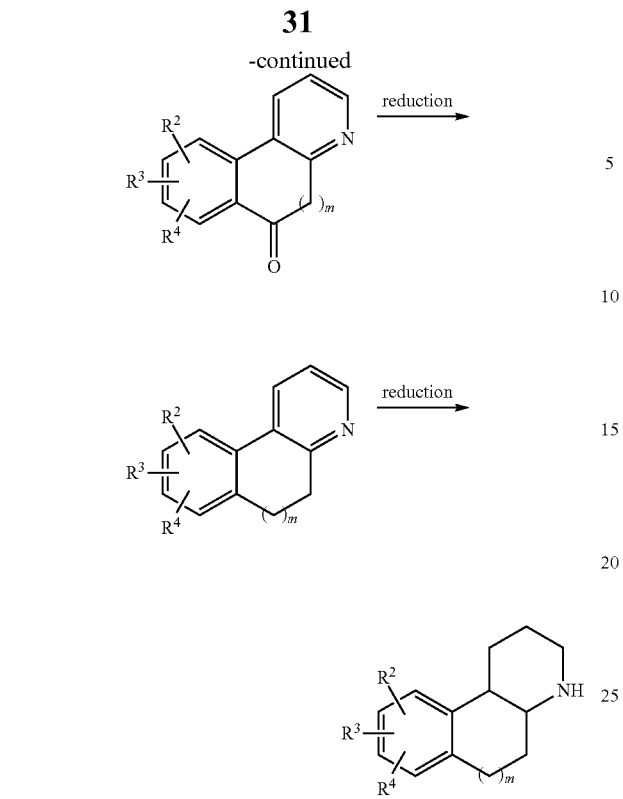

Y = e.g. Cl, Br, I, OSO$_2$CF$_3$
X = e.g. OH, OC$_{1-4}$-alkyl, or CN for COX
X preferably introduced after coupling: Cl, anhydride residue, mixed anhydride residue
M = e.g. MgCl/Br/I, B(OH)$_2$, BF$_3$K, ZnCl/Br/I, Scheme 4 describes a strategy suited for accessing the scaffold of compounds of the invention wherein m equals 0; R$^2$, R$^3$, and R$^4$ have the meanings as defined hereinbefore and hereinafter. The phenyl-pyridyl structure is assembled by a transition metal catalyzed coupling as described in Scheme 3. A nucleophilic phenyl group, bearing M, and an electrophilic pyridine group, bearing Y, are used for this purpose, though, the aromatic building blocks may be employed with opposite reactivity, i.e. phenyl bears Y and pyridine M, providing the same coupling product. The compound obtained bears two potential leaving groups, preferably fluorine, chlorine, bromine, arylsulfonate, nitro, or arylsulfonyl, one on each (hetero)aromatic ring adjacent to the phenyl-pyridyl bond. A dianionic methylene synthon, e.g. malonic acid, malonic diester, malodinitrile, cyanoacetic acid, or cyanoacetic ester, combined with a base, e.g. Cs$_2$CO$_3$, K$_2$CO$_3$, Na$_2$CO$_3$, KO$^t$Bu, NaOEt, NaOMe, NEt$_3$, $^i$Pr$_2$NEt, 1,8-diazabicyclo[5.4.0]-undec-7-ene, consecutively replaces both leaving groups by aromatic nucleophilic substitutions to establish the indenopyridine framework. N-Methylpyrrolidinone, N,N-dimethylacetamide, N,N-dimethylformamide, alcohol, e.g. ethanol, isopropanol, or tert-butanol, water, dimethyl sulfoxide, 1,4-dioxane, tetrahydrofuran, or mixtures thereof are among the preferred solvents for this transformation, which is preferably conducted at 0 to 180° C. The carboxylic electron-withdrawing groups are removed by hydrolysis with base, e.g. NaOH or KOH, or acid, e.g. HCl or H$_2$SO$_4$, in aqueous or alcoholic solution to form the carboxy group which decarboxylates spontaneously or by heating in the acidic or basic medium. This proceeding is particularly suited for compounds bearing one or more electron-withdrawing groups on the phenyl ring.

Scheme 4. Strategy 4 to build the tricyclic skeleton

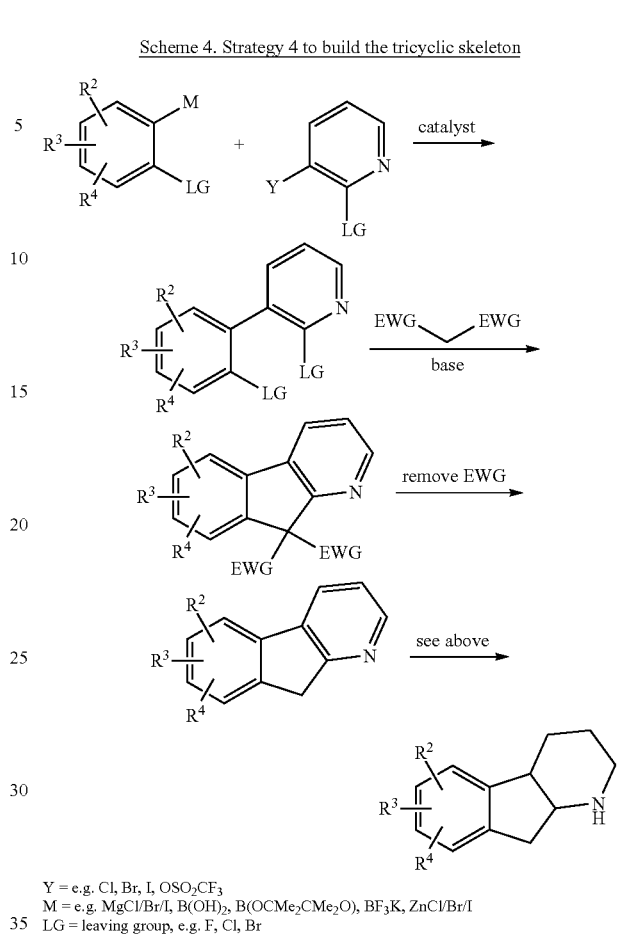

Y = e.g. Cl, Br, I, OSO$_2$CF$_3$
M = e.g. MgCl/Br/I, B(OH)$_2$, B(OCMe$_2$CMe$_2$O), BF$_3$K, ZnCl/Br/I
LG = leaving group, e.g. F, Cl, Br
EWG = electron-withdrawing group, e.g. CO$_2$H, CO$_2$C$_{1-4}$-alkyl, CN, NO$_2$, SO$_2$Ph, SO$_2$C$_{1-4}$-alkyl Scheme 5 outlines the assembly of the tricyclic scaffold of the invention starting from the corresponding pyrrolidine enamine of 2-indanones or 2-tetralones and acryl amide; R$^2$, R$^3$, R$^4$, and m have the meanings as defined hereinbefore and hereinafter. The desired tricyclic structure as a dihydropyridinone is obtained by heating the two reaction partners at 60 to 150° C. Reduction of the double bond with hydrogen in the presence of a transition metal, such as palladium on carbon, or with a hydride source, such as a trialkylsilane, e.g. triethylsilane, borohydride, e.g. NaBH$_4$, NaBH(O$_2$CCH$_3$)$_3$, or NaH$_3$BCN, or alanate, e.g. LiAlH$_4$, optionally in the presence of an additive, such as a Lewis acid, e.g. acetic acid, trifluoroacetic acid, AlCl$_3$, or BF$_3$*OEt$_2$, provides then the tricyclic piperidinone. Eventual amide reduction is preferably achieved with a hydride source, e.g. NaBH$_4$ combined with acetic acid in 1,4-dioxane, LiAlH$_4$ in tetrahydrofuran or ether, or sodium dihydrobis(2-methoxyethoxy)aluminate in ethylene glycol dimethyl ether, at 0 to 100° C.

Scheme 5. Strategy 5 to build the tricyclic skeleton

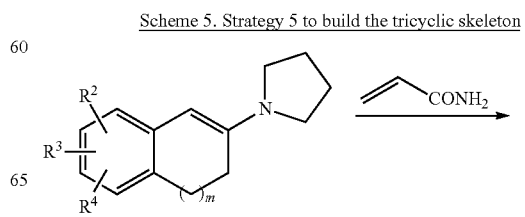

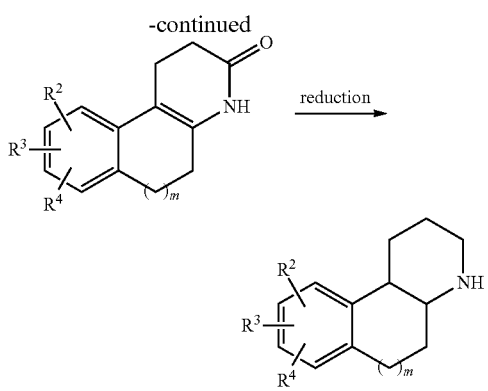

Another generally applicable approach to access the core structures of the compounds of the invention is based on an electrophilic aromatic substitution reaction (Scheme 6); $R^2$, $R^3$, $R^4$, and m have the meanings as defined hereinbefore and hereinafter. Thereby the aromatic part of the molecule reacts with a positively charged carbon atom of the piperidine ring to form the tricyclic framework. The reactive intermediate bearing the positively charged carbon atom in the azacycle may be generated by the addition of a Lewis acid to an olefinic bond or a carbonyl group or by the activation of an appropriately positioned leaving group, such as Cl, Br, I, OH, $O_3SCF_3$, $O_3SMe$, or $O_3S$-p-Tol. A huge number of Lewis acids have been described for this classical reaction that may also be employed here. The following enumeration is supposed to give a few more widely used of them: hydrobromic acid, hydroiodic acid, hydrochloric acid, sulfuric acid, phosphoric acid, $P_4O_{10}$, trifluoroacetic acid, methanesulfonic acid, toluenesulfonic acid, trifluormethanesulfonic acid, $Sc(O_3SCF_3)_3$, $InCl_3$, $InBr_3$, $SnCl_4$, $FeCl_3$, $AlBr_3$, $AlCl_3$, $SbCl_5$, $BCl_3$, $BF_3$, $ZnCl_2$, montmorillonites, $POCl_3$, and $PCl_5$. Depending on the inclination of the leaving group to be substituted and the electronic nature of the aromatic ring, a more or less powerful acid catalyst has to be used. Besides the acid catalysts mentioned, silver salts, e.g. $AgO_3SCF_3$, may be useful in the reactions using halides as leaving group. Preferred solvents are hydrocarbons such as hexane or cyclohexane, chlorinated hydrocarbons, such as dichloromethane or 1,2-dichloroethane, perfluorinated hydrocarbons, nitrobenzene, acetonitrile, chlorinated benzenes, heteroaromatics, such as quinoline, 1,2-dimethoxyethane, 1,4-dioxane, ether, ionic liquids, water, acetic acid, or mixtures thereof, though, not all of these solvents are usable with all above listed Lewis acids. The reactions are carried out between −10 and 220° C., preferably between 20° C. and 180° C. The reactions may also be conducted under microwave irradiation.

Scheme 6. Strategy 6 to build the tricyclic skeleton

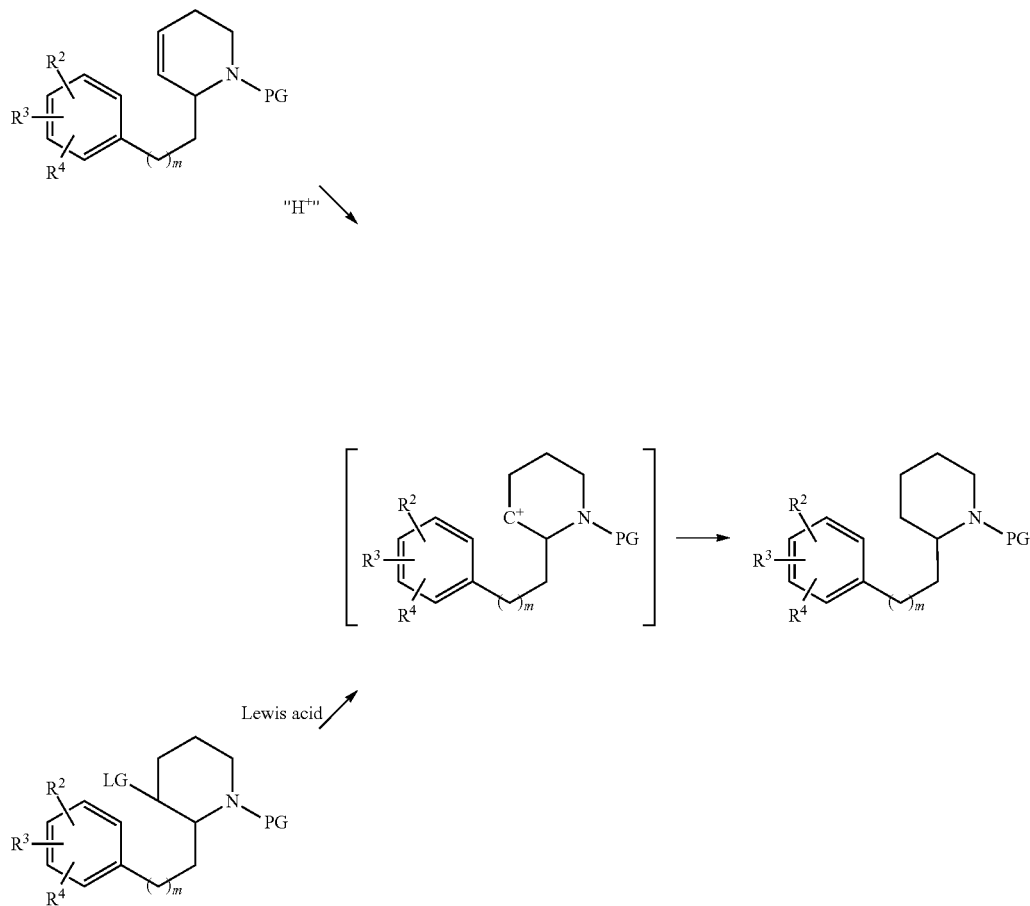

PG = protective group such as $^tBuOCO$, BnOCO, $F_3CO$, Me, Bn, Ph
LG = leaving group such as Cl, Br, I, OH, $O_3SCF_3$, $O_3STol$, $O_3SCH_3$, or =O The synthetic routes presented may rely on the use of protecting groups. Suitable protecting groups for the respective functionalities and their removal are described hereinafter and may analogously be employed (see also: *Protecting Groups, Philip J. Kocienski*, 3$^{rd}$ edition, Georg Thieme Verlag, Stuttgart, 2004 and references quoted therein).

In the following a few feasible derivatizations of compounds of general formula I or precursors thereof, obtained as described above, bearing certain functional groups to assemble other compounds of general formula I or precursors thereof are vicariously summarized. This compilation is by no means meant to be complete but is only supposed to give some possibilities by way of example.

If in the process of manufacture according to the invention a compound of general formula I or a precursor thereof is obtained which contains an amino, alkylamino, or imino group, this may be converted by acylation or sulfonylation into a corresponding acyl or sulfonyl compound of general formula I or a precursor thereof.

If a compound of general formula I or a precursor thereof is obtained which contains a hydroxy group, this may be converted by acylation or sulfonylation into a corresponding acyl or sulfonyl compound of general formula I or a precursor thereof.

If a compound of general formula I or a precursor thereof is obtained which contains a hydroxy group, this may be converted by alkylation into a corresponding ether of general formula I or a precursor thereof.

If a compound of general formula I or a precursor thereof is obtained which contains an amino, alkylamino, or imino group, this may be converted by alkylation or reductive alkylation into a corresponding alkyl compound of general formula I or a precursor thereof.

If a compound of general formula I or a precursor thereof is obtained which contains a nitro group, this may be converted by reduction into a corresponding amino compound.

If a compound of general formula I or a precursor thereof is obtained which contains an imino group, this may be converted by nitrosation and subsequent reduction into a corresponding N-amino-imino compound.

If a compound of general formula I or a precursor thereof is obtained which contains a $C_{1-4}$-alkyloxycarbonyl group, this may be converted by cleavage of the ester into the corresponding carboxy compound.

If a compound of general formula I or a precursor thereof is obtained which contains a carboxy group, this may be converted into a corresponding ester of general formula I or a precursor thereof.

If a compound of general formula I or a precursor thereof is obtained which contains a carboxy or ester group, this may be converted by reaction with an amine into a corresponding amide of general formula I or a precursor thereof.

If a compound of general formula I or a precursor thereof is obtained which contains an aromatic substructure, this may be derivatized with a chlorine, bromine, or iodine atom or a nitro, sulfonic acid, chlorosulfonyl, or acyl group by an electrophilic substitution reaction to a corresponding compound of general formula I or a precursor thereof.

If a compound of general formula I or a precursor thereof is obtained which contains an amino group that is attached to an aromatic or a heteroaromatic group, this may be transformed into a corresponding cyano, fluoro, chloro, bromo, iodo, hydroxy, mercapto, or azido derivatized compound of general formula I or a precursor thereof by diazotization and subsequent replacement of the diazo group with cyanide, fluoride, chloride, bromide, iodide, hydroxide, alkyl or hydrogen sulfide, or azide, respectively.

If a compound of general formula I or a precursor thereof is obtained which contains an amino group that is attached to an aromatic or a heteroaromatic group, this may be converted into a corresponding aryl derivatized aromatic compound of general formula I or a precursor thereof by diazotization of the amino group and subsequent replacement of the resulting diazo group with an appropriate aryl nucleophile mediated by a suited transition metal species.

If a compound of general formula I or a precursor thereof is obtained which contains a chloro, bromo, or iodo atom, or a trifluoromethylsulfonyloxy, mesyloxy, or tosyloxy group which is attached to an aromatic or a heteroaromatic group, this may be converted into a corresponding aryl, alkenyl, alkynyl, or alkyl derivatized compound of general formula I or a precursor thereof by replacement of the respective group by aryl, alkenyl, alkynyl, or alkyl using a transition metal species mediated process.

If a compound of general formula I or a precursor thereof is obtained which contains a chloro, bromo, or iodo atom, or a trifluoromethylsulfonyloxy, mesyloxy, or tosyloxy group which is attached to an aromatic or a heteroaromatic group, this may be replaced with cyano to give a corresponding aromatic compound of general formula I or a precursor thereof.

If a compound of general formula I or a precursor thereof is obtained which contains a chloro, bromo, or iodo atom, or a trifluoromethylsulfonyloxy, mesyloxy, or tosyloxy group which is attached to an aromatic or a heteroaromatic group, this may be replaced with hydrogen to give a corresponding aromatic compound of general formula I or a precursor thereof.

If a compound of general formula I or a precursor thereof is obtained which contains two heteroatoms at adjacent carbon atoms that are amino and hydroxy, amino, or mercapto, these heteroatoms may be linked via a carboxy carbon atom to form a cyclic amidine, imino ester, or imino thioester substructure that may be part of an aromatic ring.

If a compound of general formula I or a precursor thereof is obtained which contains a cyano group, this may be converted by reduction into an aminoalkyl derivatized compound of general formula I or a precursor thereof.

If a compound of general formula I or a precursor thereof is obtained which contains a cyano group, this may be converted into an N-hydroxycarbamimidoyl group by the treatment with hydroxylamine.

If a compound of general formula I is obtained which contains an N-hydroxycarbamimidoyl group, this may be converted to an oxadiazole derivatized compound of general formula I or a precursor thereof by the treatment with a carboxylic or related group.

If a compound of general formula I or a precursor thereof is obtained which contains an aminocarbonyl group, this may be converted by dehydration into a corresponding cyano compound of general formula or a precursor thereof I.

If a compound of general formula I or a precursor thereof is obtained which contains a keto or aldehydic group, this may be converted by reduction into a corresponding hydroxy compound of general formula I or a precursor thereof.

If a compound of general formula I or a precursor thereof is obtained which contains a carboxylic acid or aminocarbonyl group, this may be converted by a rearrangement reaction into a corresponding amino derivatized compound of general formula I or a precursor thereof.

If a compound of general formula I or a precursor thereof is obtained which contains a keto or aldehyde group, this may be converted into an alkenyl derivatized compound of general formula I or a precursor thereof.

If a compound of general formula I or a precursor thereof is obtained which contains an olefinic C=C double or a C≡C triple bond, this may be reduced to give the corresponding saturated compound of general formula I or a precursor thereof.

If a compound of general formula I or a precursor thereof is obtained which contains a keto or aldehydic group, this may be converted into a corresponding tertiary or secondary hydroxy compound of general formula I or a precursor thereof.

If a compound of general formula I or a precursor thereof is obtained which contains a carboxylic ester group, this may be converted into a tertiary alcohol by the addition of two equivalents of an organo metal compound.

If a compound of general formula I or a precursor thereof is obtained which contains a primary or secondary hydroxy group, this may be converted by oxidation into a corresponding carbonyl compound of general formula I or a precursor thereof.

If a compound of general formula I or a precursor thereof is obtained which contains an olefinic bond, this may be converted into a corresponding hydroxy compound of general formula I or a precursor thereof by hydroboration followed by oxidation.

If a compound of general formula I or a precursor thereof is obtained which contains an olefinic bond, this may be converted by dihydroxylation into a corresponding 1,2-dihydroxy compound of general formula I or a precursor thereof.

If a compound of general formula I or a precursor thereof is obtained which contains an olefinic bond, this may be converted by ozonolysis into a corresponding carbonyl compound compound of general formula I or a precursor thereof.

If a compound of general formula I or a precursor thereof is obtained which contains an olefinic bond, this may be converted into a corresponding hydroxy compound of general formula I or a precursor thereof by epoxidation followed by oxirane opening with a hydride source.

If a compound of general formula I or a precursor thereof is obtained which contains an olefinic bond, this may be converted by Wacker oxidation into a corresponding carbonyl compound of general formula I or a precursor thereof.

If a compound of general formula I or a precursor thereof is obtained which contains an olefinic bond, this may be converted by hydrocyanation into a corresponding cyano compound of general formula I or a precursor thereof.

If a compound of general formula I or a precursor thereof is obtained which contains a cyano group, this may be converted by water addition into a corresponding aminocarbonyl compound of general formula I or a precursor thereof.

The subsequent esterification is optionally carried out in a solvent such as methylene chloride, N,N-dimethylformamide, benzene, toluene, chlorobenzene, tetrahydrofuran, 1,4-dioxane, or mixtures thereof or particularly advantageously in the corresponding alcohol optionally in the presence of an acid, e.g. hydrochloric acid, or a dehydrating agent, e.g. isobutyl chloroformate, thionyl chloride, trimethylchlorosilane, sulfuric acid, methanesulfonic acid, p-toluenesulfonic acid, phosphorus trichloride, phosphorus pentoxide, N,N'-carbonyldiimidazole, N,N'-dicyclohexylcarbodiimide, triphenylphosphine combined with carbon tetrachloride, or combinations thereof optionally in the presence of 4-dimethylaminopyridine and/or 1-hydroxybenzotriazole. The reactions are conducted between 0 and 150° C., preferably between 0 and 80° C.

The ester formation may also be carried out by reacting a compound which contains a carboxy group with a corresponding alkyl halide in the presence of a base.

The subsequent acylation or sulfonylation is optionally carried out in a solvent such as methylene chloride, N,N-dimethylformamide, benzene, toluene, chlorobenzene, tetrahydrofuran, 1,4-dioxane, or mixtures thereof with a corresponding acyl or sulfonyl electrophile, optionally in the presence of a tertiary organic base, an inorganic base, or a dehydrating agent. Routinely used agents are e.g. isobutyl chloroformate, thionyl chloride, trimethylchlorosilane, sulfuric acid, methanesulfonic acid, p-toluenesulfonic acid, phosphorus trichloride, phosphorus pentoxide, N,N'-dicyclohexylcarbodiimide, N,N'-carbonyldiimidazole, triphenylphosphine combined with carbon tetrachloride, or combinations thereof that may be employed in the presence of 4-dimethylaminopyridine and/or 1-hydroxybenzotriazole at temperatures between 0 and 150° C., preferably between 0 and 80° C.

The subsequent alkylation is optionally carried out in methylene chloride, N,N-dimethylformamide, benzene, toluene, chlorobenzene, tetrahydrofuran, 1,4-dioxane, or mixtures thereof with an alkylating agent such as a corresponding halide or sulfonic acid ester, e.g. methyl iodide, ethyl bromide, dimethyl sulfate, or benzyl chloride, optionally in the presence of a tertiary organic base or an inorganic base at temperatures between 0 and 150° C., preferably between 0 and 100° C.

The subsequent reductive alkylation is carried out with a corresponding carbonyl compound such as formaldehyde, acetaldehyde, propionaldehyde, acetone, or butyraldehyde in the presence of a complex metal hydride, such as sodium borohydride, lithium borohydride, sodium triacetoxyborohydride, or sodium cyanoborohydride, conveniently at a pH of 6-7 and ambient temperature, or using hydrogen in the presence of a transition metal catalyst, e.g. palladium on charcoal, at hydrogen pressures of 1 to 5 bar. Methylation may also be carried out in the presence of formic acid as reducing agent at elevated temperature, e.g. between 60 and 120° C.

The subsequent reduction of a nitro group is carried out, for example, with hydrogen and a catalyst such as palladium on carbon, platinum dioxide, or Raney nickel, or using other reducing agents such as tin(II) chloride, iron, or zinc optionally in the presence of an acid such as acetic acid.

The subsequent nitrosation of an imino group followed by reduction to obtain an N-amino-imino compound is carried out, for example, with an alkyl nitrite such as isoamyl nitrite to form the N-nitroso-imino compound that is then reduced to the N-amino-imino compound using, for example, zinc in the presence of an acid such as acetic acid.

The subsequent cleaving of a $C_{1-4}$-alkyloxycarbonyl group to obtain the carboxy group is carried out, for example, by hydrolysis with an acid such as hydrochloric acid or sulfuric acid or an alkali metal hydroxide such as lithium hydroxide, sodium hydroxide, or potassium hydroxide. The tert-butyl group is preferably removed by treatment with a strong acid, e.g. trifluoroacetic acid or hydrochloric acid, in an inert solvent such as dichloromethane, 1,4-dioxane, or ethyl acetate.

The subsequent amide formation is carried out by reacting a corresponding reactive carboxylic acid derivative with a corresponding amine in a solvent such as methylene chloride, N,N-dimethylformamide, benzene, toluene, chlorobenzene, tetrahydrofuran, 1,4-dioxane, or mixtures thereof, or without an solvent in an excess of the amine, optionally in the presence of a tertiary organic base, an inorganic base, 4-dimethylaminopyridine, and/or 1-hydroxy-benzotriazole, at temperatures between 0 and 150° C., preferably between 0 and 80° C. Using the carboxylic acid may lead to the desired amide by in situ activation of the carboxy function with e.g. isobutyl chloroformate, thionyl chloride, oxalyl chloride, trimethylchlorosilane, phosphorus trichloride, phosphorus pentoxide, N,N'-carbonyldiimidazole, triphenylphosphine combined with carbon tetrachloride, 2-(1H-benzotriazol-1-yl)-1,1,3,3-tetramethyluronium tetrafluoroborate, N,N'-dicyclohexyl-carbodiimide, or combinations thereof.

The subsequent introduction of a chlorine, bromine, or iodine atom into an aromatic substructure may be carried out by reacting the aromatic compound with an appropriate electrophile of the respective halogen atom. Suited chlorine and bromine electrophiles may be e.g. N-halosuccinimide, HOCl, HOBr, tert-BuOCl, tert-BuOBr, chlorine, bromine, dibromoisocyanuric acid, pyridinium dichlorobromate, pyridinium tribromide, or sulfuryl chloride that may be used alone or in combination with an acid, e.g. hydrochloric acid, hydrobromic acid, tetrafluoroboric acid, triflic acid, sulfuric acid, or acetic acid, or a Lewis acid, e.g. iron(III) halide, boron trifluoride hydrate, boron trifluoride etherate, or aluminum halide. Further useful combinations may be LiBr and ceric ammonium nitrate, KCl or KBr with Oxone®, or KBr and sodium perborate. Suited iodine electrophiles may be generated from iodine and an oxidizing agent such as nitric acid, sulfur trioxide, manganese dioxide, $HIO_3$, hydrogen peroxide, sodium periodate, peroxydisulfates, and Oxone®. Further suited iodine electrophiles may be e.g. iodine chloride, dichloroiodates, and N-iodosuccinimide. These iodine electrophiles are optionally used without an additive or in the presence of an acid such as acetic acid, trifluoroacetic acid, or sulfuric acid or a Lewis acid such as boron trifluoride hydrate or copper salts. If a nitro group is to be introduced appropriate nitro electrophile sources may be, for instance, nitric acid, acetyl nitrate, ceric ammonium nitrate, sodium nitrate, $N_2O_5$, alkyl nitrate, and nitronium tetrafluoroborate. Some of these reagents may be used without an additive, though, several of them are better used in combination with an acid, e.g. sulfuric acid or triflic acid, acetic anhydride, trifluoroacetic anhydride, Lewis acid, e.g. ytterbium triflate or iron acetate, $P_2O_5$, or a base. The $SO_3H$ group may be introduced by reacting the aromatic compound with, for example, concentrated sulfuric acid, $SO_3$, $ClSO_3H$, or $ClSO_2NMe_2$ combined with indium triflate. Reacting the aromatic compound with $ClSO_3H$ gives the corresponding chlorosulfonylated derivative that may be hydrolyzed to the sulfonic acid. Acylating the aromatic part is conducted using an acyl electrophile that may be generated from the respective acyl halide, e.g. chloride, or acyl anhydride and a Lewis acid such as aluminum halide, diethylaluminum halide, indium halide, iron(III) halide, tin(IV) halide, boron trifluoride, titanium(IV) halide, or a Brønsted acid, e.g. sulfuric acid or triflic acid. The formyl group is preferably introduced using the so-called Vilsmeier or Vilsmeier-Haack conditions: dialkylformamide combined with phosgene, thionyl chloride, $POCl_3$, or oxalyl chloride. Preferred solvents for the electrophilic substitutions described may differ depending on the electrophile employed; in the following some more generally applicable are mentioned: methylene chloride, 1,2-dichloroethane, chlorobenzene, dichlorobenzene, ether, 1,4-dioxane, fluorinated hydrocarbons, hexanes, quinoline, and acetonitrile. Temperatures preferably applied range from 0 to 180° C.

The subsequent replacement of an amino group that is attached to an aromatic or a heteroaromatic group is initiated by diazotization of the amino group using a nitrous acid or nitrosonium source or equivalent such as a nitrite salt combined with an acid, e.g. sodium nitrite and hydrochloric acid, nitrosonium tetrafluoroborate, or an alkylnitrite, e.g. tert-butyl nitrite or iso-amyl nitrite. The diazotization is optionally carried out in methylene chloride, 1,2-dichloroethane, N,N-dimethylformamide, N-methylpyrrolidinone, benzene, toluene, chlorobenzene, tetrahydrofuran, water, ethyl acetate, alcohol, ether, 1,2-dimethoxyethane, 1,4-dioxane, or mixtures thereof at temperatures between −10 and 100° C. (diazotization of amino groups is detailed in, for example, *Angew. Chem. Int. Ed.* 1976, 15, 251). The subsequent displacement of the diazo group with a cyano group, chlorine, or bromine atom using copper cyanide, chloride, or bromide, respectively, is known as the Sandmeyer reaction (see e.g. March's Advanced Organic Chemistry, Michael B. Smith and Jerry March, John Wiley & Sons Inc., 6. Ed., New Jersey, 2007 and references quoted therein); the reaction is optionally conducted between −10 and 120° C. in one of the solvents or mixtures mentioned above. The replacement of the diazo group with a fluorine atom may be achieved with a tetrafluoroborate salt or tetrafluoroboric acid and heating to 20 to 160° C.; the reaction is known as the Schiemann reaction. Iodine may be introduced by treatment of the diazo compound with an iodide salt, e.g. sodium iodide, preferably using water or an aqueous solvent mixture at temperatures between 0 and 120° C. The diazo group is replaced with hydroxy using water or an aqueous solvent mixture at temperatures between 0 and 180° C. The reaction usually works without further additives but the addition of copper oxide or strong acid may be advantageous. Mercapto or alkylmercapto may be introduced via their corresponding disulfide salts or dialkyldisulfides at temperatures between 0 and 120° C.; depending on the sulfur species used an inert solvent or aqueous solvent system may be preferred (see e.g. *Synth. Commun.* 2001, 31, 1857 and references quoted therein).

The subsequent replacement of an amino group that is attached to an aromatic or a heteroaromatic group by an aryl group may be accomplished via the corresponding diazo compound obtainable as described above. The reaction with an aryl nucleophile, preferably an aryl boronic acid, boronic ester, trifluoroborate, zinc halide, or stannane, is conducted in the presence of a transition metal species derived from palladium, nickel, rhodium, copper, or iron, preferably palladium. The active catalyst may be a complex of the transition metal with ligands such as e.g. phosphines, phosphites, imdiazole carbenes, imidazolidine carbenes, dibenzylideneacetone, allyl, or nitriles, an elemental form of the transition metal such as palladium on carbon or nanoparticles, or salts such as chloride, bromide, acetate, or trifluoroacetate. The diazo compound is preferably employed as its tetrafluoroborate salt optionally in water, N-methylpyrrolidinone, N,N-dimethylformamide, methylene chloride, benzene, toluene, tetrahydrofuran, ethyl acetate, alcohol, ether, 1,2-dimethoxyethane, 1,4-dioxane, or mixtures thereof at temperatures between 10 and 180° C., preferably between 20 and 140° C.

The subsequent replacement of a chloro, bromo, or iodo atom or a trifluoromethylsulfonyloxy, mesyloxy, or tosyloxy group that is attached to an aromatic or a heteroaromatic group with an aryl, alkenyl, alkynyl, or alkyl residue is preferably mediated by a transition metal species derived from palladium, nickel, copper, or iron. The active catalyst may be a complex of the transition metal with ligands such as phosphines, e.g. tri-tert-butylphosphine, tricyclohexylphosphine, 2-(substituted phenyl)phenyl-dicyclohexylphosphines, 2-(substituted phenyl)phenyl-di-tert-butylphosphines, 1,1'-bis(diphenylphosphino)ferrocene, triphenylphosphine, tritolylphosphine, or trifuryl-phosphine, phosphites, 1,3-disubstituted imdiazole carbenes, 1,3-disubstituted imidazolidine carbenes, dibenzylideneacetone, allyl, or nitriles, an elemental form of the transition metal such as palladium on carbon or nanoparticles of iron or palladium, or a salt such as fluoride, chloride, bromide, acetate, triflate, or trifluoroacetate. The replacement reaction is preferably conducted with a trifluoroborate, boronic acid, or boronic ester (Suzuki or Suzuki-type reaction), zinc halide (Negishi or Negishi-type reaction), stannane (Stille or Stille-type reaction), silane (Hiyama or Hiyama-type reaction), magnesium halide (Kumada or Kumada-type reaction) of the aryl, alkenyl, or alkyl residue to be introduced. The terminal alkyne is preferably used as such or as its zinc acetylide derivative. Depending on the nature of the electrophilic and nucleophilic reaction partners additives such as halide salts, e.g. lithium chloride, potassium fluoride, tetrabutylammonium fluoride, hydroxide sources such as potassium hydroxide or potassium carbonate, silver salts such as silver oxide or triflate, and/or copper salts such as copper chloride or copper thiophene-2-carboxylate may be advantageous or even essential. Copper iodide is a preferred additive in the coupling with terminal alkynes (Sonogashira reaction). The coupling reactions are preferably conducted in benzene, toluene, ether, tetrahydrofuran, 1,2-dimethoxyethane, 1,4-dioxane, N,N-dimethylformamide, N,N-dimethylacetamide, N-methylpyrrolidinone, alcohol, water, or mixtures thereof, though, depending on the nucleophile some of them are less or not suited at all. Preferred temperatures are in the range from −10 to 180° C.

The subsequent replacement of a chlorine, bromine, or iodine atom or a mesyloxy, trifluoromethylsulfonyloxy, or tosyloxy group that is attached to an aromatic or a heteroaromatic group with a cyano group is preferably achieved via a transition metal mediated process. Copper, nickel, and palladium are the most frequently employed metals for this transformation and used as elements, salts, or complexes in combination with a cyanide source. Copper iodide, copper sulfate, copper cyanide, nickel chloride, nickel bromide, nickel cyanide, bis(triphenylphosphine)nickel dichloride, palladium on carbon, tetrakis(triphenylphosphine)palladium, tris(dibenzylideneacetone)dipalladium, palladium acetate, palladium trifluoroacetate, palladium chloride, palladium cyanide, optionally combined with a ligand, such as tricyclohexylphosphine, tri-tert-butyl-phosphine, triphenylphosphine, 1,1'-bis(diphenylphosphino)ferrocene, diadamantyl-n-butylphosphine, or Xantphos, are among the catalysts that are routinely employed. Common cyanide sources are sodium cyanide, potassium cyanide, zinc cyanide, copper cyanide, nickel cyanide, potassium hexacyanoferrate, and acetone cyanohydrin. The reactions are preferably carried out in N,N-dimethylformamide, N,N-dimethylacetamide, N-methylpyrrolidinone, dimethylsulfoxide, pyridine, acetonitrile, quinoline, toluene, tetrahydrofuran, 1,2-dimethoxyethane, 1,4-dioxane, or mixtures thereof, at 20 to 280° C., preferably at 60 to 200° C. Additives, such as zinc, sodium carbonate, potassium iodide, water, and pyridine, and or the use of microwave irradiation may be advantageous to some of the reaction conditions.

The subsequent replacement of a chlorine, bromine, or iodine atom or a trifluoromethylsulfonyloxy, mesyloxy, or tosyloxy group that is attached to an aromatic or a heteroaromatic group with a hydrogen atom is preferably mediated by a transition metal species derived from palladium, nickel, platinum, or rhodium. The active catalyst may be a complex of the transition metal with ligands, an elemental form, or a salt of the transition metal as mentioned above. Raney nickel or palladium on carbon are among the preferred catalyst species. Suited hydrogen sources may be hydrogen, preferably at pressures of 1 to 10 bar, silanes, e.g. trialkoxysilane or polymethylhydrosiloxane, boranes, hydrides, e.g. alkali metal borohydride, formic acid, or formates, e.g. ammonium formate. The reactions are preferably carried out in N,N-dimethylformamide, N,N-dimethylacetamide, N-methylpyrrolidinone, benzene, toluene, tetrahydrofuran, water, ethyl acetate, alcohol, ether, 1,2-dimethoxyethane, 1,4-dioxane, or mixtures thereof at −10 to 180° C., more preferably at 20 to 140° C.

The subsequent cyclization starting from a compound bearing two heteroatoms at adjacent carbon atoms is optionally conducted with a carboxy equivalent such as nitrile, carboxylic chloride or fluoride, carboxylic acid, ketene, carboxylic ester, or carboxylic thioester. The overall transformation comprises two reaction steps: attachment of the carboxy equivalent to one of the two heteroatoms followed by cyclization with the other heteroatom. The first step is an amide formation with the amino functionality that may be carried out as described hereinbefore. The ensuing reaction step, cyclization with the second heteroatom, may be accomplished by heating in the presence of an acid, e.g. acetic acid, trifluoroacetic acid, sulfuric acid, or hydrochloric acid, or a base, e.g. sodium hydroxide, sodium ethoxide, or sodium tert-butoxide. The use of dehydrating reagents such as anhydrides, e.g. acetic anhydride, orthoesters, e.g. trimethyl orthoformate, thionyl chloride, phosgene, diphosgene, triphosgene, phosphorous oxychloride, phosphorous pentachloride, dialkylcarbodiimides, combinations with phosphines, e.g. triphenylphosphine or trialkylphosphine with dialkyl azodicarboxylates, bromine, iodine, or 1,2-dihaloethanes, e.g. 1,2-dibromotetrafluoroethane, may be advantageous. The reactions are preferably carried out in inert solvents or mixtures such as methylene chloride, 1,2-dichloroethane, benzene, toluene, tetrahydrofuran, ether, or combinations thereof, though, cyclization in the presence of an acid or a base may also be conducted in water or an alcohol, e.g. methanol, ethanol, iso-propanol, or tert-butanol, or combinations with these solvents. The reactions are carried out at temperatures between 0 and 200° C., preferably between 20 and 140° C.

The subsequent reduction of a cyano group to obtain an aminomethyl group is preferably conducted with hydrogen in the presence of a transition metal species or with a hydride. Suited transition metals may be derived from palladium, nickel, platinum, rhodium, or ruthenium such as palladium on charcoal, palladium hydroxide, platinum oxide, or Raney nickel that may be used in solvents such as ethyl acetate, alcohols, e.g. methanol or ethanol, dichloromethane, tetrahydrofuran, ether, benzene, toluene, N,N-dimethylformamide, or N-methylpyrrolidinone at hydrogen pressures between 1 and 10 bar and at temperatures between 0 and 160° C. Additives such as acids, e.g. hydrochloric acid, methanesulfonic acid, sulfuric acid, or acetic acid, may be beneficial for the reduction with transition metal catalysts. Among the preferred hydride sources are e.g. borohydrides, e.g. sodium borohydride, potassium tri-sec-butylborohydride, borane, or lithium triethylborohydride, and alanates, e.g. lithium aluminum hydride or diisobutylaluminum hydride. Some of these reagents are best used in combination with nickel chloride or cobalt chloride as sodium borohydride. These reagents may be used in e.g. tetrahydrofuran, ether, 1,4-dioxane, 1,2-dimethoxyethane, dichloromethane, 1,2-dichloroethane, benzene, or toluene; some are also compatible with alcoholic or aqueous solutions. Preferred reaction temperatures range from −80 to 160° C., more preferred from −40 to 80° C.

The subsequent formation of a N-hydroxycarbamimidoyl group from a cyano group may be carried out by the treatment of the cyano compound with hydroxylamine. The reaction is preferably conducted in aqueous or alcoholic solvents at temperatures between 0 and 140° C.

The subsequent formation of an oxadiazole from an N-hydroxycarbamimidoyl is conducted with a carboxy equivalent such as nitrile, carboxylic chloride or fluoride, carboxylic acid, ketene, carboxylic ester, or carboxylic thioester. The transformation is related to the formation of a ring starting from two heteroatoms at adjacent carbon atoms described above and may be carried out analogously.

The subsequent formation of a cyano group from an aminocarbonyl group is preferably conducted by using a dehydrating reagent such as anhydride, e.g. acetic anhydride, trifluoroacetic anhydride, or triflic anhydride, phosgene, thionyl chloride, oxalyl chloride, $POCl_3$, $PCl_5$, $P_4O_{10}$, triphenylphosphite, or triphenyl- or trialkylphosphine combined with tetrachloromethane, 1,2-dibromotetrafluoroethane, or bromine. The reactions are preferably carried out in dichloromethane, 1,2-dichloroethane, hexanes, ether, 1,4-dioxane, benzene, toluene, acetonitrile, mixtures thereof, or without a solvent at temperatures between 0 and 140° C. Additives such as amines, e.g. pyridine or triethylamine, or N,N-dimethylformamide may be beneficial.

The subsequent reduction of a keto or an aldehydic group to obtain a secondary or primary alcohol may be carried out with a complex metal hydride such as sodium borohydride, lithium borohydride, lithium triethylborohydride, diisobutylaluminum hydride, or lithium aluminum hydride. The reductions may be conducted in e.g. dichloromethane, 1,2-dichloroethane, hexanes, ether, 1,4-dioxane, tetrahydrofuran, N,N-dimethylformamide, N-methylpyrrolidone, benzene, toluene, alcohols, e.g. methanol, water, or mixtures thereof, though, not all reducing agents are compatible with all of these solvents. Preferred temperatures range from −80 to 140° C. depending on the reducing power of the reagent. Alternatively, hydrogen in the presence of a transition metal catalyst may be used for the reduction.

The subsequent conversion of a carboxy group into an amino group by rearrangement may be accomplished by heating an acyl azide resulting in the formation of an isocyanate (Curtius rearrangement). The isocyanate may be hydrolyzed to produce the free amine or converted into a urea or carbamate derivative by treatment with an amine or an alcohol, respectively. The acyl azide may be obtained by treating an appropriate acyl electrophile, e.g. acyl chloride, carboxylic anhydride, or carboxylic ester, with an azide source, such as e.g. sodium azide or trimethylsilyl azide, in a solvent such as 1,4-dioxane, 1,2-dimethoxyethane, acetonitrile, tetrahydrofuran, dichloromethane, 1,2-dichloroethane, N-methylpyrrolidinone, N,N-dimethylformamide, toluene, benzene, hexanes, or mixtures thereof; water or alcohols may be usable in certain cases as well. The reactions are routinely carried out between −10 and 120° C. Alternatively, the acyl electrophile may be generated in situ from the acid and then converted into the acyl azide: diphenylphosphoryl azide in the presence of a base, e.g. triethylamine or ethyldiisopropylamine, in a solvent such as acetonitrile, benzene, toluene, or an alcohol at elevated temperature has proven to be an effective reagent for this direct conversion. The direct conversion may also be achieved with hydrazoic acid and an acid catalyst such as sulfuric acid in e.g. chloroform at elevated temperatures (Schmidt reaction). Another method to accomplish this overall transformation is the Lossen rearrangement: starting from an acyl electrophile such as acyl chloride the corresponding suited hydroxamic acid derivative is formed that in turn rearranges to give the isocyanate and then the amine by heating and/or treatment with a base, e.g. sodium hydroxide (see e.g. *J. Org. Chem.* 1997, 62, 3858 and *Synthesis* 1990, 1143 and references quoted therein).

An unsubstituted carboxylic amide may be converted into an amine by the so-called Hoffmann rearrangement. Among the suited reagents for this transformation are NaOBr, bromine combined with sodium methoxide, N-bromosuccinimide and sodium methoxide, $PhI(O_2CCF_3)_2$, and PhI(OH)OTs (Ts is 4-tolylsulfonyl).

The subsequent conversion of an aldehydic or a keto functionality into an olefin may be accomplished by, for example, the so-called Wittig reaction and modifications thereof, Peterson olefination, and Julia reaction and modifications thereof. These reactions have large precedence in organic syntheses and are detailed in e.g. March's Advanced Organic Chemistry, Michael B. Smith and Jerry March, John Wiley & Sons Inc., 6. Ed., New Jersey, 2007 and references quoted therein.

The subsequent reduction of a C=C double or C≡C triple bond is preferably conducted with hydrogen in the presence of a transition metal species derived from palladium, nickel, platinum, ruthenium, or rhodium, preferably Raney nickel, palladium on charcoal, platinum oxide, and $RhCl(PPh)_3$. The reactions are preferably carried out in methylene chloride, N,N-dimethylformamide, N,N-dimethylacetamide, N-methylpyrrolidinone, benzene, toluene, tetrahydrofuran, water, ethyl acetate, alcohol, ether, 1,2-dimethoxyethane, 1,4-dioxane, or mixtures thereof, at 0 to 180° C., more preferably at 20 to 140° C., and hydrogen pressures of 1 to 10 bar, preferably 1 to 5 bar.

The subsequent transformation of an aldehyde or a ketone to a secondary or tertiary alcohol is preferably accomplished by addition of a carbon nucleophile, e.g. alkyl, allyl, alkenyl, aryl, or alkynyl lithium, magnesium, or cerium compound, in tetrahydrofuran, ether, 1,4-dioxane, 1,2-dimethoxyethane, toluene, hexanes, or mixtures thereof, at −80 to 80° C.

The subsequent transformation of a carboxylic ester into a tertiary hydroxy group is preferably conducted with two or more equivalents of a carbon nucleophile, e.g. alkyl, allyl, alkenyl, aryl, or alkynyl lithium, magnesium, or cerium compound, in tetrahydrofuran, ether, 1,4-dioxane, 1,2-dimethoxyethane, toluene, hexanes, or mixtures thereof, at temperatures of −80 to 80° C.

The subsequent oxidation of a primary or secondary hydroxy compound may be achieved by using an oxidizing agent, such as dimethyl sulfoxide combined with e.g. oxalyl chloride, acetic anhydride, $SO_3$*pyridine, or dicyclohexylcarbodiimide, pyridinium chlorochromate (PCC), pyridinium dichromate (PDC), Dess-Martin periodinane, manganese dioxide, 2,2,6,6-tetramethylpiperidine-N-oxide (TEMPO) optionally combined with a co-oxidant, or tetrapropylammonium perrhutenate (TPAP) combined with a co-oxidant such as N-methyl-morpholine-N-oxide, which are optionally used in the presence of a base, e.g. triethylamine, preferably in toluene, dichloromethane, or 1,2-dichloroethane, at −70 to 60° C. Alternatively, the transformation may be performed as an Oppenauer oxidation with e.g. $Al(OtBu)_3$ and acetone.

The subsequent hydroboration and oxidation of an olefinic bond is conducted with a borane, e.g. borane complexed with tetrahydrofuran, trimethylamine, or dimethyl sulfide, diethylborane, thexylborane, 9-borabicyclo[3.3.1]nonane, $NaBH_4$ combined with $BF_3$ or $TiCl_4$, or dichloroborane, preferably used in tetrahydrofuran at −20 to 60° C. The hydroboration product is subsequently treated with e.g. hydrogen peroxide and sodium hydroxide in an aqueous solution to replace the boron group in the intermediate with hydroxy.

The subsequent dihydroxylation of an olefinic bond is preferably conducted with osmium tetroxide or potassium osmate combined with a co-oxidant, e.g. N-methyl-morpholine-N-oxide or $K_3Fe(CN)_6$, preferably in water combined with tBuOH, tetrahydrofuran, and/or 1,4-dioxane, at −20 to 60° C.

The subsequent cleavage of an olefinic bond by ozonolysis is conducted with ozone, preferably in dichloromethane at −50 to −78° C. The intermediate obtained thereafter may be transformed into a carbonyl compound by treatment with e.g. dimethyl sulfide, zinc combined with acetic acid, hydrogen in the presence of palladium, or triphenylphosphine. Treatment of the intermediate with sodium borohydride or lithium aluminum hydride affords the corresponding hydroxy compound.

The subsequent epoxidation of an olefinic bond is preferably conducted with m-chloroperbenzoic acid (mCPBA), hydrogen peroxide combined with formic acid or acetic acid, or Oxone® combined with acetone or 1,1,1-trifluoroacetone, preferably in dichloromethane at −20 to 40° C. The oxirane ring can be opened with a hydride source such as lithium aluminum hydride or lithium triethylborohydride in an inert solvent, e.g. tetrahydrofuran, to furnish the hydroxy compound.

The subsequent Wacker oxidation of an olefinic bond is preferably conducted with $PdCl_2$ and CuCl or $CuCl_2$, in the presence of oxygen, in an aqueous solvent to provide the corresponding carbonyl compound.

The subsequent hydrocyanation of an olefinic bond can be conducted with 4-tolylsulfonyl cyanide in the presence of phenylsilane and a cobalt catalyst (see e.g. *Angew. Chem.* 2007, 119, 4603-6).

The subsequent formal water addition to cyano groups can be done by treating an aqueous solution of the nitrile with a strong acid, e.g. sulfuric acid or hydrochloric acid, or a base, e.g. NaOH or KOH, optionally at elevated temperature, preferably at 0 to 140° C. Alternatively, this transformation can be achieved in an aqueous solution with a transition metal catalyst such as $PdCl_2$.

In the reactions described hereinbefore, any reactive group present, such as hydroxy, carbonyl, carboxy, amino, alkylamino, or imino, may be protected during the reaction by conventional protecting groups which are cleaved again after the reaction.

For example, a protecting group for a hydroxy group may be a trimethylsilyl, tert-butyldimethylsilyl, triisopropylsilyl, acetyl, pivaloyl, benzoyl, methyl, tert-butyl, allyl, trityl, benzyl, 4-methoxybenzyl, tetrahydropyranyl, methoxymethyl, ethoxymethyl, or 2-trimethylsilylethoxymethyl group, protecting groups for a carboxy group may be trimethylsilyl, methyl, ethyl, tert-butyl, allyl, benzyl, or tetrahydropyranyl, protecting groups for a ketone or aldehyde may be a ketal or acetal, respectively, e.g. derived from methanol, ethylene glycol, propane-1,3-diol, or propane-1,3-dithiol, protecting groups for an amino, alkylamino, or imino group may be methyl, formyl, acetyl, trifluoroacetyl, ethoxycarbonyl, tert-butoxycarbonyl, benzyloxycarbonyl, benzyl, 4-methoxybenzyl, or 2,4-dimethoxybenzyl and for the amino group additionally phthalyl and tetrachlorophthalyl, and protecting groups for a terminal alkyne may be trimethylsilyl, triisopropylsilyl, tert-butyldimethylsilyl, or 2-hydroxy-prop-2-yl.

Any acyl protecting group may be cleaved, for example, hydrolytically in an aqueous solvent, e.g. in water, isopropanol/water, acetic acid/water, tetrahydrofuran/water, or 1,4-dioxane/water, in the presence of an acid such as trifluoroacetic acid, hydrochloric acid, or sulfuric acid or in the presence of an alkali metal base such as lithium hydroxide, sodium hydroxide, or potassium hydroxide at temperatures between 0 and 120° C., preferably between 10 and 100° C. The transformation may be conducted aprotically with e.g. iodotrimethylsilane in dichloromethane or 1,2-dichlorethane at −70 to 60° C. Trifluoroacetyl is also cleaved by treating with an acid such as hydrochloric acid optionally in a solvent such as acetic acid at temperatures between 50 and 120° C. or by treating with aqueous sodium hydroxide solution optionally in an additional solvent such as tetrahydrofuran or methanol at temperatures between 0 and 80° C.

Any acetal or ketal protecting group used may be cleaved, for example, hydrolytically in an aqueous solvent, e.g. water, isopropanol/water, acetic acid/water, tetrahydrofuran/water, or 1,4-dioxane/water, in the presence of an acid such as acetic acid, trifluoroacetic acid, hydrochloric acid, or sulfuric acid at temperatures between 0 and 120° C., preferably between 10 and 100° C. Iodotrimethylsilane in dichloromethane is a variant to achieve this transformation aprotically.

A trimethylsilyl group is cleaved, for example, in water, an aqueous solvent mixture or an alcohol, such as methanol or ethanol, in the presence of a base such as lithium hydroxide, sodium hydroxide, potassium carbonate, or sodium methoxide. Acids such as e.g. hydrochloric acid, trifluoroacetic acid, or acetic acid may also be suitable. The cleavage usually takes place at comparatively low temperatures, e.g. between −60 and 60° C. Silyl groups other than trimethylsilyl are preferentially cleaved in the presence of an acid, e.g. trifluoroacetic acid, hydrochloric acid, or sulfuric acid, at temperatures between 0 and 100° C. A particularly suited cleaving method for silyl groups is based on the use of fluoride salts, e.g. tetrabutylammonium fluoride, hydrogen fluoride, or potassium fluoride, in organic solvents, such as for example diethyl ether, tetrahydrofuran, 1,4-dioxane, 1,2-dimethoxyethane, toluene, benzene, 1,2-dichloroethane, or dichloromethane at temperatures between −20 and 100° C.

A benzyl, methoxybenzyl, or benzyloxycarbonyl group is advantageously cleaved hydrogenolytically, e.g. with hydrogen in the presence of a catalyst such as palladium on carbon or palladium hydroxide, in a solvent such as methanol, ethanol, ethyl acetate, acetic acid or mixtures thereof optionally in the presence of an acid such as hydrochloric acid at temperatures between 0 and 100° C., preferably between 20 and 60° C., and at hydrogen pressures of 1 to 10 bar, preferably 3 to 5 bar. Trimethylsilyl iodide, boron trichloride, or boron trifluoride in the presence of a scavenger such as anisol, thioanisol, or pentamethylbenzene may also be used with benzylether derivatives. An electron-rich benzyl residue such as methoxybenzyl may also be cleaved oxidatively with e.g. 2,3-dichloro-5,6-dicyano-1,4-benzoquinone (DDQ) or ceric ammonium nitrate (CAN) preferably in an alcoholic or aqueous solvent at temperatures between 10 and 120° C. A 2,4-dimethoxybenzyl group is preferably cleaved in trifluoroacetic acid in the presence of a scavenger such as anisole.

A tert-butyl or tert-butyloxycarbonyl group is preferably cleaved by treating with an acid such as trifluoroacetic acid, sulfuric acid, or hydrochloric acid or by treating with iodotrimethylsilane optionally using a solvent such as methylene chloride, 1,4-dioxane, methanol, isopropanol, water, or diethylether.

A methyl group at an tertiary amine may be cleaved by the treatment with 1-chloroethyl chloroformate or vinyl chloroformate. Hydrobromic acid and boron tribromide are particularly suited for the cleavage of methylethers.

The compounds of general formula I may be resolved into their enantiomers and/or diastereomers as mentioned before. Thus, for example, cis/trans mixtures may be resolved into their cis and trans isomers and racemic compounds may be separated into their enantiomers.

The cis/trans mixtures may be resolved, for example, by chromatography into the cis and trans isomers thereof. The compounds of general formula I which occur as racemates may be separated by methods known per se (cf. Allinger N. L. and Eliel E. L. in "Topics in Stereochemistry", Vol. 6, Wiley Interscience, 1971) into their optical antipodes and diastereomeric mixtures of compounds of general formula I may be resolved into their diastereomers by taking advantage of their different physico-chemical properties using methods known per se, e.g. chromatography and/or fractional crystallization; if the compounds obtained thereafter are racemates, they may be resolved into the enantiomers as mentioned above.

The racemates are preferably resolved by column chromatography on chiral phases or by crystallization from an optically active solvent or by reacting with an optically active substance which forms salts or derivatives such as esters or amides with the racemic compound. Salts may be formed with enantiomerically pure acids for basic compounds and with enantiomerically pure bases for acidic compounds. Diastereomeric derivatives are formed with enantiomerically pure auxiliary compounds, e.g. acids, their activated derivatives, or alcohols. Separation of the diastereomeric mixture of salts or derivatives thus obtained may be achieved by taking advantage of their different physico-chemical properties, e.g. differences in solubility; the free antipodes may be released from the pure diastereomeric salts or derivatives by the action of suitable agents. Optically active acids in common use for such a purpose are e.g. the D- and L-forms of tartaric acid, dibenzoyltartaric acid, ditoloyltartaric acid, malic acid, mandelic acid, camphorsulfonic acid, glutamic acid, aspartic acid, or quinic acid. Optically active alcohols applicable as auxiliary residues may be, for example, (+) or (−)-menthol and optically active acyl groups in amides may be, for example, (+)- or (−)-menthyloxycarbonyl.

As mentioned above, the compounds of formula I may be converted into salts, particularly for pharmaceutical use into the pharmaceutically acceptable salts. As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. For example, such salts include acetates, ascorbates, benzenesulfonates (besylates), benzoates, bicarbonates, bitartrates, bromides/hydrobromides, Ca-edetates/edetates, camsylates, carbonates, chlorides/hydrochlorides, citrates, ethane disulfonates (edisylates), estolates, esylates, fumarates, gluceptates, gluconates, glutamates, glycolates, glycollylarsanilates, hexylresorcinates, hydrabamines, hydroxymaleates, hydroxynaphthoates, iodides, isothionates, lactates, lactobionates, malates, maleates, mandelates, methanesulfonates, mucates, napsylates, nitrates, oxalates, pamoates, pantothenates, phenylacetates, phosphates/diphosphates, polygalacturonates, propionates, salicylates, stearates, subacetates, succinates, sulfamides, sulfates, tannates, tartrates, teoclates, toluenesulfonates (tosylates), triethiodides, ammonium, benzathines, chloroprocaines, cholines, diethanolamines, ethylenediamines, meglumines, and procaines. Further pharmaceutically acceptable salts can be formed with cations from metals like aluminum, calcium, lithium, magnesium, potassium, sodium, zinc, and the like (also see Pharmaceutical salts, Berge, S. M. et al., J. Pharm. Sci., (1977), 66, 1-19). Some of the salts mentioned above may also be useful for purifying or isolating the compounds of the invention.

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoroacetate salts), also comprise a part of the invention.

The compounds according to the invention are advantageously also obtainable using the methods described in the examples that follow, which may also be combined for this purpose with methods known to the skilled man from the literature.

In some embodiments, the present teachings also provide methods for producing crystalline forms of a compound represented by the following structural formula (II):

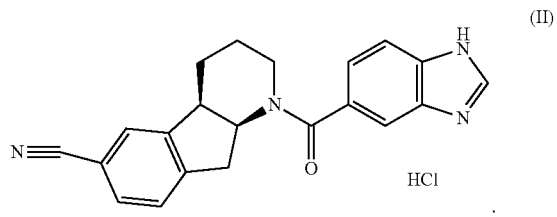 [SMILES: N#Cc1ccc2c(c1)[C@H]1CCCN(C(=O)c3ccc4[nH]cnc4c3)[C@H]1C2 ; Cl]

In some embodiments, the present teachings provide methods for producing crystalline form I of a compound represented by structural formula (II). In some embodiments, the present teachings provide methods for producing crystalline form II of a compound represented by structural formula (II).

In some embodiments, the method for producing crystalline form I of a compound represented by structural formula (II) includes dissolving a free base represented by the following structural formula (III):

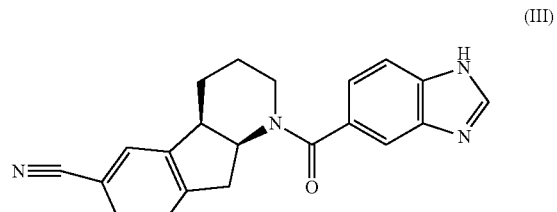

in ethanol at a temperature below about 30° C.; protonating the dissolved free base with hydrochloric acid (e.g., in an aqueous solution, such as a 30-40 wt % aqueous solution, e.g., a 36.5 wt % aqueous solution); and allowing crystalline form I to form by cooling the protonated dissolved free base (e.g., at a temperature below about 30° C.).

For example, in some embodiments, the method includes dissolving the free base in ethanol at 20-30° C., protonating the dissolved free base with hydrochloric acid (e.g., in an aqueous solution, such as a 30-40 wt % aqueous solution, e.g., a 36.5 wt % aqueous solution), and allowing crystalline form I to form at a temperature at −5° to 5° C. (or dissolving at about room temperature and crystallizing at about 0° C.). In some embodiments, the method includes dissolving the free base in ethanol at about room temperature, protonating the dissolved free base with hydrochloric acid (e.g., in an aqueous solution, such as a 30-40 wt % aqueous solution, e.g., a 36.5 wt % aqueous solution), and allowing crystalline form I to form at room temperature over a period of at least six hours, e.g., at least eight hours, e.g., at least ten hours. In still other embodiments, the method includes dissolving the free base in ethanol at a temperature above about 30° C., protonating the dissolved free base with hydrochloric acid (e.g., in an aqueous solution, such as a 30-40 wt % aqueous solution, e.g., a 36.5 wt aqueous solution) at a temperature below about 30° C., and allowing crystalline form I to form at a temperature below about 30° C.

In some embodiments, the method for producing crystalline form II of a compound represented by structural formula (II) includes contacting a compound represented by structural formula (II) (e.g., crystalline form I of a compound represented by structural formula (II)) with ethanol (e.g., 200 proof absolute ethanol) to form a suspension, and stirring the suspension for a period of time sufficient to form crystalline form II. In some embodiments, a period of time sufficient to form crystalline form II is at least about three days, at least about four days, at least about five days, at least about six days, or at least about one week.

In some embodiments, the method for producing crystalline form II of a compound represented by structural formula (II) includes dissolving a compound represented by structural formula (II) in ethyl acetate at a temperature above about 40° C. (e.g., at least about 50° C. or from 40°-60° C.); and allowing crystalline form II to form by cooling the dissolved compound (e.g., at a temperature below about 30° C. or at or below about room temperature).

In some embodiments, the method for producing crystalline form II of a compound represented by structural formula (II) includes dissolving a free base represented by structural formula (III) in isopropanol at a temperature above about 40° C. (e.g., above about 50° C., above about 60° C., or even at or above about 75° C.); protonating the dissolved free base with hydrochloric acid (e.g., in isopropanol); and allowing crystalline form II to form by cooling the dissolved protonated free base (e.g., at a temperature below about 15° C., below about 10° C. or below about 5° C.). Alternatively, the free base is dissolved at a temperature between 50°-70° C. and form II is formed at 0°-15° C.

In some embodiments, the method for producing crystalline form II of a compound represented by structural formula (II) includes dissolving a free base represented by structural formula (III) in ethanol (e.g., 200 proof absolute ethanol) at a temperature of above about 40° C. (e.g., at or above about 50° C.); protonating the dissolved free base with hydrochloric acid (e.g., in ethanol, such as 200 proof absolute ethanol); maintaining the dissolved protonated free base at the elevated temperature for at least two hours and allowing crystalline form II to form by cooling the dissolved protonated free base (e.g., at a temperature below about 15° C., below about 10° C., below about 5° C., or even at or below about 0° C.). Alternatively, the free base is dissolved at 45°-70° C., the dissolved protonated free base is maintained at 45°-70° C. for 2-3 hours and form II is formed at between 0°-25° C. or from 0°-15° C.

In some embodiments, the methods for producing crystalline forms of a compound represented by structural formula (II) further include the use of one or more seed crystals (e.g., seed crystals of crystalline form I or crystalline form II).

As already mentioned, the compounds of general formula I and the compounds of formula (II) according to the invention and the physiologically acceptable salts thereof have valuable pharmacological properties, particularly an inhibitory effect on the enzyme 11β-hydroxysteroid dehydrogenase (HSD) 1.

BIOLOGICAL EXAMPLES a) The biological properties (inhibitory activity on 11β-hydroxysteroid dehydrogenase 1) of the new compounds may be investigated as follows:

In vitro inhibition of 11β-HSD1 by test compounds is determined with HTRF (Homogeneous Time-Resolved Fluorescence) technology (cisbio international, France) detecting cortisol generated from cortisterone by human liver microsomes. Briefly, compounds are incubated for 1 hour at 37° C. in Tris buffer (20 mM tris, 5 mM EDTA, pH 6.0) containing NADPH (200 μM) and cortisone (80 nM). Cortisol generated in the reaction is then detected with a competitive immunoassay, involving two HTRF conjugates: cortisol linked to XL665 and anti-cortisol antibody labeled with Europium cryptate. The incubation period for detection reaction is typically 2 hours. The amount of cortisol is determined by reading the time-resolved fluorescence of the wells (Ex 320/75 nm; Em 615/8.5 nm and 665/7.5 nm). The ratio of the two emission signals is then calculated (Em665*10000/Em615). Each assay contains incubations with vehicle controls instead of compound as controls for non-inhibited cortisol generation (100% CTL; 'high values') and incubations with carbenoxolone as controls for fully inhibited enzyme and cortisol background (0% CTL; 'low values'). Each assay also contains a calibration curve with cortisol to transform the fluorescent data into cortisol concentrations. Percent inhibition (% CTL) of each compound is determined relative to the carbenoxolone signal and $IC_{50}$ curves are generated.

The compounds of general formula I according to the invention tested as described above for example have $IC_{50}$ values below 10000 nM, particularly below 1000 nM, most preferably below 500 nM.

TABLE 2

Inhibitory activity on 11β-HSD 1 of Examples compiled in the experimental part

| Example | $IC_{50}$ [nM] |
|---|---|
| 1 | 106 |
| 2 | 65 |
| 3 | 1380 |
| 4 | 573 |
| 5 | 861 |
| 6 | 296 |
| 7 | 410 |
| 8 | 342 |
| 9 | 481 |
| 10 | 321 |
| 11 | 94 |
| 12 | 367 |
| 13 | 257 |
| 14 | 405 |
| 15 | 1617 |
| 16 | 1412 |
| 17 | 2107 |
| 18 | 1027 |
| 19 | 1902 |
| 20 | 227 |
| 21 | 1132 |
| 22 | 123 |
| 23 | 551 |
| 24 | 1794 |
| 25 | 475 |
| 26 | 1512 |
| 27 | 297 |
| 28 | 2504 |
| 29 | 831 |
| 30 | 2210 |
| 31 | 469 |
| 32 | 954 |
| 33 | 676 |
| 34 | 651 |
| 35 | 3137 |
| 36 | 310 |
| 37 | 150 |
| 38 | 1474 |
| 39 | 1515 |

TABLE 2-continued

Inhibitory activity on 11β-HSD 1 of Examples compiled in the experimental part

| Example | IC$_{50}$ [nM] |
|---|---|
| 40 | 2148 |
| 41 | 1121 |
| 42 | 418 |
| 43 | 1629 |
| 44 | 2151 |
| 45 | 1066 |
| 46 | 3618 |
| 47 | 2157 |
| 48 | 514 |
| 49 | 1469 |
| 50 | 4266 |
| 51 | 2867 |
| 52 | 1595 |
| 53 | 979 |
| 54 | 471 |
| 55 | 4680 |
| 56 | 356 |
| 57 | 969 |
| 58 | 1112 |
| 59 | 2095 |
| 60 | 1051 |
| 61 | 821 |
| 62 | 940 |
| 63 | 1337 |
| 64 | 2871 |
| 65 | 212 |
| 66 | 631 |
| 67 | 722 |
| 68 | 435 |
| 69 | 371 |
| 70 | 350 |
| 71 | 915 |
| 72 | 656 |
| 73 | 447 |
| 74 | 1960 |
| 75 | 324 |
| 76 | 933 |
| 77 | 685 |
| 78 | 257 |
| 79 | 650 |
| 80 | 1971 |
| 81 | 1730 |
| 82 | 1338 |
| 83 | 2058 |
| 84 | 2067 |
| 85 | 1625 |
| 86 | 2110 |
| 87 | 8854 |
| 88 | 705 |
| 89 | 1319 |
| 90 | 2255 |
| 91 | 244 |
| 92 | 884 |
| 93 | 121 |
| 94 | 90 |
| 95 | 1033 |
| 96 | 1107 |
| 97 | 526 |
| 98 | 1252 |
| 99 | 3523 |
| 100 | 850 |
| 101 | 712 |
| 102 | 3119 |
| 103 | 670 |
| 104 | 847 |
| 105 | 263 |
| 106 | 31 |
| 107 | 26 |
| 108 | 150 |
| 109 | 1458 |
| 110 | 1561 |
| 111 | 1376 |
| 112 | 724 |
| 113 | 2658 |
| 114 | 185 |
| 115 | 2077 |
| 116 | 1795 |
| 117 | 1654 |
| 118 | 1067 |
| 119 | 365 |
| 120 | 383 |
| 121 | 4439 |
| 122 | 230 |
| 123 | 644 |
| 124 | 1322 |
| 125 | 484 |
| 126 | 1758 |
| 127 | 1129 |
| 128 | 1917 |
| 129 | 1490 |
| 130 | 1137 |
| 131 | 6428 |
| 132 | 320 |
| 133 | 854 |
| 134 | 389 |
| 135 | 585 |
| 136 | 527 |
| 137 | 1119 |
| 138 | 1054 |
| 139 | 484 |
| 140 | 1622 |
| 141 | 326 |
| 142 | 996 |
| 143 | 1409 |
| 144 | 609 |
| 145 | 777 |
| 146 | 55 |
| 147 | 1738 |
| 148 | 214 |
| 149 | 141 |
| 150 | 674 |
| 151 | 188 |
| 152 | 24 |
| 153 | 48 |
| 154 | 449 |
| 155 | 83 |
| 156 | 432 |
| 157 | 1155 |
| 158 | 998 |
| 159 | 1786 |
| 160 | 367 |
| 161 | 212 |
| 162 | 354 |
| 163 | 67 |
| 164 | 1315 |
| 165 | 449 |
| 166 | 182 |
| 167 | 573 |
| 168 | 313 |
| 169 | 429 |
| 170 | 248 |
| 171 | 218 |
| 174 | 67 | b) The inhibitory activity on 11β-hydroxysteroid dehydrogenase 1 of the new compounds may also be investigated as follows:

The inhibition of a microsomal preparation of 11β-HSD1 by compounds of the invention is measured essentially as previously described (K. Solly, S. S. Mundt, H. J. Zokian, G. J. Ding, A. Hermanowski-Vosatka, B. Strulovici, and W. Zheng, High-Throughput Screening of 11-Beta-Hydroxyseroid Dehydrogenase Type 1 in Scintillation Proximity Assay Format. Assay Drug Dev Technol 3 (2005) 377-384). All reactions are carried out at room temperature in 96 well clear flexible PET Microbeta plates (Perkin Elmer). The assay begins by dispensing 49 µl of substrate solution (50 mM HEPES, pH 7.4, 100 mM KCl, 5 mM NaCl, 2 mM MgCl$_2$, 2 mM NADPH and 160 nM [$^3$H]cortisone (1 Ci/mmol)) and mixing in 1 µL of the test compounds in DMSO previously diluted in half-log increments (8 points) starting at 0.1 mM. After a 10 minute pre-incubation, 50 µL of enzyme solution containing microsomes isolated from CHO cells overexpressing human 11β-HSD1 (10-20 µg/ml of total protein) is added, and the plates are incubated for 90 minutes at room temperature. The reaction is stopped by adding 50 µl of the SPA beads suspension containing 10 µM 18β-glycyrrhetinic acid, 5 mg/ml protein A coated YSi SPA beads (GE Healthcare) and 3.3 µg/ml of anti-cortisol antibody (East Coast Biologics) in Superblock buffer (Bio-Rad). The plates are shaken for 120 minutes at room temperature, and the SPA signal corresponding to [$^3$H]cortisol is measured on a Microbeta plate reader.

TABLE 3

Inhibitory activity on 11β-HSD 1 of Examples compiled in the experimental part

| Example | IC$_{50}$ [nM] | Example | IC$_{50}$ [nM] | Example | IC$_{50}$ [nM] |
|---|---|---|---|---|---|
| 172 | 5.6 | 173 | 18.6 | 174 | 3.6 |
| 175 | 58.4 | 176 | 46.5 | 177 | >100 | c) The metabolic stability of the new compounds may be investigated as follows:

The metabolic degradation of the test compound is assayed at 37° C. with pooled liver microsomes from various species. The final incubation volume of 100 µl per time point contains TRIS buffer pH 7.6 at room temperature (0.1 M), magnesium chloride (5 mM), microsomal protein (0.5 mg/mL) and the test compound at a final concentration of 1 µM. Following a short preincubation period at 37° C., the reactions are initiated by addition of beta-nicotinamide adenine dinucleotide phosphate, reduced form (NADPH, 1 mM), and terminated by transferring an aliquot into solvent after different time points. After centrifugation (10000 g, 5 min), an aliquot of the supernatant is assayed by LC-MS/MS for the amount of parent compound. The half-life is determined by the slope of the semi-logarithmic plot of the concentration-time profile.

TABLE 4

Stability in human liver microsomes of Examples compiled in the experimental part

| Example | t$_{1/2}$ [min] | Example | t$_{1/2}$ [min] | Example | t$_{1/2}$ [min] |
|---|---|---|---|---|---|
| 1 | >90 | 42 | >90 | 108 | >90 |
| 2 | 29 | 91 | >90 | 146 | >45 |
| 10 | >45 | 93 | >90 | 148 | >90 |
| 11 | 38 | 105 | 22 | 152 | >90 |
| 20 | >90 | 106 | >90 | 153 | >90 |
| 37 | >90 | 107 | >90 | 155 | 28 |

In view of their ability to inhibit the enzyme 11β-hydroxysteroid dehydrogenase (HSD) 1, the compounds of general formula I according to the invention and the corresponding pharmaceutically acceptable salts thereof, as well as the compounds of formula (II) are theoretically suitable for the treatment and/or preventative treatment of all those conditions or diseases which may be affected by the inhibition of the 11β-hydroxysteroid dehydrogenase (HSD) 1 activity. Therefore, compounds according to the invention are particularly suitable for the prevention or treatment of diseases, particularly metabolic disorders, or conditions such as type 1 and type 2 diabetes mellitus, complications of diabetes (such as e.g. retinopathy, nephropathy or neuropathies, diabetic foot, ulcers, macroangiopathies, slow or poor wound healing), metabolic acidosis or ketosis, reactive hypoglycaemia, hyperinsulinaemia, glucose metabolic disorder, insulin resistance, metabolic syndrome, dyslipidaemias of different origins, atherosclerosis and related diseases, obesity, high blood pressure, chronic heart failure, edema and hyperuricaemia. These substances may also be suitable for preventing beta-cell degeneration such as e.g. apoptosis or necrosis of pancreatic beta-cells. The substances may also be suitable for improving or restoring the functionality of pancreatic cells, and also of increasing the number and size of pancreatic beta-cells. The compounds according to the invention may also be used as diuretics or antihypertensives and are suitable for the prevention and treatment of acute renal failure.

Additionally, inhibition of 11β-hydroxysteroid dehydrogenase (HSD) 1 has been shown to lower intraocular pressure in subjects with ocular hypertension, therefore the compounds could be used to treat glaucoma.

In view of the role of 11β-hydroxysteroid dehydrogenase (HSD) 1 in modulating cortisol levels for interaction with the glucocorticoid receptor and the known role of excess glucocorticoids in bone loss, the compounds may have beneficial effects against osteoporosis.

Stress and/or glucocorticoids have been shown to influence cognitive function, and excess cortisol has been associated with brain neuronal loss or dysfunction. Treatment with an 11β-hydroxysteroid dehydrogenase (HSD) 1 inhibitor may result in amelioration or prevention of cognitive impairment. Such compounds may also be useful in treating anxiety or depression.

The dynamic interaction between the immune system and the HPA (hypothalamopituitary-adrenal) axis is known, and glucocorticoids help balance between cell-mediated responses and humoral responses. The immune reaction is typically biased towards a humoral response in certain disease states, such as tuberculosis, leprosy, and psoriasis. More appropriate would be a cell-based response. An 11β-hydroxysteroid dehydrogenase (HSD) 1 inhibitor would bolster a temporal immune response in association with immunization to ensure that a cell based response would be obtained, and as such could be useful in immunomodulation.

In particular, the compounds according to the invention, including the physiologically acceptable salts thereof, are suitable for the prevention or treatment of diabetes, particularly type 1 and type 2 diabetes mellitus, and/or diabetic complications.

In a further aspect of the present invention the present invention relates to methods for the treatment or prevention of above mentioned diseases and conditions, which method comprises the administration of an effective amount of a compound of general formula I to a human being. In a further embodiment, the present teachings relate to methods for the treatment or prevention of above mentioned diseases and conditions, which method comprises the administration of an effective amount of a compound of formula (II) to a human being.

The dosage required to achieve the corresponding activity for treatment or prevention usually depends on the compound which is to be administered, the patient, the nature and gravity of the illness or condition and the method and frequency of administration and is for the patient's doctor to decide. Expediently, the dosage may be from 1 to 100 mg, preferably 1 to 30 mg, by intravenous route, and 1 to 1000 mg, preferably 1 to 100 mg, by oral route, in each case administered 1 to 4 times a day.

The actual pharmaceutically effective amount or therapeutic dosage will of course depend on factors known by those skilled in the art such as age and weight of the patient, route of administration and severity of disease. In any case the combination will be administered at dosages and in a manner which allows a pharmaceutically effective amount to be delivered based upon patient's unique condition.

Suitable preparations for administering the compounds of formula I will be apparent to those with ordinary skill in the art and include for example tablets, pills, capsules, suppositories, lozenges, troches, solutions, syrups, elixirs, sachets, injectables, inhalatives, powders, etc. The content of the pharmaceutically active compound(s) should be in the range from 0.1 to 95 wt.-%, preferably 5.0 to 90 wt.-% of the composition as a whole.

Suitable tablets may be obtained, for example, by mixing one or more compounds according to formula I with known excipients, for example inert diluents, carriers, disintegrants, adjuvants, surfactants, binders and/or lubricants. The tablets may also consist of several layers.

For this purpose, the compounds of formula I prepared according to the invention may be formulated, optionally together with other active substances, together with one or more inert conventional carriers and/or diluents, e.g. with corn starch, lactose, glucose, microcrystalline cellulose, magnesium stearate, citric acid, tartaric acid, water, polyvinylpyrrolidone, water/ethanol, water/glycerol, water/sorbitol, water/polyethylene glycol, propylene glycol, cetylstearyl alcohol, carboxymethylcellulose or fatty substances such as hard fat or suitable mixtures thereof.

The compounds according to the invention may also be used in conjunction with other active substances, particularly for the treatment and/or prevention of the diseases and conditions mentioned above. Other active substances which are suitable for such combinations include, for example, those which potentiate the therapeutic effect of an 11β-hydroxysteroid dehydrogenase (HSD) 1 antagonist according to the invention with respect to one of the indications mentioned and/or which allow the dosage of an 11β-hydroxysteroid dehydrogenase (HSD) 1 antagonist according to the invention to be reduced. Therapeutic agents which are suitable for such a combination include, for example, antidiabetic agents such as metformin, sulfonylureas (e.g. glibenclamide, tolbutamide, glimepiride), nateglinide, repaglinide, thiazolidinediones (e.g. rosiglitazone, pioglitazone), SGLT 2 inhibitors (e.g. dapagliflozin, remogliflozin etabonate, sergliflozin, canagliflozin, 1-chloro-4-(β-D-glucopyranos-1-yl)-2-[4-((S)-tetrahydrofuran-3-yloxy)-benzyl]-benzene), PPAR-gamma-agonists (e.g. GI 262570) and antagonists, PPAR-gamma/alpha modulators (e.g. KRP 297), alpha-glucosidase inhibitors (e.g. acarbose, voglibose), DPPIV inhibitors (e.g. Sitagliptin, Vildagliptin, Saxagliptin, Alogliptin, Linagliptin), alpha2-antagonists, insulin and insulin analogues, GLP-1 and GLP-1 analogues (e.g. exendin-4) or amylin. The list also includes inhibitors of protein tyrosinephosphatase 1, substances that affect deregulated glucose production in the liver, such as e.g. inhibitors of glucose-6-phosphatase, or fructose-1,6-bisphosphatase, glycogen phosphorylase, glucagon receptor antagonists and inhibitors of phosphoenol pyruvate carboxykinase, glycogen synthase kinase or pyruvate dehydrokinase and glucokinase activators, lipid lowering agents such as for example HMG-CoA-reductase inhibitors (e.g. simvastatin, atorvastatin), fibrates (e.g. bezafibrate, fenofibrate), nicotinic acid and the derivatives thereof, PPAR-alpha agonists, PPAR-delta agonists, ACAT inhibitors (e.g. avasimibe) or cholesterol absorption inhibitors such as, for example, ezetimibe, bile acid-binding substances such as, for example, cholestyramine, inhibitors of ileac bile acid transport, HDL-raising compounds such as CETP inhibitors or ABC1 regulators or active substances for treating obesity, such as sibutramine or tetrahydrolipostatin, SDRIs, axokine, leptin, leptin mimetics, antagonists of the cannabinoid) receptor, MCH-1 receptor antagonists, MC4 receptor agonists, NPY5 or NPY2 antagonists or β3-agonists such as SB-418790 or AD-9677 and agonists of the 5HT2c receptor.

Moreover, combinations with drugs for influencing high blood pressure, chronic heart failure or atherosclerosis such as e.g. A-II antagonists or ACE inhibitors, ECE inhibitors, diuretics, β-blockers, Ca-antagonists, centrally acting antihypertensives, antagonists of the alpha-2-adrenergic receptor, inhibitors of neutral endopeptidase, thrombocyte aggregation inhibitors and others or combinations thereof are suitable. Examples of angiotensin II receptor antagonists are candesartan cilexetil, potassium losartan, eprosartan mesylate, valsartan, telmisartan, irbesartan, EXP-3174, L-158809, EXP-3312, olmesartan, medoxomil, taso-sartan, KT-3-671, GA-0113, RU-64276, EMD-90423, BR-9701, etc. Angiotensin II receptor antagonists are preferably used for the treatment or prevention of high blood pressure and complications of diabetes, often combined with a diuretic such as hydrochlorothiazide.

A combination with uric acid synthesis inhibitors or uricosurics is suitable for the treatment or prevention of gout.

A combination with GABA-receptor antagonists, Na-channel blockers, topiramat, protein-kinase C inhibitors, advanced glycation end product inhibitors or aldose reductase inhibitors may be used for the treatment or prevention of complications of diabetes.

The dosage for the combination partners mentioned above is usefully $\frac{1}{5}$ of the lowest dose normally recommended up to 1/1 of the normally recommended dose.

Therefore, in another aspect, this invention relates to the use of a compound according to the invention or a physiologically acceptable salt of such a compound combined with at least one of the active substances described above as a combination partner, for preparing a pharmaceutical composition which is suitable for the treatment or prevention of diseases or conditions which can be affected by inhibiting the enzyme 11β-hydroxysteroid dehydrogenase (HSD) 1. These are preferably metabolic diseases, particularly one of the diseases or conditions listed above, most particularly diabetes or diabetic complications.

The use of the compound according to the invention, or a physiologically acceptable salt thereof, in combination with another active substance may take place simultaneously or at staggered times, but particularly within a short space of time. If they are administered simultaneously, the two active substances are given to the patient together; while if they are used at staggered times the two active substances are given to the patient within a period of less than or equal to 12 hours, but particularly less than or equal to 6 hours.

Consequently, in another aspect, this invention relates to a pharmaceutical composition which comprises a compound according to the invention or a physiologically acceptable salt of such a compound and at least one of the active substances described above as combination partners, optionally together with one or more inert carriers and/or diluents.

Thus, for example, a pharmaceutical composition according to the invention comprises a combination of a compound of formula I according to the invention or a physiologically acceptable salt of such a compound and at least one angiotensin II receptor antagonist optionally together with one or more inert carriers and/or diluents.

The compound according to the invention, or a physiologically acceptable salt thereof, and the additional active substance to be combined therewith may both be present together in one formulation, for example a tablet or capsule, or separately in two identical or different formulations, for example as a so-called kit-of-parts.

The Examples that follow are intended to illustrate the present invention without restricting it:

Analytical HPLC and TLC parameters employed for characterization of products:

| method 1 column | Merck Cromolith Speed ROD, RP18e, 50 × 4.6 mm | method 2 column | Waters Xbridge C18, 30 × 4.6 mm, 2.5 μm |
|---|---|---|---|
| mobile phase | A: water + 0.1% $HCO_2H$<br>B: acetonitrile + 0.1% $HCO_2H$<br>TIME (min)　A %　B %<br>0.00　　　90　　10<br>4.50　　　10　　90<br>5.00　　　10　　90<br>5.50　　　90　　10 | mobile phase | A: water + 0.1% $NH_3$<br>B: methanol<br>TIME (min)　A %　B %<br>0　　　　　90　　10<br>0.15　　　　90　　10<br>4.00　　　　0　　100<br>4.40　　　　0　　100<br>4.55　　　　90　　10<br>5.00　　　　90　　10 |
| flow rate | 1.5 mL/min | flow rate | 1.6 mL/min |
| wavelength | UV 220, 230, or 254 nm | wavelength | UV 220, 230, or 254 nm |

| method 3 column | Sunfire C18, 50 × 4.6 mm, 3.5 μm, 40° C. | method 4 column | Sunfire C18, 50 × 4.6 mm, 3.5 μm, 40° C. |
|---|---|---|---|
| mobile phase | A: water + 0.1% $F_3CCO_2H$<br>B: methanol<br>TIME (min)　A %　B %<br>0.00　　　95　　　5<br>1.30　　　　0　　100<br>3.00　　　　0　　100<br>4.00　　　95　　　5 | mobile phase | A: water + 0.1% $F_3CCO_2H$<br>B: methanol<br>TIME (min)　A %　B %<br>0.00　　　95　　　5<br>1.30　　　　0　　100<br>2.50　　　　0　　100<br>2.60　　　95　　　5 |
| flow rate | 1.5 mL/min | flow rate | 1.5 mL/min |
| wavelength | UV 210-500 nm | wavelength | UV 210-500 nm |

| method 5 column | Waters Xbridge C18, 50 × 2.1 mm, 1.7 μm, 60° C. | | |
|---|---|---|---|
| mobile phase | A: water + 0.032% $NH_4OH$;<br>B: acetonitrile<br>TIME (min)　A %　B %<br>0　　　　　95　　　5<br>2.00　　　　0　　100<br>2.50　　　　0　　100<br>2.60　　　95　　　5 | TLC were conducted on Polygram ® SIL G/$UV_{254}$ plates coated with 0.2 mm silica gel | |
| flow rate | 1.3 mL/min | | |
| wavelength | UV 210-500 nm | | |

| method 6 column | StableBond SB-C18 30 × 4.6 mm, 1.8 μm | method 7 column | YMC-PACK ODS-AQ 50 × 2.0 mm, 5μm, 50° C. |
|---|---|---|---|
| mobile phase | A: water + 0.1% $F_3CCO_2H$<br>B: methanol<br>TIME (min)　A %　B %<br>0.00　　　90　　10<br>1.80　　　　0　　100<br>2.00　　　　0　　100<br>2.15　　　90　　10<br>2.35　　　90　　10 | mobile phase | A: water + 0.0375% $F_3CCO_2H$<br>B: acetonitrile + 0.0187% $F_3CCO_2H$<br>TIME (min)　A %　B %<br>0　　　　　90　　10<br>2.2　　　　20　　80<br>2.5　　　　20　　80 |
| | | flow rate | 1.0 mL/min |
| | | wavelength | UV 220 nm |
| flow rate | 1.75 mL/min | | |
| wavelength | UV 220, 230, or 254 nm | | |

In the following, whenever a benzoimidazole bearing a hydrogen on one of its two nitrogens is part of a molecule both tautomeric structures, 1H-benzoimidazole and 3H-benzoimidazole, are meant, though, only one is explicitly named or drawn.

Intermediates 1 and 2 cis-1,2,3,4,4a,5,6,10b-Octahydro-benzo[f]quinoline and trans-1,2,3,4,4a,5,6,10b-Octahydro-benzo[f]quinoline

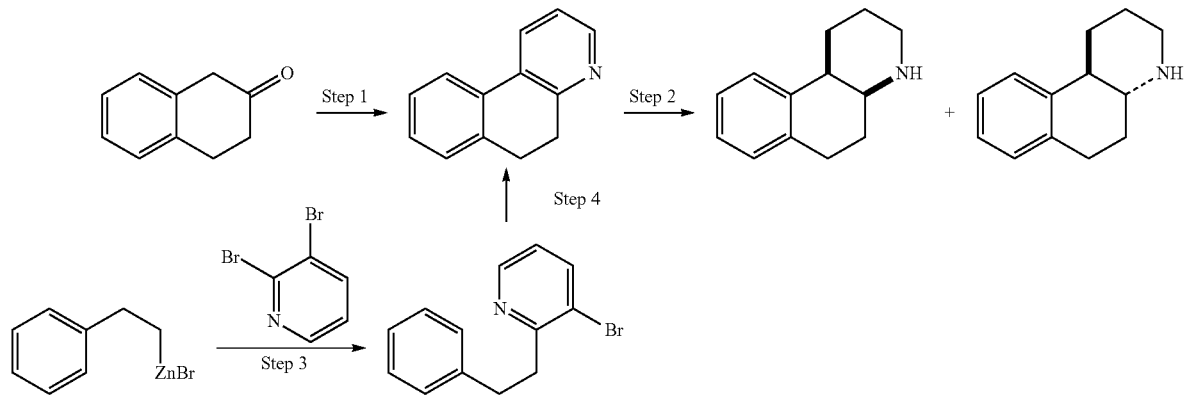

Step 1: 5,6-dihydro-benzo[f]quinoline

Propargylamine (5 mL) is added to a flask charged with a stir bar, 2-tetralone (10.00 g), NaAuCl$_4$*2H$_2$O (0.65 g), and ethanol (50 mL) (caution: a very exothermic reaction may evolve afterwards→keep an ice bath at hand). The resulting mixture is stirred at room temperature for 15 min and then at reflux temperature for 1 h. After cooling the mixture to room temperature, the solvent is evaporated and the residue is chromatographed on silica gel (cyclohexane/ethyl acetate 60:40) to afford the title compound as an oil. Yield: 6.78 g (56% of theory); LC (method 1): $t_R$=1.81 min; Mass spectrum (ESI$^+$): m/z=182 [M+H]$^+$. Alternatively, the reaction may be conducted in a microwave oven heating with microwave irradiation to 100° C. for 10 min.

Step 2: cis- and trans-1,2,3,4,4a,5,6,10b-octahydro-benzo[f]quinoline

A mixture of 5,6-dihydro-benzo[f]quinoline (8.78 g), PtO$_2$ (1.00 g), and acetic acid is shaken under hydrogen atmosphere (10 bar) at room temperature for 24 h (in case the transformation is not complete after this time, another portion of PtO$_2$ (0.20 g) is added and shaking under hydrogen is continued until completion). The catalyst is separated by filtration and the solvent is evaporated. The residue is taken up in 2 M aqueous NaOH solution and the resulting mixture is extracted with ethyl acetate. The combined extracts are dried (MgSO$_4$) and concentrated. The residue is chromatographed on silica gel (dichloromethane/methanol containing 1% NH$_3$ 95:5→80:20) to afford the two title compounds separated.

cis-1,2,3,4,4a,5,6,10b-Octahydro-benzo[f]quinoline:
Yield: 6.30 g (69% of theory); LC (method 1): $t_R$=1.85 min; Mass spectrum (ESI$^+$): m/z=188 [M+H]$^+$; $^1$H NMR (400 MHz, DMSO-d$_6$) δ 1.30-1.45 (m, 2H), 1.57-1.66 (m, 1H), 1.66-1.76 (m, 1H), 1.84-1.97 (m, 1H), 1.99-2.10 (m, 1H), 2.59-2.79 (m, 4H), 2.83-2.92 (m, 1H), 3.03-3.10 (m, 1H), 3.27 (broad s, 1H and water), 7.00-7.11 (m, 3H), 7.15-7.19 (m, 1H).

Alternatively, cis-1,2,3,4,4a,5,6,10b-octahydro-benzo[f]quinoline may be obtained in a departure of the synthesis described in J. Heterocyclic Chem. 1996, 33, 983-5 by conducting the enamide reduction with H$_2$ (3 bar) and 10% palladium on carbon in methanol containing 5% acetic acid.

trans-1,2,3,4,4a,5,6,10b-Octahydro-benzo[f]quinoline:
Yield: 0.41 g (5% of theory); Mass spectrum (ESI$^+$): m/z=188 [M+H]$^+$; $^1$H NMR (400 MHz, DMSO-d$_6$) δ 1.20-1.33 (m, 1H), 1.67-1.89 (m, 3H), 1.98-2.07 (m, 1H), ca. 2.47-2.55 (2H, m) superimposed on DMSO-d$_5$ signal, 2.59-2.68 (m, 1H), 2.70-2.80 (m, 2H), 2.82-2.90 (m, 2H), 3.12-3.20 (m, 1H), 7.05-7.18 (m, 3H), 7.25-7.31 (m, 1H).

Alternatively, trans-1,2,3,4,4a,5,6,10b-octahydro-benzo[f]quinoline may be obtained as described in J. Heterocyclic Chem. 1996, 33, 983-5.

Alternatively, 5,6-dihydro-benzo[f]quinoline may be obtained as follows:

Step 3: 3-bromo-2-phenethyl-pyridine

Tetrakis(triphenylphosphine)palladium(0) (2.0 g) is added to a flask charged with a stir bar, phenethylzinc bromide (0.5 mol/L in tetrahydrofuran, 100 mL), 2,3-dibromopyridine (10.50 g), and tetrahydrofuran (100 ml) and kept under argon atmosphere at room temperature. The resulting mixture is stirred at room temperature for 3 h and at 40° C. for another 16 h. After cooling the mixture to room temperature, the solvent is evaporated and the residue is chromatographed on silica gel (cyclohexane/ethyl acetate 90:10→75:25) to afford the title compound as an oil that solidified upon treatment with ether. Yield: 9.32 g (81% of theory); LC (method 1): $t_R$=4.28 min; Mass spectrum (ESI$^+$): m/z=262/264 (Br) [M+H]$^+$.

Step 4: 5,6-dihydro-benzo[f]quinoline

N,N-Dimethylacetamide (15 mL) is added to a flask charged with a stir bar, 3-bromo-2-phenethyl-pyridine (3.34 g), freshly dried K$_2$CO$_3$ (3.52 g), palladium(II) acetate (0.14 g), and tricyclohexylphosphonium tetrafluoroborate (0.47 g) and kept under argon atmosphere at room temperature. The flask is put into a 150° C. hot oil bath and the mixture is stirred therein for 2 h. After cooling the mixture to room temperature, the solvent is evaporated and the residue is chromatographed twice on silica gel (1. dichloromethane/methanol 98:2; 2. cyclohexane/ethyl acetate 90:10→50:50) to afford the title compound as an oil. Yield: 1.51 g (65% of theory); LC (method 1): $t_R$=1.83 min; Mass spectrum (ESI$^+$): m/z=182 [M+H]$^+$.

Intermediates 3 and 4 cis-7-Methoxy-1,2,3,4,4a,5,6,10b-octahydro-benzo[f]quinoline and trans-7-Methoxy-1,2,3,4,4a,5,6,10b-octahydro-benzo[f]quinoline

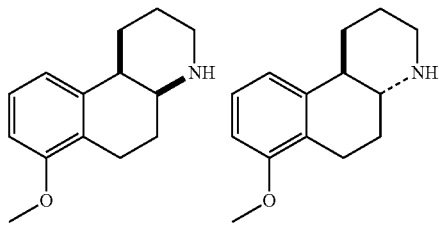

The title compounds are obtained following a route analogous to that described in Step 1 and Step 2 for Intermediates 1 and 2 employing 5-methoxy-2-tetralone and propargylamine in Step 1 and 7-methoxy-5,6-dihydro-benzo[f]quinoline in Step 2.

Step 1: 7-methoxy-5,6-dihydro-benzo[f]quinoline; Yield: 55% of theory; Mass spectrum (ESI$^+$): m/z=212 [M+H]$^+$.

Step 2: cis-7-methoxy-1,2,3,4,4a,5,6,10b-octahydrobenzo[f]quinoline; Yield: 54% of theory; LC (method 1): $t_R$=2.02 min; Mass spectrum (ESI$^+$): m/z=218 [M+H]$^+$.

trans-7-methoxy-1,2,3,4,4a,5,6,10b-octahydro-benzo[f]quinoline; Yield: 20% of theory; Mass spectrum (ESI$^+$): m/z=218 [M+H]$^+$.

Intermediates 5 and 6 cis-10-Methoxy-1,2,3,4,4a,5,6,10b-octahydro-benzo[f]quinoline and trans-10-Methoxy-1,2,3,4,4a,5,6,10b-octahydro-benzo[f]quinoline

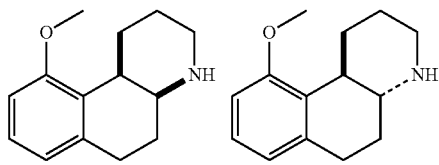

The title compounds are obtained following a route analogous to that described in Step 1 and Step 2 for Intermediates 1 and 2 employing 8-methoxy-2-tetralone and propargylamine in Step 1 and 10-methoxy-5,6-dihydro-benzo[f]quinoline in Step 2.

Step 1: 10-methoxy-5,6-dihydro-benzo[f]quinoline; Yield: 54% of theory; LC (method 1): $t_R$=2.02 min; Mass spectrum (ESI$^+$): m/z=212 [M+H]$^+$.

Step 2: cis-10-methoxy-1,2,3,4,4a,5,6,10b-octahydro-benzo[f]quinoline; Yield: 50% of theory; Mass spectrum (ESI$^+$): m/z=218 [M+H]$^+$.

trans-10-methoxy-1,2,3,4,4a,5,6,10b-octahydro-benzo[f]quinoline; Yield: 11% of theory; Mass spectrum (ESI$^+$): m/z=218 [M+H]$^+$.

Intermediates 7 and 8 cis-10b-Methyl-1,2,3,4,4a,5,6,10b-octahydro-benzo[f]quinoline and trans-10b-Methyl-1,2,3,4,4a,5,6,10b-octahydro-benzo[f]quinoline

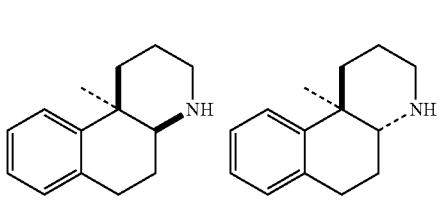

The title compounds are obtained following a route analogous to that described in Step 1 and Step 2 for Intermediates 1 and 2.

Step 1:
10b-methyl-3,5,6,10b-tetrahydro-benzo[f]quinoline

Propargylamine (0.21 mL) is added to a microwave oven suited vessel charged with a stir bar, 1-methyl-2-tetralone (0.50 mL), NaAuCl$_4$*2H$_2$O (27 mg), and ethanol (3 mL) (caution: a very exothermic reaction may evolve afterwards→keep an ice bath at hand). The resulting mixture is stirred under microwave irradiation at 100° C. for 10 min. After cooling the mixture to room temperature, the solvent is evaporated and the residue is chromatographed on silica gel (cyclohexane/ethyl acetate 25:75→0:100) to afford the title compound as an oil. Yield: 0.29 g (50% of theory); LC (method 1): $t_R$=1.78 min; Mass spectrum (ESI$^+$): m/z=198 [M+H]$^+$.

Step 2: cis-10b-methyl-1,2,3,4,4a,5,6,10b-octahydrobenzo[f]quinoline and trans-10b-methyl-1,2,3,4,4a,5,6,10b-octahydro-benzo[f]quinoline A mixture of 10b-methyl-3,5,6,10b-tetrahydro-benzo[f]quinoline (8.78 g), 10% Pd on carbon (1.00 g), acetic acid (0.3 mL), and methanol (10 mL) is shaken under hydrogen atmosphere (3 bar) at room temperature for 14 h. The catalyst is separated by filtration and the solvent is evaporated. The residue is taken up in half-concentrated aqueous Na$_2$CO$_3$ solution and the resulting mixture is extracted with ethyl acetate. The combined extracts are dried (MgSO$_4$) and then concentrated to afford the two title compounds in a ca. 3:1 mixture (cis/trans). Yield: 0.24 g (86% of theory); LC (method 1): $t_R$=1.92 min (trans-10b-methyl-1,2,3,4,4a,5,6,10b-octahydro-benzo[f]quinoline) and $t_R$=2.02 min (cis-10b- methyl-1,2,3,4,4a,5,6,10b-octahydro-benzo[f]quinoline); Mass spectrum (ESI⁺): m/z=202 [M+H]⁺.

Intermediates 9 and 10 cis-9-Methoxy-1,2,3,4,4a,5,6,10b-octahydro-benzo[f]quinoline and trans-9-Methoxy-1,2,3,4,4a,5,6,10b-octahydro-benzo[f]quinoline

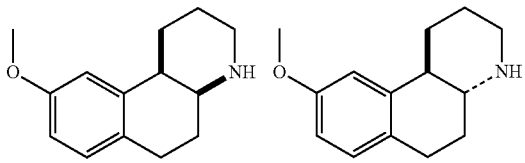

The title compounds are obtained following a route analogous to that described in Step 1 and Step 2 for Intermediates 1 and 2 employing 7-methoxy-2-tetralone and propargylamine in Step 1 and 9-methoxy-5,6-dihydro-benzo[f]quinoline in Step 2.

Step 1: 9-methoxy-5,6-dihydro-benzo[f]quinoline; Yield: 58% of theory; LC (method 1): $t_R$=1.99 min; Mass spectrum (ESI⁺): m/z=212 [M+H]⁺.

Step 2: cis-9-methoxy-1,2,3,4,4a,5,6,10b-octahydro-benzo[f]quinoline; Yield: 19% of theory; Mass spectrum (ESI⁺): m/z=218 [M+H]⁺.

trans-9-methoxy-1,2,3,4,4a,5,6,10b-octahydro-benzo[f]quinoline; Yield: 22% of theory; Mass spectrum (ESI⁺): m/z=218 [M+H]⁺.

Intermediates 11 and 12 cis-7,9-Difluoro-1,2,3,4,4a,5,6,10b-octahydro-benzo[f]quinoline and trans-7,9-Difluoro-1,2,3,4,4a,5,6,10b-octahydro-benzo[f]quinoline

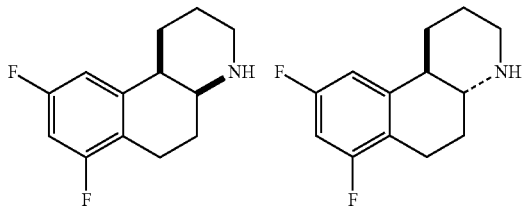

The title compounds are obtained following a route analogous to that described in Step 1 and Step 2 for Intermediates 1 and 2 employing 5,7-difluoro-2-tetralone and propargylamine in Step 1 and 7,9-difluoro-5,6-dihydro-benzo[f]quinoline in Step 2.

Step 1: 7,9-difluoro-5,6-dihydro-benzo[f]quinoline; Yield: 53% of theory; LC (method 1): $t_R$=2.54 min; Mass spectrum (ESI⁺): m/z=224 [M+H]⁺.

Step 2: cis-7,9-difluoro-1,2,3,4,4a,5,6,10b-octahydro-benzo[f]quinoline; Yield: 38% of theory; TLC: $r_f$=0.37 (silica gel, CH₂Cl₂/MeOH/32% aqueous NH₃ 90:10:1); Mass spectrum (ESI⁺): m/z=218 [M+H]⁺.

trans-7,9-difluoro-1,2,3,4,4a,5,6,10b-octahydro-benzo[f]quinoline; Yield: 26% of theory; TLC: $r_f$=0.37 (silica gel, CH₂Cl₂/MeOH/32% aqueous NH₃ 90:10:1); Mass spectrum (ESI⁺): m/z=224 [M+H]⁺.

Intermediates 13 and 14 cis-8-Methoxy-1,2,3,4,4a,5,6,10b-octahydro-benzo[f]quinoline and trans-8-Methoxy-1,2,3,4,4a,5,6,10b-octahydro-benzo[f]quinoline

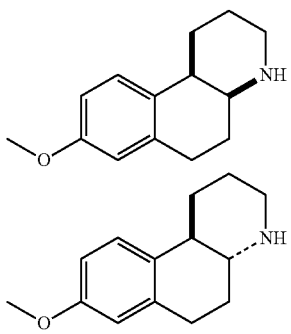

The title compounds are obtained following a route analogous to that described in Step 1 and Step 2 for Intermediates 1 and 2 employing 6-methoxy-2-tetralone and propargylamine in Step 1 and 8-methoxy-5,6-dihydro-benzo[f]quinoline in Step 2.

Step 1: 8-methoxy-5,6-dihydro-benzo[f]quinoline; Yield: 14% of theory; LC (method 1): $t_R$=1.95 min; Mass spectrum (ESI⁺): m/z=212 [M+H]⁺.

Step 2: cis-8-methoxy-1,2,3,4,4a,5,6,10b-octahydro-benzo[f]quinoline; Yield: 52% of theory; TLC: $r_f$=0.22 (silica gel, CH₂Cl₂/MeOH/32% aqueous NH₃ 90:10:1); Mass spectrum (ESI⁺): m/z=218 [M+H]⁺.

trans-8-methoxy-1,2,3,4,4a,5,6,10b-octahydro-benzo[f]quinoline; Yield: 21% of theory; TLC: $r_f$=0.28 (silica gel, CH₂Cl₂/MeOH/32% aqueous NH₃ 90:10:1); Mass spectrum (ESI⁺): m/z=218 [M+H]⁺.

Intermediates 15 and 16 cis-10-Fluoro-1,2,3,4,4a,5,6,10b-octahydro-benzo[f]quinoline and trans-10-Fluoro-1,2,3,4,4a,5,6,10b-octahydro-benzo[f]quinoline

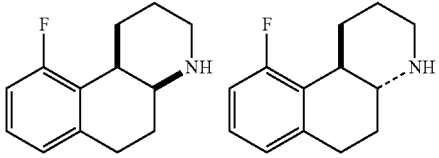

The title compounds are obtained following a route analogous to that described in Step 1 and Step 2 for Intermediates 1 and 2 employing 8-fluoro-2-tetralone and propargylamine in Step 1 and 10-fluoro-5,6-dihydro-benzo[f]quinoline in Step 2.

Step 1: 10-fluoro-5,6-dihydro-benzo[f]quinoline; Yield: 55% of theory; Mass spectrum (ESI⁺): m/z=200 [M+H]⁺.

Step 2: cis-10-fluoro-1,2,3,4,4a,5,6,10b-octahydro-benzo[f]quinoline; Yield: 63% of theory; TLC: r_f=0.38 (silica gel, CH$_2$Cl$_2$/MeOH/32% aqueous NH$_3$ 90:10:1); Mass spectrum (ESI$^+$): m/z=206 [M+H]$^+$.

trans-10-fluoro-1,2,3,4,4a,5,6,10b-octahydro-benzo[f]quinoline; Yield: 13% of theory; TLC: r_f=0.46 (silica gel, CH$_2$Cl$_2$/MeOH/32% aqueous NH$_3$ 90:10:1); Mass spectrum (ESI$^+$): m/z=206 [M+H]$^+$.

Intermediates 17 and 18 cis-8-Phenyl-1,2,3,4,4a,5,6,10b-octahydro-benzo[f]quinoline and trans-8-Phenyl-1,2,3,4,4a,5,6,10b-octahydro-benzo[f]quinoline

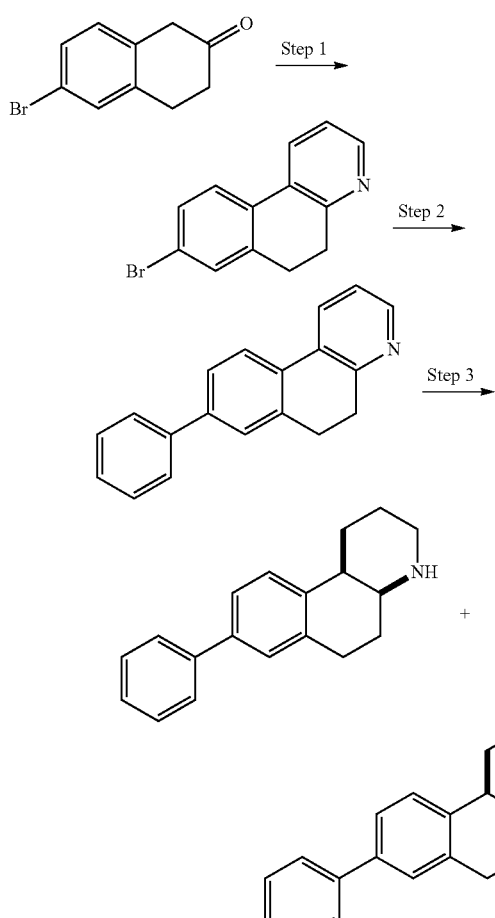

Step 1: 8-bromo-5,6-dihydro-benzo[f]quinoline

The title compound is prepared from 6-bromo-2-tetralone and propargylamine following a procedure analogous to that described in Step 1 of Intermediates 1 and 2. Yield: 69% of theory; Mass spectrum (ESI$^+$): m/z=260/262 (Br) [M+H]$^+$.

Step 2: 8-phenyl-5,6-dihydro-benzo[f]quinoline

A flask charged with a stir bar, 8-bromo-5,6-dihydro-benzo[f]quinoline (0.28 g), phenylboronic acid (0.24 g), 2 M aqueous Na$_2$CO$_3$ solution (1.1 mL), and N,N-dimethylformamide (3 ml) is sparged with argon at room temperature for 10 min. [1,1'-Bis(diphenylphosphino)-ferrocene]dichloropalladium dichloromethane complex (30 mg) is then added and the resulting mixture is heated to 90° C. and stirred at this temperature for 4 h. After cooling the mixture to room temperature, ethyl acetate and water are added and the mixture is filtered over Celite. The organic phase of the filtrate is separated and washed with brine and dried (Na$_2$SO$_4$). The solvent is evaporated and the residue is chromatographed on silica gel (cyclohexane/ethyl acetate 1:1) to afford the title compound as a solid. Yield: 0.24 g (ca. 80% pure); LC (method 1): t$_R$=3.16 min; Mass spectrum (ESI$^+$): m/z=258 [M+H]$^+$.

Step 3: cis-8-phenyl-1,2,3,4,4a,5,6,10b-octahydro-benzo[f]quinoline and trans-8-phenyl-1,2,3,4,4a,5,6,10b-octahydro-benzo[f]quinoline The title compounds are prepared from 8-phenyl-5,6-dihydro-benzo[f]quinoline following a procedure analogous to that described in Step 2 of Intermediates 1 and 2.

cis-8-Phenyl-1,2,3,4,4a,5,6,10b-octahydro-benzo[f]quinoline: Yield: 56% of theory; Mass spectrum (ESI$^+$): m/z=206 [M+H]$^+$.

trans-8-Phenyl-1,2,3,4,4a,5,6,10b-octahydro-benzo[f]quinoline: Yield: 11% of theory; Mass spectrum (ESI$^+$): m/z=206 [M+H]$^+$.

Intermediates 19 and 20 cis-1,2,3,4,4a,5,6,10b-Octahydro-benzo[f]quinoline-8-carboxylic acid methyl ester and trans-1,2,3,4,4a,5,6,10b-Octahydro-benzo[f]quinoline-8-carboxylic acid methyl ester

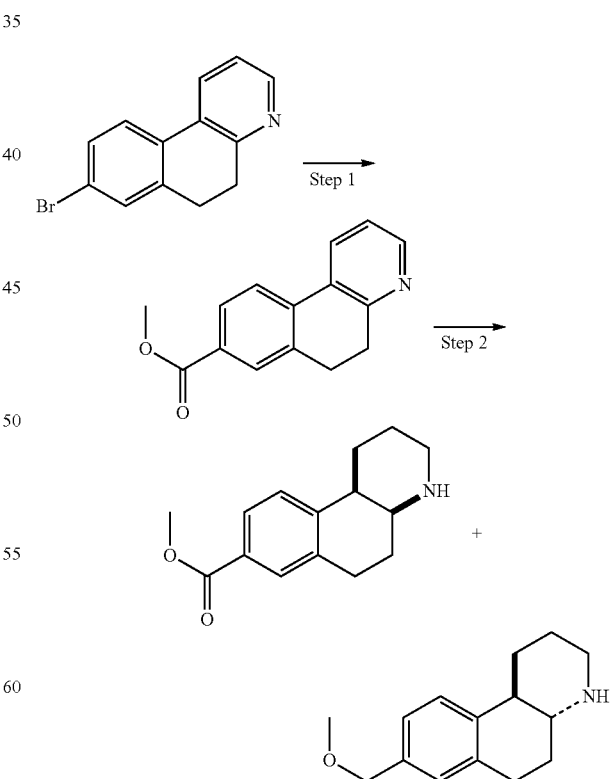

Step 1: 5,6-dihydro-benzo[f]quinoline-8-carboxylic acid methyl ester

A flask charged with 8-bromo-5,6-dihydro-benzo[f]quinoline (4.00 g), triethylamine (3.0 mL), [1,1'-bis(diphenylphosphino)ferrocene]dichloropalladium dichloromethane complex (0.63 g), N,N-dimethylformamide (5 mL), and methanol (20 ml) is flushed with argon for 5 min and with carbon monoxide for another 5 min. The mixture is then heated to 80° C. under carbon monoxide atmosphere (4 bar) and shaken at this temperature overnight. After cooling to room temperature, the mixture is filtered and concentrated under reduced pressure. The residue is taken up in ethyl acetate and washed with water and brine and dried ($Na_2SO_4$). The solvent is evaporated and the residue is chromatographed on silica gel (cyclohexane/ethyl acetate 1:1→0:1) to afford the title compound as a solid. Yield: 3.16 g (86% of theory); LC (method 1): $t_R$=2.18 min; Mass spectrum ($ESI^+$): m/z=240 $[M+H]^+$.

Step 2: cis-1,2,3,4,4a,5,6,10b-octahydro-benzo[f]quinoline-8-carboxylic acid methyl ester and trans-1,2,3,4,4a,5,6,10b-octahydro-benzo[f]quinoline-8-carboxylic acid methyl ester The title compounds are prepared from 5,6-dihydro-benzo[f]quinoline-8-carboxylic acid methyl ester following a procedure analogous to that described in Step 2 of Intermediates 1 and 2.

cis-1,2,3,4,4a,5,6,10b-octahydro-benzo[f]quinoline-8-carboxylic acid methyl ester: Yield: 79% of theory; LC (method 1): $t_R$=1.93 min; Mass spectrum ($ESI^+$): m/z=246 $[M+H]^+$.

trans-1,2,3,4,4a,5,6,10b-octahydro-benzo[f]quinoline-8-carboxylic acid methyl ester: Yield: 10% of theory; Mass spectrum ($ESI^+$): m/z=246 $[M+H]^+$.

Intermediates 21 and 22 cis-8-Benzyl-1,2,3,4,4a,5,6,10b-octahydro-benzo[f]quinoline and cis-8-Cyclohexylmethyl-1,2,3,4,4a,5,6,10b-octahydro-benzo[f]quinoline

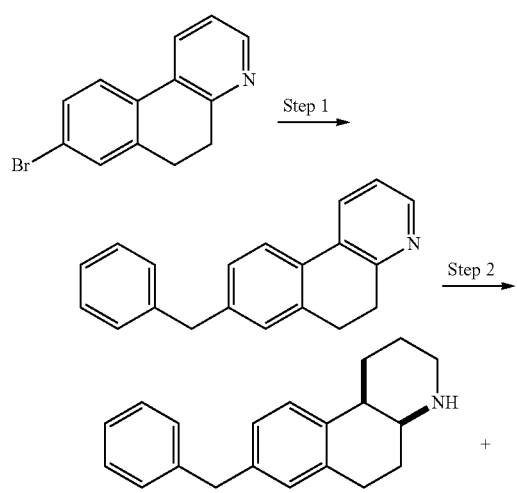

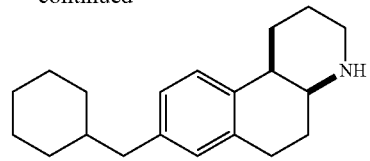

Step 1: 8-Benzyl-5,6-dihydro-benzo[f]quinoline

Benzylzinc bromide (0.5 mol/L in tetrahydrofuran, 7.7 mL) is added to a flask charged with a stir bar, tetrakis(triphenylphosphine)palladium(0) (53 mg), and 8-bromo-5,6-dihydro-benzo[f]quinoline (0.20 g) and kept under argon atmosphere at room temperature. The resulting solution is heated to reflux temperature and stirred at this temperature for 6 h. After cooling the solution to room temperature, aqueous $NH_4Cl$ solution is added and the resulting mixture is extracted with ethyl acetate. The combined extracts are washed with brine and dried ($Na_2SO_4$). The solvent is evaporated and the residue is chromatographed on silica gel (cyclohexane/ethyl acetate 4:1→1:1) to afford the title compound as an oil. Yield: 0.17 g (81% of theory); LC (method 1): $t_R$=3.08 min; Mass spectrum ($ESI^+$): m/z=272 $[M+H]^+$.

Step 2: cis-8-benzyl-1,2,3,4,4a,5,6,10b-octahydro-benzo[f]quinoline and cis-8-cyclohexyl-methyl-1,2,3,4,4a,5,6,10b-octahydro-benzo[f]quinoline The title compounds are prepared from 8-benzyl-5,6-dihydro-benzo[f]quinoline following a procedure analogous to that described in Step 2 of Intermediates 1 and 2 and obtained in a ca. 30:70 mixture that is used as such in the next reaction step. Yield: 81% of theory (ca. 30:70 mixture).

cis-8-Benzyl-1,2,3,4,4a,5,6,10b-octahydro-benzo[f]quinoline: LC-MS (method 1): $t_R$=2.91 min; Mass spectrum ($ESI^+$): m/z=278 $[M+H]^+$.

cis-8-Cyclohexyl-methyl-1,2,3,4,4a,5,6,10b-octahydro-benzo[f]quinoline: LC-MS (method 1): $t_R$=3.41 min; Mass spectrum ($ESI^+$): m/z=284 $[M+H]^+$.

Intermediate 23 cis-4-(1H-Benzoimidazole-5-carbonyl)-1,2,3,4,4a,5,6,10b-octahydro-benzo[f]quinoline-10-carboxylic acid methyl ester

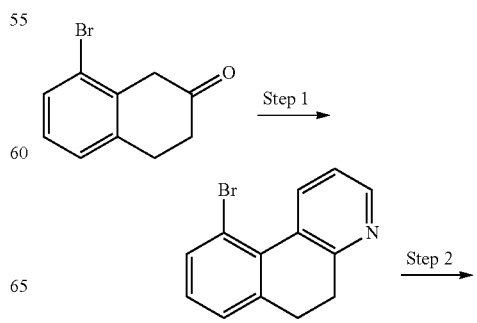

-continued

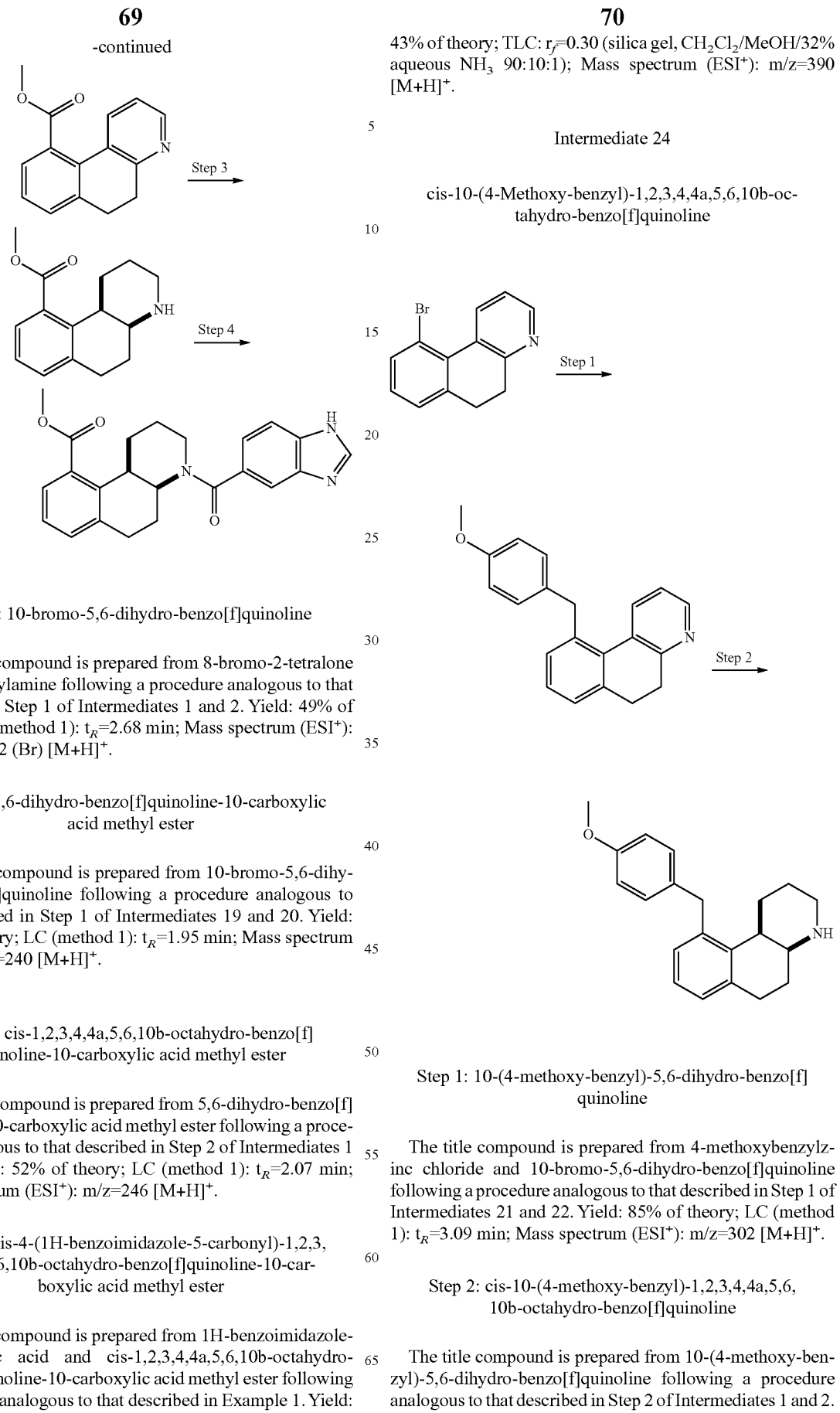

Step 1: 10-bromo-5,6-dihydro-benzo[f]quinoline

The title compound is prepared from 8-bromo-2-tetralone and propargylamine following a procedure analogous to that described in Step 1 of Intermediates 1 and 2. Yield: 49% of theory; LC (method 1): $t_R$=2.68 min; Mass spectrum (ESI$^+$): m/z=260/262 (Br) [M+H]$^+$.

Step 2: 5,6-dihydro-benzo[f]quinoline-10-carboxylic acid methyl ester

The title compound is prepared from 10-bromo-5,6-dihydro-benzo[f]quinoline following a procedure analogous to that described in Step 1 of Intermediates 19 and 20. Yield: 84% of theory; LC (method 1): $t_R$=1.95 min; Mass spectrum (ESI$^+$): m/z=240 [M+H]$^+$.

Step 3: cis-1,2,3,4,4a,5,6,10b-octahydro-benzo[f]quinoline-10-carboxylic acid methyl ester The title compound is prepared from 5,6-dihydro-benzo[f]quinoline-10-carboxylic acid methyl ester following a procedure analogous to that described in Step 2 of Intermediates 1 and 2. Yield: 52% of theory; LC (method 1): $t_R$=2.07 min; Mass spectrum (ESI$^+$): m/z=246 [M+H]$^+$.

Step 4: cis-4-(1H-benzoimidazole-5-carbonyl)-1,2,3,4,4a,5,6,10b-octahydro-benzo[f]quinoline-10-carboxylic acid methyl ester The title compound is prepared from 1H-benzoimidazole-5-carboxylic acid and cis-1,2,3,4,4a,5,6,10b-octahydro-benzo[f]quinoline-10-carboxylic acid methyl ester following a procedure analogous to that described in Example 1. Yield: 43% of theory; TLC: $r_f$=0.30 (silica gel, CH$_2$Cl$_2$/MeOH/32% aqueous NH$_3$ 90:10:1); Mass spectrum (ESI$^+$): m/z=390 [M+H]$^+$.

Intermediate 24 cis-10-(4-Methoxy-benzyl)-1,2,3,4,4a,5,6,10b-octahydro-benzo[f]quinoline

Step 1: 10-(4-methoxy-benzyl)-5,6-dihydro-benzo[f]quinoline

The title compound is prepared from 4-methoxybenzylzinc chloride and 10-bromo-5,6-dihydro-benzo[f]quinoline following a procedure analogous to that described in Step 1 of Intermediates 21 and 22. Yield: 85% of theory; LC (method 1): $t_R$=3.09 min; Mass spectrum (ESI$^+$): m/z=302 [M+H]$^+$.

Step 2: cis-10-(4-methoxy-benzyl)-1,2,3,4,4a,5,6,10b-octahydro-benzo[f]quinoline The title compound is prepared from 10-(4-methoxy-benzyl)-5,6-dihydro-benzo[f]quinoline following a procedure analogous to that described in Step 2 of Intermediates 1 and 2.

Yield: 12% of theory; LC-MS (method 1): $t_R$=2.82 min; Mass spectrum (ESI$^+$): m/z=308 [M+H]$^+$.

Intermediate 25 cis-6,6-Dimethyl-1,2,3,4,4a,5,6,10b-octahydro-benzo[f]quinoline

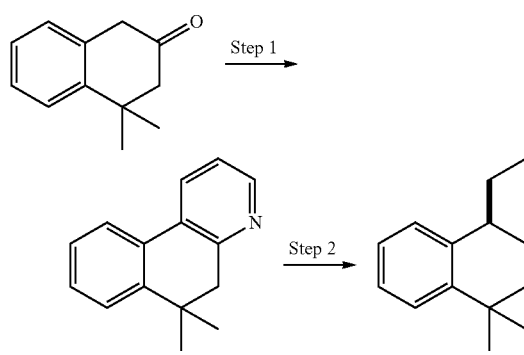

Step 1: 6,6-dimethyl-5,6-dihydro-benzo[f]quinoline

The title compound is prepared from 4,4-dimethyl-3,4-dihydro-1H-naphthalen-2-one and propargylamine following a procedure analogous to that described in Step 1 of Intermediates 1 and 2. Yield: 49% of theory; LC (method 1): $t_R$=2.40 min; Mass spectrum (ESI$^+$): m/z=210 [M+H]$^+$.

Step 2: cis-6,6-Dimethyl-1,2,3,4,4a,5,6,10b-octahydro-benzo[f]quinoline

The title compounds is prepared from 6,6-dimethyl-5,6-dihydro-benzo[f]quinoline following a procedure analogous to that described in Step 2 of Intermediates 1 and 2. Yield: 72% of theory; LC-MS (method 1): $t_R$=2.38 min; Mass spectrum (ESI$^+$): m/z=216 [M+H]$^+$.

Intermediate 26 cis-4-(1H-Benzoimidazole-5-carbonyl)-1,2,3,4,4a,5,6,10b-octahydro-benzo[f]quinoline-10-carboxylic acid

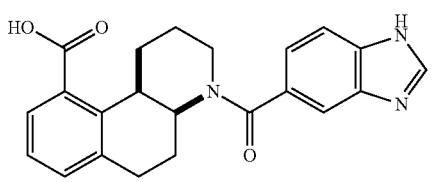

The title compound is prepared from cis-4-(1H-benzoimidazole-5-carbonyl)-1,2,3,4,4a,5,6,10b-octahydro-benzo[f]quinoline-10-carboxylic acid methyl ester following a procedure analogous to that described in Example 35 except for stirring the solution at 50° C. Yield: 69% of theory; Mass spectrum (ESI$^+$): m/z=376 [M+H]$^+$.

Intermediate 27 cis-8-(4-Methoxy-phenoxy)-1,2,3,4,4a,5,6,10b-octahydro-benzo[f]quinoline

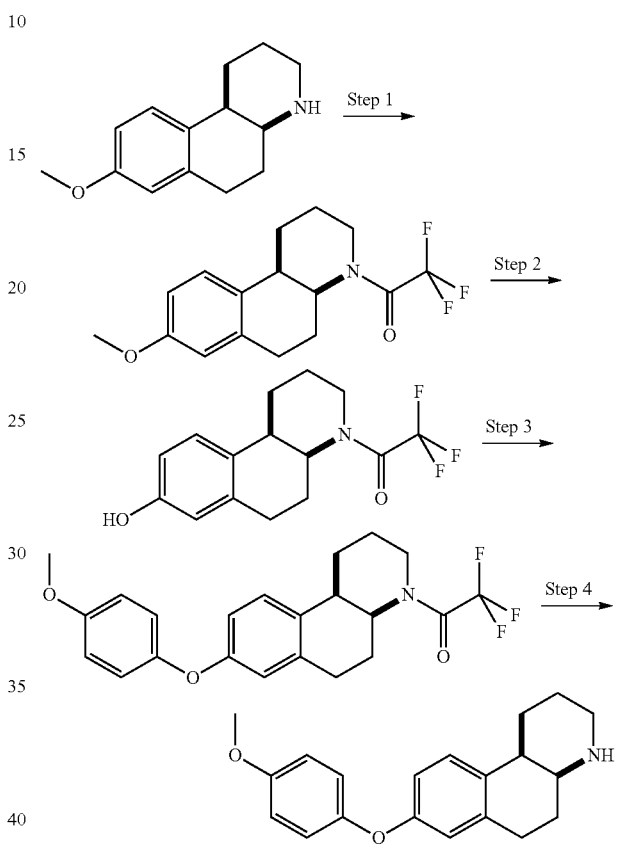

Step 1: cis-2,2,2-trifluoro-1-(8-methoxy-2,3,4a,5,6,10b-hexahydro-1H-benzo[f]quinolin-4-yl)-ethanone Trifluoroacetic anhydride (0.75 mL) is added to a solution of cis-8-methoxy-1,2,3,4,4a,5,6,10b-octahydro-benzo[f]quinoline (0.79 g) and triethylamine (0.90 mL) in dichloromethane (10 mL) chilled in an ice bath. The cooling bath is removed and the solution is stirred at room temperature overnight. Water and dichloromethane are then added and stirring is continued for another 30 min. The organic phase is separated and washed with aqueous NaHCO$_3$ solution and dried (Na$_2$SO$_4$). The solvent is evaporated to afford the title compound as a solid. Yield: 100% of theory; LC (method 1): $t_R$=4.38 min; Mass spectrum (ESI$^+$): m/z=3.14 [M+H]$^+$.

Step 2: cis-2,2,2-trifluoro-1-(8-hydroxy-2,3,4a,5,6,10b-hexahydro-1H-benzo[f]quinolin-4-yl)-ethanone The title compound is prepared from cis-2,2,2-trifluoro-1-(8-methoxy-2,3,4a,5,6,10b-hexahydro-1H-benzo[f]quinolin-4-yl)-ethanone following a procedure analogous to that described in Example 7. Yield: 93% of theory; LC (method 1): $t_R$=3.58 min; Mass spectrum (ESI$^+$): m/z=300 [M+H]$^+$.

Step 3: cis-2,2,2-trifluoro-1-[8-(4-methoxy-phenoxy)-2,3,4a,5,6,10b-hexahydro-1H-benzo[f]quinolin-4-yl]-ethanone A mixture of cis-2,2,2-trifluoro-1-(8-hydroxy-2,3,4a,5,6,10b-hexahydro-1H-benzo[f]quinolin-4-yl)-ethanone (0.98 g), 4-methoxyphenylboronic acid (1.00 g), pyridine (1.30 mL), copper(II) acetate (0.60 g), molecular sieves 3 Å (3.60 g), and dichloromethane (15 mL) is stirred in air at room temperature overnight. The mixture is diluted with dichloromethane and filtered over Celite. The filtrate is concentrated and the residue is chromatographed on silica gel (dichloromethane/methanol containing 1% NH$_3$ 99:1→95:5) to give the title compound as a colorless resin-like solid. Yield: 1.05 g (79% of theory); LC (method 1): t$_R$=5.00 min; Mass spectrum (ESI$^+$): m/z=406 [M+H]$^+$.

Step 4: cis-8-(4-methoxy-phenoxy)-1,2,3,4,4a,5,6,10b-octahydro-benzo[f]quinoline 1 M aqueous NaOH solution (10 mL) is added to a solution of cis-2,2,2-trifluoro-1-[8-(4-methoxy-phenoxy)-2,3,4a,5,6,10b-hexahydro-1H-benzo[f]quinolin-4-yl]-ethanone (0.95 g) in tetrahydrofuran (10 mL) at room temperature. The resulting solution is stirred at 35° C. overnight and then cooled to room temperature. The solution is extracted with ethyl acetate, the combined extracts are washed with brine and dried (Na$_2$SO$_4$). The solvent is evaporated and the residue is chromatographed on silica gel (dichloromethane/methanol containing 1% NH$_3$ 95:5→70:30) to give the title compound as a colorless resin-like solid. Yield: 0.64 g (88% of theory); LC (method 1): t$_R$=2.75 min; Mass spectrum (ESI$^+$): m/z=310 [M+H]$^+$.

Intermediates 28 and 29 cis-1,2,3,4,4a,5,6,10b-Octahydro-benzo[f]quinolin-9-ylamine and trans-1,2,3,4,4a,5,6,10b-Octahydro-benzo[f]quinolin-9-ylamine

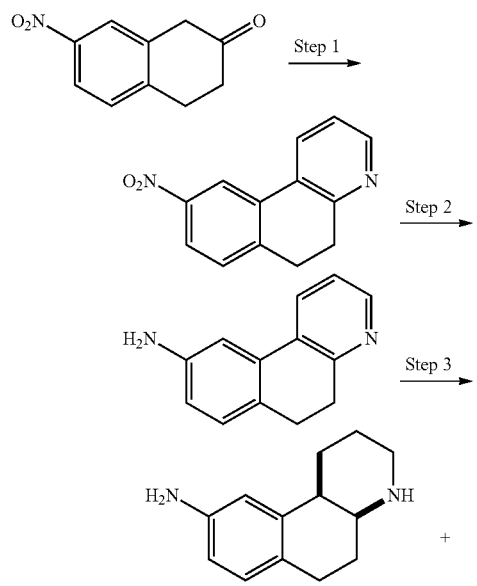

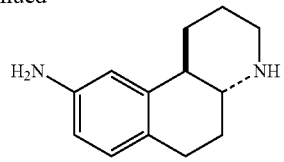

Step 1: 9-nitro-5,6-dihydro-benzo[f]quinoline

The title compound is prepared from 7-nitro-2-tetralone and propargylamine following a procedure analogous to that described in Step 1 of Intermediates 1 and 2. Yield: 41% of theory; LC (method 1): t$_R$=2.20 min; Mass spectrum (ESI$^+$): m/z=227 [M+H]$^+$.

Step 2: 9-amino-5,6-dihydro-benzo[f]quinoline

A mixture of 9-nitro-5,6-dihydro-benzo[f]quinoline (1.90 g), 10% palladium on carbon (0.20 g), and methanol (10 mL) is shaken under hydrogen atmosphere (3 bar) at room temperature for 3 h. The catalyst is then separated by filtration and the filtrate is concentrated to give an oil that is submitted to the next reaction without further purification. Yield: 1.67 g (crude); Mass spectrum (ESI$^+$): m/z=197 [M+H]$^+$.

Step 3: cis-1,2,3,4,4a,5,6,10b-octahydro-benzo[f]quinolin-9-ylamine and trans-1,2,3,4,4a,5,6,10b-octahydro-benzo[f]quinolin-9-ylamine The title compounds are prepared from 9-amino-5,6-dihydro-benzo[f]quinoline following a procedure analogous to that described in Step 2 of Intermediates 1 and 2.
cis-1,2,3,4,4a,5,6,10b-octahydro-benzo[f]quinolin-9-ylamine: Yield: 40% of theory; LC (method 2): t$_R$=2.50 min; Mass spectrum (ESI$^+$): m/z=203 [M+H]$^+$.
trans-1,2,3,4,4a,5,6,10b-octahydro-benzo[f]quinolin-9-ylamine: Yield: 24% of theory; LC (method 2): t$_R$=2.70 min; Mass spectrum (ESI$^+$): m/z=203 [M+H]$^+$.

Intermediate 30 cis-1,2,3,4,4a,5,6,10b-Octahydro-benzo[f]quinoline-9-carbonitrile

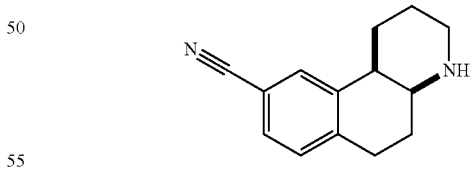

Sodium nitrite (0.12 g) dissolved in water (0.7 mL) is added dropwise to a solution of cis-1,2,3,4,4a,5,6,10b-octahydro-benzo[f]quinolin-9-ylamine (0.36 g) in half-concentrated sulfuric acid (0.6 ml) cooled to ca. −5° C. The solution is stirred for 15 min in the cooling bath prior to the addition of urea (30 mg). The resulting solution is added to a vigorously stirred solution of sodium cyanide (0.32 g) and copper(I) cyanide (0.19 g) in water (1.4 mL) cooled to ca. −5° C. The mixture is stirred in the cooling bath for another 10 min and then the cooling bath is removed. After stirring at room temperature for 10 min, the mixture is heated to 70° C. and stirred at this temperature for 1 h. The mixture is cooled to room temperature, basified with 4 M NaOH solution (1.5 mL), and extracted with dichloromethane. The combined extracts are dried (Na₂SO₄) and the solvent is evaporated. The residue is chromatographed on silica gel [dichloromethane/(dichloromethane/methanol/NH₄OH 50:48:2) 80:20→40:60] to give the title compound as a resin-like solid. Yield: 0.12 g (31% of theory); Mass spectrum (ESI⁺): m/z=213 [M+H]⁺.

Intermediate 31 trans-1,2,3,4,4a,5,6,10b-Octahydro-benzo[f]quinoline-9-carbonitrile

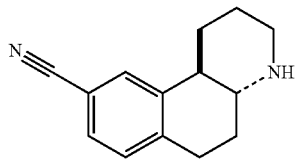

The title compound is prepared from trans-1,2,3,4,4a,5,6,10b-octahydro-benzo[f]quinolin-9-ylamine following a procedure analogous to that described for Intermediate 30. Yield: 22% of theory; LC (method 1): $t_R$=1.64 min; Mass spectrum (ESI⁺): m/z=213 [M+H]⁺.

Intermediate 32 cis-10-(6-Methyl-pyridazin-3-yloxy)-1,2,3,4,4a,5,6,10b-octahydro-benzo[f]quinoline

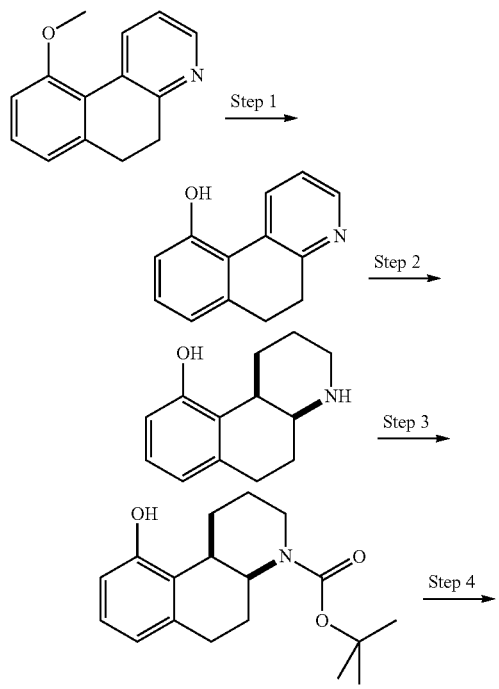

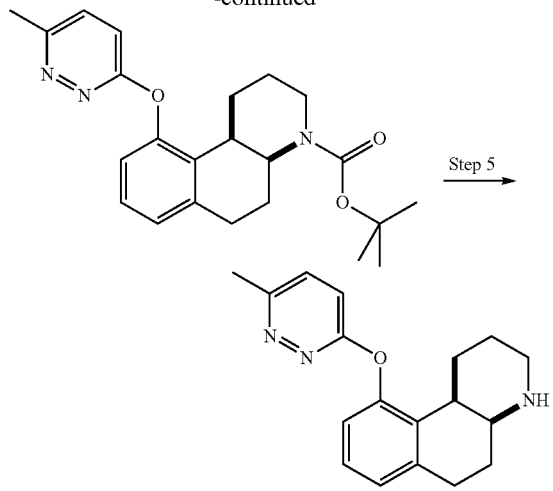

Step 1: 5,6-dihydro-benzo[f]quinolin-10-ol

The title compound is prepared from 10-methoxy-5,6-dihydro-benzo[f]quinoline following a procedure analogous to that described for Example 7. Yield: 94% of theory; LC (method 1): $t_R$=1.48 min; Mass spectrum (ESI⁺): m/z=198 [M+H]⁺.

Step 2: cis-1,2,3,4,4a,5,6,10b-octahydro-benzo[f]quinolin-10-ol

The title compound is prepared from 5,6-dihydro-benzo[f]quinolin-10-ol following a procedure analogous to that described in Step 2 of Intermediates 1 and 2. Yield: 60% of theory; LC (method 2): $t_R$=2.71 min; Mass spectrum (ESI⁺): m/z=204 [M+H]⁺.

Step 3: cis-10-hydroxy-2,3,4a,5,6,10b-hexahydro-1H-benzo[f]quinoline-4-carboxylic acid tert-butyl ester Di-tert-butyl dicarbonate (0.69 g) is added to a solution of cis-1,2,3,4,4a,5,6,10b-octahydro-benzo[f]quinolin-10-ol (0.64 g) and triethylamine (0.5 mL) in dichloromethane (25 mL) at room temperature. The solution is stirred at room temperature overnight and then diluted with dichloromethane. The resulting solution is washed with 2 M aqueous citric acid and brine, dried (Na₂SO₄), and concentrated. The residue is treated with little methanol and the precipitate formed thereafter is separated by filtration and dried to give the title compound as a colorless solid. Yield: 0.35 g (37% of theory); LC (method 1): $t_R$=4.20 min; Mass spectrum (ESI⁺): m/z=304 [M+H]⁺.

Step 4: cis-10-(6-methyl-pyridazin-3-yloxy)-2,3,4a,5,6,10b-hexahydro-1H-benzo[f]quinoline-4-carboxylic acid tert-butyl ester A mixture of cis-10-hydroxy-2,3,4a,5,6,10b-hexahydro-1H-benzo[f]quinoline-4-carboxylic acid tert-butyl ester (0.40 g), 3-chloro-6-methyl-pyridazine (0.13 g), cesium carbonate (0.35 g), and N-methylpyrrolidinone (5 mL) is stirred at 150° C. for 1.5 h. After cooling to room temperature, the mixture is diluted with ethyl acetate and washed with water and brine and dried (Na₂SO₄). The solvent is evaporated and the residue is chromatographed on silica gel (cyclohexane/ ethyl acetate 3:1→1:2) to give the title compound. Yield: 0.14 g (impure); LC (method 1): $t_R$=4.19 min; Mass spectrum (ESI$^+$): m/z=396 [M+H]$^+$.

Step 5: cis-10-(6-methyl-pyridazin-3-yloxy)-1,2,3,4, 4a,5,6,10b-octahydro-benzo[f]quinoline Hydrochloric acid (4 mol/L in 1,4-dioxane, 0.7 mL) is added to a solution of cis-10-(6-methyl-pyridazin-3-yloxy)-2,3,4a,5,6,10b-hexahydro-1H-benzo[f]quinoline-4-carboxylic acid tert-butyl ester (0.13 g) in dichloromethane (5 mL) at room temperature. The solution is stirred at room temperature for 2 h and then concentrated to give the crude title compound as its hydrochloric acid salt that is used without further purification. Yield: 0.12 g (crude); LC (method 1): $t_R$=1.90 min; Mass spectrum (ESI$^+$): m/z=296 [M+H]$^+$.

Intermediate 33 cis-2,3,4,4a,9,9a-Hexahydro-1H-indeno[2,1-b]pyridine

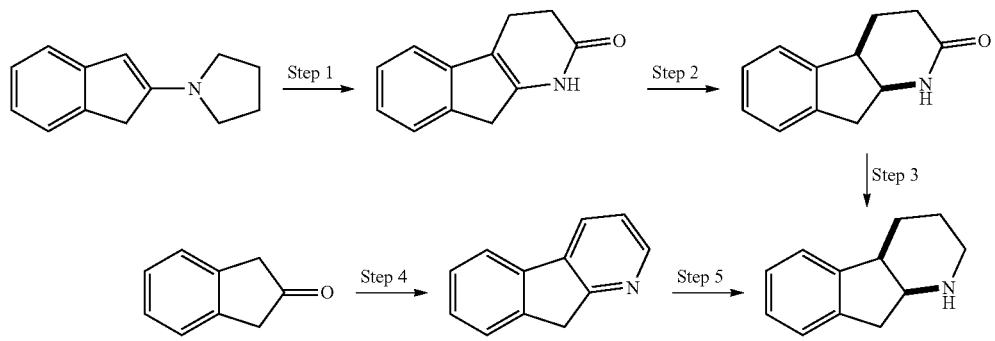

Step 1: 1,3,4,9-tetrahydro-indeno[2,1-b]pyridin-2-one

A mixture of 1-(1H-inden-2-yl)-pyrrolidine (5.34 g) and acrylamide (6.15 g) is stirred in argon atmosphere at 100° C. for 30 min. The temperature is then rised to 130° C. and stirring continued for another 15 min. After cooling to room temperature, water (50 mL) and acetic acid (5 drops) are added and the mixture is stirred for 30 min. The mixture is filtered and the organic phase of the filtrate is separated and washed with brine. After drying (MgSO$_4$) and evaporating the solvent, the residue is chromatographed on silica gel (cyclohexane/ethyl acetate 1:1→0:1) to give a brown solid that is triturated with ethyl acetate and dried to afford the title compound. Yield: 1.12 g (21% of theory); Mass spectrum (ESI$^+$): m/z=186 [M+H]$^+$.

Step 2: cis-1,3,4,4a,9,9a-hexahydro-indeno[2,1-b] pyridin-2-one

A mixture of 1,3,4,9-tetrahydro-indeno[2,1-b]pyridin-2-one (1.10 g), 10% palladium on carbon (0.15 g), acetic acid (0.75 mL), and methanol (20 mL) is shaken under hydrogen atmosphere (3 bar) at room temperature for 6 h. The catalyst is then separated by filtration and the filtrate is concentrated. The residue is triturated with tert-butyl methyl ether and dried to give the title compound as a colorless solid. Yield: 0.99 g (89% of theory); LC (method 1): $t_R$=2.53 min; Mass spectrum (ESI$^+$): m/z=188 [M+H]$^+$.

Step 3: cis-2,3,4,4a,9,9a-hexahydro-1H-indeno[2,1-b]pyridine

Lithium aluminum hydride (1 mol/L in tetrahydrofuran, 12 mL) is added to a solution of cis-1,3,4,4a,9,9a-hexahydro-indeno[2,1-b]pyridin-2-one (0.95 g) in tetrahydrofuran (15 mL) at room temperature. The resulting solution is heated to reflux temperature and stirred at this temperature for 2 h. After cooling to room temperature, the solution is poured into ice-cold water, 1 M aqueous NaOH solution and ethyl acetate are added, and the resulting mixture is filtered over Celite. The aqueous phase of the filtrate is separated and extracted with ethyl acetate and the extracts are combined with the organic phase of the filtrate. The organic phase is washed with brine and dried (MgSO$_4$). The solvent is evaporated to give the title compound as a colorless solid. Yield: 0.83 g (94% of theory); LC (method 1): $t_R$=1.29 min; Mass spectrum (ESI$^+$): m/z=174 [M+H]$^+$.

Alternatively, Intermediate 33 is obtained as follows:

Step 4: 9H-indeno[2,1-b]pyridine

The title compound is prepared from 2-indanone and propargylamine following a procedure analogous to that described in Step 1 of Intermediates 1 and 2. Yield: 56% of theory; Mass spectrum (ESI$^+$): m/z=168 [M+H]$^+$.

Step 5: cis-2,3,4,4a,9,9a-hexahydro-1H-indeno[2,1-b]pyridine

A mixture of 9H-indeno[2,1-b]pyridine (0.20 g), PtO$_2$ (70 mg), concentrated aqueous hydrochloric acid (0.1 mL), and ethanol (10 mL) is shaken under hydrogen atmosphere (2 bar) at room temperature for 16 h (in case the transformation is not complete after this time another portion of PtO$_2$ (30 mg) is added and shaking under hydrogen is continued until complete). The catalyst is separated by filtration and the solvent is evaporated to give the crude title compound as its hydrochloric acid salt that is used without further purification. Yield: 0.25 g (crude); Mass spectrum (ESI+): m/z=174 [M+H]+.

Intermediates 34 and 35 cis-1-(1H-Benzoimidazole-5-carbonyl)-2,3,4,4a,9,9a-hexahydro-1H-indeno[2,1-b]pyridine-6-carboxylic acid methyl ester and cis-1-(1H-Benzoimidazole-5-carbonyl)-2,3,4,4a,9,9a-hexahydro-1H-indeno[2,1-b]pyridine-7-carboxylic acid methyl ester

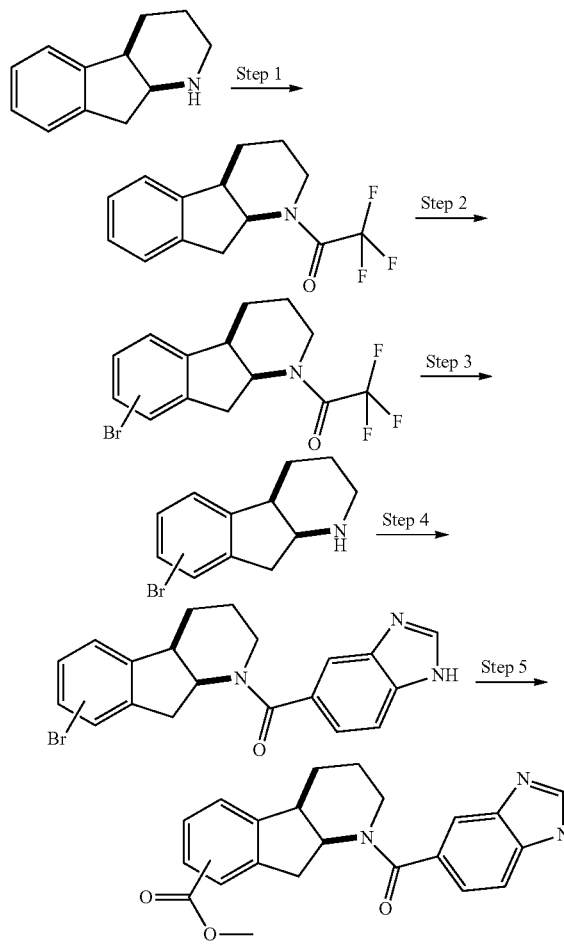

Step 1: 2,2,2-trifluoro-1-(cis-2,3,4,4a,9,9a-hexahydro-indeno[2,1-b]pyridin-1-yl)-ethanone The title compound is prepared from cis-2,3,4,4a,9,9a-hexahydro-1H-indeno[2,1-b]pyridine following a procedure analogous to that described in Step 1 of Intermediate 27. Yield: 76% of theory; Mass spectrum (ESI+): m/z=270 [M+H]+.

Step 2: cis-1-(6-bromo-2,3,4,4a,9,9a-hexahydro-indeno[2,1-b]pyridin-1-yl)-2,2,2-trifluoro-ethanone and cis-1-(7-bromo-2,3,4,4a,9,9a-hexahydro-indeno[2,1-b]pyridin-1-yl)-2,2,2-trifluoro-ethanone Bromine (0.80 mL) is added to a suspension of 2,2,2-trifluoro-1-(cis-2,3,4,4a,9,9a-hexahydro-indeno[2,1-b]pyridin-1-yl)-ethanone (4.00 g) in water (32 mL) at room temperature. The mixture is heated to 70° C. and stirred at this temperature for 4 h. After cooling to room temperature, aqueous Na2S2O3 solution is added and the resulting mixture is extracted with dichloromethane. The combined extracts are dried (Na2SO4) and the solvent is removed under reduced pressure. The residue is purified by chromatography on silica gel (cyclohexane/ethyl acetate 1:1) to give a mixture of the two title compounds and small amounts of further monobrominated isomers. Yield: 3.40 g (66% of theory); LC (method 1): $t_R$=4.70 min; Mass spectrum (ESI+): m/z=348/350 (Br) [M+H]+.

Step 3: cis-6-bromo-2,3,4,4a,9,9a-hexahydro-1H-indeno[2,1-b]pyridine and cis-7-bromo-2,3,4,4a,9,9a-hexahydro-1H-indeno[2,1-b]pyridine The title compounds are prepared from the compound mixture in Step 2 above following a procedure analogous to that described in Step 4 of Intermediate 27 and submitted as an isomeric mixture to the next step. Yield: 69% of theory.

Step 4: cis-(1H-benzoimidazol-5-yl)-(6-bromo-2,3,4,4a,9,9a-hexahydro-indeno[2,1-b]pyridin-1-yl)-methanone and cis-(1H-benzoimidazol-5-yl)-(7-bromo-2,3,4,4a,9,9a-hexahydro-indeno[2,1-b]pyridin-1-yl)-methanone The title compounds are prepared from the isomeric mixture in Step 3 above following a procedure analogous to that described for Example 1 and submitted as an isomeric mixture to the next step. Yield: 85% of theory (ca. 85% pure); Mass spectrum (ESI+): m/z=396/398 (Br) [M+H]+.

Step 5: cis-1-(1H-benzoimidazole-5-carbonyl)-2,3,4,4a,9,9a-hexahydro-1H-indeno[2,1-b]pyridine-6-carboxylic acid methyl ester and cis-1-(1H-benzoimidazole-5-carbonyl)-2,3,4,4a,9,9a-hexahydro-1H-indeno[2,1-b]pyridine-7-carboxylic acid methyl ester The title compounds are prepared from the isomeric mixture obtained in Step 4 above following a procedure analogous to that described in Step 1 of Intermediates 19 and 20 and submitted as an isomeric mixture to the next step. Yield: 80% of theory (ca. 90% pure); Mass spectrum (ESI+): m/z=376 [M+H]+.

Intermediates 36 and 37

(4a-R,9a-S)-6-Bromo-2,3,4,4a,9,9a-hexahydro-1H-indeno[2,1-b]pyridine and (4a-R,9a-S)-7-Bromo-2,3,4,4a,9,9a-hexahydro-1H-indeno[2,1-b]pyridine

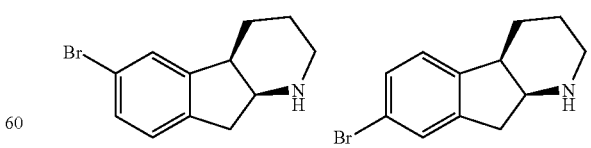

The title compounds are prepared as described in Step 3 of Intermediates 34 and 35 and the obtained isomeric mixture (2.2 g) is submitted to SFC on chiral phase (column: DAICEL IC 250×20 mm, 5 μm; mobile phase: methanol containing 0.2% diethylamine/sc carbon dioxide 20:80; flow rate: 70 mL/min) to give pure (4a-R,9a-S)-7-bromo-2,3,4,4a,9,9a-hexahydro-1H-indeno[2,1-b]pyridine [0.23 g; LC (chiral SFC as described): $t_R$=16.27 min] and a mixture of (4a-R,9a-S)-6-bromo-2,3,4,4a,9,9a-hexahydro-1H-indeno[2,1-b]pyridine with its enantiomer and another isomer which is submitted to a second SFC on chiral phase (column: DAICEL ADH 250×20 mm, 5 μm; mobile phase: isopropanol containing 0.2% diethylamine/sc carbon dioxide 15:85; flow rate: 70 mL/min) to afford pure (4a-R,9a-S)-6-bromo-2,3,4,4a,9,9a-hexahydro-1H-indeno[2,1-b]pyridine [0.21 g; LC (second chiral SFC as described): $t_R$=20.30 min].

Intermediate 38

(1H-Benzoimidazol-5-yl)-[(4a-R,9a-S)-6-bromo-2,3,4,4a,9,9a-hexahydro-1H-indeno[2,1-b]pyridin-1-yl]-methanone

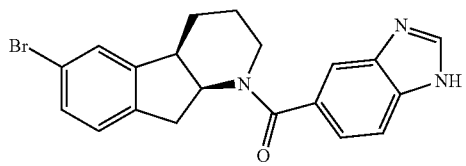 [SMILES: O=C(c1ccc2[nH]cnc2c1)N1CCC[C@@H]2c3cc(Br)ccc3C[C@@H]21]

The title compound is prepared from 1H-benzoimidazole-5-carboxylic acid and (4a-R,9a-S)-6-bromo-2,3,4,4a,9,9a-hexahydro-1H-indeno[2,1-b]pyridine following a procedure analogous to that described in Example 1. Yield: 95% of theory; LC (method 1): $t_R$=2.83 min; Mass spectrum (ESI$^+$): m/z=396/398 (Br) [M+H]$^+$.

Intermediate 39

(1H-Benzoimidazol-5-yl)-[(4a-R,9a-S)-7-bromo-2,3,4,4a,9,9a-hexahydro-indeno[2,1-b]pyridin-1-yl]-methanone

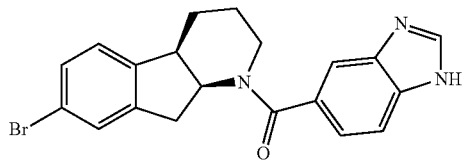 [SMILES: O=C(c1ccc2[nH]cnc2c1)N1CCC[C@@H]2c3ccc(Br)cc3C[C@@H]21]

The title compound is prepared from 1H-benzoimidazole-5-carboxylic acid and (4a-R,9a-S)-7-bromo-2,3,4,4a,9,9a-hexahydro-1H-indeno[2,1-b]pyridine following a procedure analogous to that described in Example 1. Yield: 94% of theory; LC (method 1): $t_R$=2.88 min; Mass spectrum (ESI$^+$): m/z=396/398 (Br) [M+H]$^+$.

Intermediate 40 trans-10b-Ethyl-1,2,3,4,4a,5,6,10b-octahydro-benzo[f]quinoline

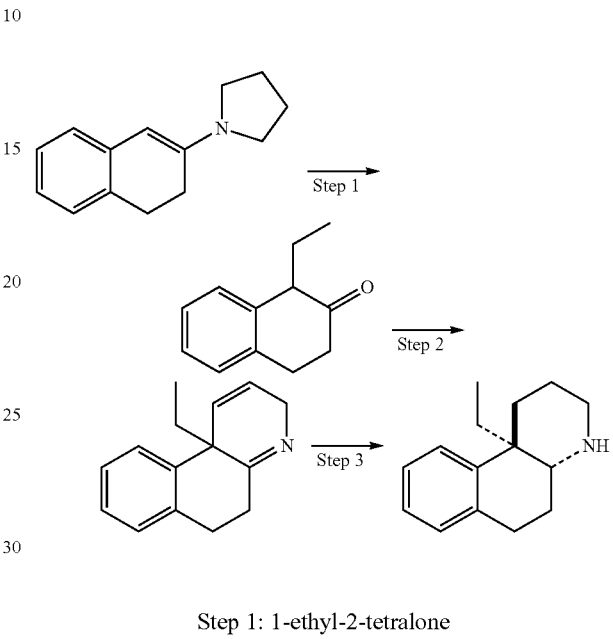

Step 1: 1-ethyl-2-tetralone

Ethyl iodide (0.81 mL) is added to a solution of 1-(3,4-dihydro-naphthalen-2-yl)-pyrrolidine (2.05 g) in acetonitrile (20 mL). The solution is heated to reflux temperature and stirred at this temperature for 4 h. Another portion of ethyl iodide (0.3 mL) is then added and stirring continued overnight. After cooling to room temperature, the solution is concentrated and treated with water and 2 M aqueous citric acid. The resulting mixture is heated to 50° C. and stirred at this temperature for 15 min. After cooling to room temperature, the mixture is extracted with ethyl acetate and the combined extracts are washed with aqueous NaHCO$_3$ solution and brine and dried (Na$_2$SO$_4$). The solvent is evaporated and the residue is chromatographed on silica gel (cyclohexane/ethyl acetate 98:2→80:20) to afford the title compound as an oil. Yield: 0.20 g (11% of theory); Mass spectrum (ESI$^+$): m/z=175 [M+H]$^+$.

Step 2: 10b-ethyl-3,5,6,10b-tetrahydro-benzo[f]quinoline

The title compound is obtained from propargylamine and 1-ethyl-2-tetralone following a procedure analogous to that described in Step 1 for Intermediates 7 and 8. Yield: 19% of theory; LC (method 1): $t_R$=2.06 min; Mass spectrum (ESI$^+$): m/z=212 [M+H]$^+$.

Step 3: trans-10b-ethyl-1,2,3,4,4a,5,6,10b-octahydro-benzo[f]quinoline

The title compound is obtained from 10b-ethyl-3,5,6,10b-tetrahydro-benzo[f]quinoline following a procedure analogous to that described in Step 2 for Intermediates 7 and 8.

Yield: 67% of theory; TLC: $r_f$=0.45 (silica gel, CH$_2$Cl$_2$/MeOH/32% aqueous NH$_3$ 90:10:1); Mass spectrum (ESI$^+$): m/z=216 [M+H]$^+$.

Intermediate 41 cis-6-Methoxy-2,3,4,4a,9,9a-hexahydro-1H-indeno[2,1-b]pyridine

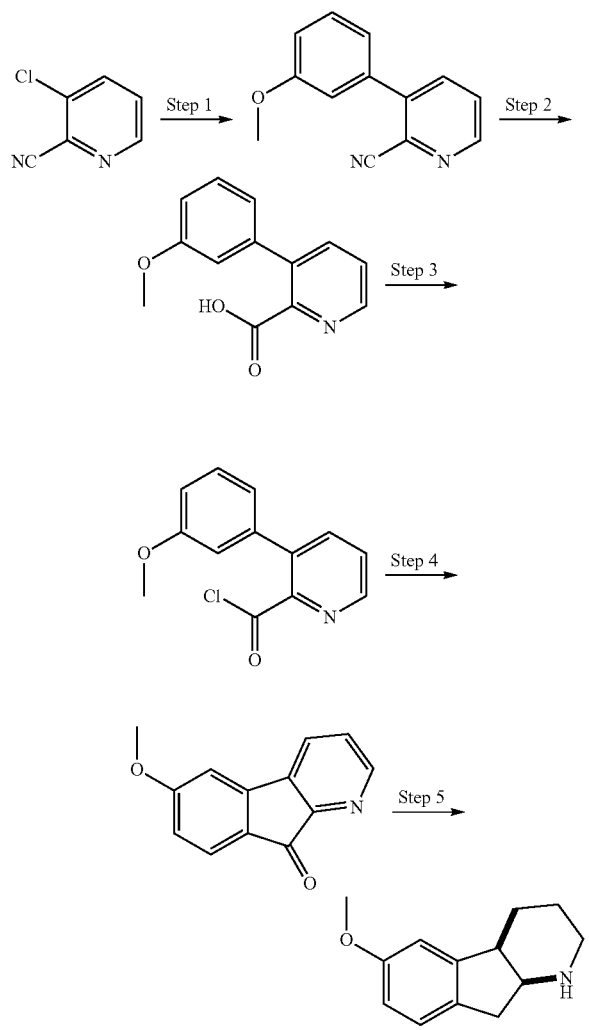

Step 1: 3-(3-methoxy-phenyl)-pyridine-2-carbonitrile

A flask charged with a stir bar, 3-chloro-2-cyanopyridine (8.16 g), 3-methoxyphenylboronic acid (13.42 g), K$_3$PO$_4$ (25.00 g), and toluene (100 mL) is sparged with argon for 10 min. Palladium(II) acetate (0.13 g) and n-butyl-di-(1-adamantyl)-phosphine (0.42 g) are added and the resulting mixture is put in a 100° C. hot oil bath and stirred in there for 3.5 h. After cooling to room temperature, ethyl acetate (250 mL) is added and the mixture is washed with 2 M aqueous NaOH solution and brine. The organic phase is dried (Na$_2$SO$_4$) and the solvent is evaporated. The residue is triturated with methanol and dried to give the title compound as a colorless solid. Yield: 12.05 g (97% of theory); LC (method 1): $t_R$=3.32 min; Mass spectrum (ESI$^+$): m/z=211 [M+H]$^+$.

Step 2: 3-(3-methoxy-phenyl)-pyridine-2-carboxylic acid

A mixture of 3-(3-methoxyphenyl)-pyridine-2-carbonitrile (12.00 g), 15 M aqueous NaOH solution (40 mL), and methanol (60 mL) is stirred at reflux temperature for 7 h. After cooling to room temperature, most of the methanol is evaporated and the residue is cooled in an ice bath and adjusted to pH value ca. 4-5 by the careful addition of concentrated hydrochloric acid. The resulting mixture is concentrated to ca. 50 ml by evaporation and extracted with dichloromethane/methanol (9:1) several times. The aqueous phase is then adjusted to pH value 2-3 using concentrated hydrochloric acid and extracted again with dichloromethane/methanol (9:1). The combined extracts are dried (Na$_2$SO$_4$) and the solvent is evaporated to give the title compound as a foam-like solid. Yield: 11.88 g (91% of theory); LC (method 1): $t_R$=1.70 min; Mass spectrum (ESI$^+$): m/z=230 [M+H]$^+$.

Step 3: 3-(3-methoxy-phenyl)-pyridine-2-carbonyl chloride

Thionyl chloride (8 mL) and N,N-dimethylformamide (few drops) are added to a solution of 3-(3-methoxy-phenyl)-pyridine-2-carboxylic acid (11.86 g) in dichloromethane (80 mL). The mixture is heated to 40° C. and stirred at this temperature overnight. The solution is then concentrated and the residue is taken up in toluene and concentrated again to give the crude title compound that is used without further purification in the next step. Yield: 12.80 g (crude).

Step 4: 6-methoxy-indeno[2,1-b]pyridin-9-one

Aluminum chloride (7.33 g) is added to a solution of 3-(3-methoxy-phenyl)-pyridine-2-carbonyl chloride (crude, 5.40 g) in dichloromethane (100 mL) chilled in an ice bath. The cooling bath is removed and the mixture is stirred at room temperature overnight. The mixture is then poured on crushed ice and the resulting mixture is extracted with dichloromethane. The combined extracts are washed with aqueous NaHCO$_3$ solution and dried (Na$_2$SO$_4$). The solvent is evaporated and the residue is triturated with a mixture of cyclohexane and ethyl acetate (1:1) and dried to give the title compound as a yellowish solid. Yield: 3.00 g (65% of theory); LC (method 1): $t_R$=2.84 min; Mass spectrum (ESI$^+$): m/z=212 [M+H]$^+$.

Step 5: cis-6-methoxy-2,3,4,4a,9,9a-hexahydro-1H-indeno[2,1-b]pyridine

A mixture of 6-methoxy-indeno[2,1-b]pyridin-9-one (2.00 g), 10% palladium on carbon (0.30 g), 4 M aqueous hydrochloric acid (6 mL), and methanol (100 mL) is shaken under hydrogen atmosphere (3 bar) at room temperature for 4 h. PtO$_2$ (0.20 g) is then added and shaking is continued under hydrogen atmosphere (1 bar) at room temperature for another 36 h. The catalysts are separated by filtration and the filtrate is concentrated. The residue is basified by the addition of 2 M aqueous NaOH solution and the resulting mixture is extracted with ethyl acetate. The combined extracts are washed with brine, dried (Na$_2$SO$_4$), and the solvent is evaporated. The residue is chromatographed on silica gel (dichloromethane/methanol containing 1% NH$_3$ 90:10→75:25) to give the title compound as a colorless oil. Yield: 1.00 g (52% of theory); LC (method 1): $t_R$=1.50 min; Mass spectrum (ESI$^+$): m/z=204 [M+H]$^+$.

Intermediate 42

Trifluoromethanesulfonic acid cis-1-(1-trifluoromethanesulfonyl-1H-benzoimidazole-5-carbonyl)-2,3,4,4a,9,9a-hexahydro-1H-indeno[2,1-b]pyridin-6-yl ester and Trifluoro-methanesulfonic acid cis-1-(3-trifluoromethanesulfonyl-3H-benzoimidazole-5-carbonyl)-2,3,4,4a,9,9a-hexahydro-1H-indeno[2,1-b]pyridin-6-yl ester

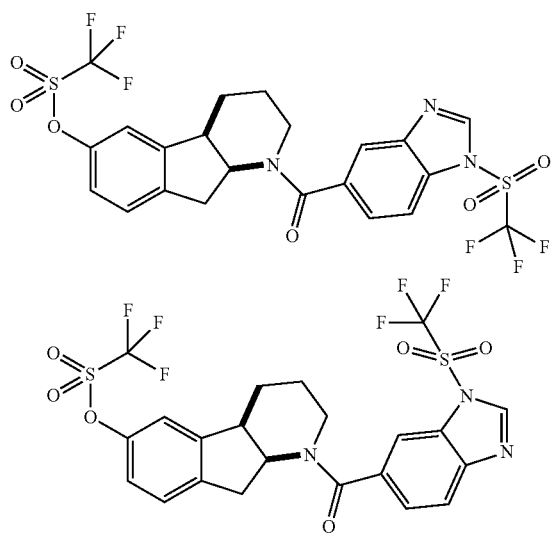

Trifluoromethanesulfonic anhydride (0.60 mL) dissolved in dichloromethane (3 mL) is added dropwise to a solution of (1H-benzoimidazol-5-yl)-(cis-6-hydroxy-2,3,4,4a,9,9a-hexahydro-indeno[2,1-b]pyridin-1-yl)-methanone (0.45 g) and pyridine (0.40 mL) in dichloromethane (10 mL) cooled to −10° C. The solution is stirred in the cooling bath for 1 h and then diluted with dichloromethane. The solution is washed with aqueous citric acid and aqueous NaHCO$_3$ solution and dried (Na$_2$SO$_4$). The solvent is evaporated to give the two title compounds as a mixture that is used as such in the next step. Yield: 0.72 g (89% of theory); LC (method 1): $t_R$=4.75 min; Mass spectrum (ESI$^+$): m/z=598 [M+H]$^+$.

Intermediate 43 cis-2,3,4,4a,9,9a-Hexahydro-1H-indeno[2,1-b]pyridin-7-ylamine

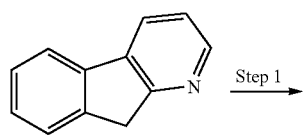

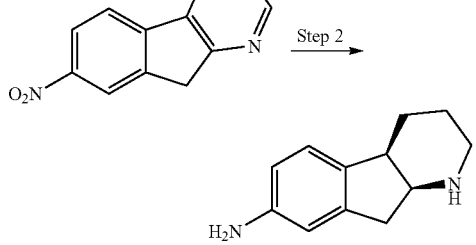

Step 1: 7-nitro-9H-indeno[2,1-b]pyridine

A ca. 10° C.-cold mixture of nitric acid (65%, 1.1 mL) and sulfuric acid (96%, 1.6 mL) is added dropwise to a solution of 9H-indeno[2,1-b]pyridine (2.44 g) in sulfuric acid (96%, 3 mL) chilled in an ice bath. The solution is stirred in the cooling bath for 1 h and poured then onto crushed ice. The precipitate formed is separated by filtration and the filtrate is neutralized using 4 M aqueous NaOH solution. The precipitate formed is separated by filtration and combined with the precipitate separated before. The precipitate is triturated with acetone and dried to give the title compound as a solid. Yield: 2.64 g (85% of theory); LC (method 1): $t_R$=2.93 min; Mass spectrum (ESI$^+$): m/z=213 [M+H]$^+$.

Step 2: cis-2,3,4,4a,9,9a-hexahydro-1H-indeno[2,1-b]pyridin-7-ylamine

A mixture of 7-nitro-9H-indeno[2,1-b]pyridine (3.25 g), 10% palladium on carbon (0.35 g), and methanol (50 mL) is shaken under hydrogen atmosphere (3 bar) at room temperature for 22 h. PtO$_2$ (0.50 g) and 4 M aqueous hydrochloric acid (3.2 mL) are then added and shaking is continued under hydrogen atmosphere (1 bar) at room temperature for another 22 h. The catalysts are separated by filtration and the filtrate is concentrated to give the crude title compound as its hydrochloric acid salt that is used without further purification or transformed to the free base by treatment with aqueous NaOH solution and extraction into ethyl acetate. Yield: 4.20 g (ca. 80% pure); LC (method 1): $t_R$=0.52 min; Mass spectrum (ESI$^+$): m/z=189 [M+H]$^+$.

Intermediate 44 cis-2,3,4,4a,9,9a-Hexahydro-1H-indeno[2,1-b]pyridin-7-ol

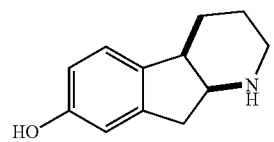

Sodium nitrite (92 mg) dissolved in water (0.5 mL) is added dropwise to a solution of cis-2,3,4,4a,9,9a-hexahydro-1H-indeno[2,1-b]pyridin-7-ylamine dihydrochloride (0.30 g) in half-concentrated sulfuric acid (0.6 ml) chilled in an ice bath. The solution is stirred for 15 min in the cooling bath prior to the addition of half-concentrated sulfuric acid (5 ml). The resulting solution is heated to 120° C. and stirred at this temperature for 3 h. The mixture is cooled to room temperature, diluted with water, and basified with 4 M NaOH. The resulting mixture is extracted with ethyl acetate and the combined extracts are dried (Na$_2$SO$_4$). The solvent is evaporated and the residue is chromatographed on silica gel [dichloromethane/(dichloromethane/methanol/NH$_4$OH 50:48:2) 80:20→40:60] to give the title compound. Yield: 0.07 g (32% of theory); LC (method 1): t$_R$=0.83 min; Mass spectrum (ESI$^+$): m/z=190 [M+H]$^+$.

Intermediate 45 cis-4-Methyl-2,3,4,4a,9,9a-hexahydro-1H-indeno[2,1-b]pyridine

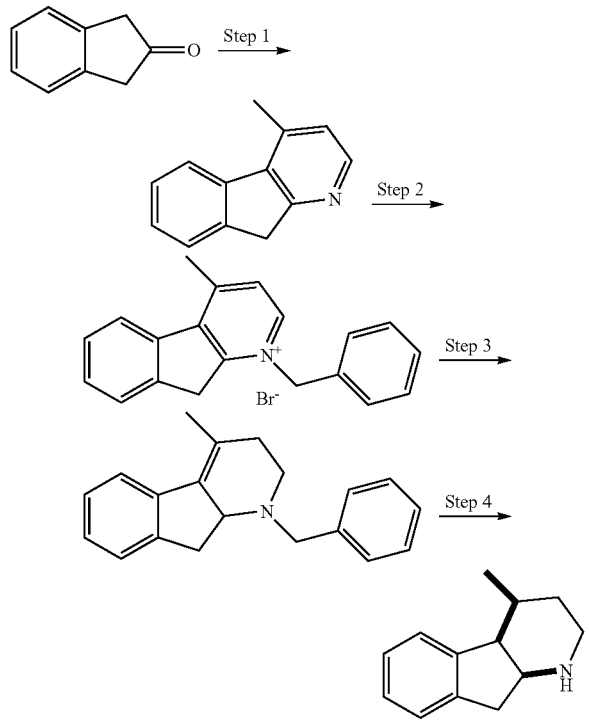

Step 1: 4-methyl-9H-indeno[2,1-b]pyridine

The title compound is prepared from indan-2-one and but-2-ynylamine following a procedure analogous to that described in Step 1 of Intermediates 1 and 2; the reaction is carried out in a microwave oven at 100° C. for 12 min. Yield: 22% of theory; LC (method 1): t$_R$=1.98 min; Mass spectrum (ESI$^+$): m/z=182 [M+H]$^+$.

Step 2: 1-benzyl-4-methyl-9H-indeno[2,1-b]pyridinium bromide

A mixture of 4-methyl-9H-indeno[2,1-b]pyridine (0.64 g) and benzyl bromide (0.42 mL) in acetone (5 mL) is stirred at reflux temperature for 4 h. After cooling to room temperature, the precipitate is separated by filtration, washed with little diethyl ether, and dried to give the title compound as a beige solid. Yield: 0.93 g (75% of theory); LC (method 1): t$_R$=2.49 min; Mass spectrum (ESI$^+$): m/z=272 [M−Br]$^+$.

Step 3: 1-benzyl-4-methyl-2,3,9,9a-tetrahydro-1H-indeno[2,1-b]pyridine

Sodium borohydride (0.15 g) is added to a suspension of 1-benzyl-4-methyl-9H-indeno[2,1-b]pyridinium bromide (0.92 g) in ethanol (10 mL) chilled in an ice bath. The cooling bath is removed and the mixture is stirred at room temperature for 1 h and at 60° C. for 2 h. More sodium borohydride (0.18 g) is added and stirring is continued at reflux temperature for 4 h. After the addition of another portion of sodium borohydride (0.10 g), the mixture is stirred at reflux temperature overnight. After cooling to room temperature, ice-cold water is added and the precipitate is separated by filtration. The precipitate is dissolved in ether, the resulting solution is dried (Na$_2$SO$_4$), and the solvent is evaporated to afford the crude product that is used without further purification. Yield: 0.66 g (crude); Mass spectrum (ESI$^+$): m/z=276 [M+H]$^+$.

Step 4: cis-4-methyl-2,3,4,4a,9,9a-hexahydro-1H-indeno[2,1-b]pyridine

A mixture of 1-benzyl-4-methyl-2,3,9,9a-tetrahydro-1H-indeno[2,1-b]pyridine (0.65 g), Pd(OH)$_2$ (200 mg), and ethanol (10 mL) is shaken under hydrogen atmosphere (5 bar) at room temperature for 16 h. Another portion of Pd(OH)$_2$ (100 mg) is then added and shaking under hydrogen atmosphere (5 bar) is continued overnight. The catalyst is separated by filtration and the solvent is evaporated to give the crude title compound that is used without further purification. Yield: 0.43 g (crude).

Intermediate 46 cis-2,3,4,4a,9,9a-Hexahydro-1H-indeno[2,1-b]pyridine-6-carbonitrile

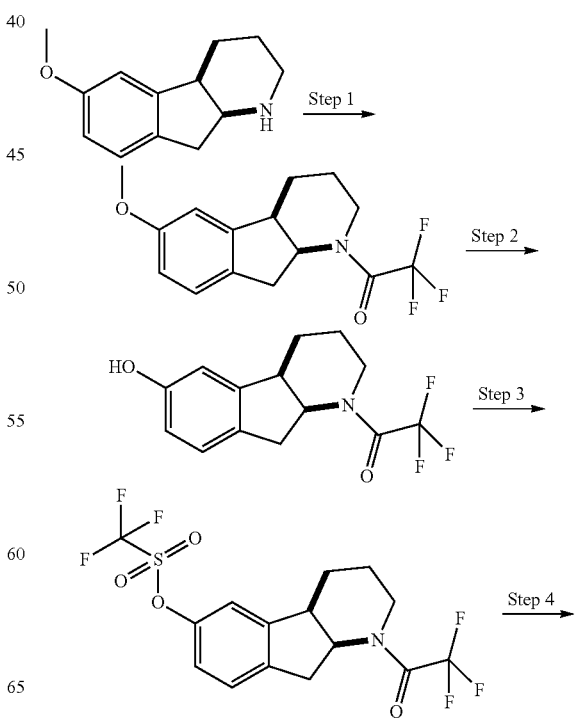

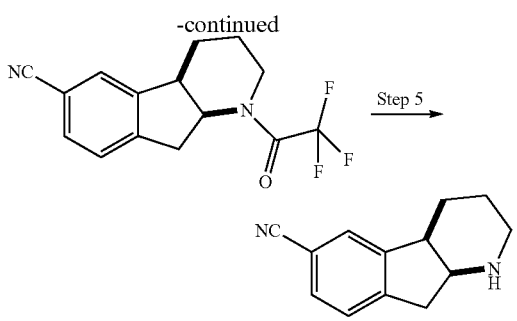

Step 1: 2,2,2-trifluoro-1-(cis-6-methoxy-2,3,4,4a,9,
9a-hexahydro-indeno[2,1-b]pyridin-1-yl)-ethanone Trifluoroacetic anhydride (4.5 mL) is added dropwise to a solution of cis-6-methoxy-2,3,4,4a,9,9a-hexahydro-1H-indeno[2,1-b]pyridine (5.0 g), triethylamine (5.6 mL), and 4-dimethylaminopyridine (ca. 5 mol %) in dichloromethane (60 mL) maintained below 10° C. The solution is stirred with cooling for 1 h and at room temperature for 2 h. The solution is diluted with dichloromethane (100 mL) and aqueous $NaHCO_3$ solution and then stirred vigorously for 15 min. The organic phase is separated, washed with 1 M hydrochloric acid (25 mL) and water (50 mL), and dried ($MgSO_4$). The solvent is evaporated to afford the title compound as an oil. Yield: 8.1 g (quantitative); LC (method 1): $t_R$=4.24 min; Mass spectrum ($ESI^+$): m/z=300 $[M+H]^+$.

Step 2: 2,2,2-trifluoro-1-(cis-6-hydroxy-2,3,4,4a,9,
9a-hexahydro-indeno[2,1-b]pyridin-1-yl)-ethanone Boron tribromide (1 mol/L in heptane, 27 mL) is added to a solution of 2,2,2-trifluoro-1-(cis-6-methoxy-2,3,4,4a,9,9a-hexahydro-indeno[2,1-b]pyridin-1-yl)-ethanone (8.1 g) in dichloromethane (120 mL) chilled in an ice bath. The resulting mixture is warmed in the cooling bath to room temperature overnight. The solution is cooled again in an ice bath, diluted with dichloromethane (50 mL), and then 25% aqueous $K_2CO_3$ (20 mL) is carefully added. The mixture is stirred for 30 min and then acidified by the addition of 4 M aqueous hydrochloric acid (60 mL). The organic phase is separated, washed with 1 M aqueous hydrochloric acid (40 mL) and dried ($MgSO_4$). The solvent is evaporated to give the title compound as a solid. Yield: 7.3 g (95% of theory); LC (method 1): $t_R$=3.43 min; Mass spectrum ($ESI^+$): m/z=286 $[M+H]^+$.

Step 3: trifluoro-methanesulfonic acid cis-1-(2,2,2-trifluoro-acetyl)-2,3,4,4a,9,9a-hexahydro-1H-indeno[2,1-b]pyridin-6-yl ester Trifluoromethanesulfonic anhydride (5.6 mL) is added dropwise to a solution of 2,2,2-trifluoro-1-(cis-6-hydroxy-2,3,4,4a,9,9a-hexahydro-indeno[2,1-b]pyridin-1-yl)-ethanone (7.3 g), triethylamine (7.2 mL), and 4-dimethylaminopyridine (50 mg) in dichloromethane (60 mL) chilled in an ice bath. The solution is stirred with cooling for 1 h and at room temperature for 2 h. Water (100 mL) and dichloromethane (100 mL) are then added and the organic phase is separated. The organic phase is washed with water (50 mL), dried ($MgSO_4$), and concentrated to give the title compound as a dark oil. Yield: 10.7 g (quantitative); TLC: $r_f$=0.50 (silica gel, cyclohexane/ethyl acetate 3:1); Mass spectrum ($ESI^+$): m/z=418 $[M+H]^+$.

Step 4: cis-1-(2,2,2-trifluoroacetyl)-2,3,4,4a,9,9a-hexahydro-1H-indeno[2,1-b]pyridine-6-carbonitrile A flask charged with a stir bar, zinc cyanide (5.0 g), trifluoro-methanesulfonic acid cis-1-(2,2,2-trifluoro-acetyl)-2,3,4,4a,9,9a-hexahydro-1H-indeno[2,1-b]pyridin-6-yl ester (10.7 g), and N,N-dimethylformamide (60 mL) is sparged with argon for 5 min. Tetrakis(triphenyl-phosphine)palladium(0) (4.0 g) is then added and the resulting mixture is stirred at 100° C. for 2 h. After cooling to room temperature, water is added and the resulting mixture is extracted with ethyl acetate. The combined extract is washed with brine, dried ($MgSO_4$), and concentrated. The residue is chromatographed on silica gel (ethyl acetate/cyclohexane 1:9→4:1) to give the title compound as a solid. Yield: 5.5 g (73% of theory); TLC: $r_f$=0.25 (silica gel, cyclohexane/ethyl acetate 3:1); Mass spectrum ($ESI^+$): m/z=295 $[M+H]^+$.

Step 5: cis-2,3,4,4a,9,9a-hexahydro-1H-indeno[2,1-b]pyridine-6-carbonitrile

A solution of cis-1-(2,2,2-trifluoroacetyl)-2,3,4,4a,9,9a-hexahydro-1H-indeno[2,1-b]pyridine-6-carbonitrile (5.50 g) and 4 M NaOH solution (5.6 mL) in methanol (30 mL) is stirred at room temperature for 2 h. Brine (150 mL) is then added and the resulting mixture is extracted with ethyl acetate (3×75 mL). The combined extract is dried ($MgSO_4$) and concentrated to give the title compound as an oil that solidified upon standing. Yield: 3.70 g (quantitative); Mass spectrum ($ESI^+$): m/z=295 $[M+H]^+$.

The racemic mixture may be separated by SFC on chiral phase (column: Daicel ADH 250×20 mm, 5 μm; mobile phase: isopropanol containing 0.2% diethylamine/sc carbon dioxide 20:80; flow rate: 70 mL/min) to give 1. (4a-R,9a-S)-2,3,4,4a,9,9a-hexahydro-1H-indeno[2,1-b]pyridine-6-carbonitrile, yield: 1.60 g (43% of theory), LC (analytical SFC on chiral phase: column: Daicel ADH 250× 4.6 mm; mobile phase: isopropanol containing 0.2% diethylamine/sc carbon dioxide 20:80; flow rate: 4 mL/min): $t_R$=4.05 min.

2. (4a-S,9a-R)-2,3,4,4a,9,9a-hexahydro-1H-indeno[2,1-b]pyridine-6-carbonitrile, yield: 1.70 g (46% of theory), LC (analytical SFC on chiral phase: column: Daicel ADH 250× 4.6 mm; mobile phase: isopropanol containing 0.2% diethylamine/sc carbon dioxide 20:80; flow rate: 4 mL/min): $t_R$=2.81 min.

The enantiomerically pure (ee>99%) Intermediate 46 is also obtained employing the following protocols:

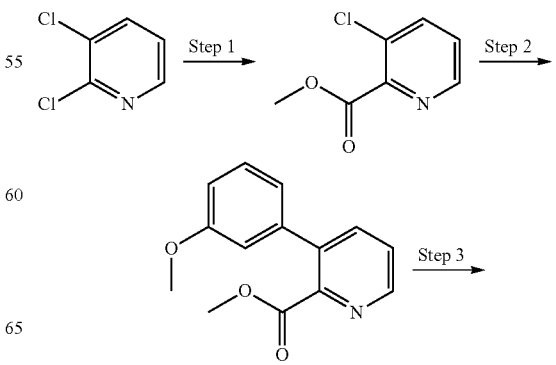

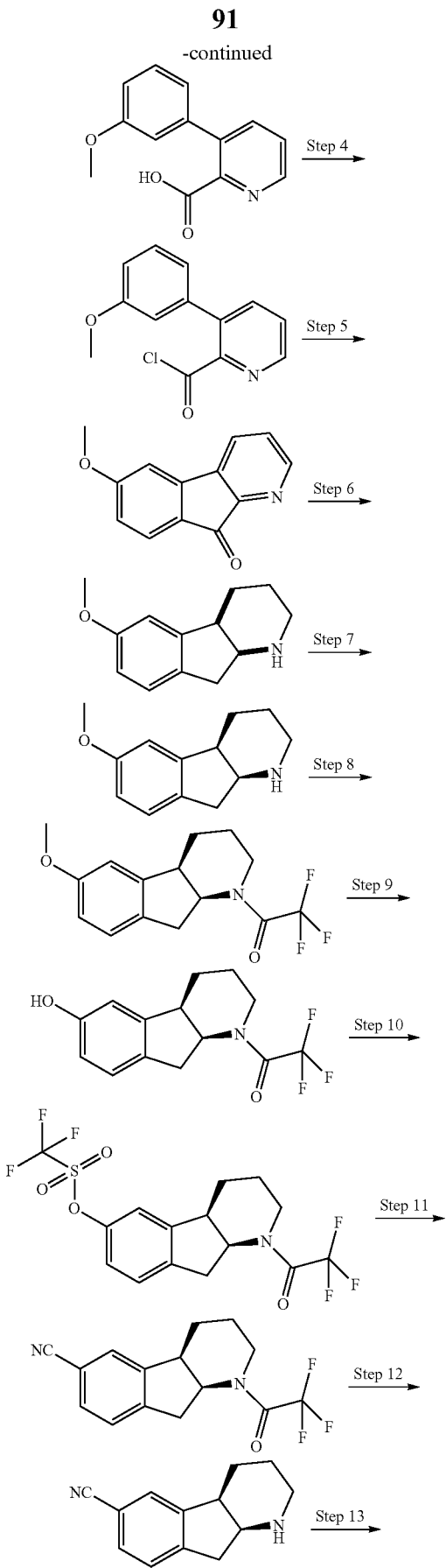

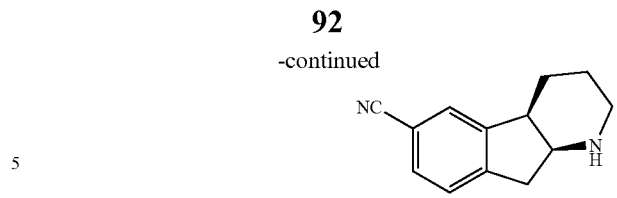

Step 1: 3-chloro-pyridine-2-carboxylic acid methyl ester

An autoclave is charged with 2,3-dichloropyridine (2.5 kg), degassed methanol (12.5 L), and triethylamine (3.42 kg). A catalyst solution [prepared as follows: a flask is charged with palladium acetate (19 g), 1,3-bis(diphenylphosphino) propane (38.5 g), and methanol (1 L). The mixture is stirred at 20-25° C. until palladium acetate is completely dissolved (ca. 30 min)] is added. After purging the apparatus with nitrogen twice and carbon monoxide twice, the mixture is stirred under carbon monoxide atmosphere (100 psi) at 60-65° C. for 20 h. After cooling to room temperature, the mixture is filtered over Celite and the filtrate is concentrated.

Steps 2/3: 3-(3-methoxy-phenyl)-pyridine-2-carboxylic acid

2-Methyl-tetrahydrofuran (500 mL) is added to crude 3-chloro-pyridine-2-carboxylic acid methyl ester (58.0 g) and the resulting solution is washed with water (200 mL) and 5% aqueous sodium chloride solution (200 mL) and concentrated (to ca. 450 mL total volume). 3-Methoxybenzeneboronic acid (61.6 g) and potassium phosphate (143.3 g) are added and the resulting mixture is sparged with nitrogen for 20 min. Palladium acetate (0.76 g) and diadamantyl-n-butylphosphine (2.42 g) are added and the resulting mixture is heated to 80° C. and stirred at this temperature for 12 h. After cooling to room temperature, the mixture is washed with water (300 mL) and 1 mol/L aqueous NaOH solution (200 mL). The organic phase is diluted with methanol (100 mL) and 30% aqueous NaOH solution (27.04 g) is added at such a rate that the solution temperature maintained below 40° C. The resulting mixture is stirred at room temperature for 2 h and then diluted with water (100 mL) and methyl tert-butyl ether (100 mL). The etheral layer is separated and concentrated hydrochloric acid (60 mL) is added to the aqueous phase (pH value ca. 2-3). The aqueous phase is extracted with dichloromethane (2×250 mL) and the combined extract is diluted with toluene (6 L). The organic solution is concentrated at below 40° C. and the crude title compound is used as is for the next step.

Steps 4/5: 6-methoxy-indeno[2,1-b]pyridin-9-one

Thionyl chloride (0.95 L) is added over 30 min to a solution of 3-(3-methoxy-phenyl)-pyridine-2-carboxylic acid (crude product; 2.0 kg) and N,N-dimethylformamide (34 mL) in dichloromethane (9 L) at 40° C. The addition vessel is rinsed with dichloromethane (1 L) and the solution is stirred at 40° C. for 2 h. The solution is diluted with toluene (10 L) and most of the solvent is evaporated (residual toluene ca. 2 L). Dichloromethane (10 L) is added to obtain a homogeneous solution. The solution is heated to 35° C. and added over 30 min to a vessel charged with aluminum chloride (1.75 kg) and dichloromethane (10 L) while keeping mild reflux. The mixture is stirred at 40° C. for 30 min and then cooled to 0° C. Water (4 L) is added at such a rate that the solution temperature maintained below 40° C. The aqueous layer is adjusted to pH value 2.5-3.5 using 2 M aqueous NaOH solution and the resulting mixture is stirred for 15 min. The organic layer is separated and the aqueous layer is extracted with dichloromethane (2×). The combined organic phase is concentrated (to ca. 10 L) and toluene (10 L) is added to the residue. The residual amount of dichloromethane is evaporated and the precipitate is separated and washed with toluene (2 L) and heptane (4 L) and dried under vacuum to give the title compound.

Step 6: cis-6-methoxy-2,3,4,4a,9,9a-hexahydro-1H-indeno[2,1-b]pyridine

A mixture of sulfuric acid (98%, 6 kg), water (6 L), and methanol (6 L) is added to an autoclave charged with 6-methoxy-indeno[2,1-b]pyridin-9-one (1.2 kg) and wet 10% palladium on carbon (50%, 0.48 kg). The autoclave is purged with nitrogen and filled then with hydrogen (100 psi). The mixture is heated to 60° C. and maintained at this temperature and hydrogen pressure until the starting material is completely consumed (2-12 h). The mixture is cooled to 50-55° C. and filtered over Celite. The Celite is washed with a warm 1:1 mixture of water and methanol several times (total 20 L). The combined filtrate is added to an autoclave charged with wet 10% palladium on carbon (50%, 0.96 kg). The autoclave is purged with nitrogen and filled then with hydrogen (100 psi). The mixture is heated to 60° C. and maintained at this temperature and hydrogen pressure until the intermediate is completely consumed (12-24 h). The mixture is cooled to ambient temperature and filtered over Celite. The Celite is washed with a mixture of methanol and water (5 L/5 L). The combined filtrate is cooled to 0-10° C. and the pH value is adjusted to 10-11 using 30% aqueous NaOH solution while maintaining the solution temperature below 40° C. Water (10 L) is added and the resulting mixture is extracted with dichloromethane (2×5 L). The combined extract is washed with 10% aqueous NaCl solution and concentrated. The residue is taken up twice in methyl ethyl ketone and concentrated again to give the crude title compound.

Step 7: (4a-R,9a-S)-6-methoxy-2,3,4,4a,9,9a-hexahydro-1H-indeno[2,1-b]pyridine

Di-p-toluoyl-D-tartaric acid (403 g) is added to crude cis-6-methoxy-2,3,4,4a,9,9a-hexahydro-1H-indeno[2,1-b]pyridine (ca. 0.53 kg of pure compound) dissolved in methyl ethyl ketone (5.3 L). The solution is heated to 50° C. and some seeds are added. The mixture is stirred at 50° C. for 1 h and at 15° C. overnight. The resulting slurry is filtered to give a white solid (386 g, 95% de). The solid is taken up in dichloromethane (6 L) and 10% aqueous NaOH solution is added. The resulting mixture is stirred at room temperature for 1 h. The organic phase is separated and concentrated to give the title compound. Yield: 170 g (95% ee).

Step 8: (4a-R,9a-S)-2,2,2-trifluoro-1-(6-methoxy-2,3,4,4a,9,9a-hexahydro-indeno[2,1-b]pyridin-1-yl)-ethanone A vessel charged with 4-dimethylaminopyridine (6.9 g), triethylamine (0.24 L), (4a-R,9a-S)-6-methoxy-2,3,4,4a,9,9a-hexahydro-1H-indeno[2,1-b]pyridine (231 g), and dichloromethane (2.3 L) is cooled to 10-15° C. Trifluoroacetic anhydride (0.21 L) is added at such a rate that the solution temperature maintained below 25° C. The mixture is heated to 20-25° C. and stirred at this temperature for 1 h. Saturated aqueous NaHCO₃ solution (1.5 L) is added and the resulting mixture is stirred for 15 min. The organic layer is separated, washed with 1 M aqueous HCl solution (1.2 L) and water (0.9 L), concentrated, and azeotropically dried using dichloromethane to give the title compound.

Step 9: (4a-R,9a-S)-2,2,2-trifluoro-1-(6-hydroxy-2,3,4,4a,9,9a-hexahydro-indeno[2,1-b]pyridin-1-yl)-ethanone Boron tribromide (0.14 kg) is added to a solution of (4a-R,9a-S)-2,2,2-trifluoro-1-(6-methoxy-2,3,4,4a,9,9a-hexahydro-indeno[2,1-b]pyridin-1-yl)-ethanone (0.34 kg) in dichloromethane (5.7 L) cooled to 10-15° C. at such a rate that the solution temperature maintained below 25° C. The solution is stirred at 20-25° C. for 5 h. The solution is poured into water (1.7 L) at such a rate that the solution temperature maintained below 35° C. and the resulting mixture is stirred for 30 min. The organic phase is separated, washed with water (1.3 L), and concentrated. The residue is azetropically dried with dichloromethane to give the title compound.

Step 10: (4a-R,9a-S)-trifluoro-methanesulfonic acid 1-(2,2,2-trifluoro-acetyl)-2,3,4,4a,9,9a-hexahydro-1H-indeno[2,1-b]pyridin-6-yl ester Trifluoromethanesulfonic anhydride (0.23 L) is added to a solution of 4-dimethylamino-pyridine (6.9 g), triethylamine (0.24 L), and (4a-R,9a-S)-2,2,2-trifluoro-1-(6-hydroxy-2,3,4,4a,9,9a-hexahydro-indeno[2,1-b]pyridin-1-yl)-ethanone (0.32 kg) in dichloromethane (3.4 L) cooled to 0-5° C. at such a rate that the solution temperature maintained between 0 and 5° C. After stirring the solution for 30 min at 0-5° C., water (1.2 L) is added at such a rate that the solution temperature maintained 0-5° C. After stirring for 15 min, the organic phase is separated, washed with water (1.2 L), and concentrated. The residue is passed through a plug of silica gel (ethyl acetate/hexane 1:2) to give the title compound as an oil. Yield: 0.42 kg (98% of theory).

Step 11: (4a-R,9a-S)-1-(2,2,2-trifluoro-acetyl)-2,3,4,4a,9,9a-hexahydro-1H-indeno[2,1-b]pyridine-6-carbonitrile A mixture of (4a-R,9a-S)-trifluoro-methanesulfonic acid 1-(2,2,2-trifluoro-acetyl)-2,3,4,4a,9,9a-hexahydro-1H-indeno[2,1-b]pyridin-6-yl ester (189 g), zinc cyanide (79.8 g), and N,N-dimethylformamide (1.9 L) is purged with nitrogen for 15 min. Tris(dibenzylidene-acetone)dipalladium(0) (16.6 g) and 1,1'-bis(diphenylphosphino)ferrocene (25.1 g) are added and the resulting mixture is purged with nitrogen at room temperature. The mixture is heated to 80° C. and stirred at this temperature for 12 h. After cooling to room temperature, water (2 L) and ethyl acetate (2 L) are added and the resulting mixture is stirred for 10 min. The organic phase is separated and the aqueous phase is extracted with ethyl acetate. The combined organic phase is washed with water (4×1 L) and concentrated. The residue is passed through a plug of silica gel (hexane/ethyl acetate 2:1.5) to give the title compound as a solid. Yield: 133 g (quantitative).

Steps 12/13: (4a-R,9a-S)-2,3,4,4a,9,9a-hexahydro-1H-indeno[2,1-b]pyridine-6-carbonitrile 2 M aqueous NaOH solution (300 mL) is added to a slurry of (4a-R,9a-S)-1-(2,2,2-trifluoro-acetyl)-2,3,4,4a,9,9a-hexahydro-1H-indeno[2,1-b]pyridine-6-carbonitrile (135 g) in methanol (600 mL) at such a rate that the slurry temperature maintained below 40° C. The mixture is stirred at room temperature for 2 h and diluted then with water (300 mL) and dichloromethane (600 mL). The organic phase is separated and the aqueous phase is extracted with dichloromethane (2×500 mL). The combined organic phase is washed with 10% aqueous NaCl solution and concentrated to give the crude title compound as an oil (90 g, 93-95% ee). The crude title compound (90 g) in isopropanol (540 mL) is heated to 50° C. and di-benzoyl-D-tartaric acid (109 g) is added. The resulting mixture is stirred at 90° C. for 1 h and at room temperature for 2 h. The precipitate is separated and washed with isopropanol (3×50 mL). The precipitate is taken up in dichloromethane (1 L) and the resulting mixture is treated with 2 M aqueous NaOH solution (500 mL). The mixture is stirred at room temperature for 1 h. The organic phase is separated, washed with 10% aqueous NaCl solution (500 mL), and concentrated to give the title compound as an oil. Yield: 80 g (>99% ee).

Intermediate 47 cis-6-Phenyl-2,3,4,4a,9,9a-hexahydro-1H-indeno[2,1-b]pyridine

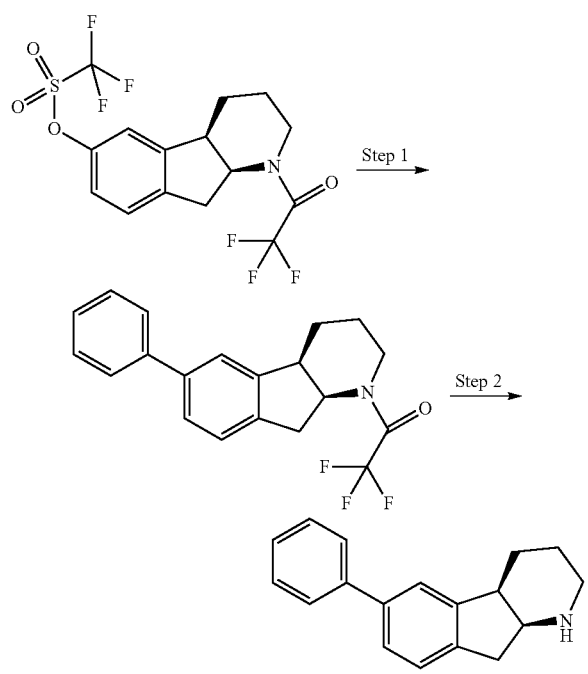

Step 1: cis-2,2,2-trifluoro-1-(6-phenyl-2,3,4,4a,9,9a-hexahydro-indeno[2,1-b]pyridin-1-yl)-ethanone The title compound is prepared from trifluoro-methanesulfonic acid cis-1-(2,2,2-trifluoro-acetyl)-2,3,4,4a,9,9a-hexahydro-1H-indeno[2,1-b]pyridin-6-yl ester and phenylboronic acid following a procedure analogous to that described in Step 2 of Intermediates 17 and 18. Yield: 70% of theory; LC (method 1): $t_R$=5.02 min; Mass spectrum (ESI$^+$): m/z=346 [M+H]$^+$.

Step 2: cis-6-phenyl-2,3,4,4a,9,9a-hexahydro-1H-indeno[2,1-b]pyridine

The title compound is prepared from cis-2,2,2-trifluoro-1-(6-phenyl-2,3,4,4a,9,9a-hexahydro-indeno[2,1-b]pyridin-1-yl)-ethanone following a procedure analogous to that described in Step 5 of Intermediate 46. Yield: 60% of theory; LC (method 1): $t_R$=2.70 min; Mass spectrum (ESI$^+$): m/z=250 [M+H]$^+$.

Intermediate 48 cis-6-Furan-3-yl-2,3,4,4a,9,9a-hexahydro-1H-indeno[2,1-b]pyridine

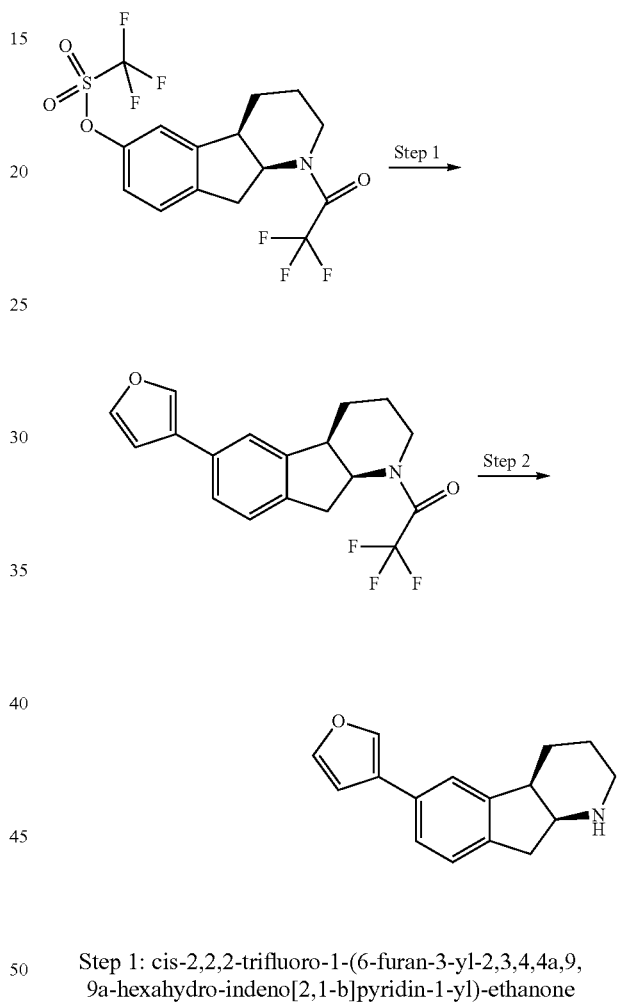

Step 1: cis-2,2,2-trifluoro-1-(6-furan-3-yl-2,3,4,4a,9,9a-hexahydro-indeno[2,1-b]pyridin-1-yl)-ethanone The title compound is prepared from trifluoro-methanesulfonic acid cis-1-(2,2,2-trifluoro-acetyl)-2,3,4,4a,9,9a-hexahydro-1H-indeno[2,1-b]pyridin-6-yl ester and furan-3-yl-boronic acid following a procedure analogous to that described in Step 2 of Intermediates 17 and 18. Yield: 61% of theory; LC (method 1): $t_R$=4.60 min; Mass spectrum (ESI$^+$): m/z=336 [M+H]$^+$.

Step 2: cis-6-furan-3-yl-2,3,4,4a,9,9a-hexahydro-1H-indeno[2,1-b]pyridine

The title compound is prepared from cis-2,2,2-trifluoro-1-(6-furan-3-yl-2,3,4,4a,9,9a-hexahydro-indeno[2,1-b]pyridin-1-yl)-ethanone following a procedure analogous to that described in Step 5 of Intermediate 46. Yield: 93% of theory; LC (method 1): $t_R$=2.27 min; Mass spectrum (ESI$^+$): m/z=240 [M+H]$^+$.

Intermediate 49 cis-6-(1-Methyl-1H-pyrazol-4-yl)-2,3,4,4a,9,9a-hexahydro-1H-indeno[2,1-b]pyridine

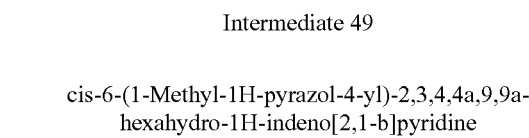

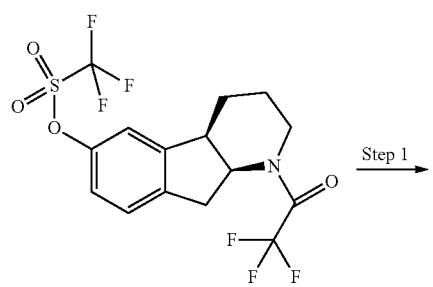

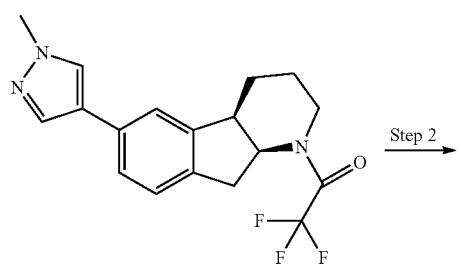

Step 1: cis-2,2,2-trifluoro-1-[6-(1-methyl-1H-pyrazol-4-yl)-2,3,4,4a,9,9a-hexahydro-indeno[2,1-b]pyridin-1-yl]-ethanone The title compound is prepared from trifluoro-methanesulfonic acid cis-1-(2,2,2-trifluoro-acetyl)-2,3,4,4a,9,9a-hexahydro-1H-indeno[2,1-b]pyridin-6-yl ester and 1-methyl-pyrazol-4-yl-boronic acid following a procedure analogous to that described in Step 2 of Intermediates 17 and 18. Yield: 32% of theory; LC (method 1): $t_R$=3.88 min; Mass spectrum (ESI$^+$): m/z=350 [M+H]$^+$.

Step 2: cis-6-(1-methyl-1H-pyrazol-4-yl)-2,3,4,4a,9,9a-hexahydro-1H-indeno[2,1-b]pyridine The title compound is prepared from cis-2,2,2-trifluoro-1-[6-(1-methyl-1H-pyrazol-4-yl)-2,3,4,4a,9,9a-hexahydro-indeno[2,1-b]pyridin-1-yl]-ethanone following a procedure analogous to that described in Step 5 of Intermediate 46. Yield: quantitative; LC (method 1): $t_R$=1.70 min; Mass spectrum (ESI$^+$): m/z=254 [M+H]$^+$.

Intermediate 50 cis-6-Methyl-2,3,4,4a,9,9a-hexahydro-1H-indeno[2,1-b]pyridine

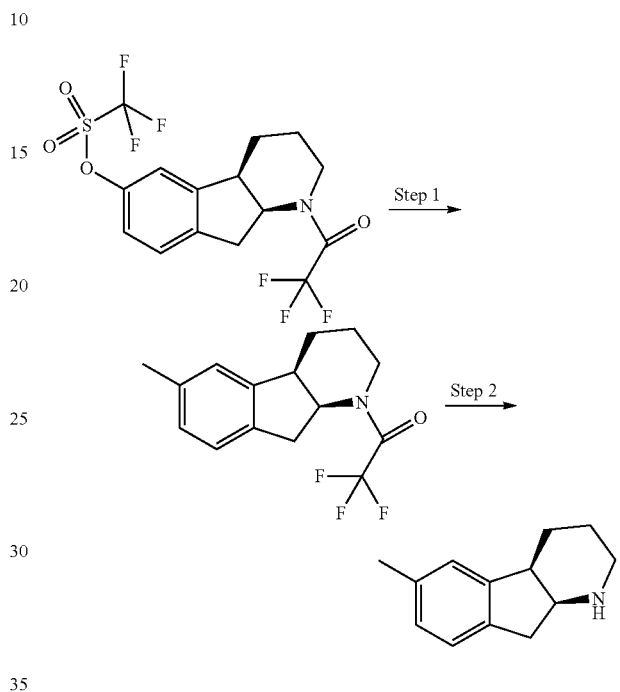

Step 1: cis-2,2,2-trifluoro-1-(6-methyl-2,3,4,4a,9,9a-hexahydro-indeno[2,1-b]pyridin-1-yl)-ethanone Tetrakis(triphenylphosphine)palladium(0) (17 mg) is added to a flask charged with a stir bar, trifluoromethanesulfonic acid cis-1-(2,2,2-trifluoro-acetyl)-2,3,4,4a,9,9a-hexahydro-1H-indeno[2,1-b]pyridin-6-yl ester (200 mg), trimethylboroxine (81 µL), K$_3$PO$_4$ (0.15 g), and 1,4-dioxane (4 mL) under argon atmosphere at room temperature. The reaction mixture is heated to 100° C. and stirred at this temperature overnight. Another portion of trimethylboroxine (40 µL) and tetrakis(triphenylphosphine)palladium(0) (17 mg) is then added and stirring is continued at 100° C. The addition of further amounts of trimethylboroxine and tetrakis(triphenylphosphine)palladium(0) is repeated after each 6 h of stirring until the starting material is completely consumed. After cooling to room temperature, water is added and the resulting mixture is extracted with ethyl acetate. The combined extract is dried (Na$_2$SO$_4$) and concentrated and the residue is chromatographed on silica gel (dichloromethane/methanol 1:0→9:1) to give the title compound. Yield: 50 mg (37% of theory); LC (method 1): $t_R$=4.62 min; Mass spectrum (ESI$^+$): m/z=284 [M+H]$^+$.

Step 2: cis-6-methyl-2,3,4,4a,9,9a-hexahydro-1H-indeno[2,1-b]pyridine

The title compound is prepared from cis-2,2,2-trifluoro-1-(6-methyl-2,3,4,4a,9,9a-hexahydro-indeno[2,1-b]pyridin-1-yl)-ethanone following a procedure analogous to that described in Step 5 of Intermediate 46. Yield: 94% of theory; LC (method 1): $t_R$=1.91 min; Mass spectrum (ESI$^+$): m/z=188 [M+H]$^+$.

Intermediate 51 cis-(3H-Benzoimidazol-5-yl)-[6-(3,6-dihydro-2H-pyran-4-yl)-2,3,4,4a,9,9a-hexahydro-indeno[2,1-b]pyridin-1-yl]-methanone

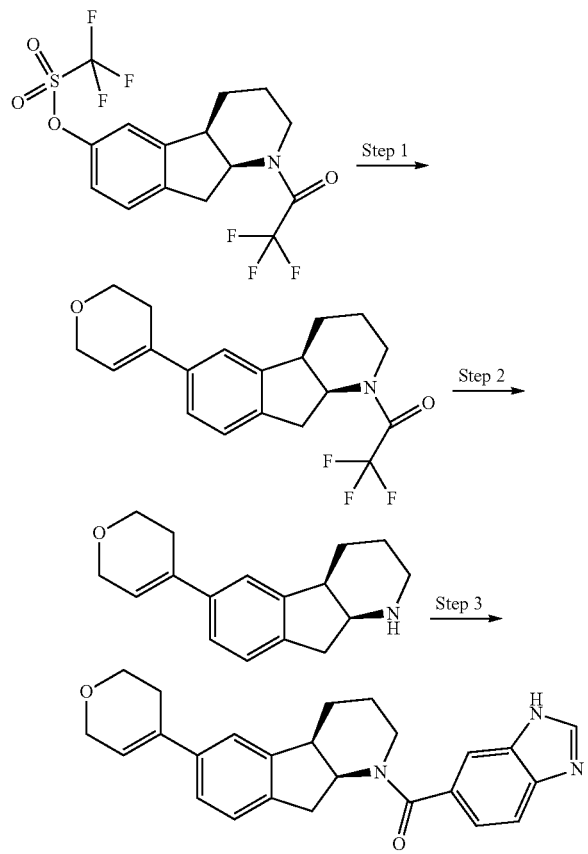

Step 1: 1-[cis-6-(3,6-dihydro-2H-pyran-4-yl)-2,3,4,4a,9,9a-hexahydro-indeno[2,1-b]pyridin-1-yl]-2,2,2-trifluoro-ethanone A flask charged with a stir bar, trifluoromethanesulfonic acid 1-(2,2,2-trifluoro-acetyl)-2,3,4,4a,9,9a-hexahydro-1H-indeno[2,1-b]pyridin-6-yl ester (0.20 g), 3,6-dihydro-2H-pyran-4-boronic acid pinacol ester (0.23 g), cesium carbonate (2 mol/L in water, 0.7 mL), tetrahydrofuran (4 ml), and toluene (1 mL) is sparged with argon for 5 min. Bis(1,1'-diphenylphosphino)ferrocene-dichloropalladium (44 mg) is added and the mixture is heated to 100° C. After stirring at 100° C. overnight, another portion of 3,6-dihydro-2H-pyran-4-boronic acid pinacol ester (0.05 g) and bis(1,1'-diphenylphosphino)ferrocene-dichloropalladium (20 mg) is added and stirring is continued at 100° C. for 5 h. After cooling to room temperature, the mixture is diluted with ethyl acetate, washed with aqueous NH$_4$Cl solution, dried (Na$_2$SO$_4$), and concentrated. The residue is chromatographed on silica gel (dichloromethane/methanol 1:0→9:1) to give the title compound.

Yield: 0.16 g (impure); LC (method 1): $t_R$=4.36 min; Mass spectrum (ESI$^+$): m/z=352 [M+H]$^+$.

Step 2: cis-6-(3,6-dihydro-2H-pyran-4-yl)-2,3,4,4a,9,9a-hexahydro-1H-indeno[2,1-b]pyridine The title compound is prepared from 1-[cis-6-(3,6-dihydro-2H-pyran-4-yl)-2,3,4,4a,9,9a-hexahydro-indeno[2,1-b]pyridin-1-yl]-2,2,2-trifluoro-ethanone following a procedure analogous to that described in Step 5 of Intermediate 46. Yield: 37% of theory; LC (method 1): $t_R$=1.97 min; Mass spectrum (ESI$^+$): m/z=256 [M+H]$^+$.

Step 3: cis-(3H-benzoimidazol-5-yl)-[6-(3,6-dihydro-2H-pyran-4-yl)-2,3,4,4a,9,9a-hexahydro-indeno[2,1-b]pyridin-1-yl]methanone The title compound is prepared from 1H-benzoimidazole-5-carboxylic acid and cis-6-(3,6-dihydro-2H-pyran-4-yl)-2,3,4,4a,9,9a-hexahydro-1H-indeno[2,1-b]pyridine following a procedure analogous to that described in Example 1. Yield: 69% of theory; LC (method 1): $t_R$=2.65 min; Mass spectrum (ESI$^+$): m/z=400 [M+H]$^+$.

Intermediate 52 cis-(3H-Benzoimidazol-5-yl)-(6-cyclopent-1-enyl-2,3,4,4a,9,9a-hexahydro-indeno[2,1-b]pyridin-1-yl)-methanone

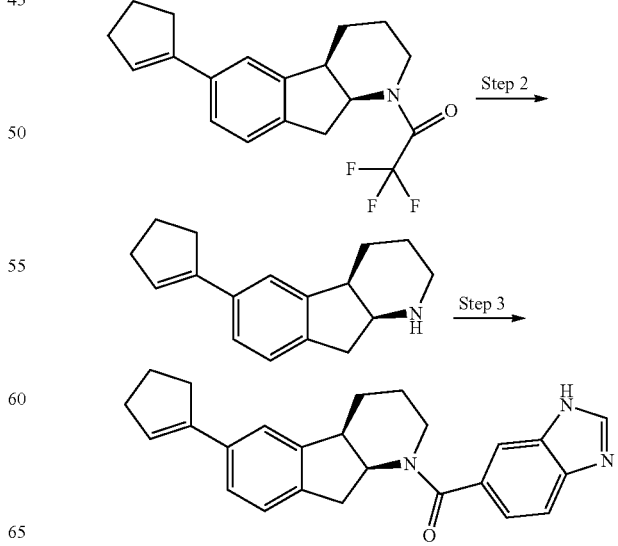

Step 1: 1-(cis-6-cyclopent-1-enyl-2,3,4,4a,9,9a-hexahydro-indeno[2,1-b]pyridin-1-yl)-2,2,2-trifluoro-ethanone The title compound is prepared from trifluoro-methanesulfonic acid 1-(2,2,2-trifluoro-acetyl)-2,3,4,4a,9,9a-hexahydro-1H-indeno[2,1-b]pyridin-6-yl ester and cyclopentenyl-1-boronic acid pinacol ester following a procedure analogous to that described in Step 1 of Intermediate 51. Yield: 31% of theory; LC (method 1): $t_R$=5.34 min; Mass spectrum (ESI$^+$): m/z=336 [M+H]$^+$.

Step 2: cis-6-cyclopent-1-enyl-2,3,4,4a,9,9a-hexahydro-1H-indeno[2,1-b]pyridine The title compound is prepared from 1-(cis-6-cyclopent-1-enyl-2,3,4,4a,9,9a-hexahydro-indeno[2,1-b]pyridin-1-yl)-2,2,2-trifluoro-ethanone following a procedure analogous to that described in Step 5 of Intermediate 46. Yield: quantitative; LC (method 1): $t_R$=2.73 min; Mass spectrum (ESI$^+$): m/z=240 [M+H]$^+$.

Step 3: cis-(3H-benzoimidazol-5-yl)-(6-cyclopent-1-enyl-2,3,4,4a,9,9a-hexahydro-indeno[2,1-b]pyridin-1-yl)-methanone The title compound is prepared from 1H-benzoimidazole-5-carboxylic acid and cis-6-cyclopent-1-enyl-2,3,4,4a,9,9a-hexahydro-1H-indeno[2,1-b]pyridine following a procedure analogous to that described in Example 1. Yield: 49% of theory; LC (method 1): $t_R$=2.64 min; Mass spectrum (ESI$^+$): m/z=384 [M+H]$^+$.

Intermediate 53

N-(cis-2,3,4,4a,9,9a-Hexahydro-1H-indeno[2,1-b]pyridin-7-yl)-acetamide

Step 1: cis-7-amino-2,3,4,4a,9,9a-hexahydro-indeno[2,1-b]pyridine-1-carboxylic acid tert-butyl ester The title compound is prepared from cis-2,3,4,4a,9,9a-hexahydro-1H-indeno[2,1-b]pyridin-7-ylamine and di-tert-butyl dicarbonate following a procedure analogous to that described in Step 3 of Intermediate 32. Yield: 25% of theory; LC (method 1): $t_R$=2.69 min; Mass spectrum (ESI$^+$): m/z=289 [M+H]$^+$.

Step 2: cis-7-acetylamino-2,3,4,4a,9,9a-hexahydro-indeno[2,1-b]pyridine-1-carboxylic acid tert-butyl ester Acetic anhydride (50 μL) is added to a solution of cis-7-amino-2,3,4,4a,9,9a-hexahydro-indeno[2,1-b]pyridine-1-carboxylic acid tert-butyl ester (140 mg) and triethylamine (70 μL) in dichloromethane (3 mL) at room temperature. The solution is stirred for 1 h at room temperature and then aqueous NaHCO$_3$ solution is added. The mixture is stirred vigorously for 20 min and then extracted with dichloromethane. The combined extract is concentrated and the residue is chromatographed (cyclohexane/ethyl acetate 7:3→1:9) to give the title compound. Yield: 100 mg (62% of theory); LC (method 1): $t_R$=3.60 min.

Step 3: N-(cis-2,3,4,4a,9,9a-hexahydro-1H-indeno[2,1-b]pyridin-7-yl)-acetamide The title compound is prepared from cis-7-acetylamino-2,3,4,4a,9,9a-hexahydro-indeno[2,1-b]pyridine-1-carboxylic acid tert-butyl ester following a procedure analogous to that described in Step 5 of Intermediate 32. Yield: quantitative; LC (method 1): $t_R$=0.92 min; Mass spectrum (ESI$^+$): m/z=231 [M+H]$^+$.

Intermediate 54

N-(cis-2,3,4,4a,9,9a-Hexahydro-1H-indeno[2,1-b]pyridin-7-yl)-methanesulfonamide

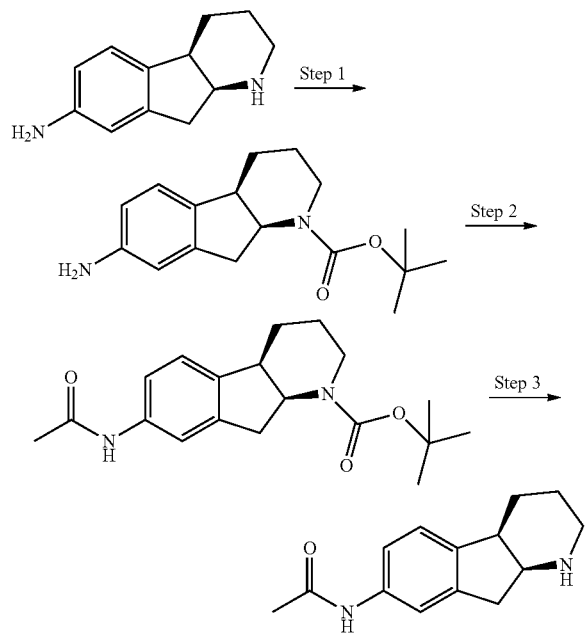

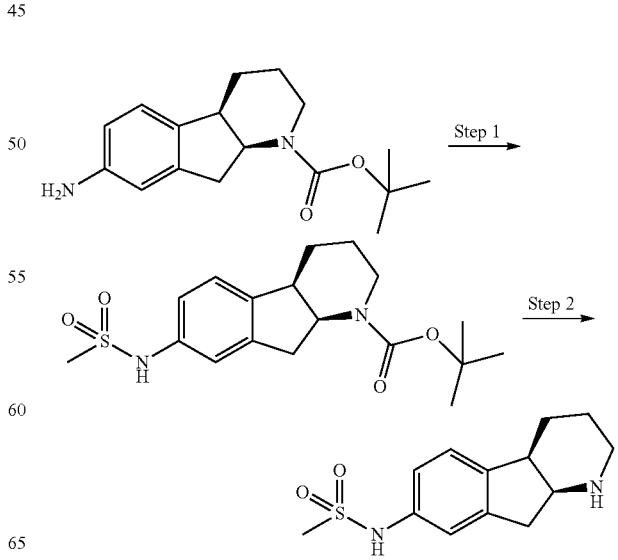

Step 1: cis-7-methanesulfonylamino-2,3,4,4a,9,9a-hexahydro-indeno[2,1-b]pyridine-1-carboxylic acid tert-butyl ester Methylsulfonyl chloride (42 µL) is added to a solution of cis-7-amino-2,3,4,4a,9,9a-hexahydro-indeno[2,1-b]pyridine-1-carboxylic acid tert-butyl ester (160 mg) and triethylamine (76 µL) in dichloromethane (3 mL) at room temperature. The solution is stirred for 1 h at room temperature and then aqueous NaHCO$_3$ solution is added. The mixture is stirred vigorously for 20 min and then extracted with dichloromethane. The combined extract is concentrated and the residue is chromatographed (cyclohexane/ethyl acetate 7:3→1:9) to give the title compound. Yield: 120 mg (59% of theory); LC (method 1): $t_R$=3.80 min; Mass spectrum (ESI$^-$): m/z=365 [M−H]$^-$.

Step 2: N-(cis-2,3,4,4a,9,9a-hexahydro-1H-indeno[2,1-b]pyridin-7-yl)-methanesulfonamide The title compound is prepared from cis-7-methanesulfonylamino-2,3,4,4a,9,9a-hexahydro-indeno[2,1-b]pyridine-1-carboxylic acid tert-butyl ester following a procedure analogous to that described in Step 5 of Intermediate 32. Yield: quantitative; LC (method 1): $t_R$=0.97 min; Mass spectrum (ESI$^+$): m/z=267 [M+H]$^+$.

Intermediate 55 cis-7-Nitro-2,3,4,4a,9,9a-hexahydro-1H-indeno[2,1-b]pyridin-6-ol

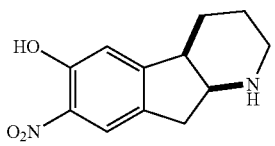

A ca. 10° C.-cold mixture of nitric acid (65%, 0.36 mL) and sulfuric acid (96%, 0.55 mL) is added dropwise to a solution of trifluoro-methanesulfonic acid cis-1-(2,2,2-trifluoroacetyl)-2,3,4,4a,9,9a-hexahydro-1H-indeno[2,1-b]pyridin-6-yl ester (2.00 g) in sulfuric acid (96%, 12 mL) chilled in an ice bath. The solution is stirred in the cooling bath for 1 h and poured then onto crushed ice. The precipitate formed is separated by filtration and taken up in methanol (10 mL). The resulting solution is treated with saturated aqueous K$_2$CO$_3$ solution (alternatively NaOH is used) until the trifluoromethylsulfonyl and trifluoroacetyl group are cleaved off (TLC or HPLC). Water is then added and the resulting mixture is extracted with ethyl acetate. The combined extract is concentrated to give the crude title compound that is used without further purification. Yield: 1.10 g (crude); LC (method 1): $t_R$=1.44 min; Mass spectrum (ESI$^+$): m/z=235 [M+H]$^+$.

Intermediate 56 cis-6-Methoxy-7-methyl-2,3,4,4a,9,9a-hexahydro-1H-indeno[2,1-b]pyridine

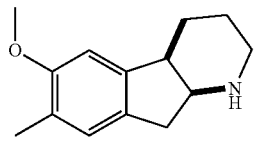

The title compound is prepared from 3-bromo-pyridine-2-carboxylic acid and 4-methyl-3-methoxyboronic acid following the synthetic sequence and protocols described for Intermediate 41; since 3-bromo-pyridine-2-carboxylic acid instead of 3-bromo-pyridine-2-carbonitrile is used for the Suzuki-Miyaura coupling (Step 1 of Intermediate 41), hydrolysis of the nitrile (Step 2 of Intermediate 41) is omitted. LC (method 7): $t_R$=0.74 min; Mass spectrum (ESI$^+$): m/z=218 [M+H]$^+$.

Intermediate 57 cis-6-Methoxy-5-methyl-2,3,4,4a,9,9a-hexahydro-1H-indeno[2,1-b]pyridine

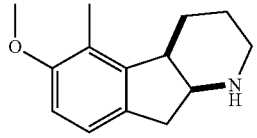

The title compound is prepared from 3-bromo-pyridine-2-carboxylic acid and 2-(3-methoxy-2-methyl-phenyl)-4,4,5,5-tetramethyl-[1,3,2]dioxaborolane (may be prepared as in WO 2001053268 described) following the synthetic sequence and protocols described for Intermediate 41; since 3-bromo-pyridine-2-carboxylic acid instead of 3-bromo-pyridine-2-carbonitrile is used for the Suzuki-Miyaura coupling (Step 1 of Intermediate 41), hydrolysis of the nitrile (Step 2 of Intermediate 41) is omitted.

Intermediate 58

Trifluoromethanesulfonic acid cis-7-methyl-1-(1-trifluoromethanesulfonyl-1H-benzoimidazole-5-carbonyl)-2,3,4,4a,9,9a-hexahydro-1H-indeno[2,1-b]pyridin-6-yl ester and Trifluoro-methanesulfonic acid cis-7-methyl-1-(3-trifluoromethanesulfonyl-3H-benzoimidazole-5-carbonyl)-2,3,4,4a,9,9a-hexahydro-1H-indeno[2,1-b]pyridin-6-yl ester

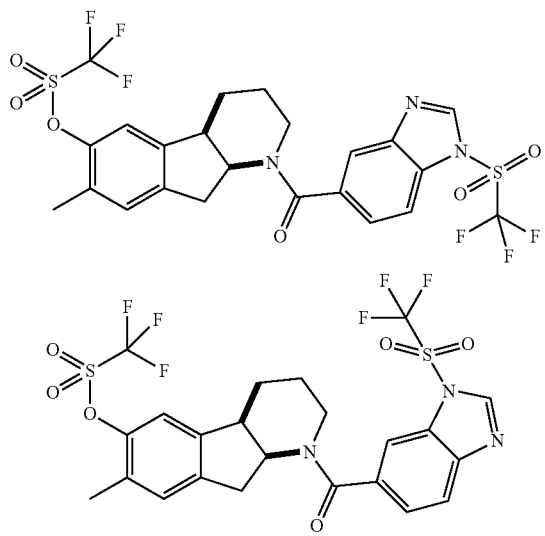

The title compounds are prepared from (1H-benzoimidazol-5-yl)-(cis-6-hydroxy-7-methyl-2,3,4,4a,9,9a-hexahydro-indeno[2,1-b]pyridin-1-yl)-methanone following a procedure analogous to that described in Intermediate 42 and used as a mixture in the following step.

Intermediate 59

(1H-Benzoimidazol-5-yl)-(cis-6-methoxy-5-methyl-2,3,4,4a,9,9a-hexahydro-indeno[2,1-b]pyridin-1-yl)-methanone

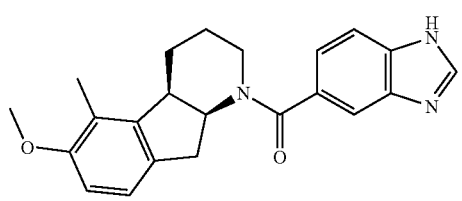 [SMILES: COc1ccc2c(c1C)[C@H]1CCCN(C(=O)c3ccc4[nH]cnc4c3)[C@H]1C2]

The title compound is prepared from 1H-benzoimidazole-5-carboxylic acid and cis-6-methoxy-5-methyl-2,3,4,4a,9, 9a-hexahydro-1H-indeno[2,1-b]pyridine following a procedure analogous to that described in Example 1.

Intermediate 60

(1H-Benzoimidazol-5-yl)-(cis-6-hydroxy-5-methyl-2,3,4,4a,9,9a-hexahydro-indeno[2,1-b]pyridin-1-yl)-methanone

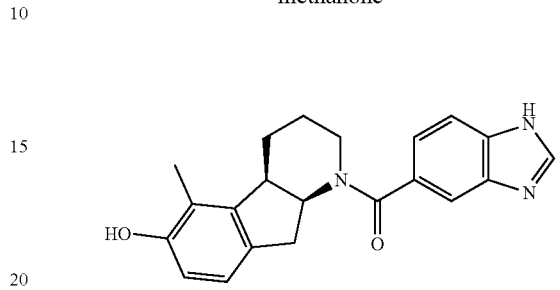

The title compound is prepared from (1H-benzoimidazol-5-yl)-(cis-6-methoxy-5-methyl-2,3,4,4a,9,9a-hexahydro-indeno[2,1-b]pyridin-1-yl)-methanone following a procedure analogous to that described in Example 7.

Intermediate 61

Trifluoromethanesulfonic acid cis-5-methyl-1-(1-trifluoromethanesulfonyl-1H-benzoimidazole-5-carbonyl)-2,3,4,4a,9,9a-hexahydro-1H-indeno[2,1-b]pyridin-6-yl ester and Trifluoro-methanesulfonic acid cis-5-methyl-1-(3-trifluoromethanesulfonyl-3H-benzoimidazole-5-carbonyl)-2,3,4,4a,9,9a-hexahydro-1H-indeno[2,1-b]pyridin-6-yl ester

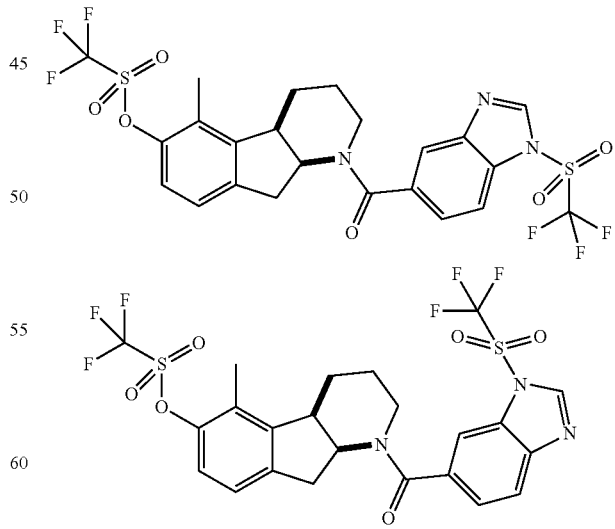

The title compounds are prepared from (1H-benzoimidazol-5-yl)-(cis-6-hydroxy-5-methyl-2,3,4,4a,9,9a-hexahydro-indeno[2,1-b]pyridin-1-yl)-methanone following a procedure analogous to that described in Intermediate 42 and used as a mixture in the following step.

Example 1

(1H-Benzoimidazol-5-yl)-(cis-2,3,4a,5,6,10b-hexahydro-1H-benzo[f]quinolin-4-yl)-methanone

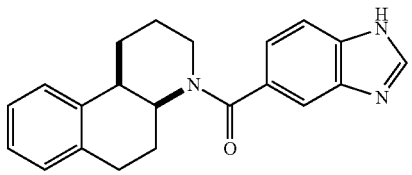

2-(1H-Benzotriazol-1-yl)-1,1,3,3-tetramethyluronium tetrafluoroborate (0.50 g; alternatively, 2-(7-aza-1H-benzotriazol-1-yl)-1,1,3,3-tetramethyluronium hexafluorophosphate may be used) is added to a solution of 1H-benzoimidazole-5-carboxylic acid (0.23 g) and ethyl-diisopropyl-amine (0.50 mL) in N,N-dimethylformamide (2 mL) at room temperature. The solution is stirred for 20 min prior to the addition of cis-1,2,3,4,4a,5,6,10b-octahydro-benzo[f]quinoline (0.30 g) dissolved in N,N-dimethylformamide (2 mL). The resulting solution is stirred at room temperature for 3 h. 32% aqueous ammonia (1 mL) in methanol (2 mL) is then added and the mixture is stirred for another 30 min. The mixture is diluted with ethyl acetate and washed with water and brine and dried ($Na_2SO_4$). The solvent is evaporated and the residue is chromatographed on silica gel (dichloromethane/methanol containing 1% $NH_3$ 95:5→80:20) to afford the title compound as a foam-like solid that is triturated with ether and dried to give a colorless solid [alternatively, the product may be purified by HPLC on reversed phase (MeOH/$H_2O$)]. Yield: 0.38 g (80% of theory); LC (method 1): $t_R$=2.53 min; Mass spectrum (ESI$^+$): m/z=332 [M+H]$^+$; $^1$H NMR (400 MHz, DMSO-$d_6$, mixture of 2 rotamers) δ 1.52-1.82 (m, 4H), 1.82-1.94 (m, 1H), 2.24-ca. 2.48 (m, 1.5H), 2.71-3.02 (m, 3H), 3.03-3.18 (m, 0.5H), 3.50-3.65 (m, 0.5H), 3.88-4.05 (m, 0.5H), 4.39-4.56 (m, 0.5H), 4.83-4.99 (m, 0.5H), 6.89-7.20 (m, 4H), 7.21-7.27 (m, 1H), 7.56-7.70 (m, 2H), 8.23-8.35 (m, 1H), 12.58 (broad s, 1H).

Example 2

(1H-Benzoimidazol-5-yl)-[(4a-S,10b-R)-2,3,4a,5,6,10b-hexahydro-1H-benzo[f]quinolin-4-yl]-methanone

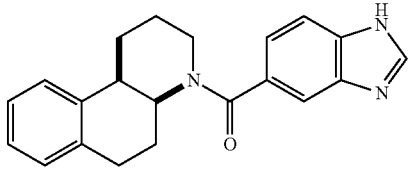

The title compound is obtained by chromatographing a racemic mixture of (1H-benzoimidazol-5-yl)-(cis-2,3,4a,5,6,10b-hexahydro-1H-benzo[f]quinolin-4-yl)-methanone (100 mg) on chiral phase (SFC; column: 1×ASH 250×10 mm, 5 μm; mobile phase: methanol containing 0.2% diethylamine/ sc carbon dioxide 25:75; flow rate: 10 mL/min). Yield: 48 mg; LC(SFC; column: Daicel ASH 250×4.6 mm, 5 μm; mobile phase: methanol containing 0.2% diethylamine/sc carbon dioxide 25:75; flow rate: 4 mL/min): $t_R$=2.73 min; Mass spectrum (ESI$^+$): m/z=332 [M+H]$^+$; for $^1$H NMR see Example 1.

Example 3

(1H-Benzoimidazol-5-yl)-[(4a-R,10b-S)-2,3,4a,5,6,10b-hexahydro-1H-benzo[f]quinolin-4-yl]-methanone

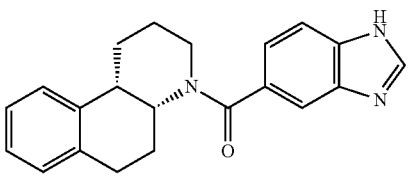 [SMILES: O=C(c1ccc2[nH]cnc2c1)N1CCC[C@H]2c3ccccc3CC[C@H]21]

The title compound is obtained by chromatographing a racemic mixture of (1H-benzoimidazol-5-yl)-(cis-2,3,4a,5,6,10b-hexahydro-1H-benzo[f]quinolin-4-yl)-methanone (100 mg) on chiral phase (SFC; column: 1×ASH 250×10 mm, 5 μm; mobile phase: methanol containing 0.2% diethylamine/ sc carbon dioxide 25:75; flow rate: 10 mL/min). Yield: 45 mg; LC(SFC; column: Daicel ASH 250×4.6 mm, 5 μm; mobile phase: methanol containing 0.2% diethylamine/sc carbon dioxide 25:75; flow rate: 4 mL/min): $t_R$=2.13 min; Mass spectrum (ESI$^+$): m/z=332 [M+H]$^+$; for $^1$H NMR see Example 1.

Example 4

(1H-Benzoimidazol-5-yl)-(trans-2,3,4a,5,6,10b-hexahydro-1H-benzo[f]quinolin-4-yl)-methanone

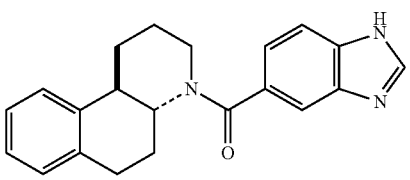

The title compound is prepared from 1H-benzoimidazole-5-carboxylic acid and trans-1,2,3,4,4a,5,6,10b-octahydro-benzo[f]quinoline following a procedure analogous to that described in Example 1. Yield: 31% of theory; TLC: $r_f$=0.40 (silica gel, $CH_2Cl_2$/MeOH/32% aqueous $NH_3$ 90:10:1); Mass spectrum (ESI$^+$): m/z=332 [M+H]$^+$; $^1$H NMR (400 MHz, DMSO-$d_6$) δ 1.32-1.46 (m, 1H), 1.53-1.76 (m, 2H), 2.14-2.24 (m, 1H), 2.30-2.43 (m, 1H), ca. 2.49-2.56 superimposed by $D_3$CSOCHD$_2$ signal (m, 1H), 2.77-2.93 (m, 2H), 3.03-3.13 (m, 1H), ca. 3.25-3.34 superimposed by $H_2O$ signal (m, 1H), 3.34-3.43 (m, 1H), 3.67-3.76 (m, 1H), 7.07-7.19 (m, 3H), 7.26-7.32 (m, 2H), 7.59-7.70 (m, 2H), 8.30 (s, 1H), 12.60 (broad s, 1H).

Example 5

4-(cis-2,3,4a,5,6,10b-Hexahydro-1H-benzo[f]quinoline-4-carbonyl)-benzamide

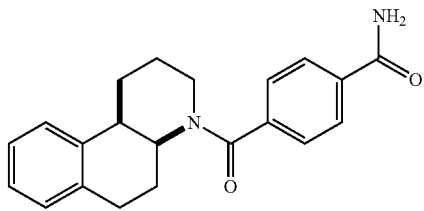

The title compound is prepared from terephthalamic acid and cis-1,2,3,4,4a,5,6,10b-octahydro-benzo[f]quinoline following a procedure analogous to that described in Example 1. Yield: 58% of theory; LC (method 1): $t_R$=3.16 min; Mass spectrum (ESI$^+$): m/z=335 [M+H]$^+$.

Example 6

(1H-Benzoimidazol-5-yl)-(cis-7-methoxy-2,3,4a,5,6,10b-hexahydro-1H-benzo[f]quinolin-4-yl)-methanone

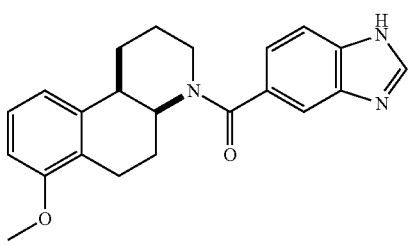

The title compound is prepared from 1H-benzoimidazole-5-carboxylic acid and cis-7-methoxy-1,2,3,4,4a,5,6,10b-octahydro-benzo[f]quinoline following a procedure analogous to that described in Example 1. Yield: 85% of theory; LC (method 1): $t_R$=2.62 min; Mass spectrum (ESI$^+$): m/z=362 [M+H]$^+$.

Example 7

(1H-Benzoimidazol-5-yl)-(cis-7-hydroxy-2,3,4a,5,6,10b-hexahydro-1H-benzo[f]quinolin-4-yl)-methanone

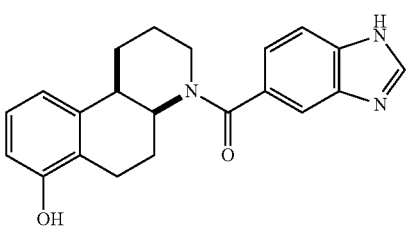

Boron tribromide (1 mol/L in dichloromethane, 0.5 mL) is added to a solution of (1H-benzoimidazol-5-yl)-(cis-7-methoxy-2,3,4a,5,6,10b-hexahydro-1H-benzo[f]quinolin-4-yl)-methanone (60 mg) in dichloromethane (5 mL) at room temperature. The resulting solution is stirred at room temperature for 2 h. Aqueous half-saturated NaHCO$_3$ solution is added and the resulting neutral mixture is extracted with dichloromethane and dichloromethane/methanol (95:5). The combined extracts are washed with brine and dried (Na$_2$SO$_4$). The solvent is evaporated and the residue is triturated with diethyl ether and dried to give the title compound as a colorless solid. Yield: 30 mg (52% of theory); TLC: $r_f$=0.45 (silica gel, CH$_2$Cl$_2$/MeOH/32% aqueous NH$_3$ 90:10:1); Mass spectrum (ESI$^+$): m/z=348 [M+H]$^+$.

Example 8

(1H-Benzoimidazol-5-yl)-(cis-10-methoxy-2,3,4a,5,6,10b-hexahydro-1H-benzo[f]quinolin-4-yl)-methanone

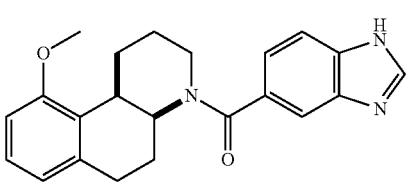

The title compound is prepared from 1H-benzoimidazole-5-carboxylic acid and cis-10-methoxy-1,2,3,4,4a,5,6,10b-octahydro-benzo[f]quinoline following a procedure analogous to that described in Example 1. Yield: 55% of theory; LC (method 1): $t_R$=2.67 min; Mass spectrum (ESI$^+$): m/z=362 [M+H]$^+$.

Example 9

(1H-Benzoimidazol-5-yl)-(trans-10-methoxy-2,3,4a, 5,6,10b-hexahydro-1H-benzo[f]quinolin-4-yl)-methanone

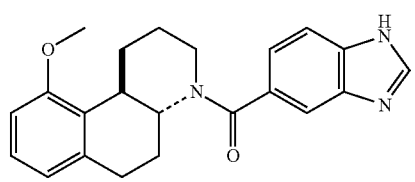

The title compound is prepared from 1H-benzoimidazole-5-carboxylic acid and trans-10-methoxy-1,2,3,4,4a,5,6,10b-octahydro-benzo[f]quinoline following a procedure analogous to that described in Example 1. Yield: 51% of theory; LC (method 2): $t_R$=3.63 min; Mass spectrum (ESI$^+$): m/z=362 [M+H]$^+$.

Example 10

(1H-Benzoimidazol-5-yl)-(cis-10b-methyl-2,3,4a,5, 6,10b-hexahydro-1H-benzo[f]quinolin-4-yl)-methanone

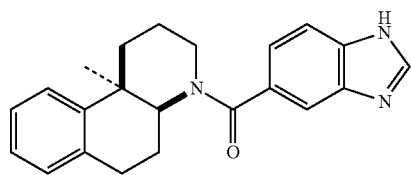

The title compound is prepared from 1H-benzoimidazole-5-carboxylic acid and an isomeric mixture of cis-10b-methyl-1,2,3,4,4a,5,6,10b-octahydro-benzo[f]quinoline and trans-10b-methyl-1,2,3,4,4a,5,6,10b-octahydro-benzo[f]quinoline following a procedure analogous to that described in Example 1 yielding a mixture of Example 10 and Example 11 which is separated by HPLC on reversed phase (MeOH/H$_2$O/NH$_4$OH). Yield: 20% of theory; LC (method 2): $t_R$=3.40 min; Mass spectrum (ESI$^+$): m/z=346 [M+H]$^+$; $^1$H NMR (400 MHz, DMSO-d$_6$, mixture of 2 rotamers) δ 1.33 (s, 3H), 1.42-1.53 (m, 2H), 1.62-1.78 (m, 1H), 2.15-2.23 (m, 1H), 2.27-2.35 (m, 1H), 2.75-2.90 (m, 3H), 3.07-3.18 (m, 1H), 3.43-3.49 (m, 1H), 3.69-3.77 (m, 1H), 7.04-7.18 (m, 3H), 7.20-7.34 (m, 2H), 7.56 (broad s, 0.75H), 7.58 (broad s, 0.25H), 7.67 (broad s, 0.75H), 7.69 (broad s, 0.25H), 8.29 (s, 1H), 12.53-12.62 (m, 1H).

Example 11

(1H-Benzoimidazol-5-yl)-(trans-10b-methyl-2,3,4a, 5,6,10b-hexahydro-1H-benzo[f]quinolin-4-yl)-methanone

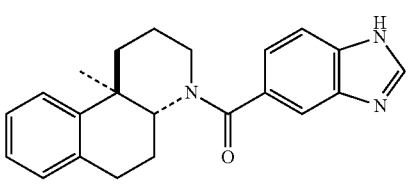

The title compound is prepared from 1H-benzoimidazole-5-carboxylic acid and an isomeric mixture of cis-10b-methyl-1,2,3,4,4a,5,6,10b-octahydro-benzo[f]quinoline and trans-10b-methyl-1,2,3,4,4a,5,6,10b-octahydro-benzo[f]quinoline following a procedure analogous to that described in Example 1 yielding a mixture of Example 10 and Example 11 which is separated by HPLC on reversed phase (MeOH/H$_2$O/NH$_4$OH). Yield: 15% of theory; LC (method 2): $t_R$=3.26 min; Mass spectrum (ESI$^+$): m/z=346 [M+H]$^+$.

Example 12

(1H-Benzoimidazol-5-yl)-(trans-7-methoxy-2,3,4a,5, 6,10b-hexahydro-1H-benzo[f]quinolin-4-4-methanone

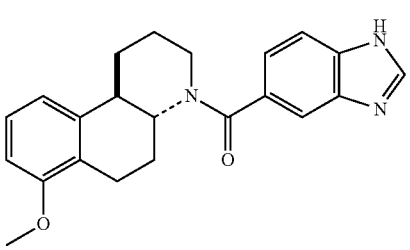

The title compound is prepared from 1H-benzoimidazole-5-carboxylic acid and trans-7-methoxy-1,2,3,4,4a,5,6,10b-octahydro-benzo[f]quinoline following a procedure analogous to that described in Example 1. Yield: 49% of theory; LC (method 1): $t_R$=2.68 min; Mass spectrum (ESI⁺): m/z=362 [M+H]⁺.

Example 13

(1H-Benzoimidazol-5-yl)-(cis-10-hydroxy-2,3,4a,5,6,10b-hexahydro-1H-benzo[f]quinolin-4-yl)-methanone

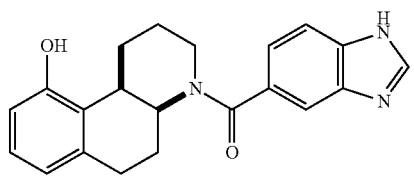

The title compound is prepared from (1H-benzoimidazol-5-yl)-(cis-10-methoxy-2,3,4a,5,6,10b-hexahydro-1H-benzo[f]quinolin-4-yl)-methanone following a procedure analogous to that described in Example 7. Yield: 68% of theory; LC (method 1): $t_R$=2.25 min; Mass spectrum (ESI⁺): m/z=348 [M+H]⁺.

Example 14

(1H-Benzoimidazol-5-yl)-(cis-9-methoxy-2,3,4a,5,6,10b-hexahydro-1H-benzo[f]quinolin-4-yl)-methanone

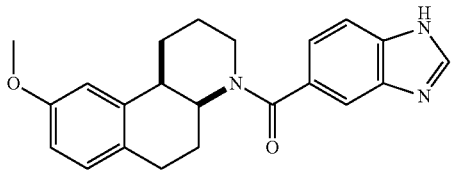

The title compound is prepared from 1H-benzoimidazole-5-carboxylic acid and cis-9-methoxy-1,2,3,4,4a,5,6,10b-octahydro-benzo[f]quinoline following a procedure analogous to that described in Example 1. Yield: 69% of theory; LC (method 1): $t_R$=2.55 min; Mass spectrum (ESI⁺): m/z=362 [M+H]⁺.

Example 15

(1H-Benzoimidazol-5-yl)-(trans-9-methoxy-2,3,4a,5,6,10b-hexahydro-1H-benzo[f]quinolin-4-4-methanone

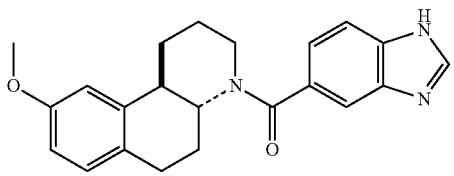

The title compound is prepared from 1H-benzoimidazole-5-carboxylic acid and trans-9-methoxy-1,2,3,4,4a,5,6,10b-octahydro-benzo[f]quinoline following a procedure analogous to that described in Example 1. Yield: 77% of theory; LC (method 1): $t_R$=2.61 min; Mass spectrum (ESI⁺): m/z=362 [M+H]⁺.

Example 16

(1H-Benzoimidazol-5-yl)-(cis-9-hydroxy-2,3,4a,5,6,10b-hexahydro-1H-benzo[f]quinolin-4-yl)-methanone

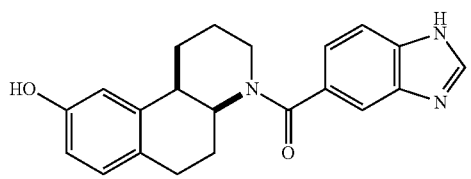

The title compound is prepared from (1H-benzoimidazol-5-yl)-(cis-9-methoxy-2,3,4a,5,6,10b-hexahydro-1H-benzo[f]quinolin-4-yl)-methanone following a procedure analogous to that described in Example 7. Yield: 58% of theory; LC (method 1): $t_R$=2.08 min; Mass spectrum (ESI⁺): m/z=348 [M+H]⁺.

Example 17

(1H-Benzoimidazol-5-yl)-(trans-9-hydroxy-2,3,4a,5,6,10b-hexahydro-1H-benzo[f]quinolin-4-yl)-methanone

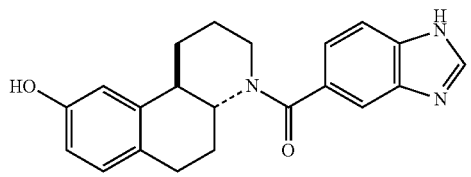

The title compound is prepared from (1H-benzoimidazol-5-yl)-(trans-9-methoxy-2,3,4a,5,6,10b-hexahydro-1H-benzo[f]quinolin-4-yl)-methanone following a procedure analogous to that described in Example 7. Yield: 61% of theory; LC (method 1): $t_R$=2.10 min; Mass spectrum (ESI⁺): m/z=348 [M+H]⁺.

Example 18

(1H-Benzoimidazol-5-yl)-(trans-10-hydroxy-2,3,4a,5,6,10b-hexahydro-1H-benzo[f]quinolin-4-yl)-methanone

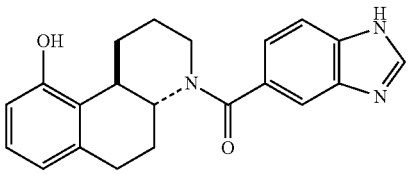

The title compound is prepared from (1H-benzoimidazol-5-yl)-(trans-10-methoxy-2,3,4a,5,6,10b-hexahydro-1H-benzo[f]quinolin-4-yl)-methanone following a procedure analogous to that described in Example 7. Yield: 14% of theory; LC (method 1): $t_R$=2.33 min; Mass spectrum (ESI⁺): m/z=348 [M+H]⁺.

Example 19

(1H-Benzoimidazol-5-yl)-(trans-7-hydroxy-2,3,4a,5,6,10b-hexahydro-1H-benzo[f]quinolin-4-yl)-methanone

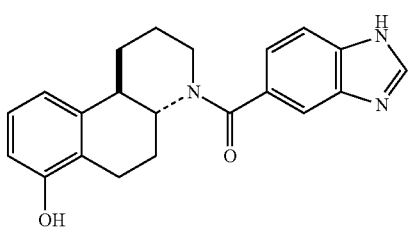

The title compound is prepared from (1H-benzoimidazol-5-yl)-(trans-7-methoxy-2,3,4a,5,6,10b-hexahydro-1H-benzo[f]quinolin-4-yl)-methanone following a procedure analogous to that described in Example 7. Yield: 36% of theory; LC (method 1): $t_R$=2.19 min; Mass spectrum (ESI⁺): m/z=348 [M+H]⁺.

Example 20

(1H-Benzoimidazol-5-yl)-(cis-7,9-difluoro-2,3,4a,5,6,10b-hexahydro-1H-benzo[f]quinolin-4-yl)-methanone

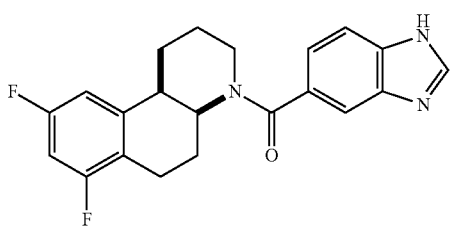

The title compound is prepared from 1H-benzoimidazole-5-carboxylic acid and cis-7,9-difluoro-1,2,3,4,4a,5,6,10b-octahydro-benzo[f]quinoline following a procedure analogous to that described in Example 1. Yield: 72% of theory; TLC: $r_f$=0.37 (silica gel, CH₂Cl₂/MeOH/32% aqueous NH₃ 90:10:1); Mass spectrum (ESI⁺): m/z=368 [M+H]⁺.

Example 21

(1H-Benzoimidazol-5-yl)-(trans-7,9-difluoro-2,3,4a,5,6,10b-hexahydro-1H-benzo[f]quinolin-4-yl)-methanone

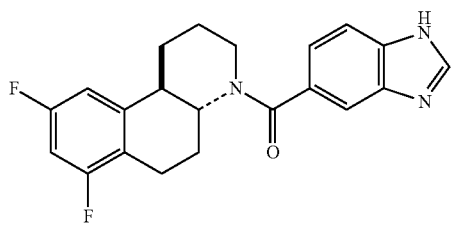

The title compound is prepared from 1H-benzoimidazole-5-carboxylic acid and trans-7,9-difluoro-1,2,3,4,4a,5,6,10b-octahydro-benzo[f]quinoline following a procedure analogous to that described in Example 1. Yield: 70% of theory; TLC: $r_f$=0.43 (silica gel, CH₂Cl₂/MeOH/32% aqueous NH₃ 90:10:1); Mass spectrum (ESI⁺): m/z=368 [M+H]⁺.

Example 22

(1H-Benzoimidazol-5-yl)-(cis-8-methoxy-2,3,4a,5,6,10b-hexahydro-1H-benzo[f]quinolin-4-yl)-methanone

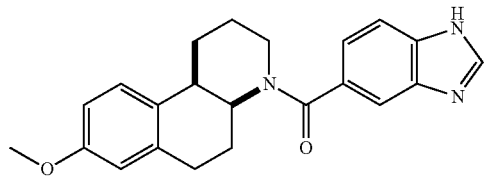

The title compound is prepared from 1H-benzoimidazole-5-carboxylic acid and cis-8-methoxy-1,2,3,4,4a,5,6,10b-octahydro-benzo[f]quinoline following a procedure analogous to that described in Example 1. Yield: 78% of theory; LC (method 1): $t_R$=2.54 min; Mass spectrum (ESI⁺): m/z=362 [M+H]⁺.

Example 23

(1H-Benzoimidazol-5-yl)-(trans-8-methoxy-2,3,4a,5,6,10b-hexahydro-1H-benzo[f]quinolin-4-yl)-methanone

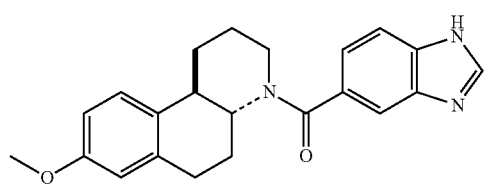

The title compound is prepared from 1H-benzoimidazole-5-carboxylic acid and trans-8-methoxy-1,2,3,4,4a,5,6,10b-octahydro-benzo[f]quinoline following a procedure analogous to that described in Example 1. Yield: 71% of theory; LC (method 1): $t_R$=2.61 min; Mass spectrum (ESI$^+$): m/z=362 [M+H]$^+$.

Example 24

(1H-Benzoimidazol-5-yl)-(trans-8-hydroxy-2,3,4a,5,6,10b-hexahydro-1H-benzo[f]quinolin-4-yl)-methanone

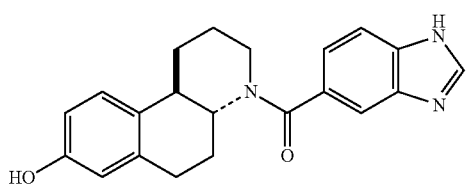

The title compound is prepared from (1H-benzoimidazol-5-yl)-(trans-8-methoxy-2,3,4a,5,6,10b-hexahydro-1H-benzo[f]quinolin-4-yl)-methanone following a procedure analogous to that described in Example 7. Yield: 48% of theory; LC (method 1): $t_R$=2.07 min; Mass spectrum (ESI$^+$): m/z=348 [M+H]$^+$.

Example 25

(1H-Benzoimidazol-5-yl)-(cis-8-hydroxy-2,3,4a,5,6,10b-hexahydro-1H-benzo[f]quinolin-4-yl)-methanone

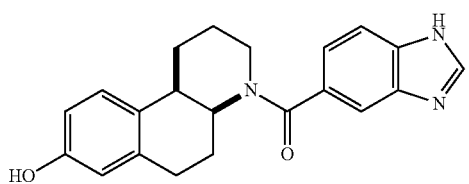

The title compound is prepared from (1H-benzoimidazol-5-yl)-(cis-8-methoxy-2,3,4a,5,6,10b-hexahydro-1H-benzo[f]quinolin-4-yl)-methanone following a procedure analogous to that described in Example 7. Yield: 39% of theory; LC (method 1): $t_R$=2.03 min; Mass spectrum (ESI$^+$): m/z=348 [M+H]$^+$.

Example 26

(1H-Benzoimidazol-5-yl)-(trans-10-fluoro-2,3,4a,5,6,10b-hexahydro-1H-benzo[f]quinolin-4-yl)-methanone

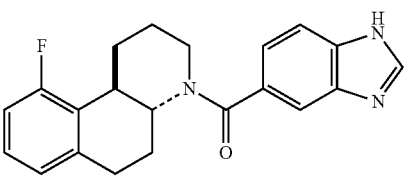

The title compound is prepared from 1H-benzoimidazole-5-carboxylic acid and trans-10-fluoro-1,2,3,4,4a,5,6,10b-octahydro-benzo[f]quinoline following a procedure analogous to that described in Example 1. Yield: 41% of theory; LC (method 1): $t_R$=2.76 min; Mass spectrum (ESI$^+$): m/z=350 [M+H]$^+$.

Example 27

(1H-Benzoimidazol-5-yl)-(cis-10-fluoro-2,3,4a,5,6,10b-hexahydro-1H-benzo[f]quinolin-4-yl)-methanone

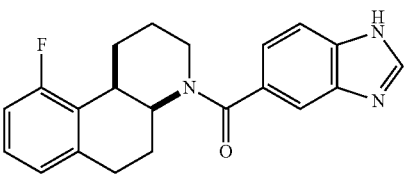

The title compound is prepared from 1H-benzoimidazole-5-carboxylic acid and cis-10-fluoro-1,2,3,4,4a,5,6,10b-octahydro-benzo[f]quinoline following a procedure analogous to that described in Example 1. Yield: 75% of theory; LC (method 1): $t_R$=2.66 min; Mass spectrum (ESI$^+$): m/z=350 [M+H]$^+$.

Example 28

(1H-Benzoimidazol-5-yl)-(trans-8-phenyl-2,3,4a,5,6,10b-hexahydro-1H-benzo[f]quinolin-4-yl)-methanone

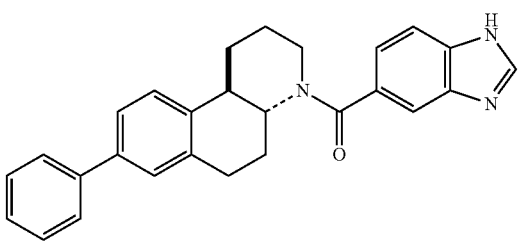

The title compound is prepared from 1H-benzoimidazole-5-carboxylic acid and trans-8-phenyl-1,2,3,4,4a,5,6,10b-octahydro-benzo[f]quinoline following a procedure analogous to that described in Example 1. Yield: 19% of theory; TLC: $r_f$=0.43 (silica gel, CH$_2$Cl$_2$/MeOH/32% aqueous NH$_3$ 90:10:1); Mass spectrum (ESI$^+$): m/z=408 [M+H]$^+$.

Example 29

(1H-Benzoimidazol-5-yl)-(cis-8-phenyl-2,3,4a,5,6,10b-hexahydro-1H-benzo[f]quinolin-4-yl)-methanone

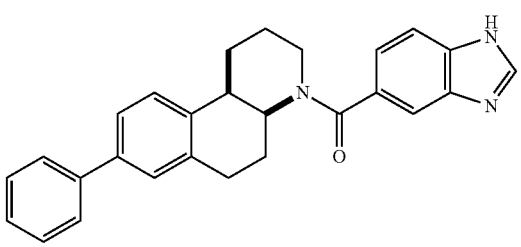

The title compound is prepared from 1H-benzoimidazole-5-carboxylic acid and cis-8-phenyl-1,2,3,4,4a,5,6,10b-octahydro-benzo[f]quinoline following a procedure analogous to that described in Example 1. Yield: 29% of theory; TLC: $r_f$=0.49 (silica gel, CH$_2$Cl$_2$/MeOH/32% aqueous NH$_3$ 90:10:1); Mass spectrum (ESI$^+$): m/z=408 [M+H]$^+$.

Example 30

(cis-2,3,4a,5,6,10b-Hexahydro-1H-benzo[f]quinolin-4-yl)-(1H-imidazo[4,5-b]pyridin-5-yl)-methanone

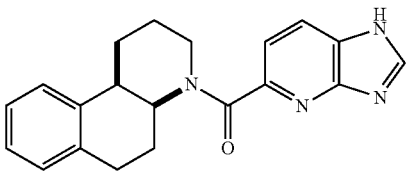

The title compound is prepared from 1H-imidazo[4,5-b]pyridine-5-carboxylic acid and cis-1,2,3,4,4a,5,6,10b-octahydro-benzo[f]quinoline following a procedure analogous to that described in Example 1 [2-(7-aza-1H-benzotriazol-1-yl)-1,1,3,3-tetramethyluronium hexa-fluorophosphate is used]. Yield: 57% of theory; LC (method 3): $t_R$=2.10 min; Mass spectrum (ESI$^+$): m/z=333 [M+H]$^+$.

Example 31

(cis-2,3,4a,5,6,10b-Hexahydro-1H-benzo[f]quinolin-4-yl)-imidazo[1,2-a]pyridin-6-yl-methanone

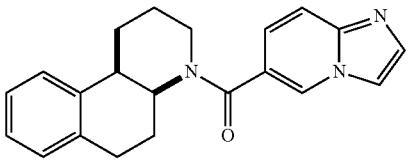

The title compound is prepared from imidazo[1,2-a]pyridine-6-carboxylic acid and cis-1,2,3,4,4a,5,6,10b-octahydro-benzo[f]quinoline following a procedure analogous to that described in Example 1 [2-(7-aza-1H-benzotriazol-1-yl)-1,1,3,3-tetramethyluronium hexa-fluorophosphate is used]. Yield: 72% of theory; LC (method 3): $t_R$=1.82 min; Mass spectrum (ESI$^+$): m/z=335 [M+H]$^+$.

Example 32

6-(cis-2,3,4a,5,6,10b-Hexahydro-1H-benzo[f]quinoline-4-carbonyl)-3H-benzothiazol-2-one

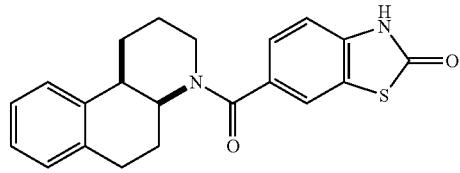

The title compound is prepared from 2-oxo-2,3-dihydro-benzothiazole-6-carboxylic acid and cis-1,2,3,4,4a,5,6,10b-octahydro-benzo[f]quinoline following a procedure analogous to that described in Example 1 [2-(7-aza-1H- benzotriazol-1-yl)-1,1,3,3-tetramethyluronium hexafluorophosphate is used]. Yield: 56% of theory; LC (method 3): $t_R$=2.32 min; Mass spectrum (ESI$^+$): m/z=365 [M+H]$^+$.

Example 33 cis-4-(1H-Benzoimidazole-5-carbonyl)-1,2,3,4,4a,5,6,10b-octahydro-benzo[f]quinoline-8-carboxylic acid methyl ester

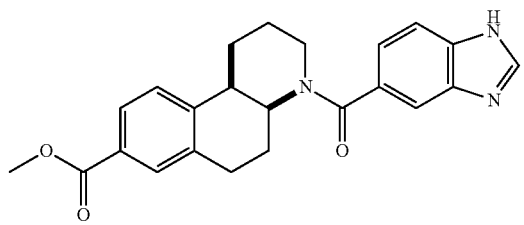

The title compound is prepared from 1H-benzoimidazole-5-carboxylic acid and cis-1,2,3,4,4a,5,6,10b-octahydro-benzo[f]quinoline-8-carboxylic acid methyl ester following a procedure analogous to that described in Example 1. Yield: 92% of theory; LC (method 1): $t_R$=2.57 min; Mass spectrum (ESI$^+$): m/z=390 [M+H]$^+$.

Example 34

(1H-Benzoimidazol-5-yl)-(cis-8-hydroxymethyl-2,3,4a,5,6,10b-hexahydro-1H-benzo[f]quinolin-4-yl)-methanone

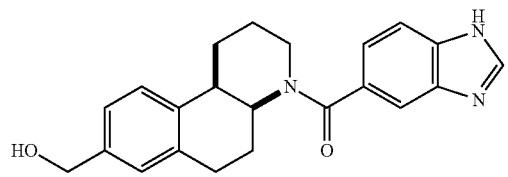

Lithium aluminum hydride (1 mol/L in tetrahydrofuran, 0.5 mL) is added to a solution of cis-4-(1H-benzoimidazole-5-carbonyl)-1,2,3,4,4a,5,6,10b-octahydro-benzo[f]quinoline-8-carboxylic acid methyl ester (150 mg) in tetrahydrofuran (6 mL) cooled to −10° C. The resulting solution is stirred for 2 h while warming to ca. −3° C. in the cooling bath. Little water is added carefully and the resulting mixture is filtered over Celite. The filtrate is diluted with ethyl acetate and dried (MgSO$_4$). The solvent is evaporated and the residue is triturated with ethyl acetate and dried to give the title compound as a solid. Yield: 56 mg (40% of theory); LC (method 1): $t_R$=2.03 min; Mass spectrum (ESI$^+$): m/z=362 [M+H]$^+$.

Example 35 cis-4-(1H-Benzoimidazole-5-carbonyl)-1,2,3,4,4a,5,6,10b-octahydro-benzo[f]quinoline-8-carboxylic acid

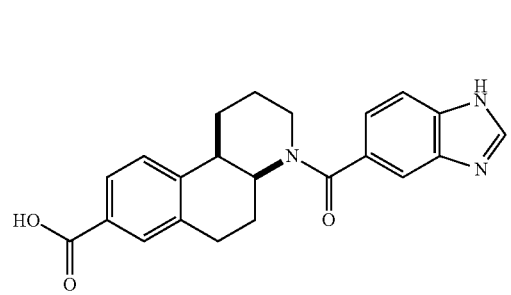

1 M aqueous NaOH solution (15 mL) is added to a solution of cis-4-(1H-benzoimidazole-5-carbonyl)-1,2,3,4,4a,5,6,10b-octahydro-benzo[f]quinoline-8-carboxylic acid methyl ester (1.60 g) in tetrahydrofuran (15 mL) at room temperature. The resulting solution is stirred at room temperature for 5 h. The solution is concentrated under reduced pressure and water (100 mL) is added to the residue. 1 M Aqueous hydrochloric acid (15 mL) is then added and the precipitate formed is separated by filtration. The precipitate is washed with water and diethyl ether and dried to afford the title compound as a solid. Yield: 1.24 g (80% of theory); LC (method 1): $t_R$=2.09 min; Mass spectrum (ESI$^+$): m/z=376 [M+H]$^+$.

Example 36 cis-4-(1H-Benzoimidazole-5-carbonyl)-1,2,3,4,4a,5,6,10b-octahydro-benzo[f]quinoline-8-carboxylic acid methylamide

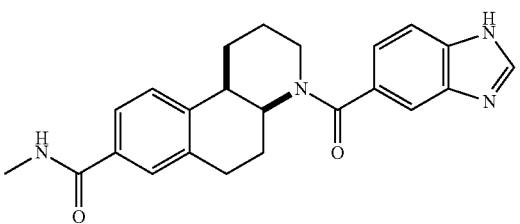

The title compound is prepared from cis-4-(1H-benzoimidazole-5-carbonyl)-1,2,3,4,4a,5,6,10b-octahydro-benzo[f]quinoline-8-carboxylic acid and methylamine (2 mol/L in tetrahydrofuran) following a procedure analogous to that described in Example 1. Yield: 75% of theory; LC (method 1): $t_R$=1.91 min; Mass spectrum (ESI$^+$): m/z=389 [M+H]$^+$.

Example 37 cis-4-(1H-Benzoimidazole-5-carbonyl)-1,2,3,4,4a,5,6,10b-octahydro-benzo[f]quinoline-8-carboxylic acid amide

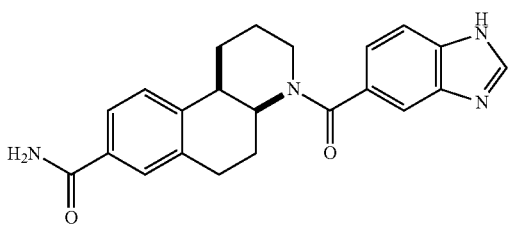

The title compound is prepared from cis-4-(1H-benzoimidazole-5-carbonyl)-1,2,3,4,4a,5,6,10b-octahydro-benzo[f]quinoline-8-carboxylic acid and ammonia (28% in water) following a procedure analogous to that described in Example 1. Yield: 58% of theory; LC (method 1): $t_R$=1.78 min; Mass spectrum (ESI$^+$): m/z=375 [M+H]$^+$.

Example 38 cis-4-(1H-Benzoimidazole-5-carbonyl)-1,2,3,4,4a,5,6,10b-octahydro-benzo[f]quinoline-8-carboxylic acid dimethylamide

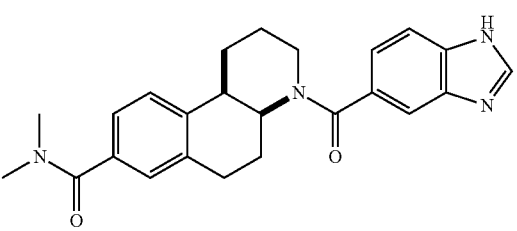

The title compound is prepared from cis-4-(1H-benzoimidazole-5-carbonyl)-1,2,3,4,4a,5,6,10b-octahydro-benzo[f]quinoline-8-carboxylic acid and dimethylamine (2 mol/L in tetrahydrofuran) following a procedure analogous to that described in Example 1. Yield: 20% of theory; LC (method 1): $t_R$=2.08 min; Mass spectrum (ESI$^+$): m/z=403 [M+H]$^+$.

Example 39

(1H-Benzoimidazol-5-yl)-[cis-8-(pyrrolidine-1-carbonyl)-2,3,4a,5,6,10b-hexahydro-1H-benzo[f]quinolin-4-yl]-methanone

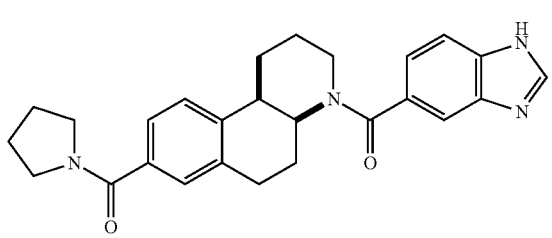

The title compound is prepared from cis-4-(1H-benzoimidazole-5-carbonyl)-1,2,3,4,4a,5,6,10b-octahydro-benzo[f]quinoline-8-carboxylic acid and pyrrolidine following a procedure analogous to that described in Example 1. Yield: 57% of theory; LC (method 1): $t_R$=2.27 min; Mass spectrum (ESI$^+$): m/z=429 [M+H]$^+$.

Example 40

(1H-Benzoimidazol-5-yl)-[cis-8-(morpholine-4-carbonyl)-2,3,4a,5,6,10b-hexahydro-1H-benzo[f]quinolin-4-yl]-methanone

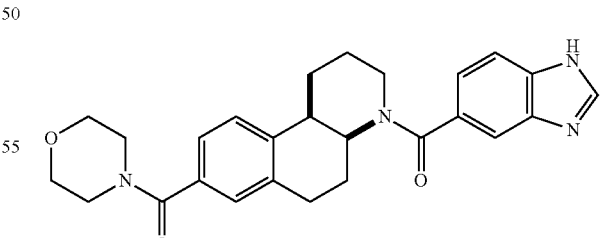

The title compound is prepared from cis-4-(1H-benzoimidazole-5-carbonyl)-1,2,3,4,4a,5,6,10b-octahydro-benzo[f]quinoline-8-carboxylic acid and morpholine following a procedure analogous to that described in Example 1. Yield: 63% of theory; LC (method 1): $t_R$=2.05 min; Mass spectrum (ESI$^+$): m/z=445 [M+H]$^+$.

Example 41

(1H-Benzoimidazol-5-yl)-[cis-8-(1-hydroxy-1-methyl-ethyl)-2,3,4a,5,6,10b-hexahydro-1H-benzo[f]quinolin-4-yl]-methanone

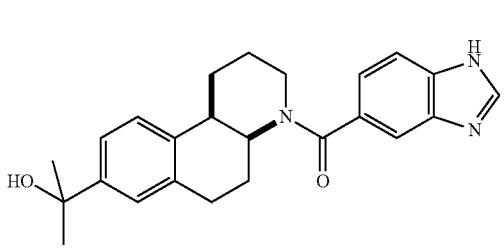

MeMgBr [1.4 mol/L in toluene/tetrahydrofuran (3:1), 1.1 mL] is added to a solution of cis-4-(1H-benzoimidazole-5-carbonyl)-1,2,3,4,4a,5,6,10b-octahydro-benzo[f]quinoline-8-carboxylic acid methyl ester (200 mg) in tetrahydrofuran (4 mL) cooled to −10° C. The resulting solution is stirred with cooling for 3 h before another portion of MeMgBr [1.4 mol/L in toluene/tetrahydrofuran (3:1), 0.8 mL] is added. The solution is warmed in the cooling bath to room temperature overnight. The solution is poured into ice-cold water and the resulting mixture is filtered over Celite. The filtrate is diluted with ethyl acetate and the organic phase is separated, washed with brine, and dried (MgSO$_4$). The solvent is evaporated and the residue is chromatographed on silica gel [dichloromethane/(dichloromethane/methanol/7 M NH$_3$ in methanol 50:48:2) 88:12→50:50] to furnish the title compound as a colorless solid. Yield: 59 mg (29% of theory); LC (method 1): $t_R$=2.27 min; Mass spectrum (ESI$^+$): m/z=390 [M+H]$^+$.

Example 42 cis-4-(1H-Benzoimidazole-5-carbonyl)-1,2,3,4,4a,5,6,10b-octahydro-benzo[f]quinoline-8-carbonitrile

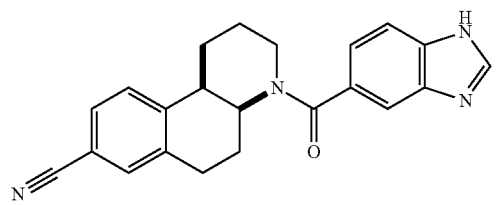

Trifluoroacetic anhydride (0.4 mL) is added to a solution of cis-4-(1H-benzoimidazole-5-carbonyl)-1,2,3,4,4a,5,6,10b-octahydro-benzo[f]quinoline-8-carboxylic acid amide (140 mg) and triethylamine (0.6 mL) in dichloromethane (4 mL) chilled in an ice bath. The cooling bath is removed and the solution is stirred at room temperature for 3 h. Another portion of trifluoroacetic anhydride (0.4 mL) and triethylamine (0.6 mL) are then added and stirring is continued at 35° C. overnight. The solution is diluted with dichloromethane and washed with water and brine. After drying (MgSO$_4$), the solvent is evaporated and the residue is chromatographed on silica gel (dichloromethane/methanol 20:1→1:1) to furnish the title compound as a yellowish solid. Yield: 50 mg (38% of theory); Mass spectrum (ESI$^+$): m/z=357 [M+H]$^+$.

Example 43

(2-Amino-benzothiazol-6-yl)-(cis-2,3,4a,5,6,10b-hexahydro-1H-benzo[f]quinolin-4-yl)-methanone

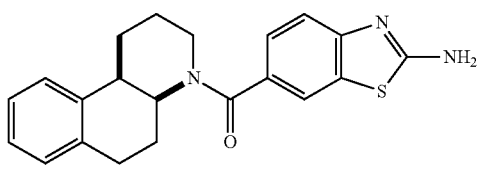

The title compound is prepared from 2-amino-benzothiazole-6-carboxylic acid and cis-1,2,3,4,4a,5,6,10b-octahydro-benzo[f]quinoline following a procedure analogous to that described in Example 1 [2-(7-aza-1H-benzotriazol-1-yl)-1,1,3,3-tetramethyluronium hexa-fluorophosphate is used]. Yield: 24% of theory; LC (method 4): $t_R$=1.80 min; Mass spectrum (ESI$^+$): m/z=364 [M+H]$^+$.

Example 44

(cis-2,3,4a,5,6,10b-Hexahydro-1H-benzo[f]quinolin-4-yl)-(3-hydroxy-4-methyl-phenyl)-methanone

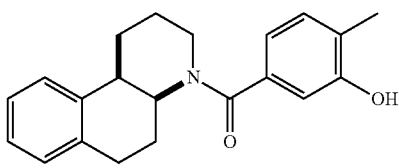

The title compound is prepared from 3-hydroxy-4-methyl-benzoic acid and cis-1,2,3,4,4a,5,6,10b-octahydro-benzo[f]quinoline following a procedure analogous to that described in Example 1 [2-(7-aza-1H-benzotriazol-1-yl)-1,1,3,3-tetramethyluronium hexa-fluorophosphate is used]. Yield: 77% of theory; LC (method 4): $t_R$=2.00 min; Mass spectrum (ESI$^+$): m/z=322 [M+H]$^+$.

Example 45

(3-Amino-4-methoxy-phenyl)-(cis-2,3,4a,5,6,10b-hexahydro-1H-benzo[f]quinolin-4-yl)-methanone

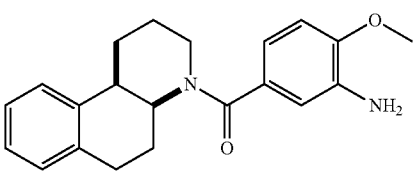

The title compound is prepared from 3-amino-4-methoxy-benzoic acid and cis-1,2,3,4,4a,5,6,10b-octahydro-benzo[f]quinoline following a procedure analogous to that described in Example 1 [2-(7-aza-1H-benzotriazol-1-yl)-1,1,3,3-tetramethyluronium hexa-fluorophosphate is used]. Yield: 63% of theory; LC (method 4): $t_R$=1.79 min; Mass spectrum (ESI$^+$): m/z=337 [M+H]$^+$.

Example 46

(cis-2,3,4a,5,6,10b-Hexahydro-1H-benzo[f]quinolin-4-yl)-(2-methyl-1H-indol-5-yl)-methanone

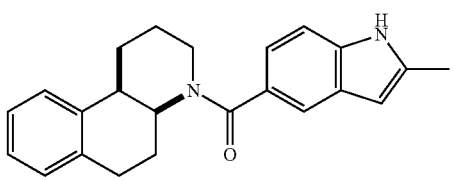

The title compound is prepared from 2-methyl-1H-indole-5-carboxylic acid and cis-1,2,3,4,4a,5,6,10b-octahydro-benzo[f]quinoline following a procedure analogous to that described in Example 1 [2-(7-aza-1H-benzotriazol-1-yl)-1,1,3,3-tetramethyluronium hexa-fluorophosphate is used]. Yield: 46% of theory; LC (method 4): $t_R$=2.03 min; Mass spectrum (ESI$^+$): m/z=345 [M+H]$^+$.

Example 47

5-(cis-2,3,4a,5,6,10b-Hexahydro-1H-benzo[f]quinoline-4-carbonyl)-1-methyl-1,3-dihydro-benzoimidazol-2-one

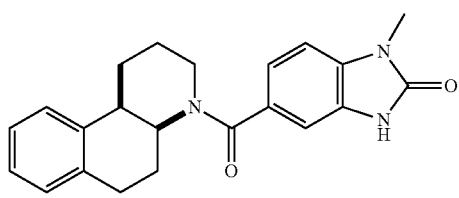

The title compound is prepared from 1-methyl-2-oxo-2,3-dihydro-1H-benzoimidazole-5-carboxylic acid and cis-1,2,3,4,4a,5,6,10b-octahydro-benzo[f]quinoline following a procedure analogous to that described in Example 1 [2-(7-aza-1H-benzotriazol-1-yl)-1,1,3,3-tetramethyluronium hexafluorophosphate is used]. Yield: 15% of theory; LC (method 4): $t_R$=1.92 min; Mass spectrum (ESI$^+$): m/z=362 [M+H]$^+$.

Example 48

(cis-2,3,4a,5,6,10b-Hexahydro-1H-benzo[f]quinolin-4-yl)-(1H-indol-6-yl)-methanone

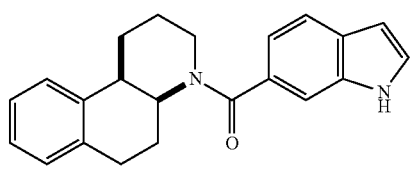

The title compound is prepared from 1H-indole-6-carboxylic acid and cis-1,2,3,4,4a,5,6,10b-octahydro-benzo[f]quinoline following a procedure analogous to that described in Example 1 [2-(7-aza-1H-benzotriazol-1-yl)-1,1,3,3-tetramethyluronium hexa-fluorophosphate is used]. Yield: 27% of theory; LC (method 4): $t_R$=2.01 min; Mass spectrum (ESI$^+$): m/z=331 [M+H]$^+$.

Example 49

5-(cis-2,3,4a,5,6,10b-Hexahydro-1H-benzo[f]quinoline-4-carbonyl)-1,3-dihydro-indol-2-one

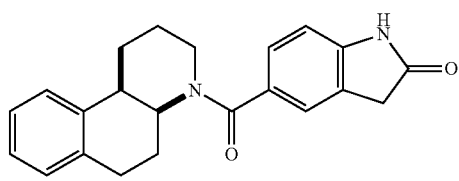

The title compound is prepared from 2-oxo-2,3-dihydro-1H-indole-5-carboxylic acid and cis-1,2,3,4,4a,5,6,10b-octahydro-benzo[f]quinoline following a procedure analogous to that described in Example 1 [2-(7-aza-1H-benzotriazol-1-yl)-1,1,3,3-tetramethyluronium hexa-fluorophosphate is used]. Yield: 25% of theory; LC (method 4): $t_R$=1.90 min; Mass spectrum (ESI$^+$): m/z=347 [M+H]$^+$.

Example 50

6-(cis-2,3,4a,5,6,10b-Hexahydro-1H-benzo[f]quinoline-4-carbonyl)-1,3-dihydro-indol-2-one

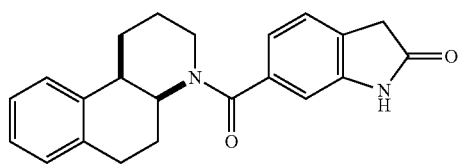

The title compound is prepared from 2-oxo-2,3-dihydro-1H-indole-6-carboxylic acid and cis-1,2,3,4,4a,5,6,10b-octahydro-benzo[f]quinoline following a procedure analogous to that described in Example 1 [2-(7-aza-1H-benzotriazol-1-yl)-1,1,3,3-tetramethyluronium hexa-fluorophosphate is used]. Yield: 12% of theory; LC (method 4): $t_R$=1.90 min; Mass spectrum (ESI$^+$): m/z=347 [M+H]$^+$.

Example 51

(cis-2,3,4a,5,6,10b-Hexahydro-1H-benzo[f]quinolin-4-yl)-(1-methyl-1H-benzoimidazol-5-yl)-methanone

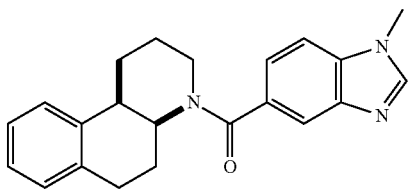

The title compound is prepared from 1-methyl-1H-benzoimidazole-5-carboxylic acid and cis-1,2,3,4,4a,5,6,10b-octahydro-benzo[f]quinoline following a procedure analogous to that described in Example 1 [2-(7-aza-1H-benzotriazol-1-yl)-1,1,3,3-tetramethyluronium hexa-fluorophosphate is used]. Yield: 83% of theory; LC (method 5): $t_R$=1.05 min; Mass spectrum (ESI$^+$): m/z=346 [M+H]$^+$.

Example 52

(cis-2.3.4a,5,6,10b-Hexahydro-1H-benzo[f]quinolin-4-yl)-(1-methyl-1H-benzotriazol-5-yl)-methanone

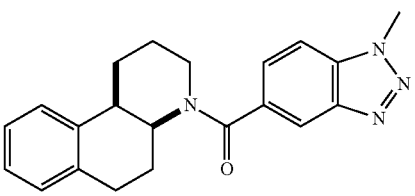

The title compound is prepared from 1-methyl-1H-benzotriazole-5-carboxylic acid and cis-1,2,3,4,4a,5,6,10b-octahydro-benzo[f]quinoline following a procedure analogous to that described in Example 1 [2-(7-aza-1H-benzotriazol-1-yl)-1,1,3,3-tetramethyluronium hexa-fluorophosphate is used]. Yield: 53% of theory; LC (method 4): $t_R$=1.90 min; Mass spectrum (ESI$^+$): m/z=347 [M+H]$^+$.

Example 53

(cis-7-Methoxy-2,3,4a,5,6,10b-hexahydro-1H-benzo[f]quinolin-4-yl)-(1-methyl-1H-indol-3-yl)-methanone

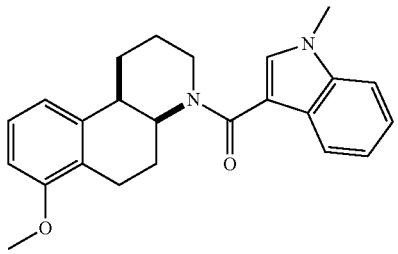

The title compound is prepared from 1-methyl-1H-indole-3-carboxylic acid and cis-7-methoxy-1,2,3,4,4a,5,6,10b-octahydro-benzo[f]quinoline following a procedure analogous to that described in Example 1. Yield: 82% of theory; LC (method 1): $t_R$=4.39 min; Mass spectrum (ESI$^+$): m/z=375 [M+H]$^+$.

Example 54

(3-Fluoro-4-hydroxy-phenyl)-(cis-2,3,4a,5,6,10b-hexahydro-1H-benzo[f]quinolin-4-yl)-methanone

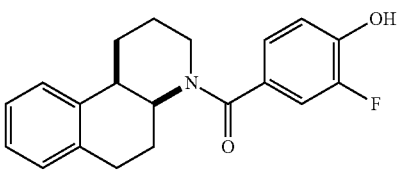

The title compound is prepared from 3-fluoro-4-hydroxy-benzoic acid and cis-1,2,3,4,4a,5,6,10b-octahydro-benzo[f]quinoline following a procedure analogous to that described in Example 1 [2-(7-aza-1H-benzotriazol-1-yl)-1,1,3,3-tetramethyluronium hexa-fluorophosphate is used]. Yield: 40% of theory; LC (method 4): $t_R$=1.94 min; Mass spectrum (ESI$^+$): m/z=326 [M+H]$^+$.

Example 55

(cis-2,3,4a,5,6,10b-Hexahydro-1H-benzo[f]quinolin-4-yl)-(2-methyl-3H-benzoimidazol-5-yl)-methanone

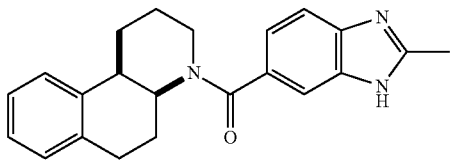

The title compound is prepared from 2-methyl-3H-benzoimidazole-5-carboxylic acid and cis-1,2,3,4,4a,5,6,10b-octahydro-benzo[f]quinoline following a procedure analogous to that described in Example 1 [2-(7-aza-1H-benzotriazol-1-yl)-1,1,3,3-tetramethyluronium hexa-fluorophosphate is used] and isolated as its trifluoroacetic acid salt. Yield: 59% of theory; LC (method 4): $t_R$=1.64 min; Mass spectrum (ESI$^+$): m/z=346 [M+H]$^+$.

Example 56

(4-Amino-3-chloro-phenyl)-(cis-2,3,4a,5,6,10b-hexahydro-1H-benzo[f]quinolin-4-yl)-methanone

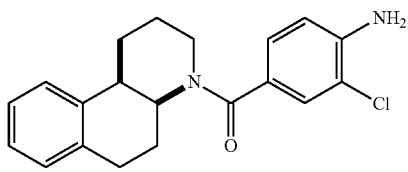

The title compound is prepared from 4-amino-3-chlorobenzoic acid and cis-1,2,3,4,4a,5,6,10b-octahydro-benzo[f]quinoline following a procedure analogous to that described in Example 1 [2-(7-aza-1H-benzotriazol-1-yl)-1,1,3,3-tetramethyluronium hexa-fluorophosphate is used]. Yield: 52% of theory; LC (method 4): $t_R$=1.99 min; Mass spectrum (ESI$^+$): m/z=341/343 (Cl) [M+H]$^+$.

Example 57

(2-Amino-3H-benzoimidazol-5-yl)-(cis-2,3,4a,5,6,10b-hexahydro-1H-benzo[f]quinolin-4-yl)-methanone

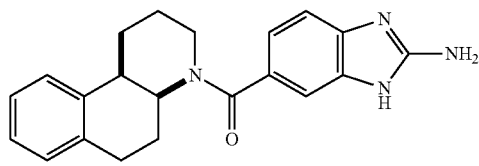

The title compound is prepared from 2-amino-3H-benzoimidazole-5-carboxylic acid and cis-1,2,3,4,4a,5,6,10b-octahydro-benzo[f]quinoline following a procedure analogous to that described in Example 1 [2-(7-aza-1H-benzotriazol-1-yl)-1,1,3,3-tetramethyluronium hexa-fluorophosphate is used] and isolated as its trifluoroacetic acid salt. Yield: 58% of theory; LC (method 4): $t_R$=1.66 min; Mass spectrum (ESI$^+$): m/z=347 [M+H]$^+$.

Example 58

Benzothiazol-6-yl-(cis-2,3,4a,5,6,10b-hexahydro-1H-benzo[f]quinolin-4-yl)-methanone

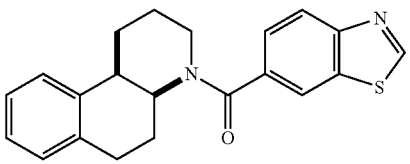

The title compound is prepared from benzothiazole-6-carboxylic acid and cis-1,2,3,4,4a,5,6,10b-octahydro-benzo[f]quinoline following a procedure analogous to that described in Example 1 [2-(7-aza-1H-benzotriazol-1-yl)-1,1,3,3-tetramethyluronium hexa-fluorophosphate is used]. Yield: 24% of theory; LC (method 4): $t_R$=1.97 min; Mass spectrum (ESI$^+$): m/z=349 [M+H]$^+$.

Example 59

(4-Chloro-3-hydroxy-phenyl)-(cis-2,3,4a,5,6,10b-hexahydro-1H-benzo[f]quinolin-4-yl)-methanone

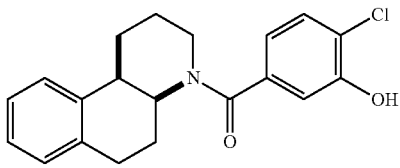

The title compound is prepared from 4-chloro-3-hydroxybenzoic acid and cis-1,2,3,4,4a,5,6,10b-octahydro-benzo[f]quinoline following a procedure analogous to that described in Example 1 [2-(7-aza-1H-benzotriazol-1-yl)-1,1,3,3-tetramethyluronium hexa-fluorophosphate is used]. Yield: 46% of theory; LC (method 4): $t_R$=1.99 min; Mass spectrum (ESI$^+$): m/z=342/344 (Cl) [M+H]$^+$.

Example 60

(cis-2,3,4a,5,6,10b-Hexahydro-1H-benzo[f]quinolin-4-yl)-(3H-imidazo[4,5-b]pyridin-5-yl)-methanone

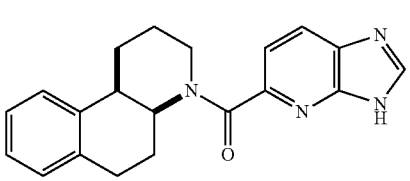

The title compound is prepared from 3H-imidazo[4,5-b]pyridine-5-carboxylic acid and cis-1,2,3,4,4a,5,6,10b-octahydro-benzo[f]quinoline following a procedure analogous to that described in Example 1 [2-(7-aza-1H-benzotriazol-1-yl)-1,1,3,3-tetramethyluronium hexa-fluorophosphate is used] and isolated as its trifluoroacetic acid salt. Yield: 40% of theory; LC (method 4): $t_R$=1.83 min; Mass spectrum (ESI$^+$): m/z=333 [M+H]$^+$.

Example 61

5-(cis-2,3,4a,5,6,10b-Hexahydro-1H-benzo[f]quinoline-4-carbonyl)-1,3-dihydro-benzoimidazol-2-one

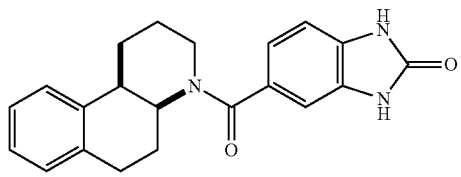

The title compound is prepared from 2-oxo-2,3-dihydro-1H-benzoimidazole-5-carboxylic acid and cis-1,2,3,4,4a,5,6,10b-octahydro-benzo[f]quinoline following a procedure analogous to that described in Example 1 [2-(7-aza-1H-benzotriazol-1-yl)-1,1,3,3-tetramethyluronium hexafluorophosphate is used]. Yield: 14% of theory; LC (method 4): $t_R$=1.89 min; Mass spectrum (ESI$^+$): m/z=348 [M+H]$^+$.

Example 62

(cis-2,3,4a,5,6,10b-Hexahydro-1H-benzo[f]quinolin-4-yl)-(3-methyl-3H-benzoimidazol-5-yl)-methanone

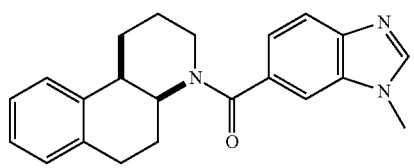

The title compound is prepared from 3-methyl-3H-benzoimidazole-5-carboxylic acid and cis-1,2,3,4,4a,5,6,10b-octahydro-benzo[f]quinoline following a procedure analogous to that described in Example 1 [2-(7-aza-1H-benzotriazol-1-yl)-1,1,3,3-tetramethyluronium hexafluorophosphate is used]. Yield: 91% of theory; LC (method 4): $t_R$=1.65 min; Mass spectrum (ESI$^+$): m/z=346 [M+H]$^+$.

Example 63

(3-Amino-4-fluoro-phenyl)-(cis-2,3,4a,5,6,10b-hexahydro-1H-benzo[f]quinolin-4-yl)-methanone

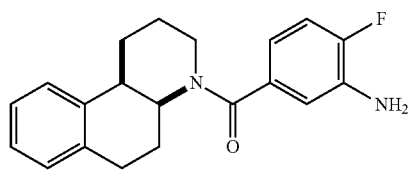

The title compound is prepared from 3-amino-4-fluoro-benzoic acid and cis-1,2,3,4,4a,5,6,10b-octahydro-benzo[f]quinoline following a procedure analogous to that described in Example 1 [2-(7-aza-1H-benzotriazol-1-yl)-1,1,3,3-tetramethyluronium hexa-fluorophosphate is used]. Yield: 47% of theory; LC (method 4): $t_R$=1.94 min; Mass spectrum (ESI$^+$): m/z=325 [M+H]$^+$.

Example 64

(cis-2,3,4a,5,6,10b-Hexahydro-1H-benzo[f]quinolin-4-yl)-imidazo[1,2-a]pyridin-7-yl-methanone

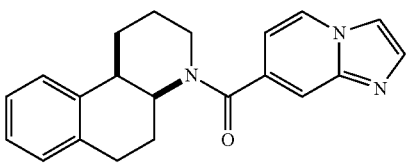

The title compound is prepared from imidazo[1,2-a]pyridine-7-carboxylic acid and cis-1,2,3,4,4a,5,6,10b-octahydro-benzo[f]quinoline following a procedure analogous to that described in Example 1 [2-(7-aza-1H-benzotriazol-1-yl)-1,1,3,3-tetramethyluronium hexa-fluorophosphate is used]. Yield: 95% of theory; LC (method 4): $t_R$=1.59 min; Mass spectrum (ESI$^+$): m/z=332 [M+H]$^+$.

Example 65

(cis-2,3,4a,5,6,10b-Hexahydro-1H-benzo[f]quinolin-4-yl)-(1H-indazol-5-yl)-methanone

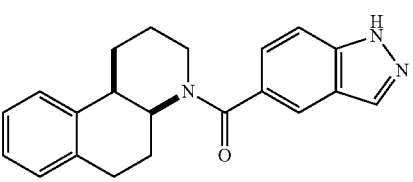

The title compound is prepared from 1H-indazole-5-carboxylic acid and cis-1,2,3,4,4a,5,6,10b-octahydro-benzo[f]quinoline following a procedure analogous to that described in Example 1 [2-(7-aza-1H-benzotriazol-1-yl)-1,1,3,3-tetramethyluronium hexa-fluorophosphate is used]. Yield: 39% of theory; LC (method 4): $t_R$=1.94 min; Mass spectrum (ESI$^+$): m/z=332 [M+H]$^+$.

Example 66

5-(cis-2,3,4a,5,6,10b-Hexahydro-1H-benzo[f]quinoline-4-carbonyl)-3,3-dimethyl-1,3-dihydro-indol-2-one

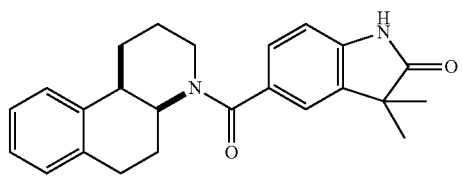

The title compound is prepared from 3,3-dimethyl-2-oxo-2,3-dihydro-1H-indole-5-carboxylic acid and cis-1,2,3,4,4a,5,6,10b-octahydro-benzo[f]quinoline following a procedure analogous to that described in Example 1 [2-(7-aza-1H-benzotriazol-1-yl)-1,1,3,3-tetramethyluronium hexafluorophosphate is used]. Yield: 19% of theory; LC (method 4): $t_R$=1.95 min; Mass spectrum (ESI$^+$): m/z=375 [M+H]$^+$.

Example 67

(4-Amino-phenyl)-(cis-2,3,4a,5,6,10b-hexahydro-1H-benzo[f]quinolin-4-yl)-methanone

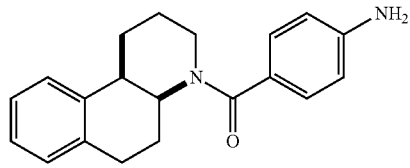

The title compound is prepared from 4-amino-benzoic acid and cis-1,2,3,4,4a,5,6,10b-octahydro-benzo[f]quinoline following a procedure analogous to that described in Example 1 [2-(7-aza-1H-benzotriazol-1-yl)-1,1,3,3-tetramethyluronium hexafluorophosphate is used]. Yield: 66% of theory; LC (method 4): $t_R$=1.81 min; Mass spectrum (ESI$^+$): m/z=307 [M+H]$^+$.

Example 68

(cis-2,3,4a,5,6,10b-Hexahydro-1H-benzo[f]quinolin-4-yl)-(4-hydroxy-phenyl)-methanone

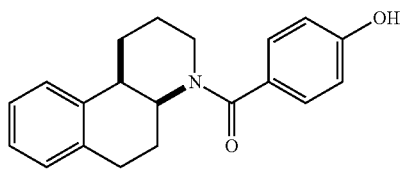

The title compound is prepared from 4-hydroxy-benzoic acid and cis-1,2,3,4,4a,5,6,10b-octahydro-benzo[f]quinoline following a procedure analogous to that described in Example 1 [2-(7-aza-1H-benzotriazol-1-yl)-1,1,3,3-tetramethyluro-nium hexafluorophosphate is used]. Yield: 28% of theory; LC (method 4): $t_R$=1.93 min; Mass spectrum (ESI$^+$): m/z=308 [M+H]$^+$.

Example 69

(cis-2,3,4a,5,6,10b-Hexahydro-1H-benzo[f]quinolin-4-yl)-(1H-indol-5-yl)-methanone

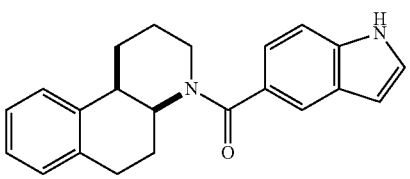

The title compound is prepared from 1H-indole-5-carboxylic acid and cis-1,2,3,4,4a,5,6,10b-octahydro-benzo[f]quinoline following a procedure analogous to that described in Example 1 [2-(7-aza-1H-benzotriazol-1-yl)-1,1,3,3-tetramethyluronium hexafluorophosphate is used]. Yield: 51% of theory; LC (method 4): $t_R$=1.99 min; Mass spectrum (ESI$^+$): m/z=331 [M+H]$^+$.

Example 70

(cis-2,3,4a,5,6,10b-Hexahydro-1H-benzo[f]quinolin-4-yl)-(1H-indol-3-yl)-methanone

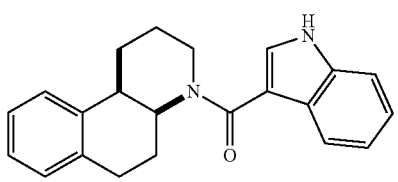

The title compound is prepared from 1H-indole-3-carboxylic acid and cis-1,2,3,4,4a,5,6,10b-octahydro-benzo[f]quinoline following a procedure analogous to that described in Example 1 [2-(7-aza-1H-benzotriazol-1-yl)-1,1,3,3-tetramethyluronium hexafluorophosphate is used]. Yield: 43% of theory; LC (method 4): $t_R$=2.01 min; Mass spectrum (ESI$^+$): m/z=331 [M+H]$^+$.

Example 71

(3,5-Dichloro-4-hydroxy-phenyl)-(cis-2,3,4a,5,6,10b-hexahydro-1H-benzo[f]quinolin-4-yl)-methanone

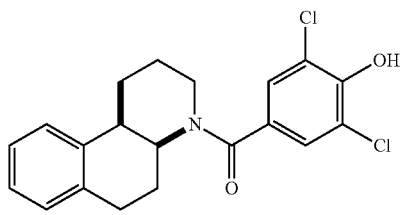

The title compound is prepared from 3,5-dichloro-4-hydroxy-benzoic acid and cis-1,2,3,4,4a,5,6,10b-octahydro-benzo[f]quinoline following a procedure analogous to that described in Example 1 [2-(7-aza-1H-benzotriazol-1-yl)-1,1,3,3-tetramethyluronium hexa-fluorophosphate is used]. Yield: 26% of theory; LC (method 4): $t_R$=2.03 min; Mass spectrum (ESI$^+$): m/z=376/378/380 (2 Cl) [M+H]$^+$.

Example 72

(1H-Benzotriazol-5-yl)-(cis-2,3,4a,5,6,10b-hexahydro-1H-benzo[f]quinolin-4-yl)-methanone

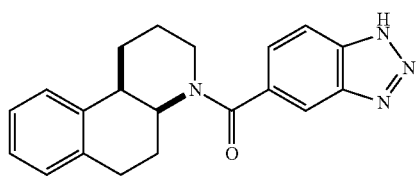

The title compound is prepared from 1H-benzotriazole-5-carboxylic acid and cis-1,2,3,4,4a,5,6,10b-octahydro-benzo[f]quinoline following a procedure analogous to that described in Example 1 [2-(7-aza-1H-benzotriazol-1-yl)-1,1,3,3-tetramethyluronium hexa-fluorophosphate is used]. Yield: 58% of theory; LC (method 4): $t_R$=1.90 min; Mass spectrum (ESI$^+$): m/z=333 [M+H]$^+$.

Example 73

(cis-2,3,4a,5,6,10b-Hexahydro-1H-benzo[f]quinolin-4-yl)-(1-methyl-1H-indol-3-yl)-methanone

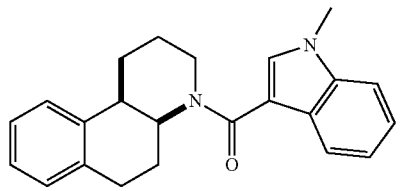

The title compound is prepared from 1-methyl-1H-indole-3-carboxylic acid and cis-1,2,3,4,4a,5,6,10b-octahydro-benzo[f]quinoline following a procedure analogous to that described in Example 1 [2-(7-aza-1H-benzotriazol-1-yl)-1,1,3,3-tetramethyluronium hexa-fluorophosphate is used]. Yield: 28% of theory; LC (method 4): $t_R$=2.05 min; Mass spectrum (ESI$^+$): m/z=345 [M+H]$^+$.

Example 74

(cis-2,3,4a,5,6,10b-Hexahydro-1H-benzo[f]quinolin-4-yl)-(3-hydroxy-4-methoxy-phenyl)-methanone

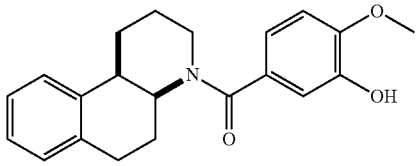

The title compound is prepared from 3-hydroxy-4-methoxy-benzoic acid and cis-1,2,3,4,4a,5,6,10b-octahydro-benzo[f]quinoline following a procedure analogous to that described in Example 1 [2-(7-aza-1H-benzotriazol-1-yl)-1,1,3,3-tetramethyluronium hexa-fluorophosphate is used]. Yield: 42% of theory; LC (method 4): $t_R$=1.93 min; Mass spectrum (ESI$^+$): m/z=338 [M+H]$^+$.

Example 75

(3-Chloro-4-hydroxy-phenyl)-(cis-2,3,4a,5,6,10b-hexahydro-1H-benzo[f]quinolin-4-yl)-methanone

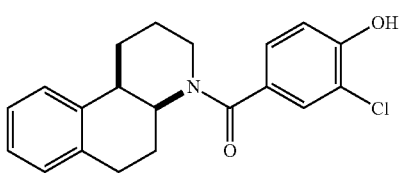

The title compound is prepared from 3-chloro-4-hydroxy-benzoic acid and cis-1,2,3,4,4a,5,6,10b-octahydro-benzo[f]

quinoline following a procedure analogous to that described in Example 1 [2-(7-aza-1H-benzotriazol-1-yl)-1,1,3,3-tetramethyluronium hexa-fluorophosphate is used]. Yield: 42% of theory; LC (method 4): $t_R$=1.98 min; Mass spectrum (ESI$^+$): m/z=342/344 (Cl) [M+H]$^+$.

Example 76

(3-Amino-4-chloro-phenyl)-(cis-2,3,4a,5,6,10b-hexahydro-1H-benzo[f]quinolin-4-yl)-methanone

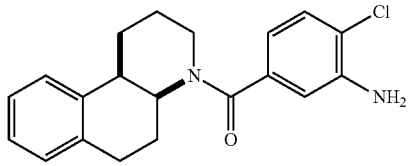

The title compound is prepared from 3-amino-4-chloro-benzoic acid and cis-1,2,3,4,4a,5,6,10b-octahydro-benzo[f]quinoline following a procedure analogous to that described in Example 1 [2-(7-aza-1H-benzotriazol-1-yl)-1,1,3,3-tetramethyluronium hexa-fluorophosphate is used]. Yield: 46% of theory; LC (method 4): $t_R$=1.28 min; Mass spectrum (ESI$^+$): m/z=341/343 (Cl) [M+H]$^+$.

Example 77

(3-Amino-4-methyl-phenyl)-(cis-2,3,4a,5,6,10b-hexahydro-1H-benzo[f]quinolin-4-yl)-methanone

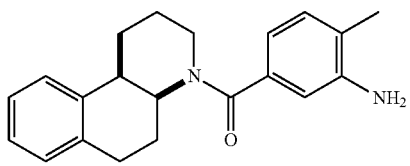

The title compound is prepared from 3-amino-4-methyl-benzoic acid and cis-1,2,3,4,4a,5,6,10b-octahydro-benzo[f]quinoline following a procedure analogous to that described in Example 1 [2-(7-aza-1H-benzotriazol-1-yl)-1,1,3,3-tetramethyluronium hexa-fluorophosphate is used]. Yield: 95% of theory; LC (method 4): $t_R$=1.85 min; Mass spectrum (ESI$^+$): m/z=321 [M+H]$^+$.

Example 78

(4-Amino-3-methoxy-phenyl)-(cis-2,3,4a,5,6,10b-hexahydro-1H-benzo[f]quinolin-4-yl)-methanone

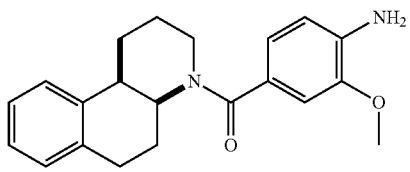

The title compound is prepared from 4-amino-3-methoxy-benzoic acid and cis-1,2,3,4,4a,5,6,10b-octahydro-benzo[f]quinoline following a procedure analogous to that described in Example 1 [2-(7-aza-1H-benzotriazol-1-yl)-1,1,3,3-tetramethyluronium hexa-fluorophosphate is used]. Yield: 64% of theory; LC (method 4): $t_R$=1.84 min; Mass spectrum (ESI$^+$): m/z=337 [M+H]$^+$.

Example 79

(4-Amino-3-fluoro-phenyl)-(cis-2,3,4a,5,6,10b-hexahydro-1H-benzo[f]quinolin-4-yl)-methanone

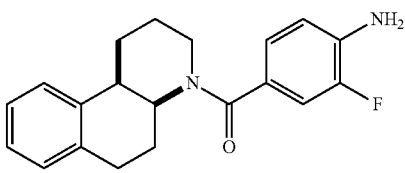

The title compound is prepared from 4-amino-3-fluoro-benzoic acid and cis-1,2,3,4,4a,5,6,10b-octahydro-benzo[f]quinoline following a procedure analogous to that described in Example 1 [2-(7-aza-1H-benzotriazol-1-yl)-1,1,3,3-tetramethyluronium hexa-fluorophosphate is used]. Yield: 64% of theory; LC (method 4): $t_R$=1.94 min; Mass spectrum (ESI$^+$): m/z=325 [M+H]$^+$.

Example 80

6-(cis-2,3,4a,5,6,10b-Hexahydro-1H-benzo[f]quinoline-4-carbonyl)-1H-quinoxalin-2-one

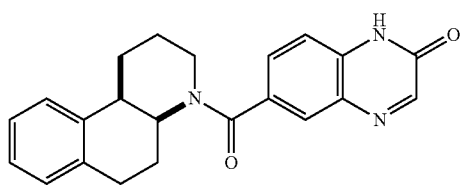

The title compound is prepared from 2-oxo-1,2-dihydro-quinoxaline-6-carboxylic acid and cis-1,2,3,4,4a,5,6,10b-octahydro-benzo[f]quinoline following a procedure analogous to that described in Example 1 [2-(7-aza-1H-benzotriazol-1-yl)-1,1,3,3-tetramethyluronium hexa-fluorophosphate is used]. Yield: 19% of theory; LC (method 4): $t_R$=1.92 min; Mass spectrum (ESI$^+$): m/z=362 [M+H]$^+$.

Example 81

(cis-7-Hydroxy-2,3,4a,5,6,10b-hexahydro-1H-benzo[f]quinolin-4-yl)-(1-methyl-1H-indol-3-yl)-methanone

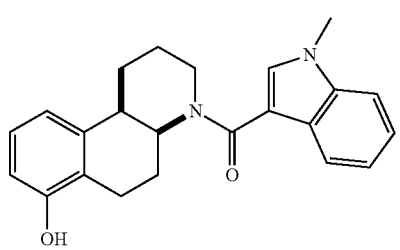

The title compound is prepared from (cis-7-methoxy-2,3,4a,5,6,10b-hexahydro-1H-benzo[f]quinolin-4-yl)-(1-methyl-1H-indol-3-yl)-methanone following a procedure analogous to that described in Example 7. Yield: 10% of theory; LC (method 1): $t_R$=3.58 min; Mass spectrum (ESI$^+$): m/z=361 [M+H]$^+$.

Example 82

(1H-Benzoimidazol-5-yl)-(cis-8-benzyl-2,3,4a,5,6,10b-hexahydro-1H-benzo[f]quinolin-4-yl)-methanone

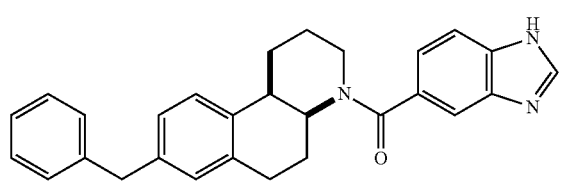

The title compound is prepared from 1H-benzoimidazole-5-carboxylic acid and a mixture of cis-8-benzyl-1,2,3,4,4a,5,6,10b-octahydro-benzo[f]quinoline and cis-8-cyclohexylmethyl-1,2,3,4,4a,5,6,10b-octahydro-benzo[f]quinoline (ca. 30:70) following a procedure analogous to that described in Example 1 and separated from the also formed Example 83 by HPLC on reversed phase (MeOH/H$_2$O/NH$_4$OH). Yield: 12% of theory; LC (method 1): $t_R$=3.35 min; Mass spectrum (ESI$^+$): m/z=422 [M+H]$^+$.

Example 83

(1H-Benzoimidazol-5-yl)-(cis-8-cyclohexylmethyl-2,3,4a,5,6,10b-hexahydro-1H-benzo[f]quinolin-4-yl)-methanone

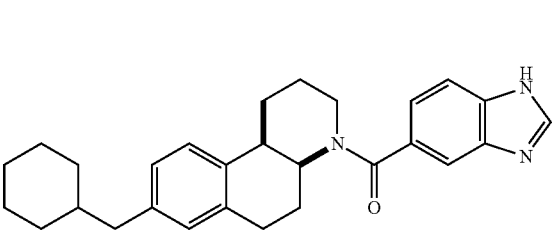

The title compound is prepared from 1H-benzoimidazole-5-carboxylic acid and a mixture of cis-8-benzyl-1,2,3,4,4a,5,6,10b-octahydro-benzo[f]quinoline and cis-8-cyclohexylmethyl-1,2,3,4,4a,5,6,10b-octahydro-benzo[f]quinoline (ca. 30:70) following a procedure analogous to that described in Example 1 and separated from the also formed Example 82 by HPLC on reversed phase (MeOH/H$_2$O/NH$_4$OH). Yield: 50% of theory; LC (method 1): $t_R$=4.06 min; Mass spectrum (ESI$^+$): m/z=428 [M+H]$^+$.

Example 84

(1H-Benzoimidazol-5-yl)-(cis-10-hydroxymethyl-2,3,4a,5,6,10b-hexahydro-1H-benzo[f]quinolin-4-yl)-methanone

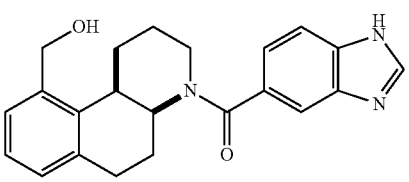

The title compound is prepared from cis-4-(1H-benzoimidazole-5-carbonyl)-1,2,3,4,4a,5,6,10b-octahydro-benzo[f]quinoline-10-carboxylic acid methyl ester following a procedure analogous to that described in Example 34. Yield: 46% of theory; TLC: $r_f$=0.27 (silica gel, $CH_2Cl_2$/MeOH/32% aqueous $NH_3$ 90:10:1); Mass spectrum (ESI$^+$): m/z=362 [M+H]$^+$.

Example 85

(1H-Benzoimidazol-5-yl)-[cis-10-(4-methoxy-benzyl)-2,3,4a,5,6,10b-hexahydro-1H-benzo[f]quinolin-4-yl]-methanone

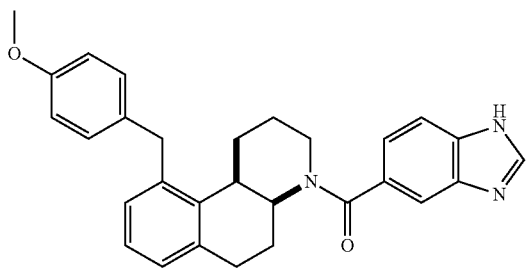

The title compound is prepared from 1H-benzoimidazole-5-carboxylic acid and cis-10-(4-methoxy-benzyl)-1,2,3,4,4a,5,6,10b-octahydro-benzo[f]quinoline following a procedure analogous to that described in Example 1. Yield: 17% of theory; LC (method 1): $t_R$=3.21 min; Mass spectrum (ESI$^+$): m/z=452 [M+H]$^+$.

Example 86

(1H-Benzoimidazol-5-yl)-(cis-6,6-dimethyl-2,3,4a,5,6,10b-hexahydro-1H-benzo[f]quinolin-4-yl)-methanone

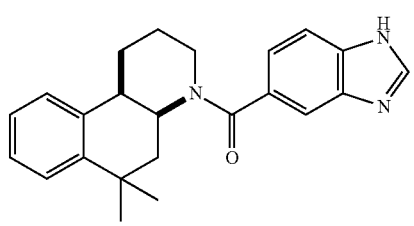

The title compound is prepared from 1H-benzoimidazole-5-carboxylic acid and cis-6,6-dimethyl-1,2,3,4,4a,5,6,10b-octahydro-benzo[f]quinoline following a procedure analogous to that described in Example 1. Yield: 58% of theory; LC (method 1): $t_R$=2.84 min; Mass spectrum (ESI$^+$): m/z=360 [M+H]$^+$.

Example 87 cis-4-(1H-Benzoimidazole-5-carbonyl)-1,2,3,4,4a,5,6,10b-octahydro-benzo[f]quinoline-10-carboxylic acid amide

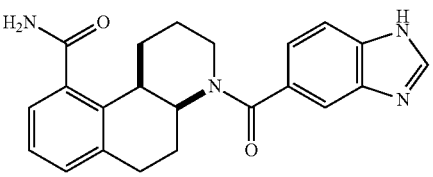

The title compound is prepared from cis-4-(1H-benzoimidazole-5-carbonyl)-1,2,3,4,4a,5,6,10b-octahydro-benzo[f]quinoline-10-carboxylic acid and ammonia (7 mol/L in methanol) following a procedure analogous to that described in Example 1. Yield: 58% of theory; TLC: $r_f$=0.24 (silica gel, $CH_2Cl_2$/MeOH/32% aqueous $NH_3$ 90:10:1); Mass spectrum (ESI$^+$): m/z=375 [M+H]$^+$.

Example 88 cis-4-(1H-Benzoimidazole-5-carbonyl)-1,2,3,4,4a,5,6,10b-octahydro-benzo[f]quinoline-10-carbonitrile

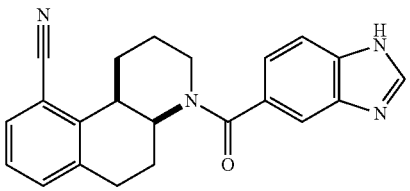

The title compound is prepared from cis-4-(1H-benzoimidazole-5-carbonyl)-1,2,3,4,4a,5,6,10b-octahydro-benzo[f]quinoline-10-carboxylic acid amide following a procedure analogous to that described in Example 42. Yield: 66% of theory; TLC: $r_f$=0.45 (silica gel, $CH_2Cl_2$/MeOH/32% aqueous $NH_3$ 90:10:1); Mass spectrum (ESI$^+$): m/z=357 [M+H]$^+$.

Example 89

(1H-Benzoimidazol-5-yl)-[cis-8-(4-methoxy-phenoxy)-2,3,4a,5,6,10b-hexahydro-1H-benzo[f]quinolin-4-yl]-methanone

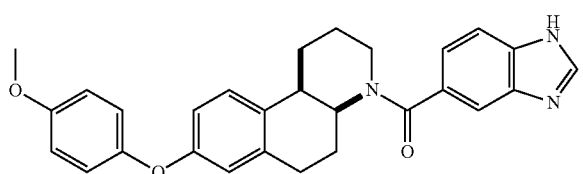

The title compound is prepared from 1H-benzoimidazole-5-carboxylic acid and cis-8-(4-methoxy-phenoxy)-1,2,3,4,4a,5,6,10b-octahydro-benzo[f]quinoline following a procedure analogous to that described in Example 1. Yield: 72% of theory; LC (method 1): $t_R$=3.16 min; Mass spectrum (ESI$^+$): m/z=454 [M+H]$^+$.

Example 90 trans-4-(1H-Benzoimidazole-5-carbonyl)-1,2,3,4,4a,5,6,10b-octahydro-benzo[f]quinoline-9-carbonitrile

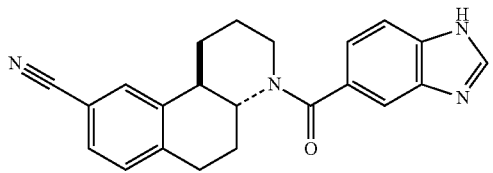

The title compound is prepared from 1H-benzoimidazole-5-carboxylic acid and trans-1,2,3,4,4a,5,6,10b-octahydro-benzo[f]quinoline-9-carbonitrile following a procedure analogous to that described in Example 1. Yield: 18% of theory; LC (method 1): $t_R$=2.49 min; Mass spectrum (ESI$^+$): m/z=357 [M+H]$^+$.

Example 91 cis-4-(1H-Benzoimidazole-5-carbonyl)-1,2,3,4,4a,5,6,10b-octahydro-benzo[f]quinoline-9-carbonitrile

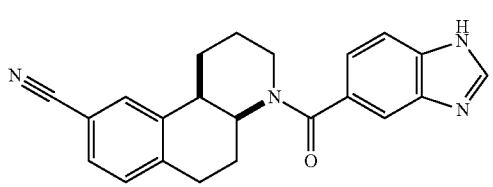

The title compound is prepared from 1H-benzoimidazole-5-carboxylic acid and cis-1,2,3,4,4a,5,6,10b-octahydro-benzo[f]quinoline-9-carbonitrile following a procedure analogous to that described in Example 1. Yield: 64% of theory; LC (method 1): $t_R$=2.40 min; Mass spectrum (ESI$^+$): m/z=357 [M+H]$^+$.

Example 92

(1H-Benzoimidazol-5-yl)-[cis-10-(6-methyl-pyridazin-3-yloxy)-2,3,4a,5,6,10b-hexahydro-1H-benzo[f]quinolin-4-yl]-methanone

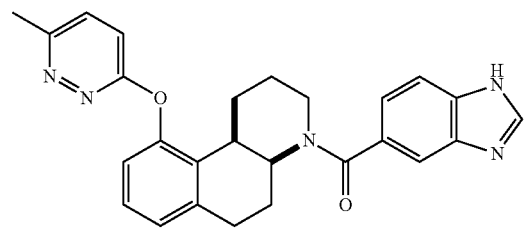

The title compound is prepared from 1H-benzoimidazole-5-carboxylic acid and cis-10-(6-methyl-pyridazin-3-yloxy)-1,2,3,4,4a,5,6,10b-octahydro-benzo[f]quinoline following a procedure analogous to that described in Example 1. Yield: 17% of theory; LC (method 1): $t_R$=2.39 min; Mass spectrum (ESI$^+$): m/z=440 [M+H]$^+$.

Example 93

(1H-Benzoimidazol-5-yl)-(cis-2,3,4,4a,9,9a-hexahydro-indeno[2,1-b]pyridin-1-yl)-methanone

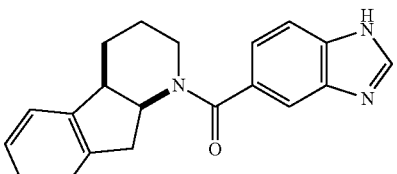

The title compound is prepared from 1H-benzoimidazole-5-carboxylic acid and cis-2,3,4,4a,9,9a-hexahydro-1H-indeno[2,1-b]pyridine following a procedure analogous to that described in Example 1. Yield: 60% of theory; LC (method 1): $t_R$=2.44 min; Mass spectrum (ESI$^+$): m/z=318 [M+H]$^+$; $^1$H NMR (400 MHz, DMSO-d$_6$, mixture of rotamers) δ 1.20-1.34 (m, 1H), 1.41-1.56 (m, 1H), 1.56-1.71 (m, 1H), 1.92-2.02 (m, 1H), 2.68-3.11 (m, 3H), 3.11-3.27 (m, 1H), 3.47-

5.43 (very broad signals, 2H), 7.07-7.30 (m, 5H), 7.54-7.62 (m, 1H), 7.64-7.72 (m, 1H), 8.29 (s, 1H), 12.51-12.65 (m, 1H).

Example 94

(1H-Benzoimidazol-5-yl)-[(4a-R,9a-S)-2,3,4,4a,9,9a-hexahydro-indeno[2,1-b]pyridin-1-yl]-methanone

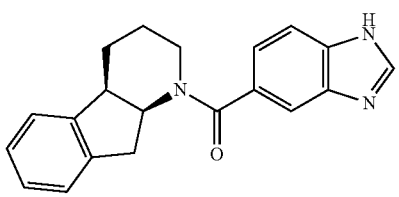 [SMILES: O=C(c1ccc2[nH]cnc2c1)N1CCC[C@@H]2c3ccccc3C[C@@H]21]

The title compound is obtained by chromatographing a racemic mixture of (1H-benzoimidazol-5-yl)-(cis-2,3,4,4a,9,9a-hexahydro-indeno[2,1-b]pyridin-1-yl)-methanone (100 mg) on chiral phase (column: 1×ASH 250×10 mm, 250 μm; mobile phase: methanol containing 0.2% diethylamine/sc carbon dioxide 25:75; flow rate: 10 mL/min). Yield: 47 mg; LC (method as above on chiral phase): $t_R$=2.35 min; Mass spectrum (ESI+): m/z=318 [M+H]+; for 1H NMR see Example 94.

Example 95

(1H-Benzoimidazol-5-yl)-[(4a-S,9a-R)-2,3,4,4a,9,9a-hexahydro-indeno[2,1-b]pyridin-1-yl]-methanone

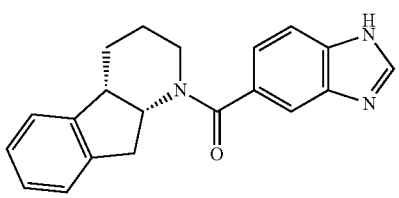 [SMILES: O=C(c1ccc2[nH]cnc2c1)N1CCC[C@H]2c3ccccc3C[C@H]21]

The title compound is obtained by chromatographing a racemic mixture of (1H-benzoimidazol-5-yl)-(cis-2,3,4,4a,9,9a-hexahydro-indeno[2,1-b]pyridin-1-yl)-methanone (100 mg) on chiral phase (column: 1×ASH 250×10 mm, 250 μm; mobile phase: methanol containing 0.2% diethylamine/sc carbon dioxide 25:75; flow rate: 10 mL/min). Yield: 44 mg; LC (method as above on chiral phase): $t_R$=1.98 min; Mass spectrum (ESI+): m/z=318 [M+H]+; for 1H NMR see Example 94.

Example 96

4-(cis-2,3,4,4a,9,9a-Hexahydro-indeno[2,1-b]pyridine-1-carbonyl)-benzamide

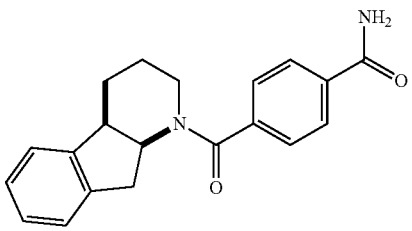

The title compound is prepared from terephthalamic acid and cis-2,3,4,4a,9,9a-hexahydro-1H-indeno[2,1-b]pyridine following a procedure analogous to that described in Example 1. Yield: 50% of theory; LC (method 1): $t_R$=3.07 min; Mass spectrum (ESI+): m/z=321 [M+H]+.

Example 97 ca. 1:1 mixture of cis-(1H-Benzoimidazol-5-yl)-(6-bromo-2,3,4,4a,9,9a-hexahydro-indeno[2,1-b]pyridin-1-yl)-methanone and cis-(1H-Benzoimidazol-5-yl)-(7-bromo-2,3,4,4a,9,9a-hexahydro-indeno[2,1-b]pyridin-1-yl)-methanone

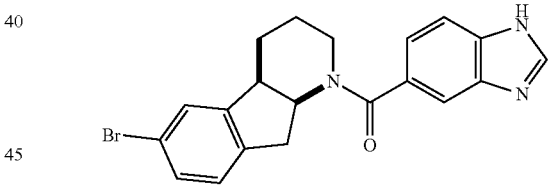

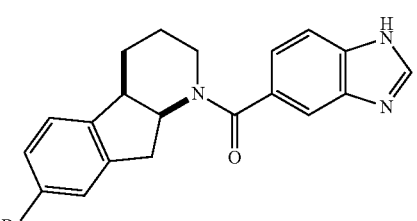

A part of the impure mixture obtained in Step 4 of Intermediates 34 and 35 is purified by HPLC on reversed phase (acetonitrile/water) to give a ca. 1:1 mixture of the title compounds. Mass spectrum (ESI+): m/z=396/398 (Br) [M+H]+.

Example 98 cis-1-(1H-Benzoimidazole-5-carbonyl)-2,3,4,4a,9,9a-hexahydro-1H-indeno[2,1-b]pyridine-6-carboxylic acid

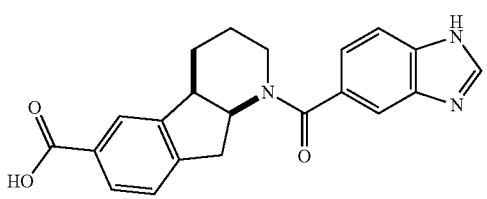

The title compound is prepared from a ca. 1:1 mixture of cis-1-(1H-benzoimidazole-5-carbonyl)-2,3,4,4a,9,9a-hexahydro-1H-indeno[2,1-b]pyridine-6-carboxylic acid methyl ester and cis-1-(1H-benzoimidazole-5-carbonyl)-2,3,4,4a,9,9a-hexahydro-1H-indeno[2,1-b]pyridine-7-carboxylic acid methyl ester following a procedure analogous to that described in Example 35 and separated from Example 99 by HPLC on reversed phase (MeCN/H2O). Yield: 4% of theory; Mass spectrum (ESI+): m/z=362 [M+H]+.

Example 99 cis-1-(1H-Benzoimidazole-5-carbonyl)-2,3,4,4a,9,9a-hexahydro-1H-indeno[2,1-b]pyridine-7-carboxylic acid

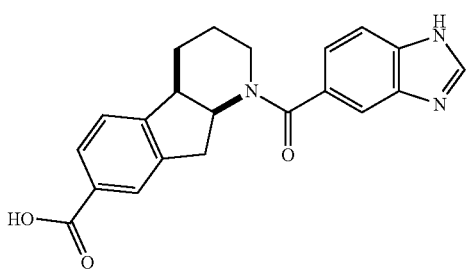

The title compound is prepared from a ca. 1:1 mixture of cis-1-(1H-benzoimidazole-5-carbonyl)-2,3,4,4a,9,9a-hexahydro-1H-indeno[2,1-b]pyridine-6-carboxylic acid methyl ester and cis-1-(1H-benzoimidazole-5-carbonyl)-2,3,4,4a,9,9a-hexahydro-1H-indeno[2,1-b]pyridine-7-carboxylic acid methyl ester following a procedure analogous to that described in Example 35 and separated from Example 98 by HPLC on reversed phase (MeCN/H2O). Yield: 5% of theory; Mass spectrum (ESI+): m/z=362 [M+H]+.

Example 100 cis-1-(1H-Benzoimidazole-5-carbonyl)-2,3,4,4a,9,9a-hexahydro-1H-indeno[2,1-b]pyridine-6-carboxylic acid amide

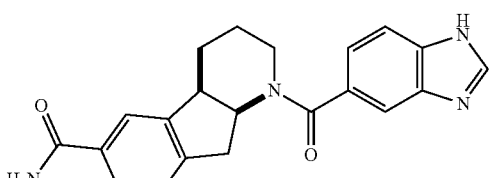

The title compound is prepared from cis-1-(1H-benzoimidazole-5-carbonyl)-2,3,4,4a,9,9a-hexahydro-1H-indeno[2,1-b]pyridine-6-carboxylic acid and ammonia (0.5 mol/L in 1,4-dioxane) following a procedure analogous to that described in Example 1. Yield: 64% of theory; LC (method 1): $t_R$=1.64 min; Mass spectrum (ESI+): m/z=361 [M+H]+.

Example 101 cis-1-(1H-Benzoimidazole-5-carbonyl)-2,3,4,4a,9,9a-hexahydro-1H-indeno[2,1-b]pyridine-7-carboxylic acid methylamide

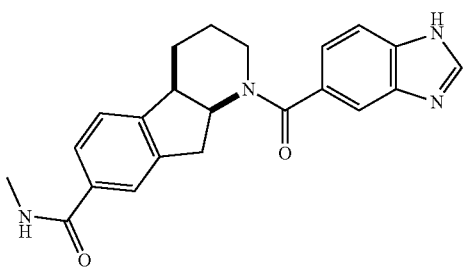

The title compound is prepared from cis-1-(1H-benzoimidazole-5-carbonyl)-2,3,4,4a,9,9a-hexahydro-1H-indeno[2,1-b]pyridine-7-carboxylic acid and methylamine (2 mol/L in tetrahydrofuran) following a procedure analogous to that described in Example 1. Yield: 19% of theory; LC (method 1): $t_R$=1.86 min; Mass spectrum (ESI$^+$): m/z=375 [M+H]$^+$.

Example 102

(cis-2,3,4,4a,9,9a-Hexahydro-indeno[2,1-b]pyridin-1-yl)-(1H-imidazo[4,5-b]pyridin-5-yl)-methanone

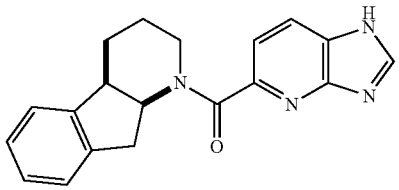

The title compound is prepared from 1H-imidazo[4,5-b]pyridine-5-carboxylic acid and cis-2,3,4,4a,9,9a-hexahydro-1H-indeno[2,1-b]pyridine following a procedure analogous to that described in Example 1 [2-(7-aza-1H-benzotriazol-1-yl)-1,1,3,3-tetramethyluronium hexa-fluorophosphate is used]. Yield: 74% of theory; LC (method 3): $t_R$=2.10 min; Mass spectrum (ESI$^+$): m/z=319 [M+H]$^+$.

Example 103

6-(cis-2,3,4,4a,9,9a-Hexahydro-indeno[2,1-b]pyridine-1-carbonyl)-3H-benzothiazol-2-one

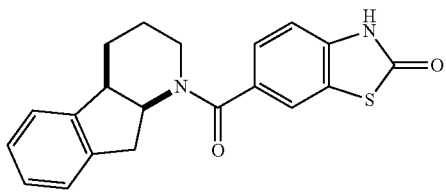

The title compound is prepared from 2-oxo-2,3-dihydro-benzothiazole-6-carboxylic acid and cis-2,3,4,4a,9,9a-hexahydro-1H-indeno[2,1-b]pyridine following a procedure analogous to that described in Example 1 [2-(7-aza-1H-benzotriazol-1-yl)-1,1,3,3-tetramethyluronium hexafluorophosphate is used]. Yield: 74% of theory; LC (method 3): $t_R$=2.28 min; Mass spectrum (ESI$^+$): m/z=351 [M+H]$^+$.

Example 104

(cis-2,3,4,4a,9,9a-Hexahydro-indeno[2,1-b]pyridin-1-yl)-imidazo[1,2-a]pyridin-6-yl-methanone

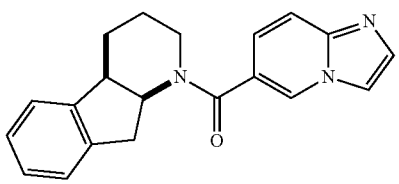

The title compound is prepared from imidazo[1,2-a]pyridine-6-carboxylic acid and cis-2,3,4,4a,9,9a-hexahydro-1H-indeno[2,1-b]pyridine following a procedure analogous to that described in Example 1 [2-(7-aza-1H-benzotriazol-1-yl)-1,1,3,3-tetramethyluronium hexa-fluorophosphate is used]. Yield: 85% of theory; LC (method 3): $t_R$=1.81 min; Mass spectrum (ESI$^+$): m/z=318 [M+H]$^+$.

Example 105

(1H-Benzoimidazol-5-yl)-(trans-10b-ethyl-2,3,4a,5,6,10b-hexahydro-1H-benzo[f]quinolin-4-yl)-methanone

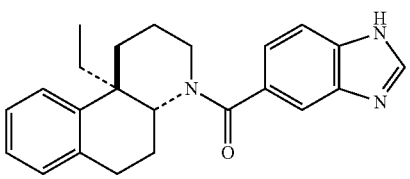

The title compound is prepared from 1H-benzoimidazole-5-carboxylic acid and trans-10b-ethyl-1,2,3,4,4a,5,6,10b-octahydro-benzo[f]quinoline following a procedure analogous to that described in Example 1. Yield: 44% of theory; TLC: $r_f$=0.42 (silica gel, CH$_2$Cl$_2$/MeOH/32% aqueous NH$_3$ 90:10:1); Mass spectrum (ESI$^+$): m/z=360 [M+H]$^+$.

Example 106 cis-1-(1H-Benzoimidazole-5-carbonyl)-2,3,4,4a,9,9a-hexahydro-1H-indeno[2,1-b]pyridine-6-carbonitrile

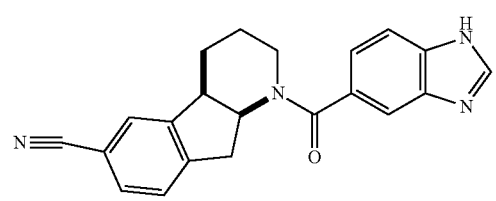

The title compound is prepared from cis-1-(1H-benzoimidazole-5-carbonyl)-2,3,4,4a,9,9a-hexahydro-1H-indeno[2,1-b]pyridine-6-carboxylic acid amide following a procedure analogous to that described in Example 42. Yield: 64% of theory; LC (method 1): $t_R$=2.33 min; Mass spectrum (ESI$^+$): m/z=343 [M+H]$^+$; for $^1$H NMR see Example 108.

The title compound is also obtained as follows:

A flask charged with a stir bar, zinc cyanide (0.32 g), trifluoromethanesulfonic acid cis-1-(1-trifluoromethanesulfonyl-1H-benzoimidazole-5-carbonyl)-2,3,4,4a,9,9a-hexahydro-1H-indeno[2,1-b]pyridine-6-yl ester (mixture of isomers regarding sulfonyl group attachment at N-1 or N-3 of the benzimidazole, 1.08 g), and N,N-dimethylformamide (5 mL) is sparged with argon for 10 min. Tetrakis(triphenylphosphine)palladium(0) (0.31 g) is then added and the resulting mixture is heated to 100° C. and stirred at this temperature for 2 h. After cooling to room temperature, 1-hydroxybenzotriazole hydrate (0.45 g) and water (1.5 mL) are added and stirring is continued at room temperature for 3 h. Ethyl acetate, little methanol, and saturated aqueous Na$_2$CO$_3$ solution are added and the mixture is filtered over Celite. The aqueous phase of the filtrate is separated and neutralized with 2 M aqueous citric acid and extracted with ethyl acetate. The organic phases are combined and washed with brine and dried (Na$_2$SO$_4$). The solvent is evaporated and the residue is chromatographed on silica gel (dichloromethane/methanol 96:4→90:10) to give the title compound as a solid. Yield: 0.42 g (68% of theory).

Example 107

(4a-R,9a-S)-1-(1H-Benzoimidazole-5-carbonyl)-2,3,4,4a,9,9a-hexahydro-1H-indeno[2,1-b]pyridine-6-carbonitrile

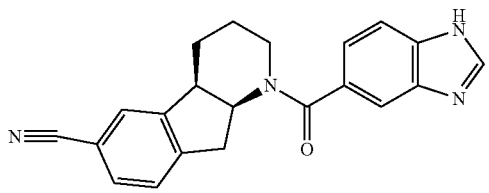 [SMILES: N#Cc1ccc2c(c1)[C@H]1CCCN(C(=O)c3ccc4[nH]cnc4c3)[C@H]1C2]

The title compound is obtained by chromatographing a racemic mixture of cis-1-(1H-benzoimidazole-5-carbonyl)-2,3,4,4a,9,9a-hexahydro-1H-indeno[2,1-b]pyridine-6-carbonitrile (600 mg) on chiral phase (SFC; column: Daicel ASH 250×20 mm, 5 µm; mobile phase: isopropanol containing 0.2% diethylamine/sc carbon dioxide 25:75; flow rate: 90 mL/min; 40° C.). Yield: 112 mg; LC (preparative SFC on chiral phase as above): $t_R$=8.45 min; Mass spectrum (ESI$^+$): m/z=318 [M+H]$^+$; for $^1$H NMR see Example 108.

Alternatively, the compound is obtained from (1H-benzoimidazol-5-yl)-[(4a-R,9a-S)-6-bromo-2,3,4,4a,9,9a-hexahydro-indeno[2,1-b]pyridin-1-yl]methanone following a procedure analogous to that described in Example 148. Yield: 26% of theory.

Alternatively, the title compound is prepared from 1H-benzoimidazole-5-carboxylic acid and (4a-R,9a-S)-2,3,4,4a,9,9a-hexahydro-1H-indeno[2,1-b]pyridine-6-carbonitrile following a procedure analogous to that described in Example 1. Yield: 81% of theory.

The title compound is also prepared as follows:

1-Hydroxybenzotriazole monohydrate (138.0 g), 1-(dimethylaminopropyl)-3-ethylcarbodiimide hydrochloride (172.7 g), and triethylamine (262 mL) are added in the given order to a solution of 1H-benzoimidazole-5-carboxylic acid (146.1 g) and (4a-R,9a-S)-2,3,4,4a,9,9a-hexahydro-1H-indeno[2,1-b]pyridine-6-carbonitrile (149.0 g) in N,N-dimethylformamide (600 mL) at room temperature. The mixture is stirred at room temperature overnight. Water (1.5 L) and dichloromethane (1.5 mL) are added and the organic phase is separated and the aqueous phase is extracted with dichloromethane (750 mL). The combined organic phase is washed with 2 mol/L aqueous NaOH solution (750 mL), 2 mol/L aqueous hydrochloric acid (630 mL), and water (3×1.5 L) and concentrated at below 50° C. Ethyl acetate (700 mL) is added to the residue and the resulting mixture is heated to obtain a homogeneous solution. The solution is cooled to room temperature overnight and the precipitate is separated by filtration and washed with ethyl acetate (2×100 mL). The precipitate is dried under vacuum at 50° C. for 5 h to give the title compound as a white solid. Yield: 208.0 g (84% pure, >99% ee).

The title compound is also prepared as follows:

(4a-R,9a-S)-2,3,4,4a,9,9a-hexahydro-1H-indeno[2,1-b]pyridine-6-carbonitrile (19.8 g) and 40 ml 2-methyltetraherofuran are added to a 500 ml reactor with overhead agitator, followed by addition of water (200 ml) and Na$_2$CO$_3$ (21.2 g, 200 mmol, 2 eq). A slurry of 1H-benzoimidazole-5-carboxylic acid chloride in 2-methyltetrahedrofuran (19.8 g, 110 mmol, 1.1 eq, in 200 ml 2-methyltetrahedrofuran) is added slowly over a period of 3 h, and the resulting two-phase reaction mixture is stirred for another 3 h. The aqueous phase is removed, and the organic organic phase is washed with 10% brine. The solution is concentrated at ~50° C. under reduced pressure, and solvent is switched to 250 mL ethyl acetate. A slurry forms at this stage and the reaction mixture is cooled to room temperature and stirred for 2 h. The precipitate is separated by filtration and washed with ethyl acetate (2×15 mL). The precipitate is dried under vacuum at 50° C. for 5 h to give the title compound as a white solid. Yield: 34.4 g (86% wt as ethyl acetate solvate, 86% yield, >99% ee).

The hydrogen chloride salt of (4a-R,9a-S)-1-(1H-benzoimidazole-5-carbonyl)-2,3,4,4a,9,9a-hexahydro-1H-indeno[2,1-b]pyridine-6-carbonitrile is obtained in two different crystalline modifications:

Crystal Form I:

(4a-R,9a-S)-1-(1H-Benzoimidazole-5-carbonyl)-2,3,4,4a,9,9a-hexahydro-1H-indeno[2,1-b]pyridine-6-carbonitrile*hydrogen chloride Hydrochloric acid (5-6 mol/L in isopropanol, 1.46 mL) is added dropwise to a stirred solution of (4a-R,9a-S)-1-(1H-benzoimidazole-5-carbonyl)-2,3,4,4a,9,9a-hexahydro-1H-indeno[2,1-b]pyridine-6-carbonitrile (2.10 g) in ethanol (10 mL) at room temperature. A seed crystal is added, and stirring is continued at room temperature for 2 h and at 0° C. for another 2 h. The precipitate is separated by filtration (the filtrate is used to prepare crystal form II, see below), washed with little ethanol, and dried (60° C.) to give an orange-colored solid (1.60 g). The solid is redissolved in ethanol (250 mL) and charcoal (1 g) is added to the solution. The mixture is stirred for 5 min and then filtered. The filtrate is concentrated to ca. 100 mL and a seed crystal is added. The solution is stirred at room temperature for 2 h and at ca. —10° C. for 30 min. The precipitate is separated by filtration (the filtrate is used to prepare crystal form II, see below) and dried (60° C.) to give the title compound as a colorless, crystalline solid (0.90 g); m$_p$ (onset)=252° C.

The seed crystals are prepared as follows: hydrochloric acid (5-6 mol/L in isopropanol, 40 µL) is added to a stirred solution of (4a-R,9a-S)-1-(1H-benzoimidazole-5-carbonyl)-2,3,4,4a,9,9a-hexahydro-1H-indeno[2,1-b]pyridine-6-carbonitrile (63 mg) in ethanol (0.5 mL). The resulting solution is stirred at room temperature overnight. The precipitate is separated by filtration, washed with little cold ethanol, and dried to give a colorless solid (30 mg).

Crystal Form I can also be prepared by the following procedure:

A solution of (4a-R,9a-S)-1-(1H-benzoimidazole-5-carbonyl)-2,3,4,4a,9,9a-hexahydro-1H-indeno[2,1-b]pyridine-6-carbonitrile (1.5 g) in ethanol (3.92 g) is prepared by heating to 50° C. The solution is then cooled to ambient temperature within 30 mins. The solution is charged with aqueous HCl (36.5 wt %; 0.4 g) and aged until the slurry forms. The slurry is filtered and dried under vacuum at −25° C.

Crystal Form II:

(4a-R,9a-S)-1-(1H-Benzoimidazole-5-carbonyl)-2,3,4,4a,9,9a-hexahydro-1H-indeno[2,1-b]pyridine-6-carbonitrile*hydrogen chloride The filtrates of the above mentioned preparation of crystal form I are concentrated, combined, and taken up in ethyl acetate (75 mL). The resulting mixture is stirred at 50° C. for 4 h. The suspension is cooled to room temperature, the precipitate is separated by filtration, washed with ethyl acetate (20 mL), and dried (60° C.) to give a colorless solid (0.58 g). This solid (0.58 g) together with a residue (ca. 1 g) obtained by concentration of a filtrate from a repeat preparation of crystal form I are stirred in ethanol at room temperature overnight. The precipitate is separated by filtration and dried (60° C.) to give the colorless, crystalline form II of the title compound (0.65 g); $m_p$ (onset)=ca. 240° C. This procedure may be scaled up to the multi-gram, hundred gram or even kilogram scale.

Crystal form II is also obtained by the following procedure:

A reaction vessel charged with (4a-R,9a-S)-1-(1H-benzoimidazole-5-carbonyl)-2,3,4,4a,9,9a-hexahydro-1H-indeno[2,1-b]pyridine-6-carbonitrile (331.5 g) and isopropanol (331.5 g) is heated at 75° C. until a homogeneous solution is formed. 5.12 mol/L HCl in isopropanol (29.7 g) is added followed by isopropanol (5 g) to rinse the addition vessel. (4a-R,9a-S)-1-(1H-Benzoimidazole-5-carbonyl)-2,3,4,4a,9,9a-hexahydro-1H-indeno[2,1-b]pyridine-6-carbonitrile hydrochloride (crystal form II; 19.88 g; the seeds are milled and slurried in 30 g isopropanol for ca. 1 h) is added followed by isopropanol (20 g) to rinse the addition vessel. The solution is aged for 1 h and then 5.12 mol/L HCl in isopropanol (171.3 g) is added over 4 h. The mixture is cooled to 0-5° C. over 1 h and aged at this temperature for 30 min. The precipitate is separated by filtration, washed with heptane (0-5° C.), and dried under vacuum at 65° C. for 8 h. Yield: 368.9 g (yield: 95%; corrected for seed charge).

Crystal form II is also obtained by the following procedure:

Crystal form I (150 mg) and absolute ethanol (0.6 mL) are stirred at room temperature for one week. The precipitate is separated by filtration, washed with little absolute ethanol and dried at 40° C.

Crystal Form II can also be prepared by the following procedure:

A solution of (4a-R,9a-S)-1-(1H-benzoimidazole-5-carbonyl)-2,3,4,4a,9,9a-hexahydro-1H-indeno[2,1-b]pyridine-6-carbonitrile (26.07 g) in 200 proof absolute ethanol (104.30 g) is prepared by heating to 50° C. The solution is charged with 4.587 g HCl in 200 proof absolute ethanol (6.55 N) at 50° C. 3.605 g Form II milled seed slurry is added (seed slurry is prepared by mixing 0.782 g milled Form II with 2.823 g EtOH) and age at 50° C. for more than 2 hrs. The solution is charged with 5.045 g HCl in EtOH (6.55 N) over 2 hrs, then cooled to 0° C. over 1 hr. The solution is aged at 0° C. for more than 1 hr. The crystals are separated by filtration and dried at 70° C. under vacuum for more than 12 hrs. This procedure may be scaled up to the multi-gram, hundred gram or even kilogram scale.

X-Ray Powder Diffraction—XRPD

X-ray powder diffraction analyses for samples of Form I and Form II were conducted on a Bruker AXS X-Ray Powder Diffractometer Model D8 Advance, using CuKα radiation (1.54 Å) in parafocusing mode with a graphite monochromator and a scintillation detector. The pattern was obtained by scanning over a range of 2°-35° 2Θ, step size of 0.05° 2Θ, step time of 4 sec per step. Exemplary XRPD spectra of Form I and Form II may be found in FIGS. 1 and 5, respectively.

Solid-State NMR—SSNMR $^{13}$C Solid-state NMR(SSNMR) data for samples of Form I and Form II was acquired on a Bruker Avance III NMR spectrometer (Bruker Biospin, Inc., Billerica, Mass.) at 9.4 T (1H=400.46 MHz, 13C=100.70 MHz). Samples were packed in 4 mm O.D. zirconia rotors with Kel-F® drive tips. A Bruker model 4BL CP BB WVT probe was used for data acquisition and sample spinning about the magic-angle (54.74°). Sample spectrum acquisition used a spinning rate of 12 kHz. A standard cross-polarization pulse sequence was used with a ramped Hartman-Hahn match pulse on the proton channel at ambient temperature and pressure. The pulse sequence used a 5 millisecond contact pulse and a 30 second recycle delay. Two-pulse phase modulated (tppm) decoupling was also employed in the pulse sequence. No exponential line broadening was used prior to Fourier transformation of the free incution decay. Chemical shifts were referenced using the secondary standard of adamantane, with the upfield resonance being set to 29.5 ppm. The magic-angle was set using the 79Br signal from KBr powder at a spinning rate of 5 kHz. Exemplary $^{13}$C SSNMR spectra of Form I and Form II may be found in FIGS. 2 and 6, respectively.

TGA

TGA analysis was performed with a Perkin Elmer Pyris 1 TGA instrument, SN 537N9120103, using general procedure, 002-GP-00342. Samples were heated from RT (~25° C.) to 300° C. and the weight loss calculated from RT to 150° C. Exemplary TGA traces of Form I and Form II may be found in FIGS. 4 and 8, respectively. Results are reported below.

| Sample ID | % Weight Loss | Ave. % Wt Loss |
|---|---|---|
| Form II | 0.041 | 0.05 |
|  | 0.066 |  |
| Form I | 2.050 | 2.09 |
|  | 2.125 |  |

DSC

DSC analysis was performed with a Diamond DSC instrument, SN 536N6102101, using general procedure, 002-GP-00343. Samples were heated from 25° C. to 300° C. and the thermal events determined. Exemplary DSC traces of Form I and Form II may be found in FIGS. 3 and 7, respectively. Results are reported below. Form I also showed a thermal event at 67.4° C. possibly due to loss of surface water as sample showed evidence of hygroscopicity.

| Sample ID | Onset of Melt w/Decomp. (° C.) |
|---|---|
| Form II | 235.5 |
| Form I | 231.7 |

Example 108

(4a-S,9a-R)-1-(1H-Benzoimidazole-5-carbonyl)-2,3,4,4a,9,9a-hexahydro-1H-indeno[2,1-b]pyridine-6-carbonitrile

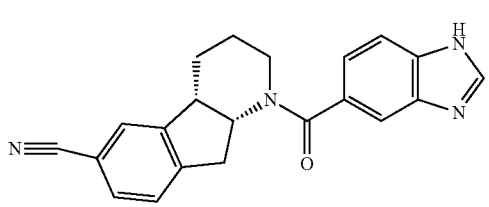 [SMILES: N#Cc1ccc2c(c1)[C@@H]1CCCN(C(=O)c3ccc4[nH]cnc4c3)[C@@H]1C2]

The title compound is obtained by chromatographing a racemic mixture of cis-1-(1H-benzoimidazole-5-carbonyl)-2,3,4,4a,9,9a-hexahydro-1H-indeno[2,1-b]pyridine-6-carbonitrile (600 mg) on chiral phase (SFC; column: Daicel ASH 250×20 mm, 5 μm; mobile phase: isopropanol containing 0.2% diethylamine/sc carbon dioxide 25:75; flow rate: 90 mL/min; 40° C.) in ca. 90% ee purity (Example 108/Example 107 ca. 95:5). Yield: 115 mg; LC (preparative SFC on chiral phase as above): $t_R$=6.00 min; Mass spectrum (ESI$^+$): m/z=318 [M+H]$^+$; $^1$H NMR (400 MHz, DMSO-d$_6$, mixture of rotamers) δ 1.22-1.35 (m, 1H), 1.42-1.56 (m, 1H), 1.57-1.69 (m, 1H), 1.96-2.06 (m, 1H), 2.86-3.18 (m, 3H), 3.20-ca. 3.29 (m, 1H), ca. 3.62-5.58 (very broad signals, 2H), 7.19-7.31 (m, 1H), 7.41-7.49 (m, 1H), 7.54-7.74 (m, 4H), 8.29 (s, 1H), 12.60 (broad s, 1H).

Example 109

(2-Amino-benzothiazol-6-yl)-(cis-2,3,4,4a,9,9a-hexahydro-indeno[2,1-b]pyridin-1-yl)-methanone

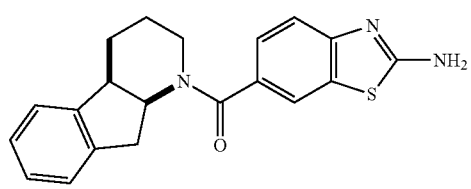

The title compound is prepared from 2-amino-benzothiazole-6-carboxylic acid and cis-2,3,4,4a,9,9a-hexahydro-1H-indeno[2,1-b]pyridine following a procedure analogous to that described in Example 1 [2-(7-aza-1H-benzotriazol-1-yl)-1,1,3,3-tetramethyluronium hexa-fluorophosphate is used]. Yield: 63% of theory; LC (method 4): $t_R$=1.76 min; Mass spectrum (ESI$^+$): m/z=350 [M+H]$^+$.

Example 110

(cis-2,3,4,4a,9,9a-Hexahydro-indeno[2,1-b]pyridin-1-yl)-(3-hydroxy-4-methyl-phenyl)-methanone

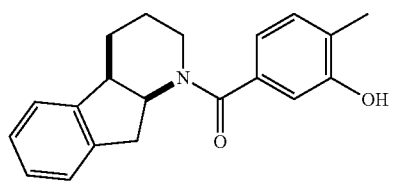

The title compound is prepared from 3-hydroxy-4-methyl-benzoic acid and cis-2,3,4,4a,9,9a-hexahydro-1H-indeno[2,1-b]pyridine following a procedure analogous to that described in Example 1 [2-(7-aza-1H-benzotriazol-1-yl)-1,1,3,3-tetramethyluronium hexa-fluorophosphate is used]. Yield: 45% of theory; LC (method 4): $t_R$=1.98 min; Mass spectrum (ESI$^+$): m/z=308 [M+H]$^+$.

Example 111

(3-Amino-4-methoxy-phenyl)-(cis-2,3,4,4a,9,9a-hexahydro-indeno[2,1-b]pyridin-1-yl)-methanone

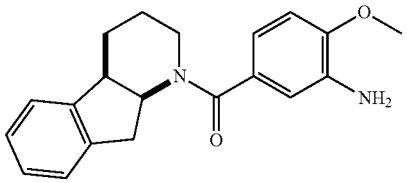

The title compound is prepared from 3-amino-4-methoxy-benzoic acid and cis-2,3,4,4a,9,9a-hexahydro-1H-indeno[2,1-b]pyridine following a procedure analogous to that described in Example 1 [2-(7-aza-1H-benzotriazol-1-yl)-1,1,3,3-tetramethyluronium hexa-fluorophosphate is used]. Yield: 77% of theory; LC (method 4): $t_R$=1.75 min; Mass spectrum (ESI$^+$): m/z=323 [M+H]$^+$.

Example 112

(cis-2,3,4,4a,9,9a-Hexahydro-indeno[2,1-b]pyridin-1-yl)-(2-methyl-1H-indol-5-yl)-methanone

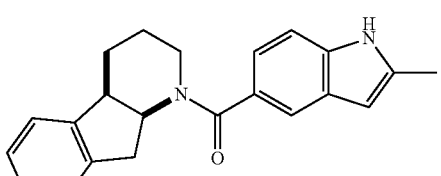

The title compound is prepared from 2-methyl-1H-indole-5-carboxylic acid and cis-2,3,4,4a,9,9a-hexahydro-1H-indeno[2,1-b]pyridine following a procedure analogous to that described in Example 1 [2-(7-aza-1H-benzotriazol-1-yl)-1,1,3,3-tetramethyluronium hexa-fluorophosphate is used]. Yield: 39% of theory; LC (method 4): $t_R$=2.01 min; Mass spectrum (ESI$^+$): m/z=331 [M+H]$^+$.

Example 113

5-(cis-2,3,4,4a,9,9a-Hexahydro-indeno[2,1-b]pyridine-1-carbonyl)-1-methyl-1,3-dihydro-benzoimidazol-2-one

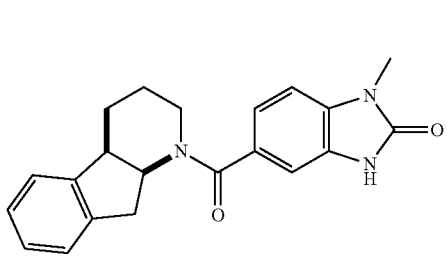

The title compound is prepared from 1-methyl-2-oxo-2,3-dihydro-1H-benzoimidazole-5-carboxylic acid and cis-2,3,4,4a,9,9a-hexahydro-1H-indeno[2,1-b]pyridine following a procedure analogous to that described in Example 1 [2-(7-aza-1H-benzotriazol-1-yl)-1,1,3,3-tetramethyluronium hexafluorophosphate is used]. Yield: 27% of theory; LC (method 4): $t_R$=1.89 min; Mass spectrum (ESI$^+$): m/z=348 [M+H]$^+$.

Example 114

(cis-2,3,4,4a,9,9a-Hexahydro-indeno[2,1-b]pyridin-1-yl)-(1H-indol-6-yl)-methanone

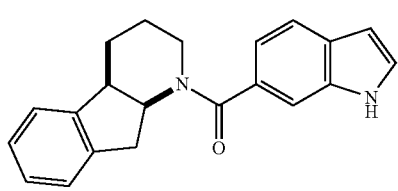

The title compound is prepared from 1H-indole-6-carboxylic acid and cis-2,3,4,4a,9,9a-hexahydro-1H-indeno[2,1-b]pyridine following a procedure analogous to that described in Example 1 [2-(7-aza-1H-benzotriazol-1-yl)-1,1,3,3-tetramethyluronium hexafluorophosphate is used]. Yield: 41% of theory; LC (method 4): $t_R$=2.00 min; Mass spectrum (ESI$^+$): m/z=317 [M+H]$^+$.

Example 115

5-(cis-2,3,4,4a,9,9a-Hexahydro-indeno[2,1-b]pyridine-1-carbonyl)-1,3-dihydro-indol-2-one

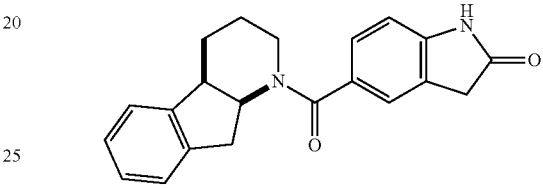

The title compound is prepared from 2-oxo-2,3-dihydro-1H-indole-5-carboxylic acid and cis-2,3,4,4a,9,9a-hexahydro-1H-indeno[2,1-b]pyridine following a procedure analogous to that described in Example 1 [2-(7-aza-1H-benzotriazol-1-yl)-1,1,3,3-tetramethyluronium hexafluorophosphate is used]. Yield: 29% of theory; LC (method 5): $t_R$=0.98 min; Mass spectrum (ESI$^+$): m/z=333 [M+H]$^+$.

Example 116

6-(cis-2,3,4,4a,9,9a-Hexahydro-indeno[2,1-b]pyridine-1-carbonyl)-1,3-dihydro-indol-2-one

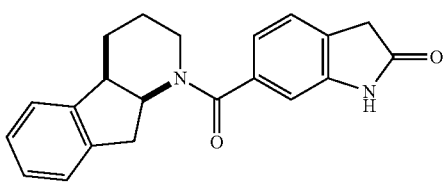

The title compound is prepared from 2-oxo-2,3-dihydro-1H-indole-6-carboxylic acid and cis-2,3,4,4a,9,9a-hexahydro-1H-indeno[2,1-b]pyridine following a procedure analogous to that described in Example 1 [2-(7-aza-1H-benzotriazol-1-yl)-1,1,3,3-tetramethyluronium

Example 117

(cis-2,3,4,4a,9,9a-Hexahydro-indeno[2,1-b]pyridin-1-yl)-(1-methyl-1H-benzoimidazol-5-yl)-methanone

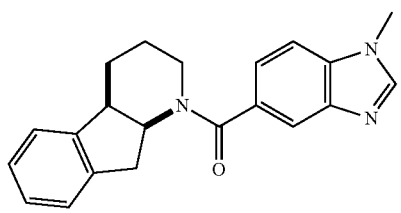

The title compound is prepared from 1-methyl-1H-benzoimidazole-5-carboxylic acid and cis-2,3,4,4a,9,9a-hexahydro-1H-indeno[2,1-b]pyridine following a procedure analogous to that described in Example 1 [2-(7-aza-1H-benzotriazol-1-yl)-1,1,3,3-tetramethyluronium hexafluorophosphate is used]. Yield: 90% of theory; LC (method 4): $t_R$=1.62 min; Mass spectrum (ESI$^+$): m/z=332 [M+H]$^+$.

Example 118

(cis-2,3,4,4a,9,9a-Hexahydro-indeno[2,1-b]pyridin-1-yl)-(1-methyl-1H-benzotriazol-5-yl)-methanone

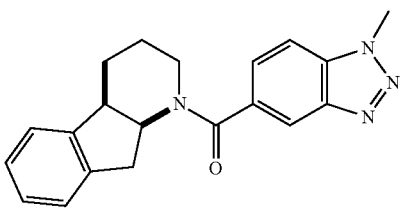

The title compound is prepared from 1-methyl-1H-benzotriazole-5-carboxylic acid and cis-2,3,4,4a,9,9a-hexahydro-1H-indeno[2,1-b]pyridine following a procedure analogous to that described in Example 1 [2-(7-aza-1H-benzotriazol-1-yl)-1,1,3,3-tetramethyluronium hexa-fluorophosphate is used]. Yield: 65% of theory; LC (method 4): $t_R$=1.88 min; Mass spectrum (ESI$^+$): m/z=333 [M+H]$^+$.

Example 119

(1H-Benzoimidazol-5-yl)-(cis-7-hydroxy-2,3,4,4a,9,9a-hexahydro-indeno[2,1-b]pyridin-1-yl)-methanone

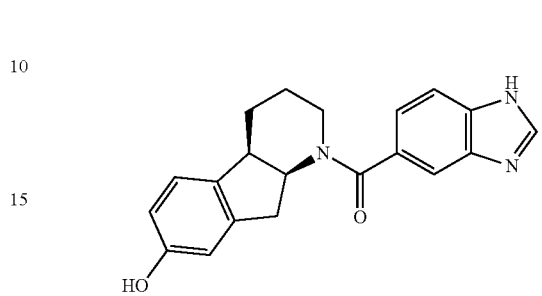

The title compound is prepared from 1H-benzoimidazole-5-carboxylic acid and cis-2,3,4,4a,9,9a-hexahydro-1H-indeno[2,1-b]pyridin-7-ol following a procedure analogous to that described in Example 1. Yield: 18% of theory; LC (method 1): $t_R$=1.97 min; Mass spectrum (ESI$^+$): m/z=334 [M+H]$^+$.

Example 120

(cis-2,3,4,4a,9,9a-Hexahydro-indeno[2,1-b]pyridin-1-yl)-(4-hydroxy-3-methyl-phenyl)-methanone

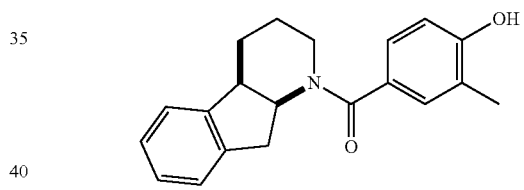

The title compound is prepared from 4-hydroxy-3-methyl-benzoic acid and cis-2,3,4,4a,9,9a-hexahydro-1H-indeno[2,1-b]pyridine following a procedure analogous to that described in Example 1 [2-(7-aza-1H-benzotriazol-1-yl)-1,1,3,3-tetramethyluronium hexa-fluorophosphate is used]. Yield: 35% of theory; LC (method 4): $t_R$=1.92 min; Mass spectrum (ESI$^+$): m/z=313 [M+H]$^+$.

Example 121

(cis-2,3,4,4a,9,9a-Hexahydro-indeno[2,1-b]pyridin-1-yl)-(2-methyl-1H-benzoimidazol-5-yl)-methanone

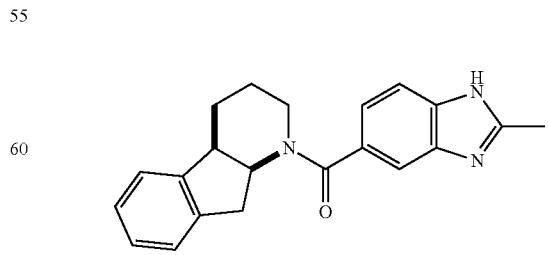

The title compound is prepared from 2-methyl-1H-benzoimidazole-5-carboxylic acid and cis-2,3,4,4a,9,9a-hexahydro-1H-indeno[2,1-b]pyridine following a procedure analogous to that described in Example 1 [2-(7-aza-1H-benzotriazol-1-yl)-1,1,3,3-tetramethyluronium hexafluorophosphate is used]. Yield: 89% of theory; LC (method 5): $t_R$=0.95 min; Mass spectrum (ESI⁺): m/z=332 [M+H]⁺.

Example 122

(4-Amino-3-chloro-phenyl)-(cis-2,3,4,4a,9,9a-hexahydro-indeno[2,1-b]pyridin-1-yl)-methanone

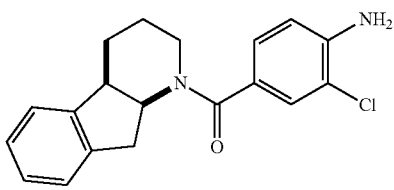

The title compound is prepared from 4-amino-3-chlorobenzoic acid and cis-2,3,4,4a,9,9a-hexahydro-1H-indeno[2,1-b]pyridine following a procedure analogous to that described in Example 1 [2-(7-aza-1H-benzotriazol-1-yl)-1,1,3,3-tetramethyluronium hexafluorophosphate is used]. Yield: 38% of theory; LC (method 4): $t_R$=1.96 min; Mass spectrum (ESI⁺): m/z=327/329 (Cl) [M+H]⁺.

Example 123

(cis-2,3,4,4a,9,9a-Hexahydro-indeno[2,1-b]pyridin-1-yl)-(1H-indazol-6-yl)-methanone

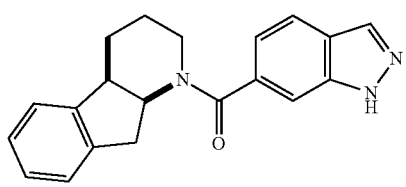

The title compound is prepared from 1H-indazole-6-carboxylic acid and cis-2,3,4,4a,9,9a-hexahydro-1H-indeno[2,1-b]pyridine following a procedure analogous to that described in Example 1 [2-(7-aza-1H-benzotriazol-1-yl)-1,1,3,3-tetramethyluronium hexafluorophosphate is used]. Yield: 5% of theory; LC (method 4): $t_R$=1.92 min; Mass spectrum (ESI⁺): m/z=318 [M+H]⁺.

Example 124

(2-Amino-1H-benzoimidazol-5-yl)-(cis-2,3,4,4a,9,9a-hexahydro-indeno[2,1-b]pyridin-1-yl)-methanone

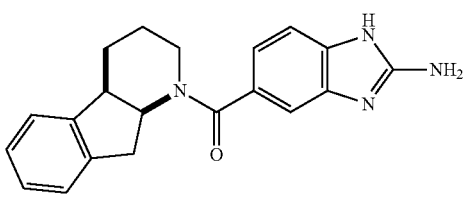

The title compound is prepared from 2-amino-1H-benzoimidazole-5-carboxylic acid and cis-2,3,4,4a,9,9a-hexahydro-1H-indeno[2,1-b]pyridine following a procedure analogous to that described in Example 1 [2-(7-aza-1H-benzotriazol-1-yl)-1,1,3,3-tetramethyluronium hexafluorophosphate is used]. Yield: 71% of theory; LC (method 4): $t_R$=1.64 min; Mass spectrum (ESI⁺): m/z=333 [M+H]⁺.

Example 125

Benzothiazol-6-yl-(cis-2,3,4,4a,9,9a-hexahydro-indeno[2,1-b]pyridin-1-yl)-methanone

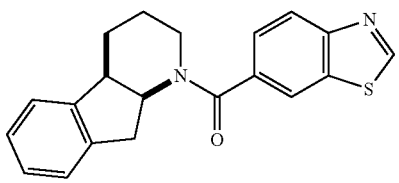

The title compound is prepared from benzothiazole-6-carboxylic acid and cis-2,3,4,4a,9,9a-hexahydro-1H-indeno[2,1-b]pyridine following a procedure analogous to that described in Example 1 [2-(7-aza-1H-benzotriazol-1-yl)-1,1,3,3-tetramethyluronium hexafluorophosphate is used]. Yield: 36% of theory; LC (method 4): $t_R$=1.94 min; Mass spectrum (ESI⁺): m/z=335 [M+H]⁺.

Example 126

(4-Chloro-3-hydroxy-phenyl)-(cis-2,3,4,4a,9,9a-hexahydro-indeno[2,1-b]pyridin-1-yl)-methanone

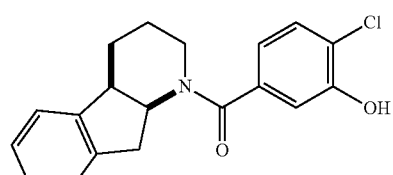

The title compound is prepared from 4-chloro-3-hydroxybenzoic acid and cis-2,3,4,4a,9,9a-hexahydro-1H-indeno[2,1-b]pyridine following a procedure analogous to that described in Example 1 [2-(7-aza-1H-benzotriazol-1-yl)-1,1,3,3-tetramethyluronium hexafluorophosphate is used]. Yield: 44% of theory; LC (method 4): $t_R$=1.97 min; Mass spectrum (ESI$^+$): m/z=328 [M+H]$^+$.

Example 127

(cis-2,3,4,4a,9,9a-Hexahydro-indeno[2,1-b]pyridin-1-yl)-(1H-imidazo[4,5-b]pyridin-6-yl)-methanone

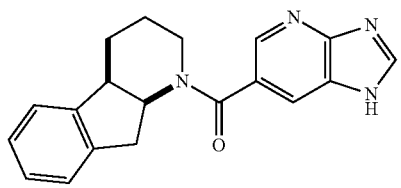

The title compound is prepared from 1H-imidazo[4,5-b]pyridine-6-carboxylic acid and cis-2,3,4,4a,9,9a-hexahydro-1H-indeno[2,1-b]pyridine following a procedure analogous to that described in Example 1 [2-(7-aza-1H-benzotriazol-1-yl)-1,1,3,3-tetramethyluronium hexafluorophosphate is used]. Yield: 71% of theory; LC (method 4): $t_R$=1.79 min; Mass spectrum (ESI$^+$): m/z=319 [M+H]$^+$.

Example 128

5-(cis-2,3,4,4a,9,9a-Hexahydro-indeno[2,1-b]pyridine-1-carbonyl)-1,3-dihydro-benzoimidazol-2-one

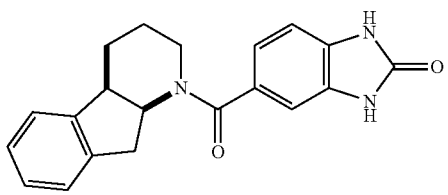

The title compound is prepared from 2-oxo-2,3-dihydro-1H-benzoimidazole-5-carboxylic acid and cis-2,3,4,4a,9,9a-hexahydro-1H-indeno[2,1-b]pyridine following a procedure analogous to that described in Example 1 [2-(7-aza-1H-benzotriazol-1-yl)-1,1,3,3-tetramethyluronium hexafluorophosphate is used]. Yield: 11% of theory; LC (method 4): $t_R$=1.86 min; Mass spectrum (ESI$^+$): m/z=334 [M+H]$^+$.

Example 129

(cis-2,3,4,4a,9,9a-Hexahydro-indeno[2,1-b]pyridin-1-yl)-(3-methyl-3H-benzoimidazol-5-yl)-methanone

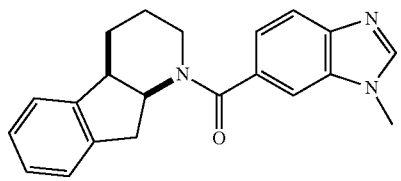

The title compound is prepared from 3-methyl-3H-benzoimidazole-5-carboxylic acid and cis-2,3,4,4a,9,9a-hexahydro-1H-indeno[2,1-b]pyridine following a procedure analogous to that described in Example 1 [2-(7-aza-1H-benzotriazol-1-yl)-1,1,3,3-tetramethyluronium hexafluorophosphate is used]. Yield: 94% of theory; LC (method 4): $t_R$=1.62 min; Mass spectrum (ESI$^+$): m/z=332 [M+H]$^+$.

Example 130

(3-Amino-4-fluoro-Phenyl)-(cis-2,3,4,4a,9,9a-hexahydro-indeno[2,1-b]pyridin-1-yl)-methanone

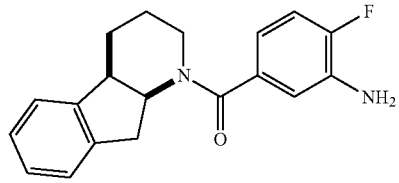

The title compound is prepared from 3-amino-4-fluorobenzoic acid and cis-2,3,4,4a,9,9a-hexahydro-1H-indeno[2,1-b]pyridine following a procedure analogous to that described in Example 1 [2-(7-aza-1H-benzotriazol-1-yl)-1,1,3,3-tetramethyluronium hexafluorophosphate is used]. Yield: 68% of theory; LC (method 4): $t_R$=1.91 min; Mass spectrum (ESI$^+$): m/z=311 [M+H]$^+$.

Example 131

(cis-2,3,4,4a,9,9a-Hexahydro-indeno[2,1-b]pyridin-1-yl)-imidazo[1,2-a]pyridin-7-yl-methanone

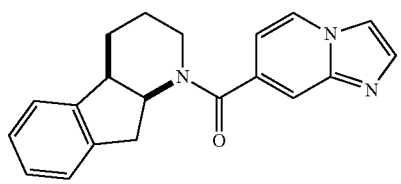

The title compound is prepared from imidazo[1,2-a]pyridine-7-carboxylic acid and cis-2,3,4,4a,9,9a-hexahydro-1H- indeno[2,1-b]pyridine following a procedure analogous to that described in Example 1 [2-(7-aza-1H-benzotriazol-1-yl)-1,1,3,3-tetramethyluronium hexafluorophosphate is used]. Yield: 18% of theory; LC (method 4): $t_R$=1.56 min; Mass spectrum (ESI$^+$): m/z=318 [M+H]$^+$.

Example 132

(cis-2,3,4,4a,9,9a-Hexahydro-indeno[2,1-b]pyridin-1-yl)-(1H-indazol-5-yl)-methanone

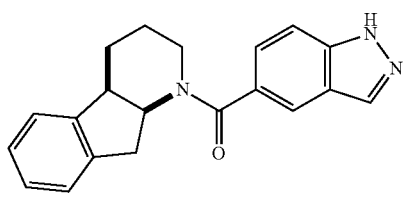

The title compound is prepared from 1H-indazole-5-carboxylic acid and cis-2,3,4,4a,9,9a-hexahydro-1H-indeno[2,1-b]pyridine following a procedure analogous to that described in Example 1 [2-(7-aza-1H-benzotriazol-1-yl)-1,1,3,3-tetramethyluronium hexafluorophosphate is used]. Yield: 31% of theory; LC (method 4): $t_R$=1.91 min; Mass spectrum (ESI$^+$): m/z=318 [M+H]$^+$.

Example 133

(4-Amino-phenyl)-(cis-2,3,4,4a,9,9a-hexahydro-indeno[2,1-b]pyridin-1-yl)-methanone

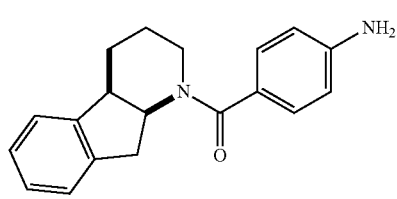

The title compound is prepared from 4-amino-benzoic acid and cis-2,3,4,4a,9,9a-hexahydro-1H-indeno[2,1-b]pyridine following a procedure analogous to that described in Example 1 [2-(7-aza-1H-benzotriazol-1-yl)-1,1,3,3-tetramethyluronium hexafluorophosphate is used]. Yield: 70% of theory; LC (method 4): $t_R$=1.77 min; Mass spectrum (ESI$^+$): m/z=293 [M+H]$^+$.

Example 134

(cis-2,3,4,4a,9,9a-Hexahydro-indeno[2,1-b]pyridin-1-yl)-(4-hydroxy-phenyl)-methanone

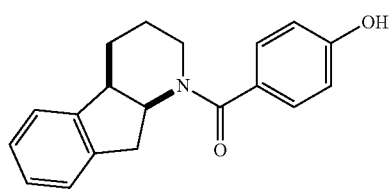

The title compound is prepared from 4-hydroxy-benzoic acid and cis-2,3,4,4a,9,9a-hexahydro-1H-indeno[2,1-b]pyridine following a procedure analogous to that described in Example 1 [2-(7-aza-1H-benzotriazol-1-yl)-1,1,3,3-tetramethyluronium hexafluorophosphate is used]. Yield: 25% of theory; LC (method 4): $t_R$=1.91 min; Mass spectrum (ESI$^+$): m/z=294 [M+H]$^+$.

Example 135

(cis-2,3,4,4a,9,9a-Hexahydro-indeno[2,1-b]pyridin-1-yl)-(1H-indol-5-yl)-methanone

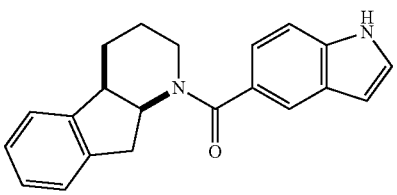

The title compound is prepared from 1H-indole-5-carboxylic acid and cis-2,3,4,4a,9,9a-hexahydro-1H-indeno[2,1-b]pyridine following a procedure analogous to that described in Example 1 [2-(7-aza-1H-benzotriazol-1-yl)-1,1,3,3-tetramethyluronium hexafluorophosphate is used]. Yield: 43% of theory; LC (method 4): $t_R$=1.97 min; Mass spectrum (ESI$^+$): m/z=317 [M+H]$^+$.

Example 136

(cis-2,3,4,4a,9,9a-Hexahydro-indeno[2,1-b]pyridin-1-yl)-(1H-indol-3-yl)-methanone

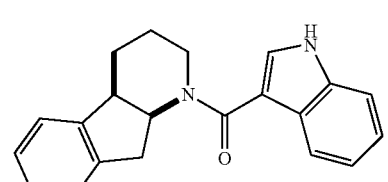

The title compound is prepared from 1H-indole-3-carboxylic acid and cis-2,3,4,4a,9,9a-hexahydro-1H-indeno[2,1-b]pyridine following a procedure analogous to that described in Example 1 [2-(7-aza-1H-benzotriazol-1-yl)-1,1,3,3-tetramethyluronium hexafluorophosphate is used]. Yield: 35% of theory; LC (method 4): $t_R$=1.99 min; Mass spectrum (ESI$^+$): m/z=317 [M+H]$^+$.

Example 137

(3,5-Dichloro-4-hydroxy-phenyl)-(cis-2,3,4,4a,9,9a-hexahydro-indeno[2,1-b]pyridin-1-yl)-methanone

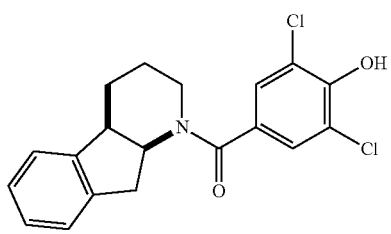

The title compound is prepared from 3,5-dichloro-4-hydroxy-benzoic acid and cis-2,3,4,4a,9,9a-hexahydro-1H-indeno[2,1-b]pyridine following a procedure analogous to that described in Example 1 [2-(7-aza-1H-benzotriazol-1-yl)-1,1,3,3-tetramethyluronium hexafluorophosphate is used]. Yield: 32% of theory; LC (method 4): $t_R$=2.01 min; Mass spectrum (ESI$^+$): m/z=362/364/366 (Cl) [M+H]$^+$.

Example 138

(1H-Benzotriazol-5-yl)-(cis-2,3,4,4a,9,9a-hexahydro-indeno[2,1-b]pyridin-1-yl)-methanone

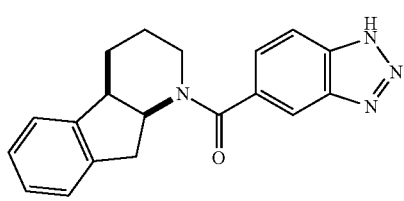

The title compound is prepared from 1H-benzotriazole-5-carboxylic acid and cis-2,3,4,4a,9,9a-hexahydro-1H-indeno[2,1-b]pyridine following a procedure analogous to that described in Example 1 [2-(7-aza-1H-benzotriazol-1-yl)-1,1,3,3-tetramethyluronium hexafluorophosphate is used]. Yield: 19% of theory; LC (method 4): $t_R$=1.87 min; Mass spectrum (ESI$^+$): m/z=319 [M+H]$^+$.

Example 139

(cis-2,3,4,4a,9,9a-Hexahydro-indeno[2,1-b]pyridin-1-yl)-(1-methyl-1H-indol-3-yl)-methanone

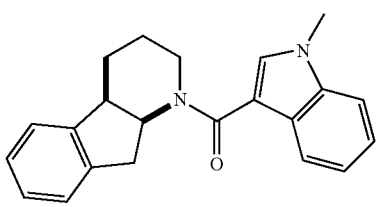

The title compound is prepared from 1-methyl-1H-indole-3-carboxylic acid and cis-2,3,4,4a,9,9a-hexahydro-1H-indeno[2,1-b]pyridine following a procedure analogous to that described in Example 1 [2-(7-aza-1H-benzotriazol-1-yl)-1,1,3,3-tetramethyluronium hexafluorophosphate is used]. Yield: 26% of theory; LC (method 4): $t_R$=2.02 min; Mass spectrum (ESI$^+$): m/z=331 [M+H]$^+$.

Example 140

(cis-2,3,4,4a,9,9a-Hexahydro-indeno[2,1-b]pyridin-1-yl)-(3-hydroxy-4-methoxy-phenyl)-methanone

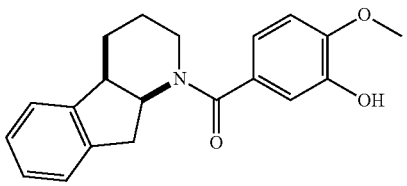

The title compound is prepared from 3-hydroxy-4-methoxy-benzoic acid and cis-2,3,4,4a,9,9a-hexahydro-1H-indeno[2,1-b]pyridine following a procedure analogous to that described in Example 1 [2-(7-aza-1H-benzotriazol-1-yl)-1,1,3,3-tetramethyluronium hexafluorophosphate is used]. Yield: 45% of theory; LC (method 4): $t_R$=1.91 min; Mass spectrum (ESI$^+$): m/z=324 [M+H]$^+$.

Example 141

(3-Chloro-4-hydroxy-phenyl)-(cis-2,3,4,4a,9,9a-hexahydro-indeno[2,1-b]pyridin-1-yl)-methanone

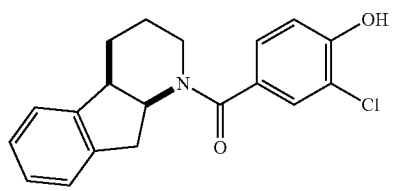

The title compound is prepared from 3-chloro-4-hydroxy-benzoic acid and cis-2,3,4,4a,9,9a-hexahydro-1H-indeno[2,1-b]pyridine following a procedure analogous to that described in Example 1 [2-(7-aza-1H-benzotriazol-1-yl)-1,1,3,3-tetramethyluronium hexa-fluorophosphate is used]. Yield: 32% of theory; LC (method 4): $t_R$=1.96 min; Mass spectrum (ESI$^+$): m/z=328/330 (Cl) [M+H]$^+$.

Example 142

(3-Amino-4-chloro-phenyl)-(cis-2,3,4,4a,9,9a-hexahydro-indeno[2,1-b]pyridin-1-yl)-methanone

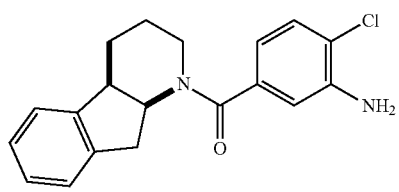

The title compound is prepared from 3-amino-4-chloro-benzoic acid and cis-2,3,4,4a,9,9a-hexahydro-1H-indeno[2,1-b]pyridine following a procedure analogous to that described in Example 1 [2-(7-aza-1H-benzotriazol-1-yl)-1,1,3,3-tetramethyluronium hexafluorophosphate is used]. Yield: 43% of theory; LC (method 4): $t_R$=1.97 min; Mass spectrum (ESI$^+$): m/z=327/329 (Cl) [M+H]$^+$.

Example 143

(3-Amino-4-methyl-phenyl)-(cis-2,3,4,4a,9,9a-hexahydro-indeno[2,1-b]pyridin-1-yl)-methanone

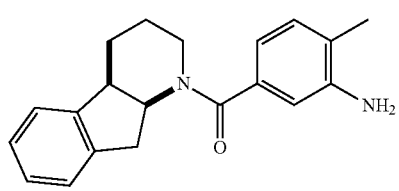

The title compound is prepared from 3-amino-4-methyl-benzoic acid and cis-2,3,4,4a,9,9a-hexahydro-1H-indeno[2,1-b]pyridine following a procedure analogous to that described in Example 1 [2-(7-aza-1H-benzotriazol-1-yl)-1,1,3,3-tetramethyluronium hexafluorophosphate is used]. Yield: 63% of theory; LC (method 4): $t_R$=1.81 min; Mass spectrum (ESI$^+$): m/z=307 [M+H]$^+$.

Example 144

(4-Amino-3-methoxy-phenyl)-(cis-2,3,4,4a,9,9a-hexahydro-indeno[2,1-b]pyridin-1-yl)-methanone

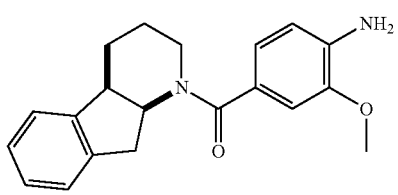

The title compound is prepared from 4-amino-3-methoxy-benzoic acid and cis-2,3,4,4a,9,9a-hexahydro-1H-indeno[2,1-b]pyridine following a procedure analogous to that described in Example 1 [2-(7-aza-1H-benzotriazol-1-yl)-1,1,3,3-tetramethyluronium hexa-fluorophosphate is used]. Yield: 59% of theory; LC (method 4): $t_R$=1.80 min; Mass spectrum (ESI$^+$): m/z=323 [M+H]$^+$.

Example 145

(4-Amino-3-fluoro-phenyl)-(cis-2,3,4,4a,9,9a-hexahydro-indeno[2,1-b]pyridin-1-yl)-methanone

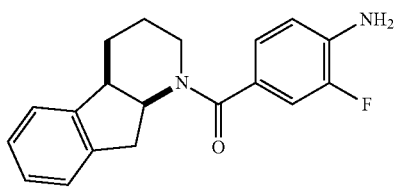

The title compound is prepared from 4-amino-3-fluoro-benzoic acid and cis-2,3,4,4a,9,9a-hexahydro-1H-indeno[2,1-b]pyridine following a procedure analogous to that described in Example 1 [2-(7-aza-1H-benzotriazol-1-yl)-1,1,3,3-tetramethyluronium hexafluorophosphate is used]. Yield: 62% of theory; LC (method 4): $t_R$=1.91 min; Mass spectrum (ESI$^+$): m/z=311 [M+H]$^+$.

Example 146

(1H-Benzoimidazol-5-yl)-(cis-4-methyl-2,3,4,4a,9,9a-hexahydro-indeno[2,1-b]pyridin-1-yl)-methanone

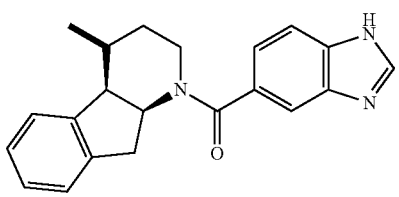 [SMILES: C[C@H]1CCN(C(=O)c2ccc3[nH]cnc3c2)[C@H]2Cc3ccccc3[C@@H]12]

The title compound is prepared from 1H-benzoimidazole-5-carboxylic acid and cis-4-methyl-2,3,4,4a,9,9a-hexahydro-1H-indeno[2,1-b]pyridine following a procedure analogous to that described in Example 1. Yield: 16% of theory; LC (method 1): $t_R$=2.68 min; Mass spectrum (ESI$^+$): m/z=332 [M+H]$^+$.

Example 147

6-(cis-2,3,4,4a,9,9a-Hexahydro-indeno[2,1-b]pyridine-1-carbonyl)-1H-quinoxalin-2-one

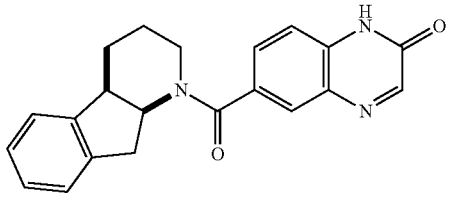

The title compound is prepared from 2-oxo-1,2-dihydroquinoxaline-6-carboxylic acid and cis-2,3,4,4a,9,9a-hexahydro-1H-indeno[2,1-b]pyridine following a procedure analogous to that described in Example 1 [2-(7-aza-1H-benzotriazol-1-yl)-1,1,3,3-tetramethyluronium hexafluorophosphate is used]. Yield: 45% of theory; LC (method 4): $t_R$=1.89 min; Mass spectrum (ESI$^+$): m/z=346 [M+H]$^+$.

Example 148

(4a-R,9a-S)-1-(1H-Benzoimidazole-5-carbonyl)-2,3,4,4a,9,9a-hexahydro-1H-indeno[2,1-b]pyridine-7-carbonitrile

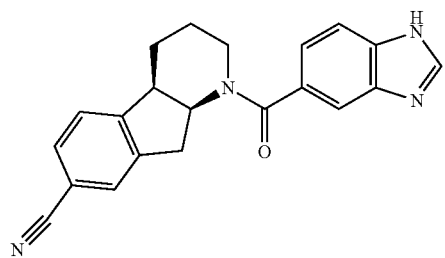 [SMILES: N#Cc1ccc2c(c1)C[C@H]1[C@@H]2CCCN1C(=O)c1ccc2[nH]cnc2c1]

A flask charged with a stir bar, zinc cyanide (94 mg), (1H-benzoimidazol-5-yl)-[(4a-R,9a-S)-7-bromo-2,3,4,4a,9,9a-hexahydro-indeno[2,1-b]pyridin-1-yl]methanone (0.30 g), and N,N-dimethylformamide (2 mL) is sparged with argon for 10 min. Tetrakis(triphenylphosphine)-palladium(0) (0.10 g) is then added and the resulting mixture is heated to 100° C. and stirred at this temperature overnight. After cooling to room temperature, methanol is added and the resulting mixture is filtered. The filtrate is concentrated and water is added to the residue. The aqueous mixture is extracted with ethyl acetate, the combined extracts are dried (Na$_2$SO$_4$), and the solvent is evaporated. The residue is purified by HPLC on reversed phase (acetonitrile/water/trifluoroacetic acid) to give the title compound as its trifluoroacetic acid salt. Yield: 0.09 g (25% of theory); LC (method 1): $t_R$=2.31 min; Mass spectrum (ESI$^+$): m/z=343 [M+H]$^+$.

Example 149

(4a-R,9a-S)-(1H-Benzoimidazol-5-yl)-(6-methoxy-2,3,4,4a,9,9a-hexahydro-indeno[2,1-b]pyridin-1-yl)-methanone

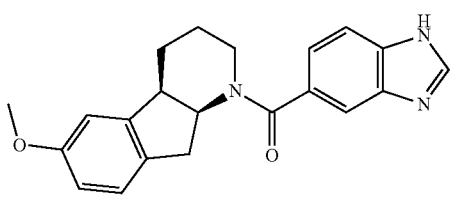 [SMILES: COc1ccc2c(c1)[C@H]1CCCN(C(=O)c3ccc4[nH]cnc4c3)[C@H]1C2]

The title compound is prepared from 1H-benzoimidazole-5-carboxylic acid and (4a-R,9a-S)-6-methoxy-2,3,4,4a,9,9a-hexahydro-1H-indeno[2,1-b]pyridine following a procedure analogous to that described in Example 1. Yield: 89% of theory; LC (method 1): $t_R$=2.43 min; Mass spectrum (ESI$^+$): m/z=348 [M+H]$^+$.

Example 150

(4a-R,9a-S)-(1H-Benzoimidazol-5-yl)-(6-hydroxy-2,3,4,4a,9,9a-hexahydro-indeno[2,1-b]pyridin-1-yl)-methanone

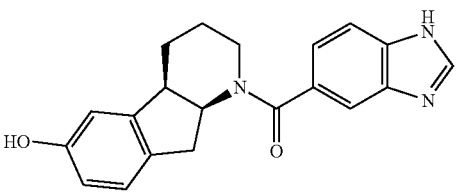 [SMILES: O=C(c1ccc2[nH]cnc2c1)N1CCC[C@@H]2c3cc(O)ccc3C[C@@H]21]

The title compound is prepared from (4a-R,9a-S)-(1H-benzoimidazol-5-yl)-(6-methoxy-2,3,4,4a,9,9a-hexahydro-indeno[2,1-b]pyridin-1-yl)-methanone following a procedure analogous to that described in Example 7. Yield: 78% of theory; LC (method 1): $t_R$=1.89 min; Mass spectrum (ESI$^+$): m/z=334 [M+H]$^+$.

Example 151

(cis-7-Amino-2,3,4,4a,9,9a-hexahydro-indeno[2,1-b]pyridin-1-yl)-(1H-benzoimidazol-5-yl)-methanone

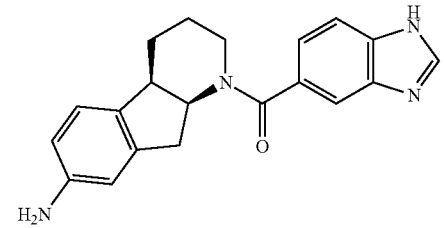 [SMILES: Nc1ccc2c(c1)C[C@H]1[C@@H]2CCCN1C(=O)c1ccc2[nH]cnc2c1]

The title compound is prepared from 1H-benzoimidazole-5-carboxylic acid and cis-2,3,4,4a,9,9a-hexahydro-1H-indeno[2,1-b]pyridin-7-ylamine following a procedure analogous to that described in Example 1. Yield: 30% of theory; LC (method 1): $t_R$=0.79 min; Mass spectrum (ESI+): m/z=333 [M+H]+.

Example 152

(4a-R,9a-S)-1-(7-Methyl-1H-benzoimidazole-5-carbonyl)-2,3,4,4a,9,9a-hexahydro-1H-indeno[2,1-b]pyridine-6-carbonitrile

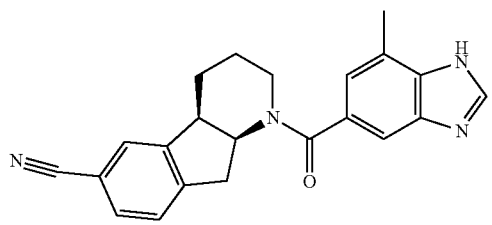 [SMILES: Cc1cc(C(=O)N2CCC[C@@H]3c4cc(C#N)ccc4C[C@@H]32)cc2nc[nH]c12]

The title compound is prepared from 7-methyl-1H-benzoimidazole-5-carboxylic acid and (4a-R,9a-S)-2,3,4,4a,9,9a-hexahydro-1H-indeno[2,1-b]pyridine-6-carbonitrile following a procedure analogous to that described in Example 1. Yield: 53% of theory; LC (method 6): $t_R$=1.05 min; Mass spectrum (ESI+): m/z=357 [M+H]+.

Example 153

(4a-R,9a-S)-1-(6-Methyl-1H-benzoimidazole-5-carbonyl)-2,3,4,4a,9,9a-hexahydro-1H-indeno[2,1-b]pyridine-6-carbonitrile

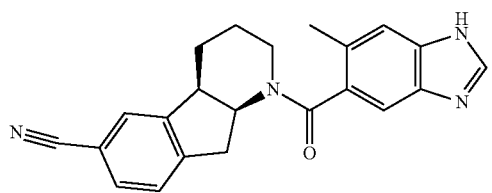 [SMILES: Cc1cc2[nH]cnc2cc1C(=O)N1CCC[C@@H]2c3cc(C#N)ccc3C[C@@H]21]

The title compound is prepared from 6-methyl-1H-benzoimidazole-5-carboxylic acid and (4a-R,9a-S)-2,3,4,4a,9,9a-hexahydro-1H-indeno[2,1-b]pyridine-6-carbonitrile following a procedure analogous to that described in Example 1. Yield: 69% of theory; LC (method 6): $t_R$=0.99 min; Mass spectrum (ESI+): m/z=357 [M+H]+.

Example 154 cis-1-(1H-Benzoimidazole-5-carbonyl)-2,3,4,4a,9,9a-hexahydro-1H-indeno[2,1-b]pyridine-6-carboxylic acid methyl ester

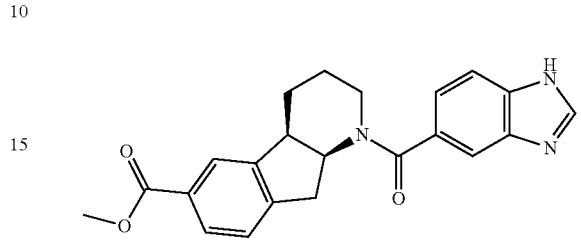

A flask charged with a stir bar, trifluoromethanesulfonic acid cis-1-(1-trifluoromethane-sulfonyl-1H-benzoimidazole-5-carbonyl)-2,3,4,4a,9,9a-hexahydro-1H-indeno[2,1-b]pyridin-6-yl ester (mixture of isomers regarding sulfonyl group attachment to N-1 or N-3 of the benzimidazole, 0.50 g), triethylamine (0.18 mL), N,N-dimethylformamide (2 mL), and methanol (1 ml) is sparged with argon for 5 min. [1,1'-Bis(diphenylphosphino)ferrocene]-dichloropalladium dichloromethane complex (53 mg) is added and the mixture is sparged with carbon monoxide for another 5 min. The mixture is then heated to 70° C. under carbon monoxide atmosphere (4 bar) and shaken at this temperature overnight. After cooling to room temperature, the mixture is filtered and the filtrate is concentrated under reduced pressure. The residue is chromatographed on silica gel (dichloromethane/methanol 1:0→9:1) to afford the title compound. Yield: 0.27 g (87% of theory); LC (method 1): $t_R$=2.43 min; Mass spectrum (ESI+): m/z=376 [M+H]+.

Example 155

(1H-Benzoimidazol-5-yl)-(cis-6-ethynyl-2,3,4,4a,9,9a-hexahydro-indeno[2,1-b]pyridin-1-yl)-methanone

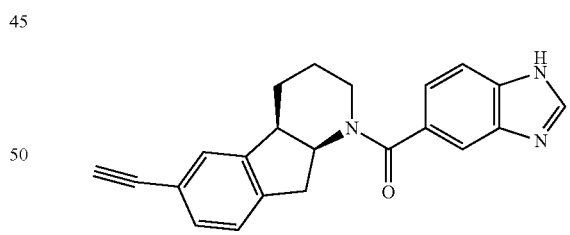

A flask charged with a stir bar, trifluoromethanesulfonic acid cis-1-(1-trifluoromethane-sulfonyl-1H-benzoimidazole-5-carbonyl)-2,3,4,4a,9,9a-hexahydro-1H-indeno[2,1-b]pyridin-6-yl ester (mixture of isomers regarding sulfonyl group attachment to N-1 or N-3 of the benzimidazole, 0.20 g) and N,N-dimethylformamide (2 mL) is sparged with argon for 5 min. Copper(1) iodide (13 mg), Pd(PPh₃)₂Cl₂ (25 mg), triethylamine (0.31 mL), and trimethylsilylacetylene (0.14 mL) are added in the given order, the vessel is sealed, and the resulting mixture is heated to 60° C. After stirring the mixture at 60° C. overnight, it is cooled to room temperature and aqueous K₂CO₃ solution is added. The resulting mixture is extracted with ethyl acetate, the combined extract is dried (Na$_2$SO$_4$), and the solvent is evaporated. The residue is chromatographed on silica gel (dichloromethane/methanol 1:0→9:1) to afford the trimethylsilylated title compound which is taken up in methanol (3 mL) and treated with saturated aqueous K$_2$CO$_3$ solution at room temperature for 2 h. The mixture is then concentrated, water is added to the residue, and the resulting mixture is extracted with ethyl acetate. The combined extract is dried (Na$_2$SO$_4$) and concentrated. The residue is chromatographed on silica gel (dichloromethane/methanol 1:0→9:1) to afford the title compound. Yield: 0.03 g (26% of theory); LC (method 1): $t_R$=2.65 min; Mass spectrum (ESI$^+$): m/z=342 [M+H]$^+$.

Example 156

(1H-Benzoimidazol-5-yl)-(cis-6-hydroxymethyl-2,3,4,4a,9,9a-hexahydro-indeno[2,1-b]pyridin-1-yl)-methanone

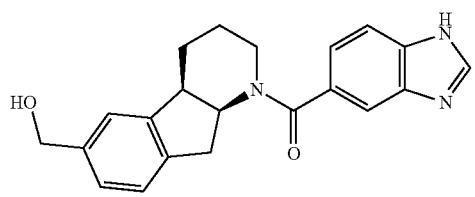 [SMILES: O=C(c1ccc2[nH]cnc2c1)N1CCC[C@@H]2c3cc(CO)ccc3C[C@@H]21]

The title compound is prepared from cis-1-(1H-benzoimidazole-5-carbonyl)-2,3,4,4a,9,9a-hexahydro-1H-indeno[2,1-b]pyridine-6-carboxylic acid methyl ester following a procedure analogous to that described in Example 34. Yield: 30% of theory; LC (method 1): $t_R$=1.87 min; Mass spectrum (ESI$^+$): m/z=348 [M+H]$^+$.

Example 157

(1H-Benzoimidazol-5-yl)-[cis-6-(1-hydroxy-1-methyl-ethyl)-2,3,4,4a,9,9a-hexahydro-indeno[2,1-b]pyridin-1-yl]-methanone

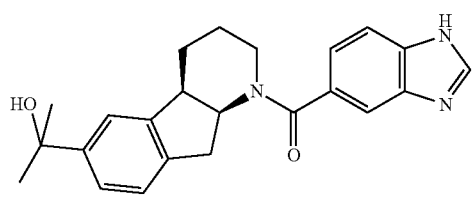 [SMILES: CC(C)(O)c1ccc2c(c1)[C@H]1CCCN(C(=O)c3ccc4[nH]cnc4c3)[C@H]1C2]

The title compound is prepared from cis-1-(1H-benzoimidazole-5-carbonyl)-2,3,4,4a,9,9a-hexahydro-1H-indeno[2,1-b]pyridine-6-carboxylic acid methyl ester following a procedure analogous to that described in Example 41 except for using MeLi instead of MeMgBr. Yield: 21% of theory; LC (method 1): $t_R$=2.13 min; Mass spectrum (ESI$^+$): m/z=376 [M+H]$^+$.

Example 158

(1H-Benzoimidazol-5-yl)-(cis-6-phenyl-2,3,4,4a,9,9a-hexahydro-indeno[2,1-b]pyridin-1-yl)-methanone

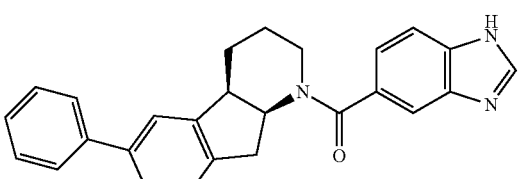

The title compound is prepared from 1H-benzoimidazole-5-carboxylic acid and cis-6-phenyl-2,3,4,4a,9,9a-hexahydro-1H-indeno[2,1-b]pyridine following a procedure analogous to that described in Example 1. Yield: 63% of theory; LC (method 1): $t_R$=3.28 min; Mass spectrum (ESI$^+$): m/z=394 [M+H]$^+$.

Example 159

(1H-Benzoimidazol-5-yl)-(cis-6-phenylethynyl-2,3,4,4a,9,9a-hexahydro-indeno[2,1-b]pyridin-1-yl)-methanone

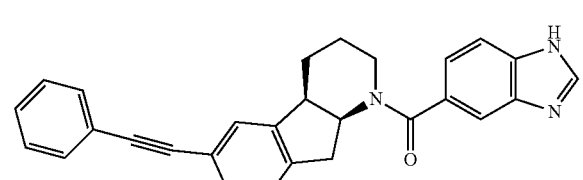

The title compound is prepared from cis-1-(1-trifluoromethane-sulfonyl-1H-benzoimidazole-5-carbonyl)-2,3,4,4a,9,9a-hexahydro-1H-indeno[2,1-b]pyridin-6-yl ester (mixture of isomers regarding sulfonyl group attachment to N-1 or N-3 of the benzimidazole) and phenylacetylene following a procedure analogous to that described in Example 155; in case the sulfonyl group on one of the benzimidazole nitrogens is not completely removed after the reaction, the mixture is treated with 1-hydroxy-benzotriazole and water.

Yield: 24% of theory; LC (method 1): $t_R$=3.58 min; Mass spectrum (ESI⁺): m/z=418 [M+H]⁺.

Example 160

(1H-Benzoimidazol-5-yl)-(cis-6-furan-3-yl-2,3,4,4a,9,9a-hexahydro-indeno[2,1-b]pyridin-1-yl)-methanone

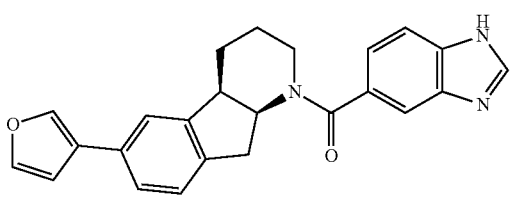 [SMILES: O=C(c1ccc2[nH]cnc2c1)N1CCC[C@@H]2c3cc(-c4ccoc4)ccc3C[C@@H]21]

The title compound is prepared from 1H-benzoimidazole-5-carboxylic acid and cis-6-furan-3-yl-2,3,4,4a,9,9a-hexahydro-1H-indeno[2,1-b]pyridine following a procedure analogous to that described in Example 1. Yield: 14% of theory; LC (method 1): $t_R$=2.89 min; Mass spectrum (ESI⁺): m/z=384 [M+H]⁺.

Example 161

(1H-Benzoimidazol-5-yl)-(cis-6-prop-1-ynyl-2,3,4,4a,9,9a-hexahydro-indeno[2,1-b]pyridin-1-yl)-methanone

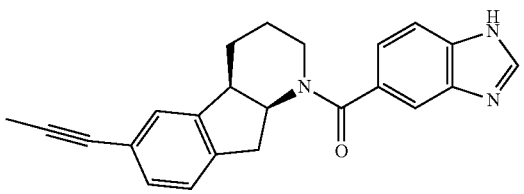 [SMILES: CC#Cc1ccc2c(c1)[C@H]1CCCN(C(=O)c3ccc4[nH]cnc4c3)[C@H]1C2]

The title compound is prepared from cis-1-(1-trifluoromethane-sulfonyl-1H-benzoimidazole-5-carbonyl)-2,3,4,4a,9,9a-hexahydro-1H-indeno[2,1-b]pyridin-6-yl ester (mixture of isomers regarding sulfonyl group attachment to N-1 or N-3 of the benzimidazole) and propyne following a procedure analogous to that described in Example 155; in case the sulfonyl group on one of the benzimidazole nitrogens is not completely removed after the reaction, the mixture is treated with 1-hydroxy-benzotriazole and water. Yield: 30% of theory; LC (method 1): $t_R$=2.92 min; Mass spectrum (ESI⁺): m/z=356 [M+H]⁺.

Example 162

(1H-Benzoimidazol-5-yl)-[cis-6-(1-methyl-1H-pyrazol-4-yl)-2,3,4,4a,9,9a-hexahydro-indeno[2,1-b]pyridin-1-yl]-methanone

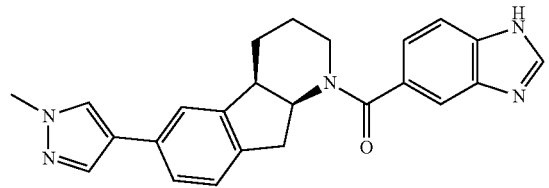 [SMILES: Cn1cc(-c2ccc3c(c2)[C@H]2CCCN(C(=O)c4ccc5[nH]cnc5c4)[C@H]2C3)cn1]

The title compound is prepared from 1H-benzoimidazole-5-carboxylic acid and cis-6-(1-methyl-1H-pyrazol-4-yl)-2,3,4,4a,9,9a-hexahydro-1H-indeno[2,1-b]pyridine following a procedure analogous to that described in Example 1. Yield: 78% of theory; LC (method 1): $t_R$=2.35 min; Mass spectrum (ESI⁺): m/z=398 [M+H]⁺.

Example 163

(1H-Benzoimidazol-5-yl)-(cis-6-methyl-2,3,4,4a,9,9a-hexahydro-indeno[2,1-b]pyridin-1-yl)-methanone

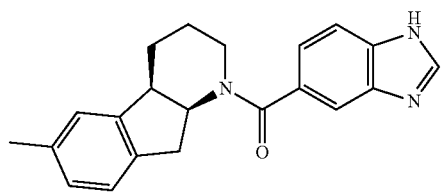 [SMILES: Cc1ccc2c(c1)[C@H]1CCCN(C(=O)c3ccc4[nH]cnc4c3)[C@H]1C2]

The title compound is prepared from 1H-benzoimidazole-5-carboxylic acid and cis-6-methyl-2,3,4,4a,9,9a-hexahydro-1H-indeno[2,1-b]pyridine following a procedure analogous to that described in Example 1. Yield: 60% of theory; LC (method 1): $t_R$=2.75 min; Mass spectrum (ESI⁺): m/z=332 [M+H]⁺.

Example 164

(1H-Benzoimidazol-5-yl)-(cis-6-(tetrahydro-pyran-4-yl)-2,3,4,4a,9,9a-hexahydro-indeno[2,1-b]pyridin-1-yl)-methanone

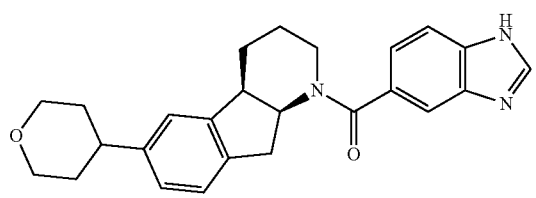 [SMILES: O=C(c1ccc2[nH]cnc2c1)N1CCC[C@@H]2c3cc(C4CCOCC4)ccc3C[C@@H]21]

A mixture of (1H-benzoimidazol-5-yl)-[6-(3,6-dihydro-2H-pyran-4-yl)-2,3,4,4a,9,9a-hexahydro-indeno[2,1-b]pyridin-1-yl]methanone (48 mg), 10% palladium on carbon (10 mg), and methanol (3 mL) is shaken under hydrogen atmosphere (5 bar) at room temperature overnight. The catalyst is then separated by filtration and the filtrate is concentrated. The residue is purified by chromatography on silica gel (dichloromethane/methanol 1:0→9:1) to afford the title compound. Yield: 15 mg (31% of theory); LC (method 1): $t_R$=2.63 min; Mass spectrum (ESI$^+$): m/z=402 [M+H]$^+$.

Example 165

(1H-Benzoimidazol-5-yl)-(cis-6-cyclopentyl-2,3,4,4a,9,9a-hexahydro-indeno[2,1-b]pyridin-1-yl)-methanone

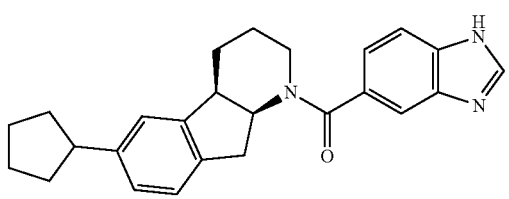 [SMILES: O=C(c1ccc2[nH]cnc2c1)N1CCC[C@@H]2c3cc(C4CCCC4)ccc3C[C@@H]21]

The title compound is prepared from (1H-benzoimidazol-5-yl)-(6-cyclopent-1-enyl-2,3,4,4a,9,9a-hexahydro-indeno[2,1-b]pyridin-1-yl)-methanone following a procedure analogous to that described in Example 164. Yield: 50% of theory; LC (method 1): $t_R$=3.53 min; Mass spectrum (ESI$^+$): m/z=386 [M+H]$^+$.

Example 166

N-[cis-1-(1H-Benzoimidazole-5-carbonyl)-2,3,4,4a,9,9a-hexahydro-1H-indeno[2,1-b]pyridin-7-yl]-acetamide

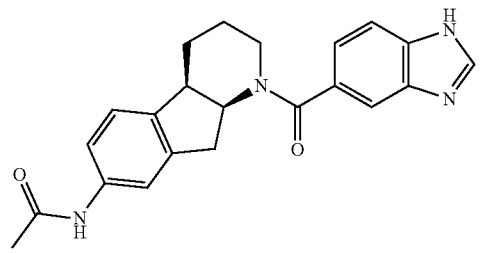 [SMILES: CC(=O)Nc1ccc2c(c1)C[C@H]1[C@@H]2CCCN1C(=O)c1ccc2[nH]cnc2c1]

The title compound is prepared from 1H-benzoimidazole-5-carboxylic acid and N-(cis-2,3,4,4a,9,9a-hexahydro-1H-indeno[2,1-b]pyridin-7-yl)-acetamide following a procedure analogous to that described in Example 1. Yield: 34% of theory; LC (method 1): $t_R$=1.97 min; Mass spectrum (ESI$^+$): m/z=375 [M+H]$^+$.

Example 167

N-[cis-1-(1H-Benzoimidazole-5-carbonyl)-2,3,4,4a,9,9a-hexahydro-1H-indeno[2,1-b]pyridin-7-yl]-methanesulfonamide

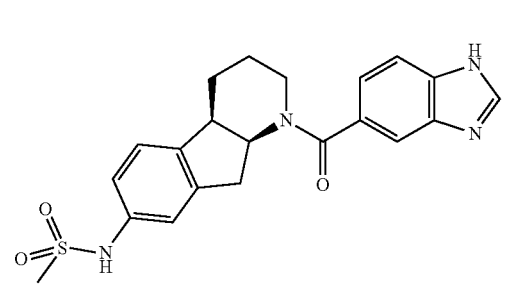 [SMILES: CS(=O)(=O)Nc1ccc2c(c1)C[C@H]1[C@@H]2CCCN1C(=O)c1ccc2[nH]cnc2c1]

The title compound is prepared from 1H-benzoimidazole-5-carboxylic acid and N-(cis-2,3,4,4a,9,9a-Hexahydro-1H-indeno[2,1-b]pyridin-7-yl)-methanesulfonamide following a procedure analogous to that described in Example 1. Yield: 7% of theory; LC (method 1): $t_R$=2.07 min; Mass spectrum (ESI$^+$): m/z=411 [M+H]$^+$.

Example 168

(1H-Benzoimidazol-5-yl)-(cis-6-hydroxy-7-nitro-2,3,4,4a,9,9a-hexahydro-indeno[2,1-b]pyridin-1-yl)-methanone

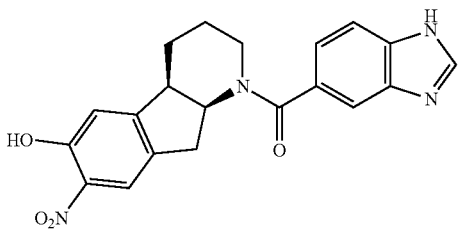

The title compound is prepared from 1H-benzoimidazole-5-carboxylic acid and cis-7-nitro-2,3,4,4a,9,9a-hexahydro-1H-indeno[2,1-b]pyridin-6-ol following a procedure analogous to that described in Example 1. Yield: 32% of theory; LC (method 1): $t_R$=2.43 min; Mass spectrum (ESI$^+$): m/z=379 [M+H]$^+$.

Example 169

(cis-7-Amino-6-hydroxy-2,3,4,4a,9,9a-hexahydro-indeno[2,1-b]pyridin-1-yl)-(1H-benzoimidazol-5-yl)-methanone

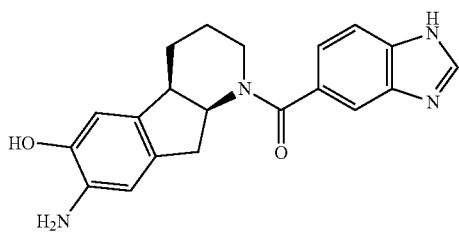 [SMILES: O=C(c1ccc2[nH]cnc2c1)N1CCC[C@@H]2c3cc(O)c([N+](=O)[O-])cc3C[C@@H]21]

A mixture of (1H-benzoimidazol-5-yl)-(cis-6-hydroxy-7-nitro-2,3,4,4a,9,9a-hexahydro-indeno[2,1-b]pyridin-1-yl)-methanone (0.56 g), 10% palladium on carbon (50 mg), and methanol (10 mL) is shaken under hydrogen atmosphere (1 bar) at room temperature for 3 h. The catalyst is separated by filtration and the filtrate is concentrated. The residue is chromatographed (dichloromethane/methanol 1:1→7:3) to give the title compound. Yield: 0.32 g (63% of theory); LC (method 1): $t_R$=0.65 min; Mass spectrum (ESI$^+$): m/z=349 [M+H]$^+$.

Example 170

(1H-Benzoimidazol-5-yl)-(cis-2-methyl-4b,5,6,7,8a,9-hexahydro-3-oxa-1,8-diaza-cyclopenta[b]fluoren-8-yl)-methanone

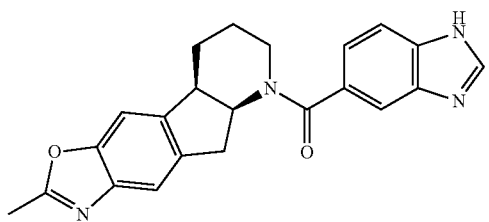 [SMILES: Cc1nc2cc3c(cc2o1)[C@H]1CCCN(C(=O)c2ccc4[nH]cnc4c2)[C@H]1C3]

(cis-7-Amino-8-hydroxy-2,3,4,4a,9,9a-hexahydro-indeno[2,1-b]pyridin-1-yl)-(1H-benzoimidazol-5-yl)-methanone (0.10 g) in triethyl orthoformate (0.5 mL) is stirred at 60° C. for 2 h. After cooling to room temperature, the mixture is concentrated and the residue is chromatographed on silica gel (dichloromethane/methanol 1:0→7:3) to afford the title compound. Yield: 64% of theory; LC (method 1): $t_R$=2.28 min; Mass spectrum (ESI$^+$): m/z=373 [M+H]$^+$.

Example 171

(1H-Benzoimidazol-5-yl)-(cis-4b,5,6,7,8a,9-hexahydro-3-oxa-1,8-diaza-cyclopenta[b]fluoren-8-yl)-methanone

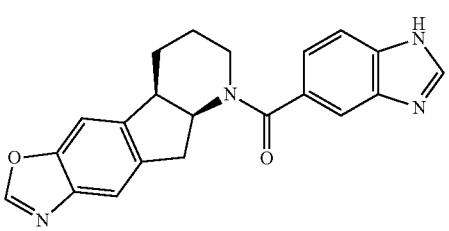 [SMILES: O=C(c1ccc2[nH]cnc2c1)N1CCC[C@@H]2c3cc4ocnc4cc3C[C@@H]21]

A mixture of (cis-7-amino-8-hydroxy-2,3,4,4a,9,9a-hexahydro-indeno[2,1-b]pyridin-1-yl)-(1H-benzoimidazol-5-yl)-methanone (100 mg), 4-toluenesulfonic acid hydrate (5 mg), triethyl orthoformate (40 μL), and methanol (1 mL) is stirred at 60° C. for 2 h. After cooling to room temperature, the mixture is concentrated and the residue is dissolved in ethyl acetate. The resulting solution is washed with 1 M NaOH solution, dried (Na$_2$SO$_4$), and concentrated to give the title compound. Yield: 50 mg (49% of theory); LC (method 1): $t_R$=2.24 min; Mass spectrum (ESI$^+$): m/z=359 [M+H]$^+$.

Example 172

(1H-Benzoimidazol-5-yl)-(cis-6-methoxy-7-methyl-2,3,4,4a,9,9a-hexahydro-indeno[2,1-b]pyridin-1-yl)-methanone

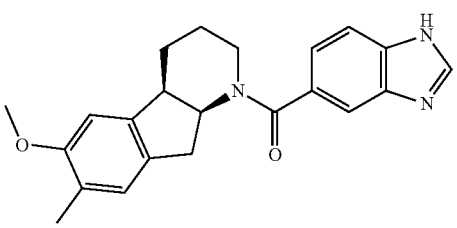 [SMILES: COc1cc2c(cc1C)C[C@H]1[C@@H]2CCCN1C(=O)c1ccc2[nH]cnc2c1]

The title compound is prepared from 1H-benzoimidazole-5-carboxylic acid and cis-6-methoxy-7-methyl-2,3,4,4a,9,9a-hexahydro-1H-indeno[2,1-b]pyridine following a procedure analogous to that described in Example 1. LC (method 7): $t_R$=1.04 min; Mass spectrum (ESI$^+$): m/z=362 [M+H]$^+$.

Example 173

(1H-Benzoimidazol-5-yl)-(cis-6-hydroxy-7-methyl-2,3,4,4a,9,9a-hexahydro-indeno[2,1-b]pyridin-1-yl)-methanone

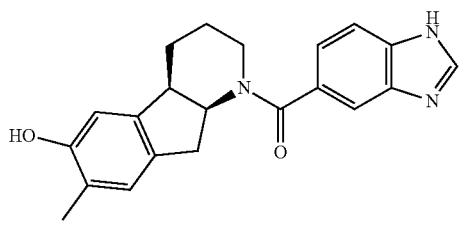 [SMILES: Cc1cc2c(cc1O)[C@H]1CCCN(C(=O)c3ccc4[nH]cnc4c3)[C@H]1C2]

The title compound is prepared from (1H-benzoimidazol-5-yl)-(cis-6-methoxy-7-methyl-2,3,4,4a,9,9a-hexahydro-indeno[2,1-b]pyridin-1-yl)-methanone following a procedure analogous to that described in Example 7. LC (method 7): $t_R$=0.82 min; Mass spectrum (ESI$^+$): m/z=348 [M+H]$^+$.

Examples 174 and 175

(4a-R,9a-S)-1-(1H-Benzoimidazole-5-carbonyl)-7-methyl-2,3,4,4a,9,9a-hexahydro-1H-indeno[2,1-b]pyridine-6-carbonitrile (174) and (4a-S,9a-R)-1-(1H-Benzoimidazole-5-carbonyl)-7-methyl-2,3,4,4a,9,9a-hexahydro-1H-indeno[2,1-b]pyridine-6-carbonitrile (175) (the Absolute Configuration of the Two Compounds is Arbitrarily Assigned)

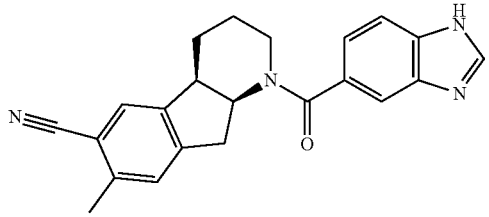

174

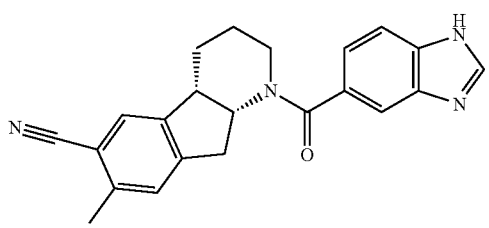

175

The title compounds are prepared from trifluoromethanesulfonic acid cis-7-methyl-1-(1-trifluoromethanesulfonyl-1H-benzoimidazole-5-carbonyl)-2,3,4,4a,9,9a-hexahydro-1H-indeno[2,1-b]pyridin-6-yl ester (mixture of isomers regarding sulfonyl group attachment at N-1 or N-3 of the benzimidazole) and zinc cyanide following a procedure analogous to that described in Example 106; the title compounds are separated by SFC on chiral phase. (4a-R,9a-S)-1-(1H-Benzoimidazole-5-carbonyl)-7-methyl-2,3,4,4a,9,9a-hexahydro-1H-indeno[2,1-b]pyridine-6-carbonitrile (174): LC (method 7): $t_R$=0.88 min; Mass spectrum (ESI$^+$): m/z=357 [M+H]$^+$, 379 [M+Na]$^+$. (4a-S,9a-R)-1-(1H-Benzoimidazole-5-carbonyl)-7-methyl-2,3,4,4a,9,9a-hexahydro-1H-indeno[2,1-b]pyridine-6-carbonitrile (175): LC (method 7): $t_R$=0.88 min; Mass spectrum (ESI$^+$): m/z=357 [M+H]$^+$, 379 [M+Na]$^+$.

Examples 176 and 177

(4a-R,9a-S)-1-(1H-Benzoimidazole-5-carbonyl)-5-methyl-2,3,4,4a,9,9a-hexahydro-1H-indeno[2,1-b]pyridine-6-carbonitrile (176) and (4a-S,9a-R)-1-(1H-Benzoimidazole-5-carbonyl)-5-methyl-2,3,4,4a,9,9a-hexahydro-1H-indeno[2,1-b]pyridine-6-carbonitrile (177) (the Absolute Configuration of the Two Compounds is Arbitrarily Assigned)

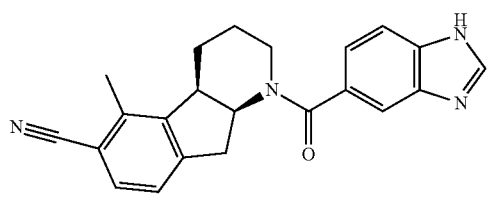

176

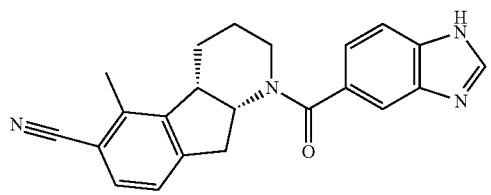

177

The title compounds are prepared from trifluoromethanesulfonic acid cis-5-methyl-1-(1-trifluoromethanesulfonyl-1H-benzoimidazole-5-carbonyl)-2,3,4,4a,9,9a-hexahydro-1H-indeno[2,1-b]pyridin-6-yl ester (mixture of isomers regarding sulfonyl group attachment at N-1 or N-3 of the benzimidazole) and zinc cyanide following a procedure analogous to that described in Example 106; the title compounds are separated by SFC on chiral phase. (4a-R,9a-S)-1-(1H-Benzoimidazole-5-carbonyl)-5-methyl-2,3,4,4a,9,9a-hexahydro-1H-indeno[2,1-b]pyridine-6-carbonitrile (176): LC (method 7): $t_R$=0.89 min; Mass spectrum (ESI$^+$): m/z=357 [M+H]$^+$, 379 [M+Na]$^+$. (4a-S,9a-R)-1-(1H-Benzoimidazole-5-carbonyl)-5-methyl-2,3,4,4a,9,9a-hexahydro-1H-indeno[2,1-b]pyridine-6-carbonitrile (177): LC (method 7): $t_R$=0.89 min; Mass spectrum (ESI$^+$): m/z=357 [M+H]$^+$, 379 [M+Na]$^+$.

Some examples of formulations will now be described in which the term "active substance" denotes one or more compounds according to the invention, including the salts thereof. In the case of one of the combinations with one or additional active substances as described previously, the term "active substance" also includes the additional active substances.

Example A

Tablets Containing 100 mg of Active Substance

Composition:

| 1 tablet contains: | |
|---|---|
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Method of Preparation:

The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.

Weight of tablet: 220 mg
Diameter: 10 mm, biplanar, facetted on both sides and notched on one side.

Example B

Tablets Containing 150 mg of Active Substance

Composition:

| 1 tablet contains: | |
|---|---|
| active substance | 150.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation:

The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture.

Weight of tablet: 300 mg
die: 10 mm, flat

Example C

Hard Gelatine Capsules Containing 150 mg of Active Substance

Composition:

| 1 capsule contains: | |
|---|---|
| active substance | 150.0 mg |
| corn starch (dried) approx. | 180.0 mg |
| lactose (powdered) approx. | 87.0 mg |
| magnesium stearate | 3.0 mg |
| approx. | 420.0 mg |

Preparation:

The active substance is mixed with the excipients, passed through a screen with a mesh size of 0.75 mm and homogeneously mixed using a suitable apparatus. The finished mixture is packed into size 1 hard gelatine capsules.

Capsule filling: approx. 320 mg
Capsule shell: size 1 hard gelatine capsule.

Example D

Suppositories Containing 150 mg of Active Substance

Composition:

| 1 suppository contains: | |
|---|---|
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

Preparation:

After the suppository mass has been melted the active substance is homogeneously distributed therein and the melt is poured into chilled moulds.

Example E

Ampoules Containing 10 mg Active Substance

Composition:

| | |
|---|---|
| active substance | 10.0 mg |
| 0.01 N hydrochloric acid q.s. | |
| double-distilled water ad | 2.0 mL |

Preparation:

The active substance is dissolved in the necessary amount of 0.01 N HCl, made isotonic with common salt, filtered sterile and transferred into 2 mL ampoules.

Example F

Ampoules containing 50 mg of active substance

Composition:

| | |
|---|---|
| active substance | 50.0 mg |
| 0.01 N hydrochloric acid q.s. | |
| double-distilled water ad | 10.0 mL |

Preparation:

The active substance is dissolved in the necessary amount of 0.01 N HCl, made isotonic with common salt, filtered sterile and transferred into 10 mL ampoules.

We claim:

1. A solid pharmaceutical composition comprising a pharmaceutically acceptable carrier or diluent; and a compound represented by the following structural formula:

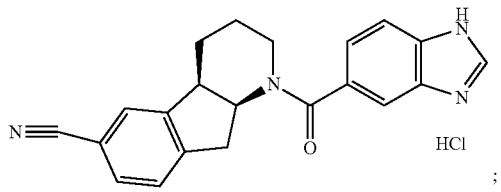 [SMILES: N#Cc1ccc2c(c1)[C@H]1CCCN(C(=O)c3ccc4[nH]cnc4c3)[C@H]1C2 ; Cl]

wherein at least 50% by weight of the compound is a single crystalline form characterized by x-ray powder diffraction peaks at 2Θ angles selected from 13.7°, 17.6°, 21.3°, 21.9°, 23.3°, 25.6° and 26.5°.

2. A method of treating a disease or condition selected from type 1 and type 2 diabetes mellitus, a metabolic disorder, retinopathy, nephropathy, neuropathy, hypoglycemia, hyperinsulinemia, insulin resistance, metabolic syndrome, dyslipidemia, atherosclerosis, obesity, high blood pressure, chronic heart failure, edema, hyperuricemia, acute renal failure, glaucoma, osteoporosis, cognitive impairment, anxiety, depression, tuberculosis, leprosy, and psoriasis, comprising administering a compound represented by the following structural formula:

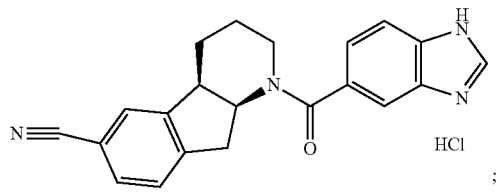 [SMILES: N#Cc1ccc2c(c1)[C@H]1CCCN(C(=O)c3ccc4[nH]cnc4c3)[C@H]1C2 ; Cl]

wherein at least 50% by weight of the compound is a single crystalline form characterized by x-ray powder diffraction peaks at 2Θ angles selected from 13.7°, 17.6°, 21.3°, 21.9°, 23.3°, 25.6° and 26.5°.

3. The solid pharmaceutical composition of claim 1, wherein at least 90% by weight of the compound is a single crystalline form characterized by x-ray powder diffraction peaks at 2Θ angles selected from 13.7°, 17.6°, 21.3°, 21.9°, 23.3°, 25.6° and 26.5°.

4. The solid pharmaceutical composition of claim 3, wherein at least 99% by weight of the compound is a single crystalline form characterized by x-ray powder diffraction peaks at 2Θ angles selected from 13.7°, 17.6°, 21.3°, 21.9°, 23.3°, 25.6° and 26.5°.

5. The method of claim 2, wherein at least 90% by weight of the compound is a single crystalline form characterized by x-ray powder diffraction peaks at 2Θ angles selected from 13.7°, 17.6°, 21.3°, 21.9°, 23.3°, 25.6° and 26.5°.

6. The method of claim 5, wherein at least 99% by weight of the compound is a single crystalline form characterized by x-ray powder diffraction peaks at 2Θ angles selected from 13.7°, 17.6°, 21.3°, 21.9°, 23.3°, 25.6° and 26.5°.

* * * * *